United States Patent
Van Ness et al.

(10) Patent No.: US 6,361,940 B1
(45) Date of Patent: Mar. 26, 2002

(54) COMPOSITIONS AND METHODS FOR ENHANCING HYBRIDIZATION AND PRIMING SPECIFICITY

(75) Inventors: Jeffrey Van Ness, Seattle; John C. Tabone, Bothell; Lori K. Garrison, Seattle, all of WA (US)

(73) Assignee: QIAGEN Genomics, Inc., Bothell, WA (US)

( * ) Notice: Subject to any disclaimer, the term of this patent is extended or adjusted under 35 U.S.C. 154(b) by 0 days.

(21) Appl. No.: 09/053,831

(22) Filed: Apr. 1, 1998

Related U.S. Application Data

(63) Continuation-in-part of application No. 09/002,051, filed on Dec. 31, 1997, now abandoned, which is a continuation-in-part of application No. 08/933,924, filed on Sep. 23, 1997, now abandoned.

(60) Provisional application No. 60/026,621, filed on Sep. 24, 1996.

(51) Int. Cl.$^7$ .................. C12Q 1/68; C07H 19/00; C07H 21/00; C07H 21/02; C07H 21/04
(52) U.S. Cl. ............ 435/6; 435/91.1; 435/91.2; 536/22.1; 536/23.1; 536/24.3; 536/25.3
(58) Field of Search .............. 435/6, 91.1, 91.2; 536/22.1, 23.1, 24.3, 25.3

(56) References Cited

U.S. PATENT DOCUMENTS

| | | | | |
|---|---|---|---|---|
| 4,405,717 A | * | 9/1983 | Urbas | 435/140 |
| 4,683,195 A | | 7/1987 | Mullis et al. | 435/6 |
| 4,683,202 A | | 7/1987 | Mullis | 435/91 |
| 4,800,159 A | | 1/1989 | Mullis et al. | 435/172.3 |
| 4,851,331 A | | 7/1989 | Vary et al. | 435/6 |
| 4,873,192 A | | 10/1989 | Kunkel | 435/172.3 |
| 5,066,584 A | | 11/1991 | Gyllensten et al. | 435/91 |
| 5,137,806 A | | 8/1992 | LeMaistre et al. | 435/6 |
| 5,210,015 A | | 5/1993 | Gelfand et al. | 435/6 |
| 5,219,727 A | | 6/1993 | Wang et al. | 435/6 |
| 5,407,801 A | | 4/1995 | Miller | 435/6 |
| 5,589,335 A | | 12/1996 | Kearney et al. | 435/6 |
| 5,595,890 A | | 1/1997 | Newton et al. | 435/91.2 |
| 5,633,129 A | * | 5/1997 | Karger et al. | 435/6 |
| 5,641,658 A | | 6/1997 | Adams et al. | 435/91.2 |
| 5,698,391 A | * | 12/1997 | Cook et al. | 435/5 |

FOREIGN PATENT DOCUMENTS

| | | |
|---|---|---|
| EP | 237 362 A1 | 9/1987 |
| EP | 420 260 A2 | 4/1991 |
| EP | 628 571 A1 | 12/1994 |
| EP | 731 177 A2 | 9/1996 |
| EP | 742 287 A2 | 11/1996 |
| WO | WO 87/06621 | 11/1987 |

(List continued on next page.)

OTHER PUBLICATIONS

Wilk et al "Backbone–modified oligonucleotides containing a butanediol–1,3 moiety as a 'vicarious segment' for tehdeoxyribosyl moiety –synthesis and enzyme studies" Nucleic Acids Research, vol. 18, No. 8 pp. 2065–2068, 1990.*

(List continued on next page.)

*Primary Examiner*—Jezia Riley
(74) *Attorney, Agent, or Firm*—Seed Intellectual Property Law Group PLLC

(57) ABSTRACT

Compositions and methods are provided for increasing the specificity of a probe nucleic acid for a target nucleic acid in a hybridization solution. An abasic residue, deoxyNebularine residue, or a hybotrope is used to increase specificity. A method is provided for identifying useful hybotropes, including salts, water miscible organic solvents, aprotic solvents and organic solvents, on the basis of enthalpy considerations. Hybotropic hybridization and modified oligonucleotides may be used in amplification reactions, such as PCR, sequence analysis methods, and genomic screening methods.

97 Claims, 30 Drawing Sheets

FOREIGN PATENT DOCUMENTS

| WO | WO 89/01941 | 3/1989 |
|---|---|---|
| WO | WO 90/12116 | 10/1990 |
| WO | WO 92/15708 | 9/1992 |
| WO | WO 92/18649 | 10/1992 |
| WO | WO 93/20234 | 10/1993 |
| WO | WO 94/06815 | 3/1994 |
| WO | WO 95/19776 | 7/1995 |
| WO | WO 95/30774 | 11/1995 |
| WO | WO 97/46711 | 12/1997 |

OTHER PUBLICATIONS

Pease et al. "Light–generated oligonucleotide arrays for rapid DNA sequence analysis" PNAS, vol. 91, pp. 5022–5026, 1994.*

Aerschot et al., "An acyclic 5–nitroindazole nucleoside analogue as ambiguous nucleoside," *Nucleic Acids Research* 23 (21):4363–4370, 1995.

Bergstrom et al., "Comparision of the base pairing properties of a series of nitroazole nucleobase analogs in the oligodeoxyribonucleotide sequence 5'-d(CGCXAAT-TYGCG)-3'," *Nucleic Acids Research* 25 (10):1935–1942, 1997.

Bergstrom et al., "Synthesis, Structure, and Deoxyribonucleic Acid Sequencing with a Universal Nucleoside: 10(2'–Deoxy–β–D–ribofuranosyl)–3–nitropyrrole," *J. Am. Chem. Soc.* 117:1201–1209, 1995.

Birnboim and Doly, "A rapid alkaline extraction procedure for screening recombinant plasmid DNA," *Nucleic Acids Research* 7 (6):1513–1523, 1979.

Chen and Seeburg, "Laboratory Methods. Supercoil Sequencing: A Fast and Simple Method for Sequencing Plasmid DNA," *DNA* 4 (2):165–170, 1985.

Chengzhi et al., "Synthesis of a Pyrimidine Isostere of the N–Methyl–D–Aspartate Antagonist SDZ EAB 515," *Tetrahedron* 50 (19): 5735–5740, 1994.

De and Roychowdhury, "Crystal and molecular structure of an isostere of purine ring system: 7–benzylamino–2–methylmercaptothiazolo [5,4–d] pyrimidine," *Zeitschrift füKristallographie* 188:69–75, 1989.

Fernández–Resa and Stud, "Synthesis of 2–S–Dioxo Isosteres of Purine and Pyrimidine Nucleosides. II(1)," *J. Heterocyclic Chem.* 19: 305–307, 1982.

Frey et al., "The Nucleotide Analog 2–Aminopurine as a Spectroscopic Probe of Nucleotide Incorporation by the Klenow Fragment of *Escherichia coli* Polymerase I and Bacteriophage T4 DNA Polymerase," *Biochemistry* 34: 9185–9192, 1995.

Gi et al., "Synthesis of Dihydroisoxazole Nucleoside and Nucleotide Analogs," *J. Org. Chem.* 62: 88–92, 1997.

Guilfoyle et al., "Ligation–mediated PCR amplification of specific fragments from a Class–II restriction endonuclease total digest," *Nucleic Acids Research* 25(9): 1854–1858, 1997.

Guo et al., "Enhanced discrimination of single nucleotide polymorphisms by artificial mismatch hybridization," *Nature Biotechnology* 15:331–335, 1997.

Johnson et al., "The synthesis and stability of oligodeoxyribonucleotides containing the deoxyadenosine mimic 1–(2'–deoxy–β–D–ribofuranosyl)imidazole–4–carboxamide," *Nucleic Acids Research* 25(3):559–567, 1997.

Kelley et al., "1–(Fluorobenzyl)–4–amino–1H–1,2,3–triazolo[4,5–c]pyridines: Synthesis and Anticonvulsant Activity," *J. Med. Chem.* 38:4131–4134, 1995.

Lane et al., "The thermodynamic advantage of DNA oligonucleotide 'stacking hybridization' reactions: energetics of a DNA nick," *Nucleic Acids Research* 25(3):611–616, 1997.

Lim et al., "Synthesis of the Pyrrol[3,2–d]Pyrimidine C–Nucleoside Isostere of Inosine," *Tetrahedron Letters* 21:1013–1016, 1980.

Loakes et al., "3–Nitropyrrole and 5–nitroindole as universal bases in primers for DNA sequencing and PCR," *Nucleic Acids Research* 23(13):2361–2366, 1995.

Luo et al., "Improving the fidelity of Thermus thermophilus DNA ligase," *Nucleic Acids Research* 24(14):3071–3078, 1996.

Majumdar and Thakur, "Melting transition of covalently closed DNA with supercoil–induced cruciforms," *Nucleic Acids Research* 13(16):5883–5893, 1985.

Marguet and Forterre, "DNA stability at temperatures typical for hypertheromophiles," *Nucleic Acids Research* 22(9):1681–1686, 1994.

Moran et al., "Difluorotoluene, a Nonpolar Isostere for Thymine, Codes Specifically and Efficiently for Adenine in DNA Replication," *J. Am. Chem. Soc.* 119:2056–2057, 1997.

Nishikawa et al., "Construction of a Human Genomic Library of Clones Containing Poly(dG–dA) ●Poly(dT–dC) Tracts by $Mg^{2+}$–dependent Triplex Affinity Capture," *The Journal of Biological Chemistry* 270 (16):9258–9264, 1995.

Pouwels et al., "Structure of the Replicative Form of Bacteriophage ØX DNA," *J. Mol. Biol.* 32:169–182, 1968.

Ram et al., "Chemotherapeutic Agents. XXIV Synthesis of Pyrazolo [3,4–d] pyrimidines as Isostere of Purines," *Journal für prakitische Chemi Chemiker–Zeitung* 334: 190–192, 1992.

Ren et al., "Synthetic Studies of the Thieno[3,2–d]pyrimidine C–Nucleoside Isostere of Inosine," *J. Org. Chem.* 47:4633–4637, 1982.

Sala et al., "Ambiguous base pairing of the purine analogue 1–2(2–deoxy–β–D–ribofuranosyl)–imidazole–4–carboxamide during PCR," *Nucleic Acids Research* 24(17):3302–3306, 1996.

Schweitzer and Kool, "Aromatic Nonpolar Nucleosides as Hydrophobic Isosteres of Pyrimidine and Purine Nucleosides," *J. Org. Chem.* 59:7238–7242, 1994.

Shah et al., "Synthesis of Amino–Acid–Derived Nucleo(side/tide) Analogs for Peptide–Derived Enantiospecific Nucleic Acid Analogs," *Bioorganic Chemistry* 24(Article No. 0017): 194–200, 1996.

Thumm et al., "Energy–structure correlations of plasmid DNA in different topological forms," *Nucleic Acids Research* 16(24):11737–11757, 1988.

Valenzuela and Siddiqui, "Bidirectional Sequencing of Supercoiled Plasmid DNA," *Analyticla Biochemistry* 183:258–262, 1989.

Van Ness and Chen, "the use of oligodeoxynucleotide probes in chaotrope based hybridization solutions," *Nucleic Acids Research* 19(19):5143–5151, 1991.

Vinograd et al., "Early and Late Helix–Coil Transitions in Closed Circular DNA The Number of Superhelical Turns in Polyoma DNA," *J. Mol. Biol.* 33:173–197, 1968.

Wetmur, "DNA Probes: Applications of the Principles of Nucleic Acid Hybridization," *Critical Reviews in Biochemistry and Molecular Biology* 26(¾):227–259, 1991.

Randall K. Saiki et al., "Primer–Directed Enzymatic Amplification of DNA with a Thermostable DNA Polymerase," *Science* 239:487–491, 1998.

* cited by examiner

COMPOSITIONS AND METHODS FOR ENHANCING HYBRIDIZATION AND PRIMING SPECIFICITY

CROSS-REFERENCE TO RELATED APPLICATIONS

This application is a continuation-in-part of U.S. patent application Ser. No. 09/002,051, filed Dec. 31, 1997, (now abandoned), which in turn is a continuation-in-part of U.S. patent application Ser. No. 08/933,924, filed Sep. 23, 1997, (now abandoned), which claims the benefit of U.S. Provisional Application No. 60/026,621, filed Sep. 24, 1996 (now abandoned), where these three applications are incorporated herein by reference.

TECHNICAL FIELD

The present invention relates generally to compositions and methods for hybridization of oligonucleotides, and more specifically to certain solutions and/or oligonucleotide analogues which may increase hybridization and priming specificity.

BACKGROUND OF THE INVENTION

The detection of diseases is increasingly important in prevention and treatments. While multifactorial diseases are difficult to devise genetic tests for, more than 200 known human disorders are caused by a defect in a single gene, often a change of a single amino acid residue (Olsen, *Biotechnology: An industry comes of age*, National Academic Press, 1986). Many of these mutations result in an altered amino acid that causes a disease state.

Sensitive mutation detection techniques offer extraordinary possibilities for mutation screening. For example, analyses may be performed even before the implantation of a fertilized egg (Holding and Monk, *Lancet* 3:532, 1989). Increasingly efficient genetic tests may also enable screening for oncogenic mutations in cells exfoliated from the respiratory tract or the bladder in connection with health check-ups (Sidransky et al., *Science* 252:706, 1991). Also, when an unknown gene causes a genetic disease, methods to monitor DNA sequence variants are useful to study the inheritance of disease through genetic linkage analysis. However, detecting and diagnosing mutations in individual genes poses technological and economic challenges. Several different approaches have been pursued, but none are both efficient and inexpensive enough for truly widescale application.

Mutations involving a single nucleotide can be identified in a sample by physical, chemical, or enzymatic means. Generally, methods for mutation detection may be divided into scanning techniques, which are suitable to identify previously unknown mutations, and techniques designed to detect, distinguish, or quantitate known sequence variants.

Several scanning techniques for detection of mutations have been developed on the observation that heteroduplexes of mismatched complementary DNA strands exhibit an abnormal behavior, especially when denatured. This phenomenon is exploited in denaturing and temperature gradient gel electrophoresis (DGGE and TGGE, respectively) methods. Duplexes mismatched in even a single nucleotide position can partially denature, resulting in retarded migration, when electrophoresed in an increasingly denaturing gradient gel (Myers et al., *Nature* 313:495, 1985; Abrams et al., *Genomics* 7:463, 1990; Henco et al., *Nucl. Acids Res.* 18:6733, 1990). Although mutations may be detected, no information is obtained regarding the precise location of a mutation. Mutant forms must be further isolated and subjected to DNA sequence analysis.

Alternatively, a heteroduplex of an RNA probe and a target strand may be cleaved by RNase A at a position where the two strands are not properly paired. The site of cleavage can then be determined by electrophoresis of the denatured probe. However, some mutations may escape detection because not all mismatches are efficiently cleaved by RNase A.

Mismatched bases in a duplex are also susceptible to chemical modification. Such modification can render the strands susceptible to cleavage at the site of the mismatch or cause a polymerase to stop in a subsequent extension reaction. The chemical cleavage technique allows identification of a mutation in target sequences of up to 2 kb and it provides information on the approximate location of mismatched nucleotide(s) (Cotton et al., *PNAS USA* 85:4397, 1988; Ganguly et al., *Nucl. Acids Res.* 18:3933, 1991). However, this technique is labor intensive and may not identify the precise location of the mutation.

An alternative strategy for detecting a mutation in a DNA strand is by substituting (during synthesis) one of the normal nucleotides with a modified nucleotide, thus altering the molecular weight or other physical parameter of the product. A strand with an increased or decreased number of this modified nucleotide relative to the wild-type sequence exhibits altered electrophoretic mobility (Naylor et al., *Lancet* 337:635, 1991). This technique detects the presence of a mutation, but does not provide the location.

Two other strategies visualize mutations in a DNA segment by altered gel migration. In the single-strand conformation polymorphism technique (SSCP), mutations cause denatured strands to adopt different secondary structures, thereby influencing mobility during native gel electrophoresis. Heteroduplex DNA molecules, containing internal mismatches, can also be separated from correctly matched molecules by electrophoresis (Orita, *Genomics* 5:874, 1989; Keen, *Trends Genet.* 7:5, 1991). As with the techniques discussed above, the presence of a mutation may be determined but not the location. As well, many of these techniques do not distinguish between a single and multiple mutations.

All of the above-mentioned techniques indicate the presence of a mutation in a limited segment of DNA and some of them allow approximate localization within the segment. However, sequence analysis is still required to unravel the effect of the mutation on the coding potential of the segment. Sequence analysis is a powerful tool, allowing, for example, screening for the same mutation in individuals of an affected family, monitoring disease progression in the case of malignant disease, or for detecting residual malignant cells in bone marrow before autologous transplantation. Despite these advantages, the procedure is unlikely to be adopted as a routine diagnostic method because of the high expense involved.

A large number of other techniques have been developed to analyze known sequence variants. Automation and economy are very important considerations for implementation of these types of analyses. In this regard, none of the alternative techniques discussed below combine economy and automation with the required specificity.

A number of strategies for nucleotide sequence distinction all depend on enzymes to identify sequence differences (Saiki, *PNAS USA* 86:6230, 1989; Zhang, *Nucl. Acids Res.* 19:3929, 1991).

For example, restriction enzymes recognize sequences of about 4–8 nucleotides. Based on an average G+C content, approximately half of the nucleotide positions in a DNA segment can be monitored with a panel of 100 restriction enzymes. As an alternative, artificial restriction enzyme recognition sequences may be created around a variable position by using partially mismatched PCR primers. With this technique, either the mutant or the wild-type sequence alone may be recognized and cleaved by a restriction enzyme after amplification (Chen et al., *Anal. Biochem.* 195:51, 1991; Levi et al., *Cancer Res.* 51:3497, 1991).

Another method exploits the property that an oligonucleotide primer that is mismatched to a target sequence at the 3' penultimate position exhibits a reduced capacity to serve as a primer in PCR. However, some 3' mismatches, notably G-T, are less inhibitory than others, thus limiting its usefulness. In attempts to improve this technique, additional mismatches are incorporated into the primer at the third position from the 3' end. This results in two mismatched positions in the three 3' nucleotides of the primer hybridizing with one allelic variant, and one mismatch in the third position in from the 3' end when the primer hybridizes to the other allelic variant (Newton et al., *Nucl. Acids Res.* 17:2503, 1989). For this technique to be successful, it is necessary to define amplification conditions that significantly disfavor amplification in the presence of a 1 bp (basepair) mismatch. In fact, this technique is rarely successful (see, e.g., Sininsky, *J. Nucl. Acids Res.*, 1990).

DNA polymerases have also been used to distinguish allelic sequence variants by determining which nucleotide is added to an oligonucleotide primer immediately upstream of a variable position in the target strand. Based on this approach, a ligation assay has been developed. In this method, two oligonucleotide probes hybridizing in immediate juxtaposition on a target strand are joined by a DNA ligase. Ligation is inhibited if there is a mismatch where the two oligonucleotide probes abut.

Mutations may be identified via their destabilizing effects on the hybridization of short oligonucleotide probes to a target sequence (see Wetmur, *Crit. Rev. Biochem. Mol. Biol.* 26:227, 1991). Generally, this technique, allele-specific oligonucleotide hybridization, involves amplification of target sequences and subsequent hybridization with short oligonucleotide probes. An amplified product can be scanned for many possible sequence variants by determining its hybridization pattern to an array of immobilized oligonucleotide probes. Many of these techniques, especially allele-specific oligonucleotide hybridization, require establishing conditions that favor the hybridization of an exact match over a mismatch. As is well known, such conditions are difficult to achieve. One approach to improving hybridization is the addition of a chaotrope.

Chaotropes decrease the melting temperature of an oligonucleotide duplex (see Van Ness and Chen, *Nucleic Acids Research* 19:5143, 1991). Oligonucleotide probes (12–50 mers) possess some functional properties that are not shared by long DNA probes. These parameters include different rates of duplex formation as a function of (a) the difference between the hybridization temperature and the $T_m$, (b) stringency requirements for maximal selectivity/specificity of hybridization, and (c) sequence-specific anomalous behavior.

Chaotropes are useful in DNA probe-based diagnostic assays, as they can simultaneously lyse the cells of organisms of interest, inhibit nucleases and proteases, and provide adequate hybridization stringency without chemically altering the target analyte. Chaotropic lysis and hybridization solutions eliminate the need to isolate nucleic acid prior to conducting the DNA probe assay, and facilitate the development of rapid and simple assay formats (see Van Ness and Chen, *Nucleic Acids Research* 19:5143, 1991, for review). However, the commonly used chaotropes do not substantially increase the differential hybridization of matched/mismatched sequences. Furthermore, they do not neutralize the dependence of $T_m$ and $T_d$ on G+C content.

In addition, special problems arise when hybridization methods are employed that involve the use of mixed pools of oligonucleotide probes (12- to 50-mers) having differing base sequences and G+C content. Many applications utilize mixed pools of oligonucleotides and are frustrated by a host of problems. For example, many gene isolation strategies involve the reverse translation of a known polypeptide sequence into a set of all possible DNA sequences that can encode that protein (Jaye et al., *Nucl. Acids Res.* 11:2325–2335, 1983). A pool of oligonucleotide probes, homologous to the set of possible protein encoding DNA sequences, are then used to screen a genomic or cDNA library from the relevant organism or cell type in order to identify the desired gene sequence. While the length of all of the oligonucleotide probes is the same, the G+C content of each probe may vary significantly, making the selection of hybridization conditions that are suitable and specific for each oligonucleotide problematic. As a result, often many false positive clones will be selected when screening highly complex libraries for genes of low abundance.

This problem of simultaneously and accurately hybridizing many differing oligonucleotides of differing G+C content is even greater for sequence analysis of a specific region of DNA or identifying single base change mutations using large arrays of oligonucleotides (which may vary from 100% A+T to 100% G+C) bound to a fixed surface (Southern et al., *Genomics* 13:1008–1017, 1992; Maskos and Southern, *Nucl. Acids Res.* 20:1675–1678, 1992). These methods, while theoretically powerful, have been sorely limited by the inability to identify hybridization conditions that will facilitate accurate hybridization (i.e., no mismatch hybrid duplexes formed) and allow all possible perfect hybrids to be stably formed.

One attempted solution has been to use a class of salts composed of small alkylammonium ions (most commonly tetramethylammonium (TMA+) and tetraethylammonium (TEA+)), that can greatly decrease the effect of base composition on DNA melting (Marky et al., *Biochemistry* 20:1427–1431, 1981; De Murcia et al., *Biophys. Chem.* 8:377–383, 1978; Melchior and Von Hippel, *Proc. Nat. Acad. Sci. USA* 70:298–302, 1973). Of the tetraalkylammonium salts, only TMA+ and TEA+ are small enough to fit into the major groove of the B-form DNA double helix where they bind to the A+T base pairs of DNA (perhaps to the O-2 of thymine) (see De Murcia et al., *Biophysical Chemistry* 8:377 1978). The overall effect on stability is two-fold with the first being that the tetraalkylammonium salts increase the non-polar character of the solvent which destabilizes the base stacking interactions in native DNA (see Rees et al., *Biochemistry* 32:137, 1993). The second effect is that the A+T base pairs are stabilized. Specifically, TMACl prevents DNA premelting by decreasing the transient openings between the base pairs from occurring below the melting temperature (see De Murcia et al., *Biophysical Chemistry* 8:377 1978; Marky et al., *Biochemistry* 20:1427, 1981). The exact nature of TEACl stabilization is not known. Overall, the A+T pairing is stabilized resulting in a rise in the melting temperature for the A+T pairs (see Marky et al., *Biochemistry* 20:1427 1981; De Murcia et al., *Biophysical Chemistry* 8:377 1978). For 100% A+T oligonucleotide duplexes, the $T_m$ in TMACl is actually 6° C. higher than that found in a sodium solution (see Marky et al., *Biochemistry* 20:1427, 1981).

When genomic DNA is melted in TMACl or TEACl at the specific concentrations of 3 M and 2.4 M, respectively, identical melting temperatures are exhibited for A+T and G+C pairs (see Melchior et al., *Proc. Natl. Acad. Sci. USA* 70:298, 1973). Usually what is observed is that synthetic DNA duplex stability in concentrated TMACl and TEACl stability is somewhat diminished and has little base compositional dependence (see Wood et al., *Proc. Natl. Acad. Sci. USA* 82:1585 1985; Marky et al., *Biochemistry* 20:1427 1981; Jacobs et al., *Nucleic Acids Res.* 16:4637, 1988). For example, a series of 19-mers ranging from 26% G+C to 79% G+C content had melting temperatures over a range of 18° C. in 2×SSC, while in 3 M TMACl the range narrowed to 5° C. and in 2.4 M TEACl, the temperatures were virtually unchanged negating all influence from G+C content (see Jacobs et al., *Nucleic Acids Res.* 16:4637, 1988). TEACl had the added benefit of reducing the melting temperature approximately 22° C. over TMACl and SSC (see Jacobs et al., *Nucleic Acids Res.* 16:4637, 1988). When various lengths of hybridization probes are measured and the corresponding melting temperatures plotted versus length, the plot is a smooth curve even though the G+C content varied from 31–66% (see Wood et al., *Proc. Natl. Acad. Sci. USA* 82:1585 1985).

In the context of gene isolation from complex libraries, the number of false positive clones isolated using a 17-mer mixed oligo pool (G+C range of 47% to 71%) was reduced 100-fold when performed in 3 M TMACl rather than using a NaCl hybridization solution (Wood et al., *Proc. Nat. Acad. Sci. USA* 82:1585–1588, 1985). However, even when using TMACl to eliminate the base composition effect on $T_m$, a significant number of false positive clones are still isolated due to formation of mismatched hybrids.

Using deoxyinosine at the third codon position (Honoré et al., *J. Biochem. Biophys. Methods* 27:39–48, 1993) of highly degenerate oligonucleotide pools from backtranslated protein sequences allows the oligonucleotide pool size to be significantly reduced. However, when screening a more complex genomic library for clones, the isolation of false positive clones may still be a significant problem (Jacobs et al., *Nucl. Acids Res.* 16:4637–4650, 1988). While the presence of tetramethylammonium and tetraethylammonium salts made oligonucleotide melting independent of base composition, there was no or little effect of mismatches on the thermal melting of oligonucleotides. That is, duplexes containing a mismatch had a similar $T_m$ to duplexes which were perfectly base-paired.

Another method used to enhance specificity in hybridization reactions creates base mismatches using base analogs to replace any of the A, G, C, or T nucleotides. Research has shown that some primers containing a base pair mismatch have increased specificity when the mismatch is placed in precise locations (see Wenham et al., *Clinical Chemistry* 37:241, 1991; Newton et al., *Nucleic Acids Research* 17:2503, 1989; Ishikawa et al., *Human Immunology* 42:315, 1995). However, differences of as little as 0.5° C. in the melting temperatures are equally common between perfectly matched hybrids and the same hybrid with a single base mismatch introduced (see Tibanyenda et al., *European Journal of Biochemistry* 139:19, 1984; Wemtges et al., *Nucleic Acids Research* 14:3773, 1986). Even better specificity has been noted between one and two base mismatched duplexes than has been observed between a perfectly matched duplex and the same duplex with a single mismatch (see Guo et al., *Nature Biotechnology* 15:331, 1997). Guo et al. found a ($T_m$ of 4° C. between zero and one mismatches and a $\Delta T_m$ of 13° C. between one and two adjacent mismatches for a 20-mer duplex. However, even with two mismatches, often there is still little destabilization of the duplex. This inability to consistently discriminate mismatches lends to the lack of specificity in PCR.

The use of more than one base pair mismatch per hybridization employing at least one nucleotide analog has been evaluated (see Guo et al., *Nature Biotechnology* 15:331, 1997). In this case, the analog compound consists of 3-nitropyrrole replacement of the purine or pyrimidine bases. 3-Nitropyrrole has the ability to minimally hydrogen bond with all four bases (see Nichols et al., *Nature* 369:492, 1994; Bergstrom et al., *Journal of the American Chemical Society* 117:1201, 1995). By introducing an artificial mismatch, large differences in the duplex melting temperatures occur ranging from approximately 5° C. to 15° C. with the largest difference occurring when the mismatch is located at the center of the 15-mer hybridizing oligo. Significant differences in $\Delta T_m$ occur when an artificial nucleotide is introduced into a duplex that already contains a base mismatch creating a two-mismatch duplex. The degree of destabilization depends upon the type of base mismatch (e.g., G/T) and the separation between the two mismatches. In experimental examination, the base analog nucleotide ranged from 1 to 7 bases to the 3' side of the base mismatch, which was held in the center of the 15-mer. Differences in $\Delta T_m$ for the three different base mismatched 15-mers ranged from a 2° C. stabilization (in the C/T mismatch case only and when the mismatches are adjacent) to a 7° C. further destabilization with the maximum destabilization consistently occurring at a 3 or 4 base mismatch separation (see Guo et al., *Nature Biotechnology* 15:331, 1997).

When two artificial mismatches are introduced, the proximity of the artificial bases greatly influences the degree of destabilization. The two artificial mismatches were centered on the middle of a 21-mer duplex beginning with a separation of 6 bp. The destabilization, or $\Delta T_m$, is minimally 12° C. when compared to the perfectly matched duplex. The greatest difference of over 20° C. occurs when the two artificial mismatches are 10 base pairs apart. This difference corresponds to one helical turn and indicates that some kind of interaction occurs between the two artificial bases that decreases the stability of the duplex.

Experimentally, when the PCR primer utilized contained one or two artificial mismatches between the primer and the DNA sample, the PCR gave results as would be expected for a perfectly matched primer (see Guo et al., *Nature Biotechnology* 15:331, 1997). However, when the primer contained both a true and an artificial mismatch, the PCR failed to produce any measurable results; while PCR with perfectly matched and true mismatches all produced measurable amounts of PCR product. The same study found similar results when using hybridization probes: those with perfect matches, true mismatches and artificial mismatches annealed while the probes containing artificial and true mismatches did not. These studies indicate greater ispecificity is created when artificial base mismatches are incorporated in hybridization reactions such that when naturally occurring mismatches occur, they are thermodynamically less stable than a perfectly matched hybridization reaction and thus less likely to produce a false positive in an assay or PCR. Interestingly, however, the difference in thermodynamic stability noted above for duplexes containing only artificial mismatches is not manifested in the experimental situation.

A further means of effecting hybridization discrimination is through differences in the stability between hybridization duplexes that contain nicks and gaps. In these reactions, duplexes are formed from tandernly stacked short oligomers hybridized to a longer strand that either align contiguously or non-contiguously leaving a few base pair gap. Hybridizations that result in a nick are subject to "stacking hybridization" where another DNA strand hybridizes across the nick site. Stacking hybridization does not occur where gaps are present in the non-contiguous oligomers. The stacking has the effect of increased discrimination as evidenced by decreased dissociation rates and greater thermodynamic stability than the non-contiguous counterparts (see Lane et al., *Nucleic Acids Res.* 25:611, 1997). Thermodynamic measurements show differences between the hybridization stacked duplexes standard free energy change ($\Delta G$) and the gapped duplexes is 1.4 to 2.4 kcal/mol. Therefore, discrimination in hybridization can be afforded through the use of multiple short probes.

Most of the base mimics in current use are the result of the pursuit for a universal base. Many utilize nitroazole base analogues and have demonstrated reduced discrimination in base pairing. A series of nitroazole nucleobase analogues have been studied in attempts to gain additional insight into the significance of electronic structure and heterocyclic size in base pairing for the development of more effective universal bases (see Bergstrom et al., *Nucleic Acids Res.* 25:1935, 1997). In this work, the thermodynamic properties of the deoxyribonucleosides of 3-nitropyrrole, 4-nitropyrazole, 4-nitroimidazole, and 5-nitroindole were measured. For comparison, thermodynamic measurements were also made on the deoxyribonucleosides of hypoxanthine and pyrazole as well an abasic spacer, 1,2-dideoxyribose. Four oligonucleotides were synthesized for each modified nucleoside in order to obtain duplexes in which each of the four natural bases was placed opposite the base mimic. All of the base mimics analyzed proved to be far less stable than the natural base pairings (A+T: $T_m$=65.7° C., C+G: $T_m$=70.5° C.) with the $T_m$s ranging from 35–46° C. for 5-nitroindole to 18–29° C. for the other nitroazole bases analyzed. The only exception was 4-nitroimidazole paired with dGTP where the $T_m$ was 40.9° C. In analyzing the free energy for the duplex melting, the 3-nitropyrrole base mimic was found to have the least discrimination when pairing with any of the four naturally occurring bases with an overall $\Delta G$ of 0.4 kcal/mol. The next least discriminating was 5-nitroindole with a $\Delta G$ of 0.8 kcal/mol. Both of these values are less than the $\Delta G$ of 1.1 kcal/mol found between the natural base pairings of A+T and G+C. 4-Nitropyrazole showed a slight preference for pairing with A with a $\Delta G$ of 1 kcal/mol more stable than C, G, and T free energies. Finally, 4-nitroimidazole showed a high selectivity for pairing to G (as was evidenced by its high $T_m$ value) due to the ability of the imidazole N3 to hydrogen bond with the deoxyguanosine N1. It should be noted, however, that the above values are dependent upon the nearest base neighbors to the mimic. Further studies altered the nearest neighbors and found that 3-nitropyrrole and 5-nitroindole are quite non-discriminating base pairing partners.

Of interest, the enthalpy and entropy changes were found to track one another (i.e., a large enthalpy change correlates to a large entropy change) regardless of the base mimic utilized implying that the correlation between AS and AH is independent of the mode of association of the bases. What was observed was that small enthalpy and entropy changes were found in the non-hydrogen bonding base mimics. The low values for entropy change reflect the greater degree of freedom of movement possible for bases that are not locked into the duplex by hydrogen bonding interactions. The small enthalpy changes reflect alterations in hydrogen bonding interactions as a result of the loss of hydrogen bonding interactions for the base opposite the base mimic. If a natural base remains stacked in the helix without an opposing hydrogen bonding partner then it has lost hydrogen bonding interactions with water without regaining a new donor/acceptor partner.

A similar study involved examining acyclic nucleoside analogues with carboxamido- or nitro-substituted heterocyclic bases (see Aerschot et al., *Nucleic Acids Res.* 23:4363, 1995). Utilization of acyclic nucleosides endows the constructs with enough flexibility to allow good base stacking as well as allow the base mimics to obtain an orientation to best base-pair with the corresponding base. The heterocyclic bases examined included: 4,5-imidazoledicarboxamide, 4-nitroimidazole, and 5-nitroindazole. These complexes were referenced against acyclic hypoxanthine, 1-(2(-deoxy-(-D-ribofuranosyl)-3-nitropyrrole, 5-nitroindole, and 2-deoxyinosine. All the new acyclic complexes had melting temperatures 7–20° C. less than those observed for the natural bases. 5-Nitroindazole when paired against each of the four natural bases had the least spread in $\Delta T_m$ of only 2.2° C. while the 4-nitroimidazole had a spread of 8.0° C. with dG being significantly out of line with the other three bases as had similarly been observed above. Of the reference compounds, deoxyinosine had a $\Delta T_m$ of 5.6° C., 5-nitroindole's $\Delta T_m$ was 1.0° C., 1-(2(-deoxy-(-D-ribofuranosyl)-3-nitropyrrole had a $\Delta T_m$ of 5.1° C., and the $\Delta T_m$ of acyclic hypoxanthine was 4.8° C. However, all base mimics showed about the same destabilization ($\Delta T_m$ of 4–5° C.) when placed in an oligo consisting almost exclusively of adenosines with exception of 4-nitroimidazole and acyclic deoxyinosine that had $\Delta T_m$s of 7.0° C. and 8.9° C., respectively.

Aerschot and co-workers also examined the effect of incorporation of multiple base mimics into an oligo (see Aerschot et al., *Nucleic Acids Res.* 23:4363, 1995). Overall, melting temperatures dropped but most markedly with the incorporation of three base mimics. The nitroindoles, however, showed the least amount of temperature differential.

Another base mimic, 1-(2(-deoxy-(-D-ribofuranosyl) imidazole-4-carboxamide (*Nucleoside* 1), mimics preferentially dA as well as dC nucleosides (see Johnson et al., *Nucleic Acids Res.* 25:559, 1997). The ability to substitute for both dA and dC results from rotation about the carboxamide/imidazole bond as well as the bond between the imidazole and furanose ring. When the imidazole is anti to the furanose and the carboxamide group is anti to the imidazole, the lone pair on the oxygen and one of the amide NH hydrogens is in a position that mimics the $NH_2$ and N-1 of adenosine. Imidazole rotation about the glycosidic bond to the syn orientation places the amide group in a position that approximately matches the positions of the $NH_2$ and N-3 of cytosine.

When Nucleoside 1 is substituted for any naturally occurring nucleoside, the enthalpy increases with the greatest increase for a dG substitution for the 1-C pairing (from $\Delta H$=74.7 (kcal/mol)/$\Delta G$=−16.5 (kcal/mol) for the G/C pairing to $\Delta H$=−45.5 (kcal/mol)/$\Delta G$=−5.8 (kcal/mol)). The smallest enthalpy change occurs for a dA substitution ($\Delta H$=−72.9 (kcal/mol)/$\Delta G$=−15.4 (kcal/mol) for A/T pairing to $\Delta H$=−66.7 (kcal/mol)/$\Delta G$=−11.7 (kcal/mol) for the 1-T pairing). Correspondingly, $T_m$ significantly decreases from 65.7° C. and 70.5° C. for the A-T and C-G couples, respectively, to 46.6° C. for the 1-T pairing, 43.4° C. for 1-G, 27.6° C. for 1-A, and 14.6° for 1-C.

When used in a PCR reaction, Nucleoside 1 and its N-propyl derivative are preferentially incorporated as dATP analogues (see Sala et al., *Nucleic Acids Res.* 24:3302, 1996). However, once incorporated into a DNA template, their ambiguous hydrogen bonding potential gave rise to misincorporation of any of the naturally occurring bases at frequencies of $3\times10^{-2}$ per base per amplification. Most of the substitutions (primarily consisting of G) were a result of rotation about the carboxamide bond when part of the template. Between 11–15% of the substitutions were due to rotation of the imidazole moiety about the glycosidic bond. As part of a DNA template, the N-propyl derivative behaved in the same way as Nucleoside 1 despite its propyl moiety. This study indicates that while Nucleoside 1 preferentially behaves as dATP, it has the ability in a PCR type environment to behave as all four naturally occurring nucleotides as well. From this and the above studies, it is evident that a wide range of duplex stability can be obtained through variations in base mimics and their placement within an oligonucleotide.

Petrruska et al., *Proc. Natl. Acad. Sci. USA* 85:6252–6256, 1988, have reported on the correlation between the thermodynamic stability of mismatched primers and DNA polymerase fidelity. By analyzing the melting profiles of a perfectly based paired primer with a A/T correct match at the 3'-end compared to primers that had either the incorrect base pair G/T, C/T, or T/T it was noted that there was a shift in free energy changes upon dissociation ($\Delta\Delta G^\circ$) of 0.2, 0.3 and 0.4 kcal/mole for the terminal A/T compared to the G/T, C/T, or T/T mismatches. Interestingly, the A/T mismatch was extended (Drosphilia DNA polymerase) about 200 times faster than the G/T mismatch and about 1400 and 2500 times faster than the C/T and T/T mismatched respectively. The authors hypothesized that the binding cleft of the polymers excludes water and amplifies by amplifying free energy differences by increasing enthalpy differences in mismatched primers.

Many DNA hybridization-based diagnostic tests are being developed to identify persons who might be suffering from (or be predisposed to) specific genetic diseases (see for example, Norari et al., *Gene* 43:23–28, 1986) or to determine a genetic histocompatibility profile, which is useful for tissue matching between donor and patient (e.g., for a bone marrow transplant) (Sorg et al., *Eur. J. Immunogen* 19:391–401, 1992). However, significant problems are encountered when trying to develop simple and reliable hybridization methods using allele-specific oligonucleotide probes that differ in sequence at one nucleotide position. Norari et al. solved the mismatch hybridization problem by the addition of 10-times more unlabeled complementary oligonucleotide than the mismatched labeled oligonucleotide. However, this is an impractical solution when multiplex hybridization methods are being used.

Diagnostic tests that rely on the polymerase chain reaction (PCR) technique also experience problems associated with the hybridization of oligonucleotides. Rychlik (*BioTechniques* 18:84–90, 1995) examined the effects on PCR of varying the G+C content of primers at either the 5' or 3' end of a priming oligonucleotide. Using standard PCR buffers and conditions, oligonucleotides having a high G+C content at the 3' end (the end used to extend DNA synthesis during PCR) results in high priming efficiency, but also promotes false priming due to greater tolerance for mismatches at the 5' end. Moreover, the effects of mismatches in PCR are variable; mismatches located in the middle of a primer-template duplex do not significantly affect the efficiency of PCR amplification, while 3'-terminal base mismatches sometimes strongly affects PCR product yield. As a further complication, the strength of the effect that the various base pair mismatches have on PCR amplification is not the same as that observed for oligonucleotide hybrid formation and stability (Ikuta et al., *Nucl. Acids. Res.* 15:797–811, 1987; Jacobs et al., *Nucl. Acids Res.* 16:4637–4650, 1988).

The present invention provides methods and compositions for detecting base changes by improving the specificity and accuracy of oligonucleotide hybridization and PCR priming reactions, and further provides other related advantages.

SUMMARY OF THE INVENTION

This invention generally provides compositions and methods to increase the specificity of hybridization of nucleic acids and priming of nucleic acids in PCR.

In one aspect, the invention provides a composition comprising a nucleic acid and a salt, the salt comprising an anion and a cation, the anion selected from halogenated acetate, propionate and halogenated propionate, the cation selected from primary, secondary and tertiary ammonium comprising 1–36 carbon atoms, and quaternary ammonium comprising 4–48 carbon atoms.

In another aspect, the invention provides a composition which is non-flowing comprising an oligonucleotide of 6–100 nucleotides and a salt, the salt comprising an anion and a cation, the anion selected from acetate, halogenated acetate, propionate, and halogenated propionate, the cation selected from primary, secondary and tertiary ammonium comprising 1–36 carbon atoms, and quaternary ammonium comprising 4–48 carbon atoms.

In another aspect, the invention provides a composition which is free from organic solvent, comprising an oligonucleotide of 6–100 nucleotides and a salt, the salt comprising an anion and a cation, the anion selected from acetate, halogenated acetate, propionate, and halogenated propionate, the cation selected from primary, secondary and tertiary ammonium comprising 1–36 carbon atoms, and quaternary ammonium comprising 4–48 carbon atoms.

In another aspect, the invention provides a composition which includes a nucleic acid and a salt, the nucleic acid immobilized on a solid support, the salt .comprising an anion and a cation, the anion selected from acetate, halogenated acetate, propionate and halogenated propionate, the cation selected from primary, secondary and tertiary ammonium comprising 1–36 carbons, and quaternary ammonium comprising 4–48 carbons.

In another aspect, the invention provides a salt selected from the group:

(a) an acetate salt of a cation of the formula $HN(CH_3)_2R_a$ wherein $R_a$ is a $C_4$–$C_7$hydrocarbyl;

(b) a halogenated acetate salt of a cation of the formula $HN(CH_3)_2R_b$ wherein $R_b$ is a $C_7$–$C_{12}$hydrocarbyl;

(c) acetate and halogenated acetate salts of a cation of the formula $H_2N(C_5$–$C_7$cycloalkyl)$R_c$ where $R_c$ is a $C_1$–$C_{12}$hydrocarbyl; and (d) acetate and halogenated acetate salts of N-substituted piperdine, wherein the nitrogen of piperidine is substituted with $C_1$–$C_{12}$hydrocarbyl.

In another aspect, the invention provides an oligonucleotide in solution, where the oligonucleotide is formed from constituents including a plurality of fragments, each fragment shown schematically by structure (1)

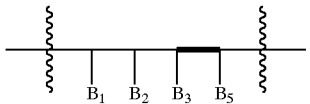
(1)

wherein,

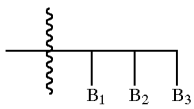

represents a sequence of at least three nucleotides as found in wild-type DNA, where "B" represents a base independently selected at each location;

—— represents a series of covalent chemical bonds termed a "specificity spacer," which separates and connects two bases $B_3$ and $B_5$;

the specificity spacer having steric and chemical properties such that (a) it does not prevent hybridization between a fragment of structure (1) and an oligonucleotide fragment having a complementary base sequence, as shown schematically as structure (2)

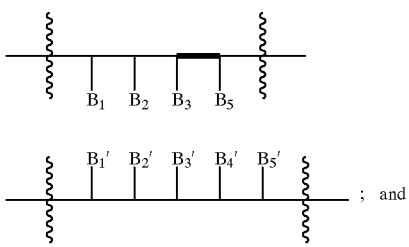
; and and (b) it cannot enter into hydrogen bonding with a base positioned opposite itself in a hybridized complementary base sequence of structure (2).

In another aspect, the invention provides an array which includes a plurality of oligonucleotides immobilized in an array format to a solid support, each oligonucleotide of the plurality formed from components which include a plurality of fragments, each fragment shown schematically by structure (1)

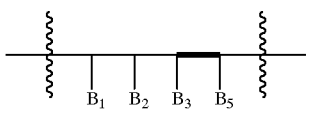
(1)

wherein,

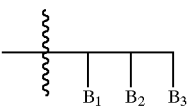

represents a sequence of at least three nucleotides as found in wild-type DNA, where "B" represents a base independently selected at each location;

—— represents a series of covalent chemical bonds termed a "specificity spacer," which separates and connects two bases $B_3$ and $B_5$;

the specificity spacer having steric and chemical properties such that (a) it does not prevent hybridization between a fragment of structure (1) and an oligonucleotide fragment having a complementary base sequence, as shown schematically as structure (2)

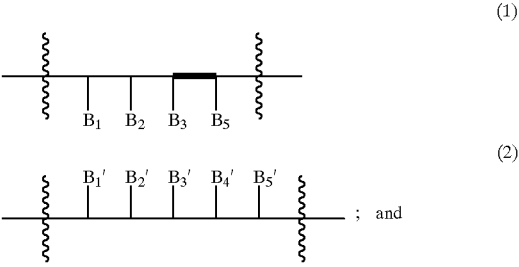
; and and (b) it cannot enter into hydrogen bonding with a base positioned opposite itself in a hybridized complementary base sequence of structure (2).

In another aspect, the invention provides an oligonucleotide in solution, where the oligonucleotide is formed from components including a plurality of fragments, each fragment shown schematically by structure (1)

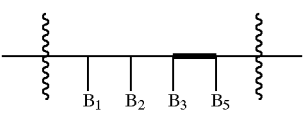
(1)

wherein,

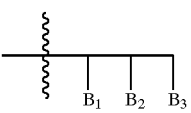

represents a sequence of at least three nucleotides as found in wild-type DNA, where "B" represents a base independently selected at each location;

—— represents a series of covalent chemical bonds termed a "specificity spacer," which separates and connects two bases $B_3$ and $B_5$;

the specificity spacer having steric and chemical properties such that (a) it does not prevent hybridization between a fragment of structure (1) and an oligonucleotide fragment having a complementary base sequence, as shown schematically as structure (2)

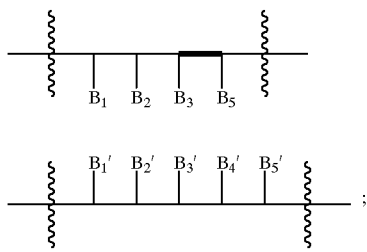

(b) it enters into hydrogen bonding with a base positioned opposite itself in a hybridized complementary base sequence of structure (2); and (c) it does not hydrogen-bond through any of adenine, guanine, cytosine, thymine or uracil.

In another aspect, the invention provides an array including a plurality of oligonucleotides immobilized in an array format to a solid support, each oligonucleotide of the plurality formed from components including a plurality of fragments, each fragment shown schematically by structure (1)

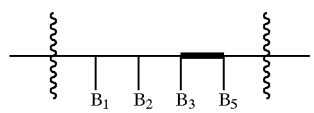

wherein,

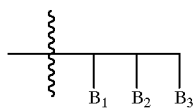

represents a sequence of at least three nucleotides as found in wild-type DNA, where "B" represents a base independently selected at each location;

—— represents a series of covalent chemical bonds termed a "specificity spacer," which separates and connects two bases $B_3$ and $B_5$;

the specificity spacer having steric and chemical properties such that (a) it does not prevent hybridization between a fragment of structure (1) and an oligonucleotide fragment having a complementary base sequence, as shown schematically as structure (2)

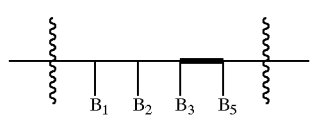

-continued

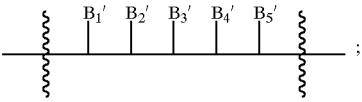

(b) it enters into hydrogen bonding with a base positioned opposite itself in a hybridized complementary base sequence of structure (2); and (c) it does not hydrogen-bond through any of adenine, guanine, cytosine, thymine or uracil.

The invention also provides a method of distinguishing between hybridization of a complementary nucleic acid target and a nucleic acid probe in which the probe and target are perfectly complementary and in which the probe and target have one or more base mismatches, comprising:

(a) mixing the nucleic acid target with the nucleic acid probe in a solution comprising a hybotrope;

(b) hybridizing at a discriminating temperature; and (c) detecting probe hybridized to target, thereby determining whether the nucleic acid probe and target are perfectly complementary or mismatched.

In a preferred embodiment, the nucleic acid probe is labeled with a radioactive molecule, fluorescent molecule, mass-spectrometry tag or enzyme. In preferred embodiments, the nucleic acid probe and/or the target nucleic acid is from 6 to 40 bases. Preferably, the hybotrope is an ammonium salt as defined herein. Specific preferred ammonium salt hybotropes of the present invention include, without limitation, bis(2-methoxyethyl)amine acetate, 1-ethylpiperidine acetate, 1-ethylpiperidine trichloroacetate, 1-ethylpiperidine trifluoroacetate, 1-methylimidizole acetate, 1-methylpiperidine acetate, 1-methylpiperidine trichloroacetate, 1-methylpyrrolidine acetate, 1-methylpyrrolidine trichloroacetate, 1-methylpyrrolidine trifluoroacetate, 2-methoxyethylamine acetate, N,N-dimethylcyclohexylamine acetate, N,N-dimethylcyclohexylamine trifluoroacetate, N,N-dimethylcyclohexylamine, N,N-dimethylheptylamine acetate, N,N-dimethylheptylamine acetate, N,N-dimethylhexylamine acetate, N,N-dimethylhexylamine acetate, N,N-dimethylisopropylamine acetate, N-ethylbutylamine acetate, N-ethylbutylamine trifluoroacetate, N,N-dimethylaminobutane trichloroacetate, N,N-dimethylisopropylamine trichloroacetate, triethanolamine acetate, triethylamine acetate, triethylamine trichloroacetate, tripropylamine acetate, and tetraethylammonium acetate. Other suitable hybotropes include LiTCA, RbTCA, GuSCN, NaSCN, NaClO$_4$, KI, TMATCA TEATCA, TMATBA, TMTCA, TMTBA, TBATCA and TBATBA. Preferably, the hybotrope is present at a molarity of from about 0.005 M to about 6 M. Preferably, the probe nucleic acid is DNA or RNA, and the target nucleic acid is DNA or RNA. Preferably, the target nucleic acid is affixed to a solid substrate. Preferably, the method further comprises polymerase chain reaction.

The invention also provides a method of distinguishing between hybridization of a complementary nucleic acid target and a nucleic acid probe in which the probe and target are perfectly complementary and in which the probe and target have one or more base mismatches, comprising:

(a) mixing a nucleic acid target with a nucleic acid probe containing at least one abasic or deoxyNebularine substitution;

(b) hybridizing at a discriminating temperature; and (c) detecting probe bound to the target,
thereby determining whether the nucleic acid probe and target are perfectly complementary or mismatched.

Preferably, the nucleic acid probe is labeled with a radioactive molecule, fluorescent molecule, mass-spectrometry tag or enzyme. In preferred embodiments, the nucleic acid probe is from 6 to 40 bases and/or the target nucleic acid is from 6 to 40 bases. Preferably, the method further comprises the use of a hybotrope, where the hybotrope may be an ammonium salt. Specific preferred ammonium salt hybotropes of the present invention include, without limitation, bis(2-methoxyethyl)amine acetate, 1-ethylpiperidine acetate, 1-ethylpiperidine trichloroacetate, 1-ethylpiperidine trifluoroacetate, 1-methylimidizole acetate, 1-methylpiperidine acetate, 1-methylpiperidine trichloroacetate, 1-methylpyrrolidine acetate, 1-methylpyrrolidine trichloroacetate, 1-methylpyrrolidine trifluoroacetate, 2-methoxyethylamine acetate, N,N-dimethylcyclohexylamine acetate, N,N-dimethylcyclohexylamine trifluoroacetate, N,N-dimethylcyclohexylamine, N,N-dimethylheptylamine acetate, N,N-dimethylheptylamine acetate, N,N-dimethylhexylamine acetate, N,N-dimethylhexylamine acetate, N,N-dimethylisopropylamine acetate, N-ethylbutylamine acetate, N-ethylbutylamine trifluoroacetate, N,N-dimethylaminobutane trichloroacetate, N,N-dimethylisopropylamine trichloroacetate, triethanolamine acetate, triethylamine acetate, triethylamine trichloroacetate, tripropylamine acetate, and tetraethylammonium acetate. Other suitable hybotropes include one or more of LiTCA, RbTCA, GuSCN, NaSCN, NaClO$_4$, KI, TMATCA TEATCA, TMATBA, TMTCA, TMTBA, TBATCA and TBATBA. Preferably, the hybotrope is present at a molarity of from about 0.005 M to about 6 M. Preferably, the probe nucleic acid is DNA or RNA and the target nucleic acid is DNA or RNA. Preferably, the target nucleic acid is affixed to a solid substrate.

The invention also provides a method of increasing discrimination in a nucleic acid synthesis procedure, comprising:
(a) mixing a single-stranded nucleic acid target with an oligonucleotide primer in a solution comprising a hybotrope and a polymerase;
(b) annealing the primer to the target at a discriminating temperature; and
(c) synthesizing a complementary strand to the target to form a duplex.

Preferably, the nucleic acid primer is labeled with a radioactive molecule, fluorescent molecule, mass-spectrometry tag or enzyme. Preferably, the nucleic acid primer is from 6 to 40 bases. Preferably, the method includes using a hybotrope, where the hybotrope may be an ammonium salt. Specific preferred ammonium salt hybotropes of the present invention include, without limitation, bis(2-methoxyethyl)amine acetate, 1-ethylpiperidine acetate, 1-ethylpiperidine trichloroacetate, 1-ethylpiperidine trifluoroacetate, 1-methylimidizole acetate, 1-methylpiperidine acetate, 1-methylpiperidine trichloroacetate, 1-methylpyrrolidine acetate, 1-methylpyrrolidine trichloroacetate, 1-methylpyrrolidine trifluoroacetate, 2-methoxyethylamine acetate, N,N-dimethylcyclohexylamine acetate, N,N-dimethylcyclohexylamine trifluoroacetate, N,N-dimethylcyclohexylamine, N,N-dimethylheptylamine acetate, N,N-dimethylheptylamine acetate, N,N-dimethylhexylamine acetate, N,N-dimethylhexylamine acetate, N,N-dimethylisopropylamine acetate, N-ethylbutylamine acetate, N-ethylbutylamine trifluoroacetate, N,N-dimethylaminobutane trichloroacetate, N,N-dimethylisopropylamine trichloroacetate, triethanolamine acetate, triethylamine acetate, triethylamine trichloroacetate, tripropylamine acetate, and tetraethylammonium acetate. Other suitable hybotrope salts include LiTCA, RbTCA, GuSCN, NaSCN, NaClO$_4$, KI, TMATCA TEATCA, TMATBA, TMTCA, TMTBA, TBATCA and TBATBA. Preferably, the hybotrope is present at a molarity of from about 0.005 M to about 6 M. Preferably, the steps of (a), (b), and (c) are repeated multiple times.

The invention also provides a method of distinguishing a single base change in a nucleic acid molecule from a wild-type sequence, comprising:
(a) mixing a single-stranded nucleic acid target with an oligonucleotide primer in a solution comprising an amine-based salt and a polymerase, wherein the oligonucleotide primer has a 3'-most base complementary to the wild-type sequence or the single base change;
(b) annealing the primer to the target at a discriminating temperature;
(c) extending the primer, wherein a complementary strand to the target is synthesized when the 3'-most base of the primer is complementary to the target; and
(d) detecting the extension of the primer.

Primer extension may be detected by methods well known in the art. For instance, direct detection of the duplex may be achieved visually using dyes, or a label may be incorporated into the primer or extension product. Suitable labels include radiolabels and fluorescent labels. The duplex may be denatured and the presence of extension product detected by any of the methods known in the art. For instance, the extension product may collected and run on a gel.

DETAILED DESCRIPTION OF THE INVENTION

Figure 1:
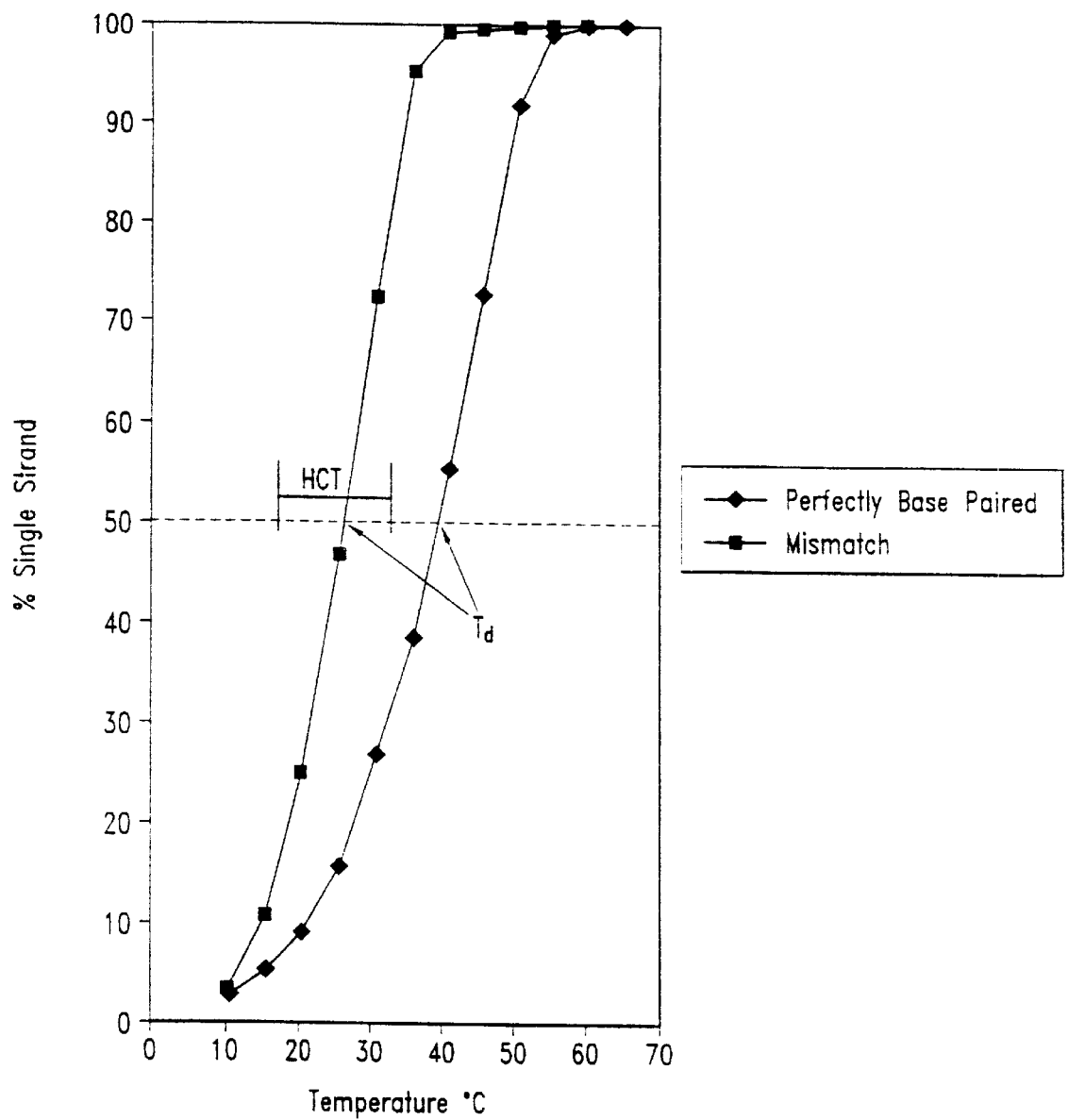
FIG. 1 is a graph illustrating thermal melt profiles of oligonucleotide duplexes. Percentage single strand DNA ($\alpha$, y-axis) is plotted versus temperature (x-axis). The $T_d$ of the duplex is defined as the temperature at which 50% of the strands are in single strand form. The helical coil transition (HCT) is defined as the temperature difference between an $\alpha$ of 0.2 (or 20%) and 0.8 (or 80%). The melting curve denoted by the squares represents the behavior of a duplex in contact with a hybotrope (e.g., LiTCA) and the melting curve denoted by the diamonds represents the behavior of an oligonucleotide duplex in a NaCl-based hybridization solution.

Prior to setting forth the invention, it may be helpful to an understanding thereof to define certain terms used herein.

As used herein, "hybotrope" refers to any chemical or any mixture of a chemical in an aqueous or organic environment with buffers, chelators, salts and/or detergents that can change the enthalpy of a nucleic acid duplex by at least 20% when referenced to a standard salt solution (0.165 M NaCl, 0.01 M Tris pH 7.2, 5 mM EDTA and 0.1% SDS) when the hybotrope is present in the environment within a molarity range of 0.1 M to 10 M. That is, the energy content of the nucleic acid duplexes is decreased. The reference oligonucleotide is 5'-GTCATACTCCTGCTTGCTGATCCACATCTG-3' (SEQ ID NO: 1) as the immobilized oligonucleotide and 5'-TGTGGATCAGCAAGCAGGAGTATG-3' (SEQ ID NO: 2) as the solution nucleotide which is typically labeled at the 5'-end with a fluorochrome such as Texas Red. The oligonucleotide duplex (24 nucleotides in length) has a helical to coil transition (HCT) of 25° C. or less. The HCT is the difference between the temperatures at which 80% and 20% of the duplex is single stranded. The average minimum slope for a solution to be defined as a hybotrope is the first derivative of the HCT and is equal to 2.4 in units of 1/temperature in degrees C. ((80% single strand–20% single-strand)/25° C.).

Although a hybotrope of the present invention may achieve the above-described effect on the enthalpy of a nucleic acid duplex, the present invention does not require that the hybotrope be present within a concentration range of 0.1 M to 10 M in the methods of the present invention. Indeed, lower hybotrope concentrations (i.e., lower than 0.1 M) may be advantageously employed in methods of the present invention. For example, in the presence of enzymes or polymerases the hybotrope can be diluted to 0.005 M to 1.0 M.

As used herein, "stringency" is the percentage of mismatched base pairs that are tolerated for hybridization under a given condition.

As used herein, "discrimination" is the difference in $T_d$ between a perfectly base-paired duplex and a duplex containing a mismatch.

As used herein, a "discrimination temperature" is a temperature at which a hybridization reaction is performed that allows detectable discrimination between a mismatched duplex and a perfectly matched duplex. As shown herein, a range of temperatures satisfy criteria of a discrimination temperature. As used herein, the discrimination temperature can equal the annealing temperature in a reaction like the polymerase chain reaction.

As used herein, an "abasic residue" in an oligonucleotide refers to a molecular fragment (MF) within an oligonucleotide chain (e.g., polyA, so the oligonucleotide having the abasic residue may be represented by polyA-MF-polyA), where the molecular fragment approximates the length of a ribofuranose or a deoxyribofuranose sugar in such a way that bases adjacent to the molecular fragment are separated from one another by the same, or effectively the same, distance as if a ribofuranose or a deoxyribofuranose sugar of any of A, G, C, T, or U were present in place of the abasic residue. The abasic residue may incorporate a ribofuranose or deoxyribofuranose ring as in native A, G, C, T, or U. However, the abasic residue does not contain a base or other molecule that can interact with the base on the opposite strand of a duplex which is formed with the abasic residue-containing oligonucleotide. Thus, an abasic residue may be an apurine or apyrimidine structure, a base analog, or an analogue of a phosphate backbone. The abasic substitution may also consist of a backbone of N-(2-aminoethyl)-glycine linked by amide bonds.

As used herein, a "base analog" or "base analog residue" in an oligonucleotide refers to a molecular fragment that includes a ribofuranose sugar and is substituted at the beta anomeric position with a group that has a three-dimensional size and shape similar to that of at least one of the A, C, G, T, or U bases, so that a polymerase will read through the base analog, however, the base analog does not hydrogen bond to the base on the opposite strand of a duplex using classical Watson-Crick hydrogen bonding. "DeoxyNebularine", which refers to a 2'-deoxyNebularine, more specifically 9-(beta-D-2'-deoxyribofuranosyl) purine (Eritja et al., *Nucl. Acids Res.* 14:8135, 1986), having a molecular formula is $C_{10}H_{12}N_4O_4$, is an exemplary base analog.

As used herein, "nucleic acid" or "nucleic acid molecule" refers to any of deoxyribonucleic acid (DNA), ribonucleic acid (RNA), oligonucleotides, fragments generated by the polymerase chain reaction (PCR), and fragments generated by any of ligation, scission, endonuclease action, and exonuclease action. Nucleic acids can be composed of monomers that are naturally-occurring nucleotides (such as deoxyribonucleotides and ribonucleotides), or analogs of naturally-occurring nucleotides (e.g., α-enantiomeric forms of naturally-occurring nucleotides or base analogs), or a combination of both. Modified nucleotides can have modifications in sugar moieties and/or in pyrimidine or purine base moieties. Sugar modifications include, for example, replacement of one or more hydroxyl groups with halogens, alkyl groups, amines, and azido groups, or sugars can be functionalized as ethers or esters. Moreover, the entire sugar moiety can be replaced with sterically and electronically similar structures, such as aza-sugars and carbocyclic sugar analogs. Examples of modifications in a base moiety include alkylated purines and pyrimidines, acylated purines or pyrimidines, or other well-known heterocyclic substitutes. Nucleic acid monomers can be linked by phosphodiester bonds or analogs of such linkages. Analogs of phosphodiester linkages include phosphorothioate, phosphorodithioate, phosphoroselenoate, phosphorodiselenoate, phosphoroanilothioate, phosphoranilidate, phosphoramidate, and the like. The term "nucleic acid molecule" also includes oligonucleotides incorporating one or more specificity spacers (as defined herein) where abasic residue and base analog residues are exemplary specificity spacers. The term "nucleic acid" also includes so-called "peptide nucleic acids," which comprise naturally-occurring or modified nucleic acid bases attached to a polyamide backbone. Nucleic acids can be either single stranded or double stranded.

As used herein, the term "nucleic acid fragment" means a molecule which is complementary to a selected target nucleic acid molecule (i.e., complementary to all or a portion thereof), and may be derived from nature or synthetically or recombinantly produced, including non-naturally occurring molecules, and may be in double or single stranded form where appropriate; and includes an oligonucleotide (e.g., DNA or RNA), a primer, a probe, a nucleic acid analog (e.g., PNA), an oligonucleotide which is extended in a 5' to 3' direction by a polymerase, a nucleic acid which is cleaved chemically or enzymatically, a nucleic acid that is terminated with a dideoxy terminator or capped at the 3' or 5' end with a compound that prevents polymerization at the 5' or 3' end, and combinations thereof. The complementarity of a nucleic acid fragment to a selected target nucleic acid molecule generally means the exhibition of at least about 70% specific base pairing throughout the length of the fragment. Preferably the nucleic acid fragment exhibits at least about 80% specific base pairing; and most preferably at least about 90%. Assays for determining the percent mismatch (and thus the percent specific base pairing) are well known in the art and are based upon the percent mismatch as a function of the $T_m$ when referenced to the fully base paired control.

As used herein, "$T_m$" is the temperature at which half the molecules of a nucleic acid duplex are single stranded. $T_m$ is measured in solution, while $T_d$ is measured for the duplex affixed to a solid support, and both terms indicate the temperature at which half of a duplex are single stranded.

A. Hybotropes

As noted above, the present invention provides compositions, including hybotropes, that can change the enthalpy of a nucleic acid duplex (i.e., that can decrease the energy content of the oligonucleotide duplex, so that the cooperativity of the melting processes is increased, as discussed in more detail below). Generally, enthalpy of a duplex in a solution containing a hybotrope is increased at least 20%, and preferably, 30–100% over a duplex in a reference solution comprising 0.165 M NaCl.

Figure 4:
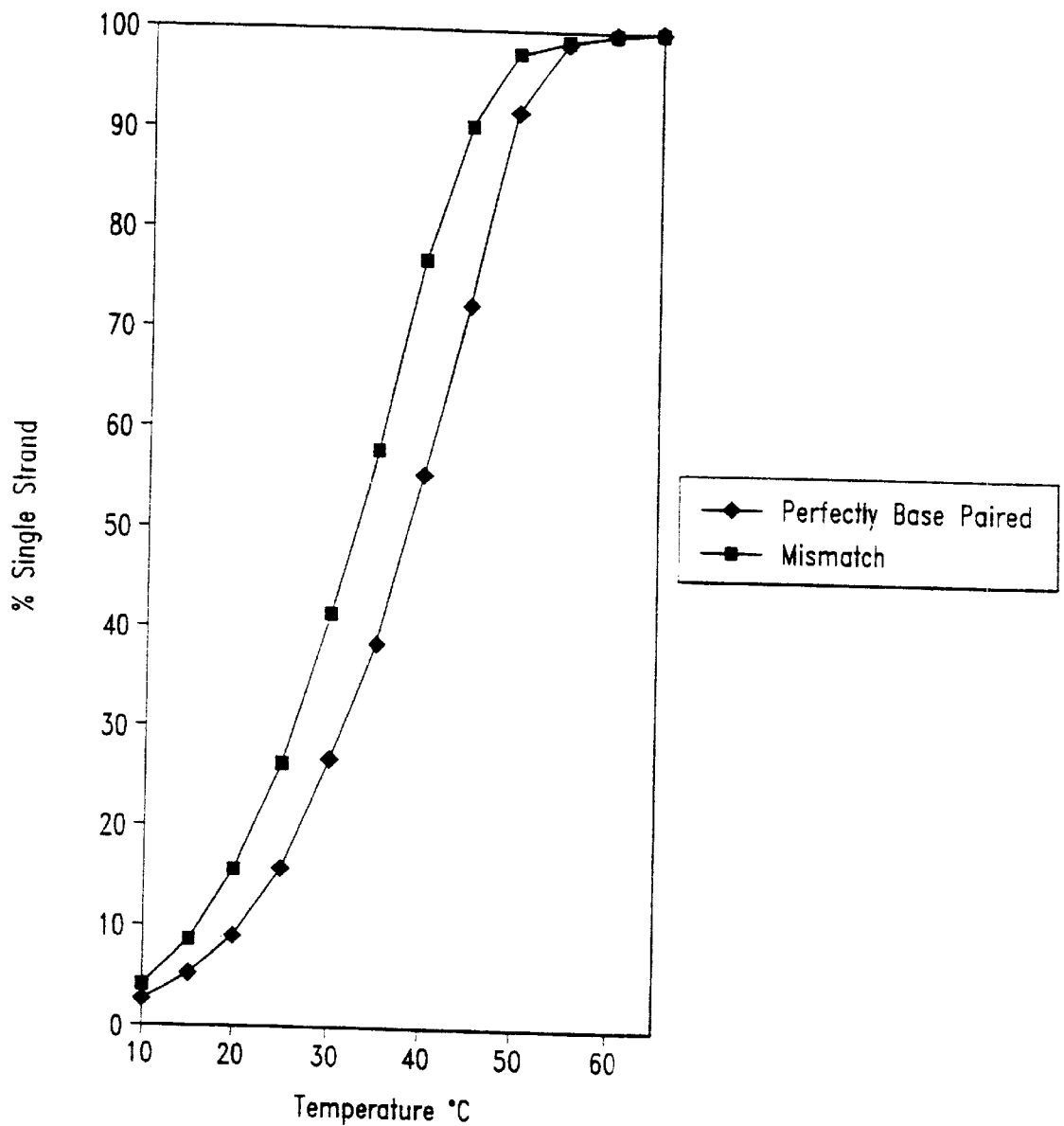
FIG. 4 is a graph displaying melting profiles for an 18-mer oligonucleotide duplex that is perfectly based paired (diamonds) and the same oligonucleotide duplex that contains a central mismatch (squares A/A, position 9). The $\Delta T_d$ is 6° C. The melting profiles were determined in 2.0 M LiTCA. The percentage single strand (y-axis) is plotted versus temperature (° C.; x-axis).
Figure 5:
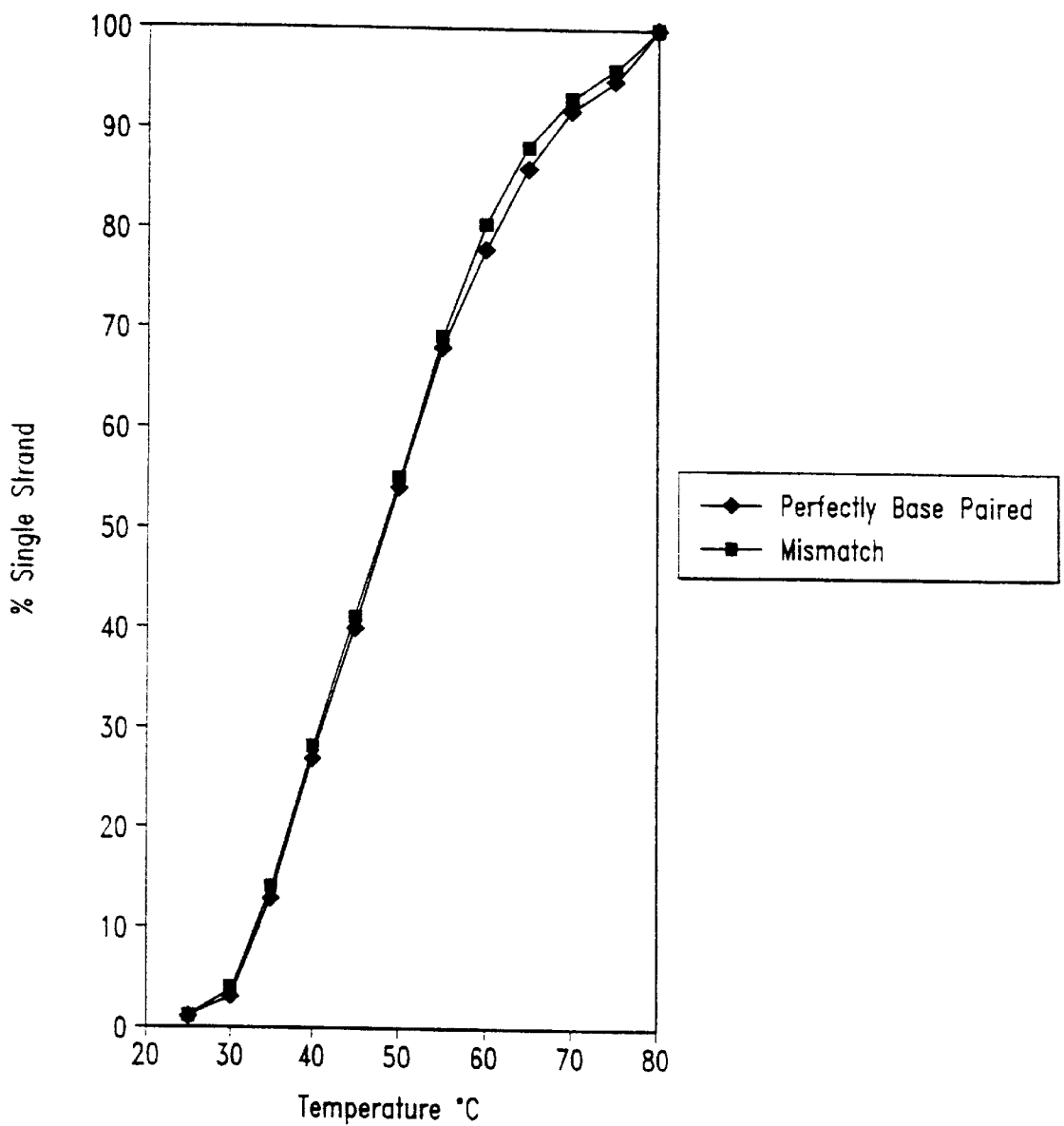
FIG. 5 is a graph illustrating melting profiles for an 18-mer oligonucleotide duplex that is perfectly based-paired (diamonds) and the same oligonucleotide duplex that contains a central mismatch (squares; A/A, position 9). The melting curves are determined in QY low stringency hybridization buffer (Promega, Madison, Wis.). The percentage single strand (y-axis) is plotted versus temperature (° C.; x-axis).

Several consequences flow from increased enthalpy. Importantly, the temperature range over which a duplex melts is decreased, likely due to increased cooperativity of melting. The difference between a hybrotropic solution and a hybridization solution used in most molecular biology protocols is illustrated in FIG. 4 and FIG. 5. In FIG. 4, the difference in $T_d$ between a duplex containing a mismatch and duplex which is perfectly base-paired is about 5° C. and is clearly distinguished. The hybotrope in FIG. 4 is LiTCA. In FIG. 5 the difference in $T_d$ between a duplex containing a mismatch and duplex which is perfectly base-paired is less than 2° C. and is not distinct. Also, the HCT of the hybotrope in FIG. 4 is less than 25° C. and the HCT of the SSC-based solution is greater than 25° C.

Figure 3:
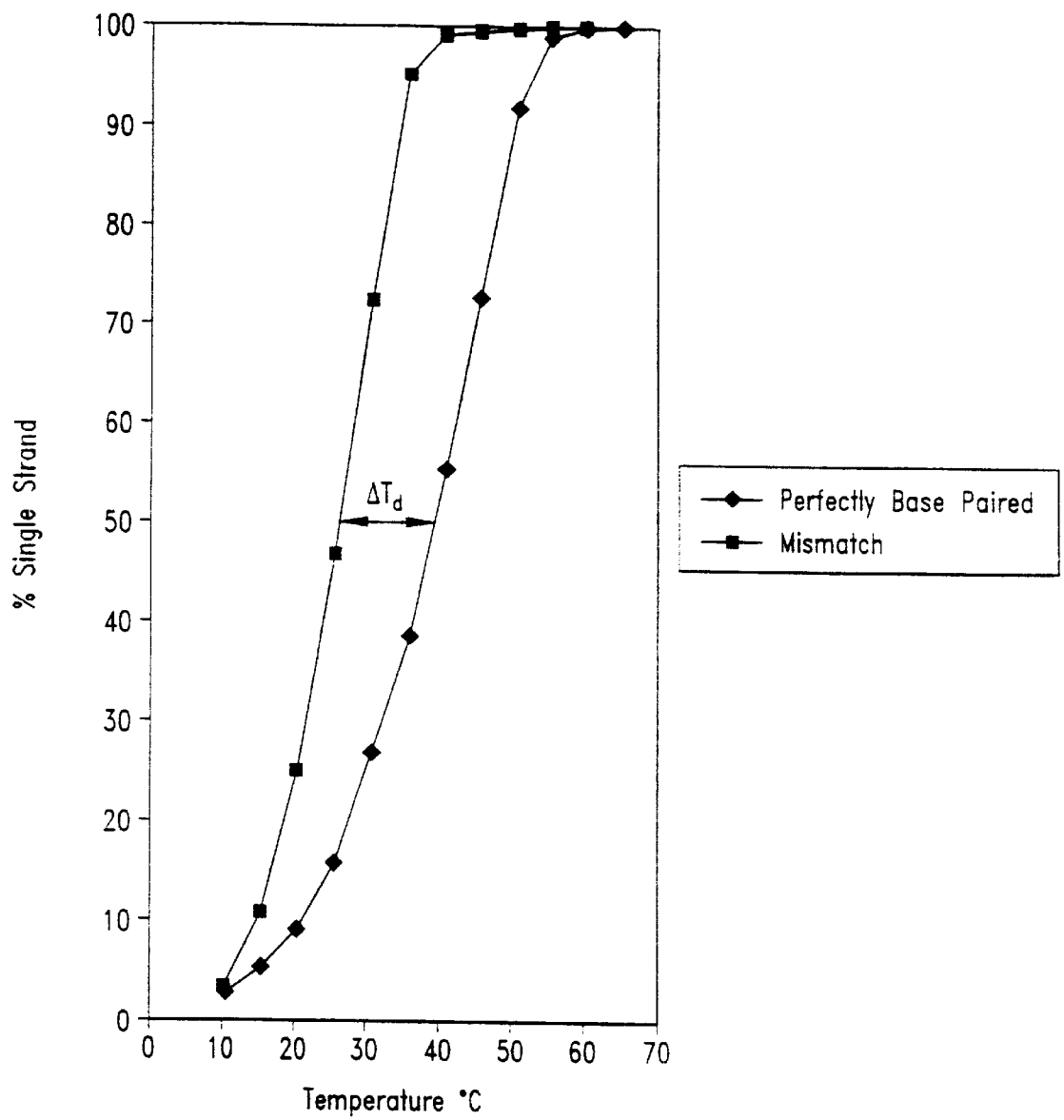
FIG. 3 is a graph showing the difference in $T_d$ between two duplexes, one that is perfectly based-paired and the other that contains a single mismatch. The temperature difference between any two $T_d$s at $\alpha$=0.5 is defined as the $\Delta T_d$. The percentage of single strand DNA (y-axis) is plotted versus temperature (° C.; x-axis).

Because the temperature range of a melt is smaller in a hybotropic solution, there is a greater difference in the $T_m$ of a perfectly complementary duplex and a duplex containing one or more mismatched base pairs (e.g., base pairing other than A:T, G:C, A:U). This property is illustrated in FIG. 3 in which an 18 mer duplex perfectly complement or containing a 1 bp mismatch is melted in a solution comprising a hybotrope. As shown, the difference in $T_d$ between the two duplexes is substantial. In general, a hybotrope causes an increase in $\Delta T_d$ of $\geq 2°$ C. (e.g., $\geq 2°$ C., $\geq 2.5°$ C., $\geq 3°$ C, $\geq 3.5°$ C., $\geq 4°$ C.) over the $\Delta T_d$ of the matched and mismatched duplexes in a reference solution (e.g., 0.18 M Na+). For a 6 to 18 base pair duplex (50% G+C) a hybotrope induces a $\Delta T_d$ of $\geq 2°$ C. (e.g., $\geq 2°$ C., $\geq 2.5°$ C., $\geq 3°$ C., $\geq 3.5°$ C., $\geq 4°$ C., $\geq 4.5°$ C., $\geq 5°$ C.), for a 19 to 24 base pair duplex, a hybotrope induces a $\Delta T_d$ of $\geq 1°$ C. (e.g., $\geq 1°$ C., $\geq 1.5°$ C., $\geq 2°$ C., $\geq 2.5°$ C., $\geq 3°$ C., $\geq 3.5°$ C., $\geq 3°$ C, $\geq 4°$ C., $\geq 4.5°$ C., $\geq 5°$ C.) and for a 25 to 36 base pair duplex, a hybotrope induces a $\Delta T_d$ of $\geq 0.5°$ C. (e.g., $\geq 0.5°$ C., $\geq 1°$

C., ≧1.5° C., ≧2° C., ≧2.5° C., ≧3° C., ≧3.5° C., ≧4° C., ≧4.5° C., ≧5° C.).

In performing PCR with hybotropes, standard PCR conditions are 10 mM Tris-HCl pH 8.3, 50 mM KCl, 1.25 mM MgCl$_2$, 200 µM dNTP's, 0.5% formamide, 5 µM primers, 1/250 dilution of the template, and 1.25 units of TAQ polymerase. The thermocycling conditions are typically 94° C. for 3 minutes, 25 cycles of 94° C. for 30 seconds, 60° C. for 30 seconds, 72° C. for 1 minute, and a final extension step of 72° C. for 5 minutes.

The melting of a duplex causes a transition from a helical state (duplex) to a coil state (single stranded). The transition, called HCT (helical to coil transition) is readily measured and is expressed in units of temperature. As used herein, HCT is the temperature difference between which a duplex is 80% ($\alpha$=0.8) and 20% ($\alpha$=0.2) single-stranded.

A hybotrope may be identified as any chemical or any mixture of a chemical in an aqueous or organic environment with buffers, chelators, salts and/or detergents that can decrease the enthalpy of a nucleic acid duplex by 20% when referenced to a standard salt solution (0.165 M NaCl, 0.01 M Tris pH 7.2, 5 mM EDTA and 0.1% SDS) when the hybotrope is present in the environment within a molarity range of 0.1 M to 10 M. The reference oligonucleotide is 5'-GTCATACTCCTGCTTGCTGATCCACATCTG-3' (SEQ ID NO: 1) as the immobilized oligonucleotide and 5'-TGTGGATCAGCAAGCAGGAGTATG-3' (SEQ ID NO: 2) as the solution nucleotide which is typically labeled at the 5'-end with a fluorochrome such as Texas Red. The oligonucleotide duplex (24 nucleotides in length) has a helical to coil transition (HCT) of 25° C. or less. The HCT is the difference between the temperatures at which 80% and 20% of the duplex is single stranded.

1. Relationship of Hybotrope to HCT

In FIG. 1, the characteristic parameters of a thermal melting profile (helical coil transition) of an oligonucleotide duplex in two different hybridization solutions are presented. The squares represent the melting profile of an oligonucleotide duplex in NaCl based hybridization solution (e.g., SSPE, SSC). 20×SSPE is 173.5 g NaCl, 27.6 g NaHPO4, and 7.4 g EDTA at pH 7.4 in 1 L water. 20×SSC is 175.3 g NaCl, 88.2 g NaCitrate at pH 7 in 1 L water. The diamonds represent the melting profile of the same oligonucleotide duplex in a hybotrope-based hybridization solution, in this case LiTCA (lithium trichloroacetate). $T_d$ is the temperature (° C.) at which half of the molecules in a population are single-strand and half of the molecules are double-stranded. The HCT (helical coil transition) is the width of the melting curve from a value of 20% single-strand to 80% single-strand and possesses the unit of temperature (e.g., ° C., ° K). The stringency factor is the value of the slope (partial derivative) of the helical coil transition at the $T_d$. Either stringency factor or HCT may be used to identify a hybotrope.

In Table 1, the slope (k) of the linear equation that relates concentration of solute to $T_d$, the helical coil transition, and the $\Delta T_d$ for 9 different hybotropic and hybridization solutions is presented. An 18 bp oligonucleotide duplex was melted in 15 the respective solutions and the values are obtained as described in the examples.

TABLE 1

| Hybridization Solution Type | Slope (k) | HCT* | Stringency Factor |
|---|---|---|---|
| LiTCA | 19 | 8 | 7.5 |
| GuSCN | 13 | 10 | 6.0 |

TABLE 1-continued

| Hybridization Solution Type | Slope (k) | HCT* | Stringency Factor |
|---|---|---|---|
| NaSCN | 8.5 | 11 | 5.4 |
| NaClO$_4$ | 7 | 12 | 5.0 |
| KI | 5 | 15 | 4.0 |
| NaCl | 4.5 | 17.5 | 3.4 |
| GuCl | 3.5 | 18 | 3.3 |
| CsTFA | 2.5 | 18 | 3.3 |
| 30% formamide | ND** | 20 | 3.0 |

* = ° C.
** = not determined

Figure 2:
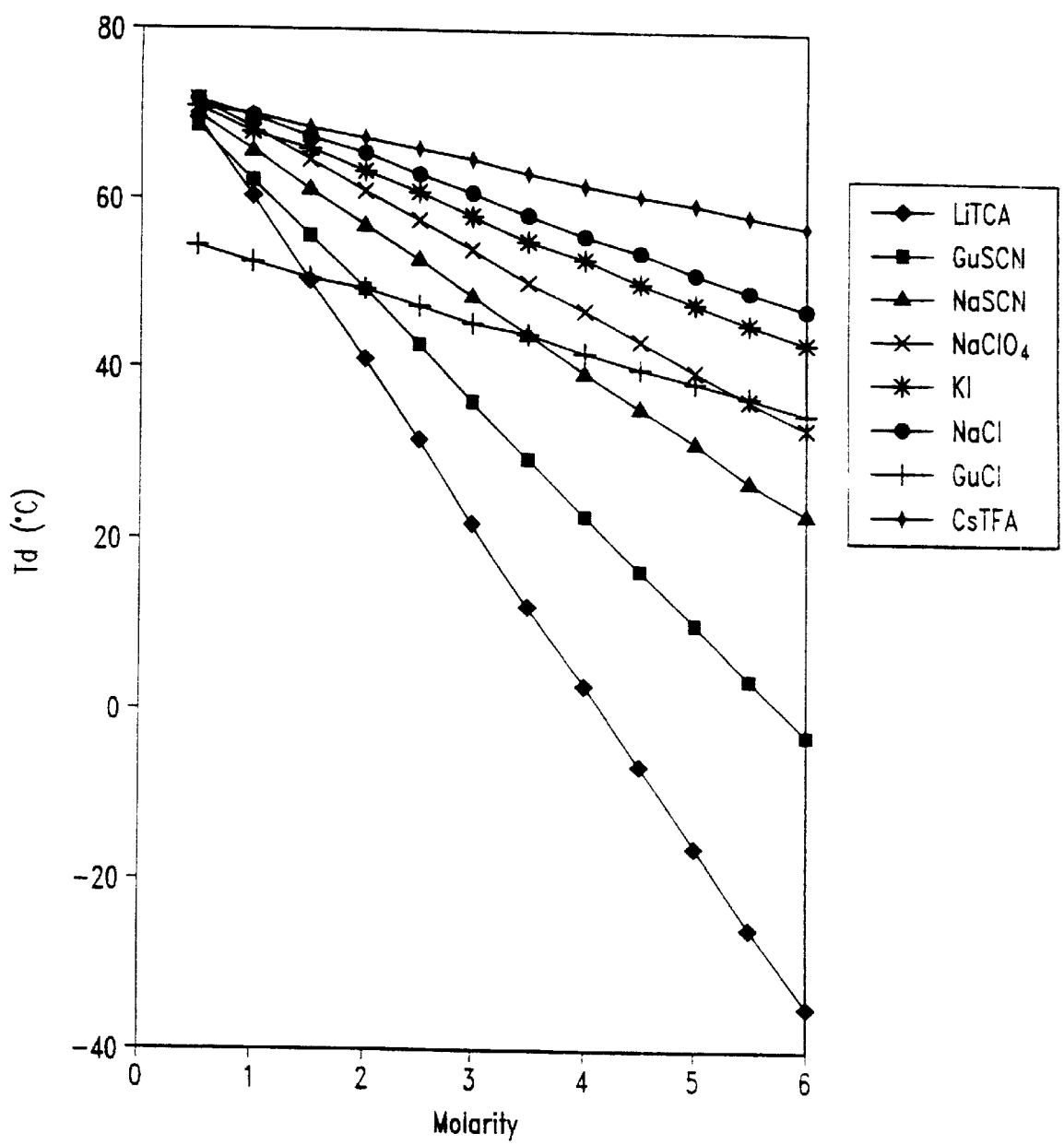
FIG. 2 is a graph illustrating the relationship of the $T_d$ of an oligo duplex and salt concentration in hybridization solutions (LiTCA, GuSCN, NaSCN, NaClO$_4$, KI, NaCl, GuCl, CsTFA). The $T_d$ in degrees C. is plotted versus molarity of the salt.

Thus, from these data, HCT is inversely proportional to the stringency factor for a given hybridization solution type; the lower the value of HCT, the higher the stringency factor. The HCT increases as the slope of the linear function that relates salt concentration to $T_d$ decreases (($T_d$[salt]=$T_d$[0]−k[Cx$^-$]), where $T_d$[0] is the extrapolated $T_d$ at zero salt concentration, k is the salt specific constant and Cx$^-$ is the concentration of the salt or hybotrope; see FIG. 2).

2. Relationship of HCT to Discrimination

Either stringency factor or HCT is related directly to another readily measurable parameter of oligonucleotide duplexes. This parameter, $\Delta T_d$, is the temperature difference between the $T_d$ of an oligonucleotide duplex that is perfectly base paired and the $T_d$ of the same oligonucleotide duplex that contains a mismatch at some position in the duplex (see FIG. 3). As shown herein, the temperature difference between a perfectly base paired duplex and a duplex containing a mismatch is a function of the stringency factor (or HCT) of a given hybridization solution or If hybotrope. The relationship is expressed as: $\Delta T_d$ increases as the stringency factor of a solution increases. In Table 2, this relationship is presented for 18 bp oligonucleotide duplexes. The duplex is melted in the respective hybridization solution and HCT and $\Delta T_d$ is determined as described herein.

TABLE 2

| Hybridization Solution Type | Slope (k) | HCT (° C.) | $\Delta T_d$ (° C.) |
|---|---|---|---|
| LiTCA | 19 | 8 | 7.5 |
| GuSCN | 13 | 10 | 6.0 |
| NaSCN | 8.5 | 11 | 5.5 |
| NaClO$_4$ | 7 | 12 | 4.5 |
| KI | 5 | 15 | 3.0 |
| NaCl | 4.5 | 17.5 | 1.5 |
| GuCl | 3.5 | 18 | 1.2 |
| CsTFA | 2.5 | 18 | 1.2 |
| 30% formamide | ND* | 20 | 1.5 |

* = not determined

The data presented in Table 2 show that HCT is inversely proportional to the $\Delta T_d$ between a perfectly base paired duplex and a duplex containing a mismatch. That is, either stringency factor or HCT predicts the ability of given hybridization solution to discriminate mismatched duplexes. This aspect of hybotrope-based hybridization is further illustrated in FIGS. 4 and 5. FIG. 4 is a graph showing melting profiles in 2.0 M LiTCA for an 18-mer oligonucleotide duplex that is perfectly based paired (diamonds) and the same oligonucleotide duplex that contains a central mismatch (A/A, position 9). The $\Delta T_d$ is 6° C. FIG. 5 is a graph showing melting profiles for an 18-mer oligonucleotide duplex in QY low stringency hybridization buffer (Promega, Madison, Wis.) that is perfectly based paired (squares) and the same oligonucleotide duplex that contains a central mismatch (A/A, position 9). The $\Delta T_d$ is 0° C. Therefore, the $\Delta T_d$ value relates to the ability of a chemical to discriminate between perfectly base paired duplexes and duplexes that contain a mismatch. The practical utility of this result is discussed below.

In addition, transition enthalpies between a fully base-paired and base stacked double helix to two unpaired and unstacked single strands can be calculated. (Breslauer, K. J., Chapter 15, "Methods for Obtaining Thermodynamic Data on Oligonucleotide Transitions," in *Thermodynamic Data for Biochemistry and Biotechnology*, ed. H. Hinz, Academic Press, New York, N.Y., 1986.) The difference between a non-cooperative and cooperative transition is expressed in terms of $\Delta H_{vH}$ (van't Hoff enthalpy). In a cooperative transition, the value of $(d\alpha/dT)T_d$ is high, and therefore, the $\Delta H_{vH}$ is also high. In a non-cooperative transition, the value of $(d\Delta/dT)T_d$ is low, and therefore, the $\Delta H_{vH}$ is also low. (The term $(d\alpha/dT)T_d$ is the derivative of the slope of the melting curve at the $T_d$, $\alpha$ is defined as the % single strand on the ordinate axis.)

In this regard, thermodynamic parameters for two different sets of oligonucleotides (42% G+C; 63% G+C) in three types of hybridization solution are shown in Table 3. The data show that the enthalpy values are inversely related to the values obtained for the temperature range of the thermal coil transition of the duplex (HCT).

In Table 2, EP represents 1-ethyl piperidine, and DMCHAA represents dimethylcyclohexylamine acetate.

TABLE 3

| Solution Type | % G + C | $\Delta T_d$ | $T_d$(° C.) | HCT (° C.) | $\Delta H_{vH}$ (kcal/mol) |
|---|---|---|---|---|---|
| 0.5 M EP | 42 | 5° C. | 55.5 | 24 | −50.8 |
| 1 M DMHCAA | 63 | 6° C. | 40.0 | 18.0 | −41.2 |
| 2 M LiTCA | 42 | 5° C. | 35.5 | 12 | −52.8 |
| 2 M TMATCA | 42 | 4° C. | 55.4 | 18 | −47.0 |
| 3 M TMATCA | 42 | 4° C. | 43.0 | 11.5 | −60.7 |
| 3 M TMACl | 42 | 1° C. | 60.0 | 15.5 | −46.2 |
| 2 M LiTCA | 63 | | 42.0 | 15 | −42.0 |
| 2 M TMATCA | 63 | | 48.0 | 19.5 | −38.6 |
| 3 M TMATCA | 63 | | 47.0 | 13 | −61.8 |
| 3 M TMACl | 63 | | 59.0 | 17.5 | −39.7 |

* = ° C.

3. Characterization of a Hybotrope a. Characteristics of a Hybotrope

As noted herein, a hybotrope is useful within the context of the present invention if it is a solution or is miscible from about 0.001 M to about 10 M in water, other protic, or aprotic solvent. In certain preferred embodiments, the hybotrope does not inactivate polymerases.

As indicated above, a hybotrope is a chemical that can increase the enthalpy of an oligonucleotide or nucleic acid duplex by at least 20% when referenced to a standard salt solution (i.e., 0.165 M NaCl) when the hybotrope is present in the environment within a molarity range of 0.1 M to 10 M. Enthalpy is measured by plotting the slope of the thermal transition, $\alpha$, versus temperature (see FIG. 1) and applying the following:

The van't Hoff enthalpy can be obtained from the differentiated equilibrium melting curve (Marky and Breslauer, 1987) by plotting $d\alpha$ versus temperature. Briefly, thermodynamic data provide a basis for predicting the stability ($\Delta G'$) and temperature-dependent melting behavior (also described here as the helical coil transition (HCT), ($\Delta H^0$)) from the primary sequence of bases in the duplex. We use a thermally induced helical coil transition (from double strand to single strand) to obtain values for the $\Delta H_{vH}$. The analysis of the shape of the helical coil transition is used to calculate the van't Hoff transition enthalpy. As described by Marky and Breslauer, (1987), $\alpha$ is equal to the fraction of single strands in the duplex state. If $\alpha$ is plotted versus temperature the temperature at which $\alpha$ takes the value of 0.5 is defined as the $T_d$. The equilibrium constant K for any transition can be expressed in the form of $\alpha$, the van't Hoff enthalpy can be expressed as:

$$\Delta - H_{vH} = RT2[d \ln K/dT] \text{ or } \Delta - H_{vH} = -R[d\ln K/d(1/T)]$$

To solve the general expression when $\alpha$ takes the value of 0.5 in terms of $\alpha$ the foregoing equation is differentiated and solved for $\alpha$ at the $T_d$;

$$\Delta - H_{vH} = (2+2n)RT2(\partial\alpha/\partial T)_{T-Td}$$

which can also be written:

$$\Delta - H_{vH} = (2+2n)R(\partial\alpha/\partial(1/T)_{T-Td}$$

In this series of experiments it is assumed that a bi-molecularity exists where n=2 for the preceding equations and therefore the corresponding coefficient is equal to 6. Another assumption employed is that there is no dependence of $T_d$ on concentration since at every temperature increment the concentration of single strands is zero (recall that all unhybridized material is washed away from the solid support prior to the melting process and that at each 5° C. temperature increment, the solid support is placed in a fresh solution). For any process at equilibrium, $\Delta G = -RT(\ln K_{eq})$ and $\Delta G = \Delta H - T\Delta S$ it is possible to write $-RT (\ln K) = \Delta H - T\Delta S$.

As has been shown by Gralla and Crothers (Gralla, J., and Crothers, D. M., *J. Mol. Biol.* 73:497–511, 1973) for bimolecular transitions, the full width or half-width of a differentiated melt curve at the half-height is inversely proportional to the van't Hoff transition enthalpy. As suggested, for an equilibrium of the form $nA \leftrightarrow A_n$, the general forms of the van't Hoff equation are:

$$\Delta - H_{vH} = B/((1/T_1)-(1/T_2)) \text{ (for the full width at half-height)}$$

$$\Delta - H_{vH} = B'/((1/T_{max})-(1/T_2)) \text{ (for the upper half-width at half-height)}$$

where $T_{max}$ is the temperature at the maximum, and $T_1$ and $T_2$ correspond to the upper and lower temperatures at which value the change in the plotted temperature is equal to one-half of $[(\partial\alpha/\partial(1/T)_{max}]$. For a molecularity of 2, −B=10.14 and −B'=4.38. The detailed derivations are given in Marky and Breslauer, (1987). This approach of measuring the van't Hoff enthalpies is particularly amenable to melting duplexes off solid supports as all problems associated with baselines and background are completely eliminated.

The equilibrium constant K for a helical transition of a molecularity of 2 can be expressed as the extent of $\alpha$ (the fraction of single strand molecules in a duplex). The value of K is usually determined at the $T_m$ of the helical coil transition where $\alpha$=0.5. This value of the $T_m$ is then extrapolated to some reference temperature (e.g., 298 K) using the empirically determined $T_m$ (or $T_d$) and the calculated van't Hoff enthalpy (assumed to be temperature independent) and the integrated form of the van't Hoff equation:

$$\ln [K(T_m)/K(T_{ref})] = \Delta H^0/R(1/T - 1/T_m)$$

From the empirically determined value of $K(T_{ref})$, it is possible to determine $\Delta G^0$ for the helical coil transition using the relation $\Delta G^0 = \Delta H^0 - T\Delta S^0$. Since the melting curves described here are concentration independent, the $\ln(K_{Tm})=0$ since K=1 at the $T_m$. Therefore the van't Hoff equation reduces to:

$$-\ln K(T) = \Delta H^0 / R(1/T - 1/T_m),$$

which upon multiplying both sides by RT, provides $$-RT \ln K(T) = \Delta H'(1 - T/T_m) = \Delta G^0$$

This expression can be used to calculate the transition free energy $\Delta G^0$ at any temperature of interest (T) from the experimentally measured values of $T_m$ and $\Delta H_{vH}$. The corresponding $\Delta S^0$ can be calculated from relation $\Delta G^0 = \Delta H^0 - T\Delta S^0$.

As a result of reducing the HCT, a hybotrope increases the stringency factor of a hybridization solution or solvent, where the stringency factor is the value of the slope (partial derivative) of the helical coil transition at the value of the $T_m$. As discussed above, the stringency factor can be used to identify a hybotrope.

A hybotrope is generally soluble or miscible in water, polar, apolar or organic solvent from about 0.05 to 10 M, or a hybotrope can be composed solely of a polar, apolar or organic solvent.

b. Structure of Hybotropes

The hybotropes of the present invention are salts, and more specifically are amine-based salts. In common with all salts, the hybotrope salts are formed of an anion and a cation. The hybotrope salts are referred to as amine-based salts because the cationic part of the hybotrope is one of a primary, secondary, tertiary or quaternary amine, and is preferably a primary, secondary or tertiary amine, and is more preferably a secondary or tertiary amine, and is most preferably a tertiary amine.

In order for the hybotrope to function in a hybridization buffer of the invention, the hybotrope should not be too hydrophobic. Thus, the total number of carbon atoms in the cationic portion of the hybotrope typically does not exceed about 36 when the cation is a primary, secondary or tertiary amine, and preferably does not exceed about 48 when the cation is a quaternary amine. Preferably, the cation has from 2 to 20 carbons. Preferably, the primary, secondary, tertiary and quaternary amines contain only carbon and hydrogen atoms in addition to a single nitrogen atom, and thus may be referred to as having only hydrocarbon groups bonded to the central nitrogen.

Non-carbon atoms may or may not be present as part of the cation structure, where such non-carbon atoms include oxygen and nitrogen. Typically, there are no more than about 5 non-carbon atoms present in the cation, and thus the invention provides amine-based hybotrope salts with 0–5 oxygens and 0–5 nitrogens, in addition to carbon and, of course, hydrogen atoms. The cation containing non-carbon atoms has a central amine nitrogen with substituents selection from, for example, hydroxyarylalkyl, N-monosubstituted alkylcarboxyamide, N,N-dialkyl-substituted alkylcarboxyamide, acyl, hydroxyalkyl, and cyanoalkyl, to name a few.

The cation which is a quaternary amine has the structure $N(R)_4$ where R is preferably a $C_1$–$C_{12}$hydrocarbyl and any two R groups may join together to form a cyclic structure with the nitrogen. As used herein, a "$C_x$–$C_y$ hydrocarbyl" is a group having at least "x" and as many "y" carbon atoms, where those atoms may be arranged in a linear, branched or cyclic fashion, and bonds between any two atoms may be saturated or unsaturated, even to the extent of being aromatic. The hydrocarbyl group is formed entirely from carbon and hydrogen atoms. Any two R groups may join together to form a cyclic structure with the nitrogen, and thus the quaternary amine may be a heterocyclic structure, including monocyclic and bicyclic structures. Dimethylpiperidine is an example of a monoheterocyclic quaternary amine of the invention. Preferably, R at each occurrence is independently selected from $C_1$–$C_{12}$alkyl, $C_3$–$C_{12}$cycloalkyl and $C_1$–$C_{12}$arylalkyl.

The cation which is based on a tertiary amine has the structure $HN(R)_3$ wherein R is a $C_1$–$C_{12}$hydrocarbyl and any two R groups may join together to form a cyclic structure with the nitrogen. Preferably, R at each occurrence is independently selected from $C_1$–$C_{12}$alkyl, $C_3$–$C_{12}$cycloalkyl and $C_7$–$C_{12}$arylalkyl.

The cation which is based on a secondary amine has the structure $N(H)_2(R)_2$ wherein R is a $C_1$–$C_{12}$hydrocarbyl and the two R groups may join together to form a cyclic structure with the nitrogen. Preferably, R at each occurrence is independently selected from $C_1$–$C_{12}$alkyl, $C_3$–$C_{12}$cycloalkyl and $C_7$–$C_{12}$arylalkyl.

The cation which is based on a primary amine has the structure $N(H_3)R$ wherein R is a $C_1$–$C_{12}$hydrocarbyl group, and is preferably selected from $C_1$–$C_{12}$alkyl, $C_3$–$C_{12}$cycloalkyl and $C_7$–$C_{12}$arylalkyl.

The cation is preferably based on a primary, secondary or tertiary amine. When present in a salt form, tertiary amines in particular typically provide superior performance to quaternary ammonium salts.

Preferred amines which, upon protonation form the cation of the hybotrope salt include, without limitation, ethylbutylamine, 1-methylimidizole, 1-methylpiperidine, 1-methylpyrrolidine, 3-methoxypropylamine, triethylamine, bis(2-methoxyethyl)amine, diallylamine, dibutylamine, diisobutylamine, N,N-dimethylaminobutane, N,N-dimethylcyclohexylamine, N,N-dimethylheptylamine, N,N-dimethylhexylamine, triethanolamine, 1-ethylpiperidine, dicyclohexylamine, diisopropylainine, dipropylamine, N,N-dimethylisopropylamine, N-ethylbutylamine, tetraethylammonium, tripropylamine, 2-methoxyethylamine, and N,N-dimethyloctylamine. The protonated forms of 1-ethylpiperidine and is a preferred cation in a hybotrope of the present invention.

The anionic portion of the hybotrope salt is preferably selected from short chain organic carboxylates, such as acetate and propionate, as well as halogenated derivatives thereof. Halogenated derivatives include fluorinated, chlorinated, brominated and iodinated derivatives of the short chain organic carboxylate. Preferred halogenated derivatives are fluorinated and chlorinated carboxylates, such as trichloroaceate and trifluoroacetate. Acetate and halogenated derivatives thereof are preferred, with acetate typically being most preferred. Other suitable anions for hybotrope salts of the invention include halide, and preferably bromide or chloride, as well as short-chain (ca. $C_3$–$C_6$) dicarboxylates as present in, for example, malic acid, succinic acid and adipic acid. Other suitable anions are phosphate, nitrate, sulfate and organic sulfonates.

Preferred hybotrope salts of the invention are selected from the following: (a) an acetate salt of a cation of the formula $HN(CH_3)_2R_a$ wherein Ra is a $C_4$–$C_7$hydrocarbyl; (b) a halogenated acetate salt of a cation of the formula $HN(CH_3)_2R_b$ wherein $R_b$ is a $C_7$–$C_{12}$hydrocarbyl; (c) acetate and halogenated acetate salts of a cation of the formula $H_2N(C_5$–$C_7$cycloalkyl)$R_c$ where $R_c$ is a $C_1$–$C_{12}$hydrocarbyl; and (d) acetate and halogenated acetate salts of N-substituted piperdine, wherein the nitrogen of piperidine is substituted with $C_1$–$C_{12}$hydrocarbyl. In any of these salts, the hydrocarbyl is preferably selected from alkyl, alkenyl, alkynyl, cycloalkyl, cycloalkenyl, aryl, aralkyl, and alkylaryl. A preferred composition of the invention includes any of these salts in combination with a nucleic acid molecule.

Other preferred hybotropes are the following: 3,3-dimethylpiperidine acetate, 2-ethylpiperidine acetate, 3,5-dimethylpiperidine acetate, dipiperidinomethane acetate, 1-methylpiperidine, 1,1-methylenebis(3'methylpiperidine), n-methyldicyclohexylammonium acetate, n-tertbutylcyclohexylammonium acetate, isopropylcyclohexylammonium acetate, diethanolammonium acetate, diethylammonium acetate, dimethylaminopropylammonium acetate, ethylenediammonium acetate, isopropylammonium acetate, monoethanol ammonium acetate, morpholine acetate, triethanolammonium acetate, triethylammonium acetate, mono-n-propyl ammonium acetate, di-n-propyl ammonium acetate, tri-n-propyl ammonium acetate, monoisopropyl ammonium acetate, dimethylaminopropyl ammonium acetate, mono-n-butyammonium acetate, di-N-butylammonium acetate, tri-n-butylammonium acetate, monoisobutylammonium acetate, diisobutylammonium acetate, ethyl-n-butylammonium acetate, monoethyl ammonium acetate, 1,8-diazabicyclo[5.4.0]undec-7-ene acetate, dimethylaminopropylammonium acetate, n-ethylcyclohexylammonium acetate, n-ethyl-1,2-dimethylpropylammonium acetate, 2-methylcyclohexyl ammonium acetate, mixed polycycloaliphatic ammonium acetates, bis(p-aminocyclohexyl)methane acetate, tetramethylimino-bis-propyl ammonium acetate, n,n,n1,n1-tetramethyl 1,3 propane diammonium acetate, 1-amino-4-cyclopentylpiperazine, 2-methylpiperazine, 2,6-dimethylpiperazine, 2,5-dimethylpiperazine, homopiperazine, methylhomopiperazine, n-methylpiperazine, n-ethylpiperazine, and n-isobutylpiperazine.

Hybotropes formed from tertiary amines, i.e., hybotropes wherein the cationic portion is a protonated tertiary amine (HNR$_3$) are preferred components of the buffer solutions described herein. Within this category, a preferred tertiary amine is an N-alkyl substituted cyclic amine, e.g., a 4- to 8-membered nitrogen containing heterocyclic ring wherein the ring nitrogen is substituted with an alkyl group. Preferred alkyl groups are $C_1$–$C_{10}$, more preferably $C_2$–$C_5$alkyl. Preferred heterocyclic rings have 4–6 carbon atoms in addition to a nitrogen atom which form the ring. Piperidine is a preferred heterocyclic ring. The heterocyclic ring may be substituted at any ring carbon with a $C_1$–$C_{10}$alkyl group. N,N-dialkyl-substituted piperazine is another tertiary amine which may be used to form the hybotrope of the invention. Preferred counterions to the tertiary amine are acetic acid and haloacetic acid (e.g., trichloroacetic acid and trifluoroacetic acid).

Additional specific preferred hybotropes of the present invention include, without limitation, bis(2-methoxyethyl) amine acetate, 1-ethylpiperidine acetate, 1-ethylpiperidine trichloroacetate, 1-ethylpiperidine trifluoroacetate, 1-methylimidizole acetate, 1-methylpiperidine acetate, 1-methylpiperidine trichloroacetate, 1-methylpyrrolidine acetate, 1-methylpyrrolidine trichloroacetate, 1-methylpyrrolidine trifluoroacetate, 2-methoxyethylamine acetate, N,N-dimethylcyclohexylamine acetate, N,N-dimethylcyclohexylamine trifluoroacetate, N,N-dimethylcyclohexylamine, N,N-dimethylheptylamine acetate, N,N-dimethylheptylamine acetate, N,N-dimethylhexylamine acetate, N,N-dimethylhexylamine acetate, N,N-dimethylisopropylamine acetate, N-ethylbutylamine acetate, N-ethylbutylamine trifluoroacetate, N,N-dimethylaminobutane trichloroacetate, N,N-dimethylisopropylamine trichloroacetate, triethanolamine acetate, triethylamine acetate, triethylamine trichloroacetate, tripropylamine acetate, and tetraethylammonium acetate.

Upon protonation, each of a primary, secondary and tertiary amine is converted to an ammonium cationic form. Upon deprotonation, a carboxylic acid is converted to a carboxylate anionic form. When any of a primary, secondary and tertiary amine is contacted with a carboxylic acid, the proton from the carboxylic acid may transfer to the nitrogen of the amine, to provide a carboxylate anion and an ammonium cation, i.e., a salt. Thus, in solution, there is an equilibrium present between the carboxylic acid/carboxylate forms and the amine/ammonium forms, so that the precise species present in the solution, and the concentrations thereof, depends in part on the pH of the solution. The hybotrope-containing compositions of the present invention may have any pH. Thus, so long as either the salt form itself, or the corresponding amine and carboxylic acid forms are added to a hybridization buffer, the composition will contain a hybotrope according to the present invention, regardless of whether additional chemicals and agents are added to the composition which may affect the pH and/or the concentration of the cation and the anion of the hybotrope salt.

Preferably, the hybotrope salt is in combination with water, preferably completely dissolved in the water, and when dissolved the salt is preferably at a concentration of from 1.0 mM to 6 M at room temperature. In general, hybotrope solubility may be measured by making a saturated solution with the respective salt, filtering off undissolved salt, removing the liquid or aqueous material and then determining the weight of the remaining salt.

In one embodiment, the invention provides a composition which includes a nucleic acid molecule and a salt, where the salt is comprises an anion and a cation. The anion is selected from halogenated acetate, propionate and halogenated propionate, while the cation is selected from primary, secondary and tertiary ammonium comprising 1–36 carbon atoms, and quaternary ammonium comprising 4–48 carbons.

In another embodiment, the invention provides a composition which is non-flowing and includes a nucleic acid molecule of 6–100 nucleotides and a salt, where the salt comprising an anion and a cation. The anion is selected from acetate, halogenated acetate, propionate, and halogenated propionate, while the cation is selected from primary, secondary and tertiary ammonium comprising 1–36 carbons, and quaternary ammonium comprising 4–48 carbons. The composition is "non-flowing" in the sense that it is not being pumped or otherwise being made to flow through a chromatography column. The hybotrope-containing compositions of the present invention are useful as hybridization buffers, and in this utility are essentially static within a container, possibly experiencing some stirring, however are not flowing.

In another embodiment, the invention provides a composition which is free from organic solvent, and includes a nucleic acid molecule of 6–100 nucleotides and a salt. The salt comprising an anion and a cation, where the anion is selected from acetate, halogenated acetate, propionate, and halogenated propionate, and the cation is selected from primary, secondary and tertiary ammonium comprising 1–36 carbons, and quaternary ammonium comprising 4–48 carbons. Organic solvents are liquids that contain carbon atoms, such as alcohols, ethers, ketones and the like.

As used herein, the following terms have the indicated meanings.

Alkyl refers to an aliphatic hydrocarbon radical, —$(CH_2)_n$ $CH_3$, either branched or unbranched such as methyl, ethyl, N-propyl, iso-propyl, N-butyl, iso-butyl, sec-butyl, tert-butyl, dodecyl or the like. An alkenyl group is essentially an alkyl group wherein a double bond (rather than a single bond) is present between at least two carbon atoms. An alkynyl group is essentially an alkyl group wherein a triple bond is present between at least two carbon atoms.

Aryl refers to a radical derived from an aromatic hydrocarbon by removal of one hydrogen atom such as phenyl, α-naphthyl, β-naphthyl, biphenyl, anthryl and the like.

Arylalkyl, —(CH$_2$)$_n$—Ar, refers to an alkyl radical as defined above joined to an aryl radical.

Alkylcarboxyamide refers to a radical, —(CH$_2$)$_n$—CONH$_2$.

Hydroxyarylalkyl refers to an arylalkyl radical where the aryl radical is an hydroxyaryl.

N-mono-substituted alkylcarboxyamide refers to a radical,

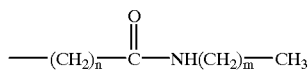

where n=10 to 20 carbons and m=1 to 5 carbons.

N,N-dialkyl-substituted alkylcarboxyamide refers to a radical,

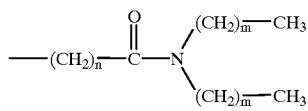

where each alkyl can be the same or different and where n=10 to 20 carbons and m=1 to 5 carbons.

Acyl includes any organic radical derived from an organic acid, such as a carboxylic acid by elimination of the hydroxyl group. It is represented by the formula R$_s$—CO, wherein it is preferred that R$_s$ be an alkyl of 1 to 20 carbons or a cycloalkyl.

Hydroxyalkyl refers to a radical —(CH$_2$)$_n$OH, where n=1 to 20.

Cycloalkane or cycloalkyl refers to a radical of a saturated hydrocarbon in a ring structure such as cyclopropyl, cyclobutyl, cyclopentyl, cyclohexyl, cycloheptyl, adamantyl and the like.

Cyanoalkyl refers to a radical of a cyano group, having the formula —C≡N joined to an alkyl group, as defined above.

Unless otherwise stated, all number ranges are inclusive of the stated range (e.g, 1 to 5 carbons, includes to and 5 carbons).

Halogen refers to chlorine, bromine, iodine or fluorine.

c. Hybotrope-containing Compositions

As stated above, the present invention provides (a) a composition that includes a nucleic acid molecule, preferably having 6–100 nucleotides, and a hybotrope salt; (b) a non-flowing composition that includes a nucleic acid molecule of 6–100 nucleotides and a hybotrope salt; (c) a composition which is free from organic solvent, and includes a nucleic acid molecule of 6–100 nucleotides and a hybotrope salt. In one embodiment, the nucleic acid molecule is DNA. In another embodiment, the nucleic acid molecule is RNA. In yet another embodiment, the nucleic acid molecule is cDNA.

Additional components may be present in the compositions of the invention. For instance, the compositions preferably include water, so that the nucleic acid molecule and hybotrope salt are in aqueous solution. In a solution, the nucleic acid molecule is preferably present at a concentration of from $10^{-6}$ to $10^{-22}$ g/mL. The compositions may also contain an enzyme, such as a polymerase and/or a ligase. The presence of the polymerase is desirable when the hybotrope-containing compositions are used in amplification reactions. Preferably, the hybotrope does not inactivate the polymerase, where polymerase activity in a hybotropic solution may be measured according to the use of the polymerase. For example, in amplification reactions, duplicate reactions with and without the hybotrope are run. The hybotrope does not inactivate the enzyme if 10% of activity is retained. Other suitable optional components include, without limitation, at least one of a buffer, detergent and chelator.

Figure 6:
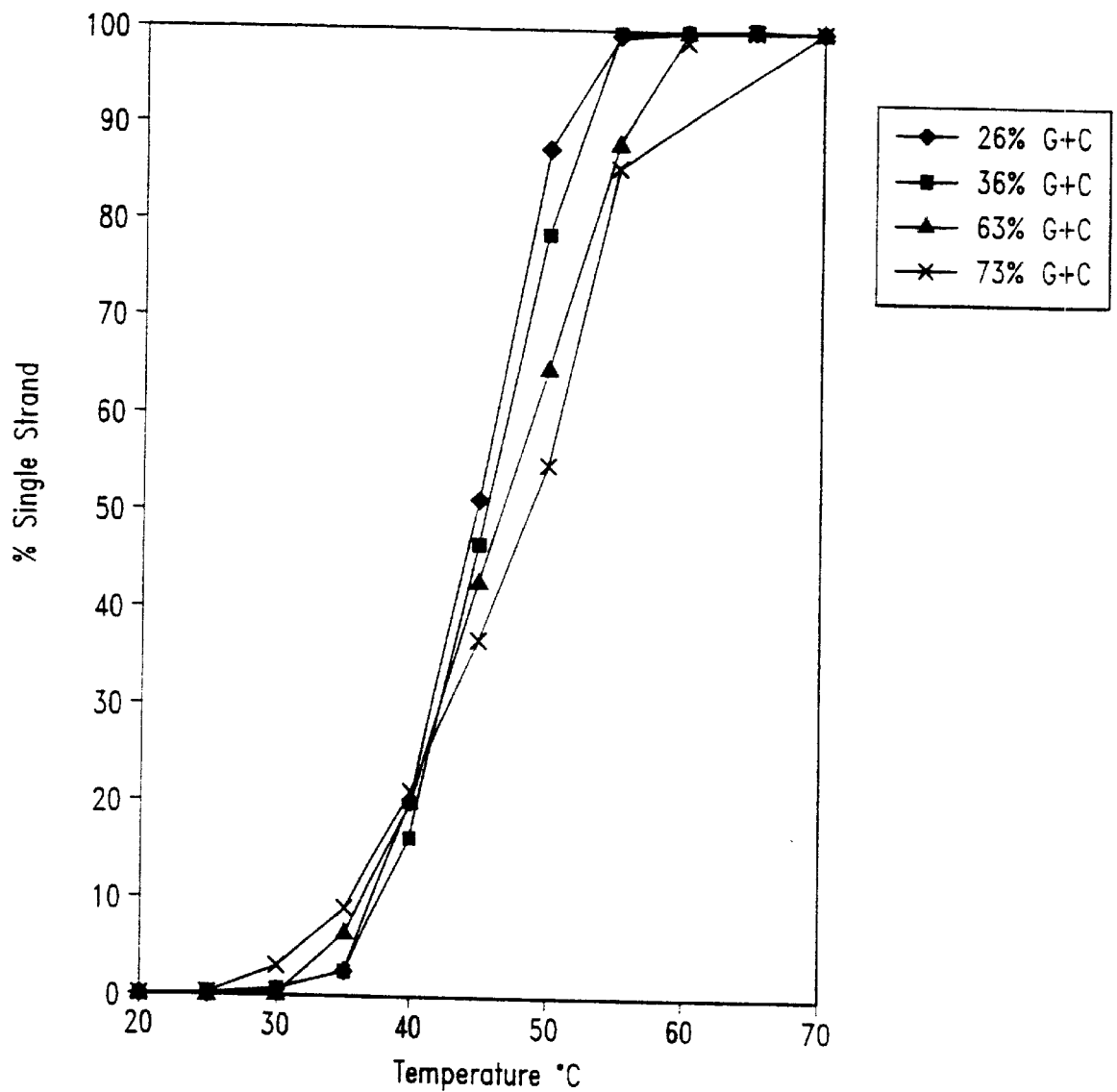
FIG. 6 is a graph showing melting profiles for a set of 19-mer oligonucleotides duplexes that vary in G+C composition from 26% to 73%. All of the duplexes are perfectly based paired. The $\Delta T_d$ is 5° C. across the entire G+C range. The melting profiles are determined in 3 M TMATCA. The % single strand (y-axis) is plotted versus temperature (° C.; x-axis).
Figure 7:
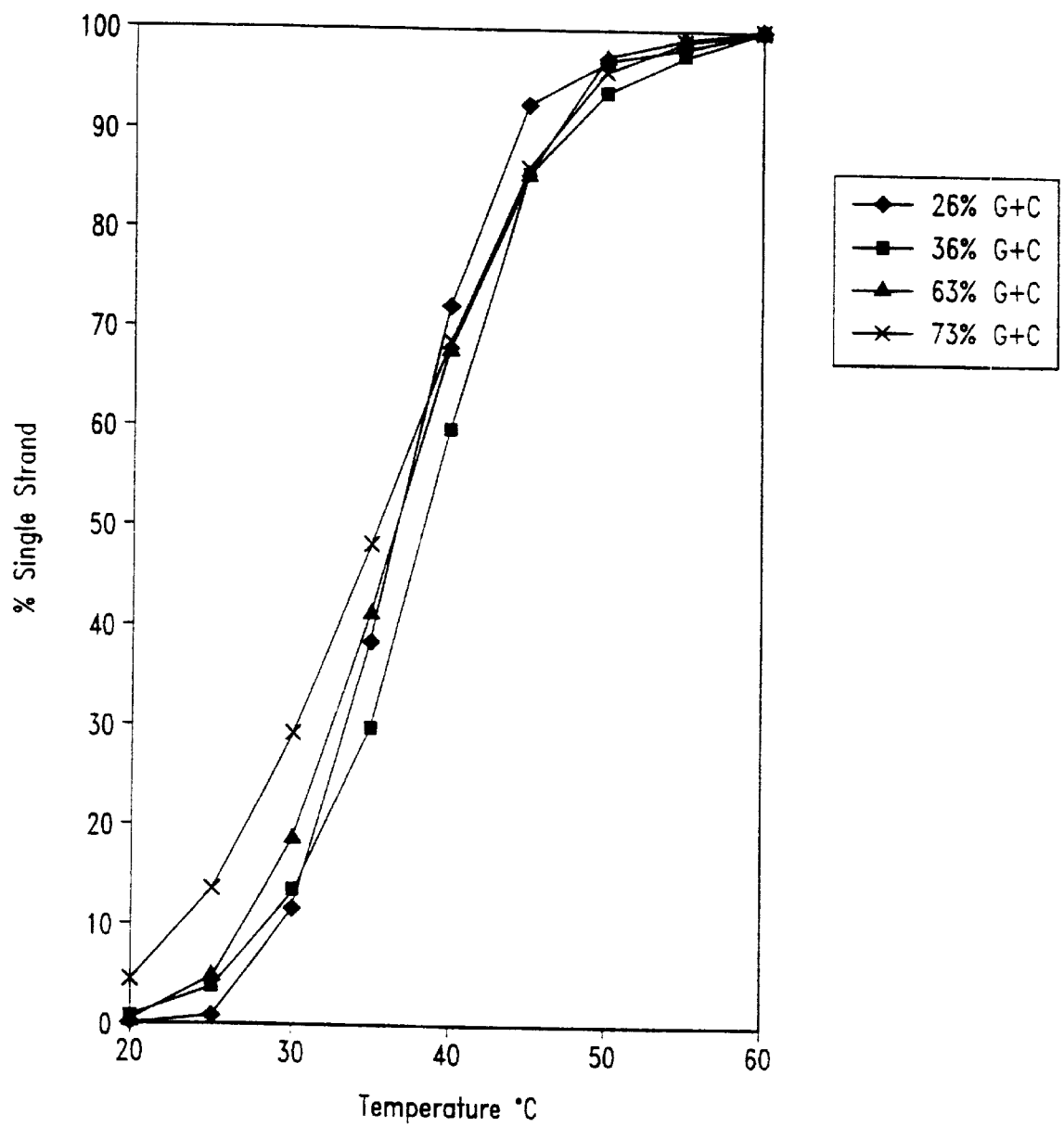
FIG. 7 is a graph displaying melting profiles for a set of 19-mer oligonucleotides duplexes that vary in G+C composition from 26% to 73%. All of the duplexes are perfectly based paired. The $\Delta T_d$ is 4° C. across the entire G+C range. The melting profiles are determined in 3 M TEATCA. The % single strand (y-axis) is plotted versus temperature (° C.; x-axis).
Figure 8:
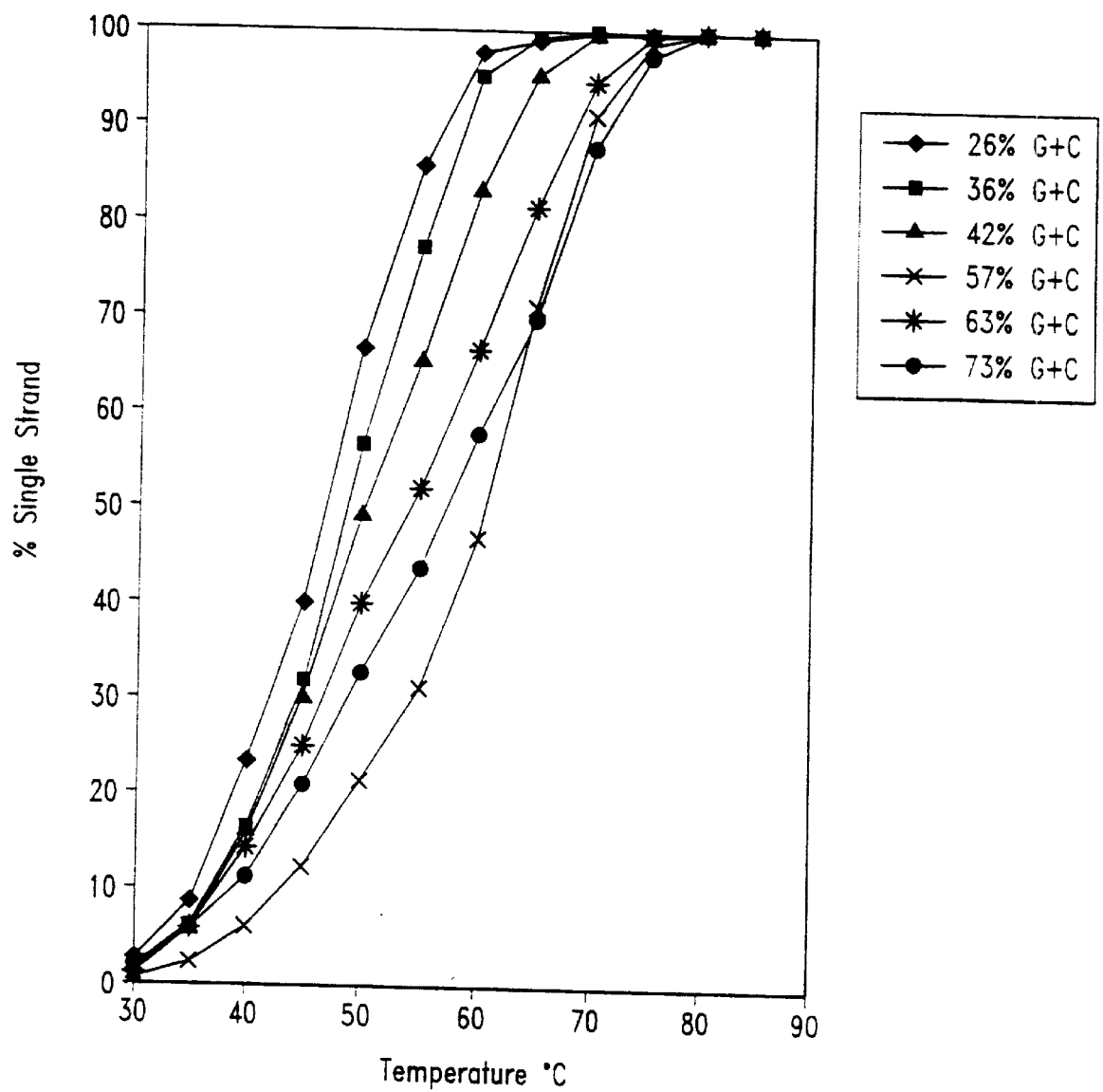
FIG. 8 is a graph illustrating melting profiles for a set of 19-mer oligonucleotide duplexes that vary in G+C composition from 26% to 73%. All of the duplexes are perfectly base-paired. The $\Delta$-$T_m$ is 16° C. across the entire G+C range. The melting profiles are determined in 0.165 M NaCi. The % single strand (y-axis) is plotted versus temperature (° C.; x-axis).

Some of the hybotropes disclosed herein form novel hybridization solutions that improve the specificity of oligonucleotide probes. For example, diisopropylammonium acetate (DIIPAA) and 1-ethylpiperidine acetate (EPA) confer a high level of hybridization stringency. Moreover, these hybotropes neutralize the influence of G+C content on T$_d$. In the Examples, random oligonucleotide probes (all 19-mers) differing in G+C content from 25% to 73% are shown to possess a T$_d$ within 5° C. of each other in the presence of TMATCA (see FIG. 6); the average T$_d$ in 3 M TMATCA was 45° C. Similar results are obtained with TEATCA (see FIG. 7). As a control, the T$_d$s of these 19 mers were determined in 3 M TEACl. The resulting differences in T$_d$ was 6° C. and the average T$_d$ of the 6 oligonucleotides was about 62° C. Furthermore, in 30% formamide, the 6 oligonucleotide probes differed in T$_d$ by 15° C.; in 0.165 M NaCl, the range in T$_d$ values was 15° C. (see FIG. 8); and in 2 M LiTCA, the difference in T$_d$ was about 10° C. Most significantly, however, the HCT in TMATCA ranges from 8° C. for the 25% G+C content oligo to 14° C. for the 73% G+C oligonucleotide. The HCT in TMACl ranges from 12.5° C. for the 25% G+C content oligo to 17.5° C. for the 73% G+C oligonucleotide.

Novel hybridization solutions have also been identified which neutralize the effects of G+C content on the melting behavior of nucleic acid duplexes. These solutions are in some cases hybotropes and in other cases can be used as PCR buffers or as hybridization solutions which minimize the effects of G+C content on nucleic acid duplexes. These new hybridization solutions, their properties, and their preparation are described in the Examples.

Figure 14:
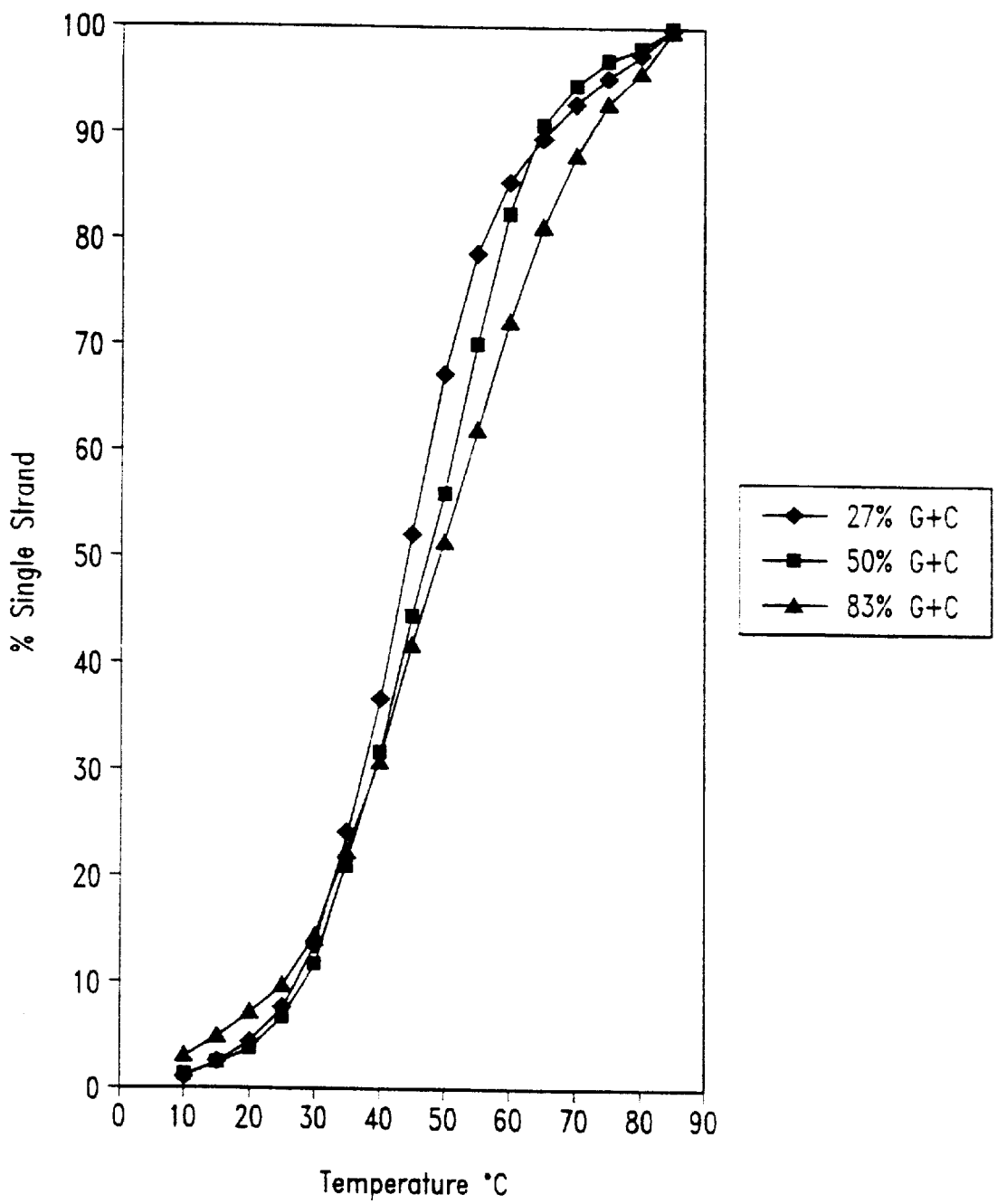
FIG. 14 is a graph showing the difference in $T_d$ between three duplexes, that vary in G+C content from 27% to 83%. The percentage of single strand DNA (y-axis) is plotted versus temperature (° C.; x-axis). The melting solution was 100 mM 2-methoxyethylamine trifluoroacetate.
Figure 15:
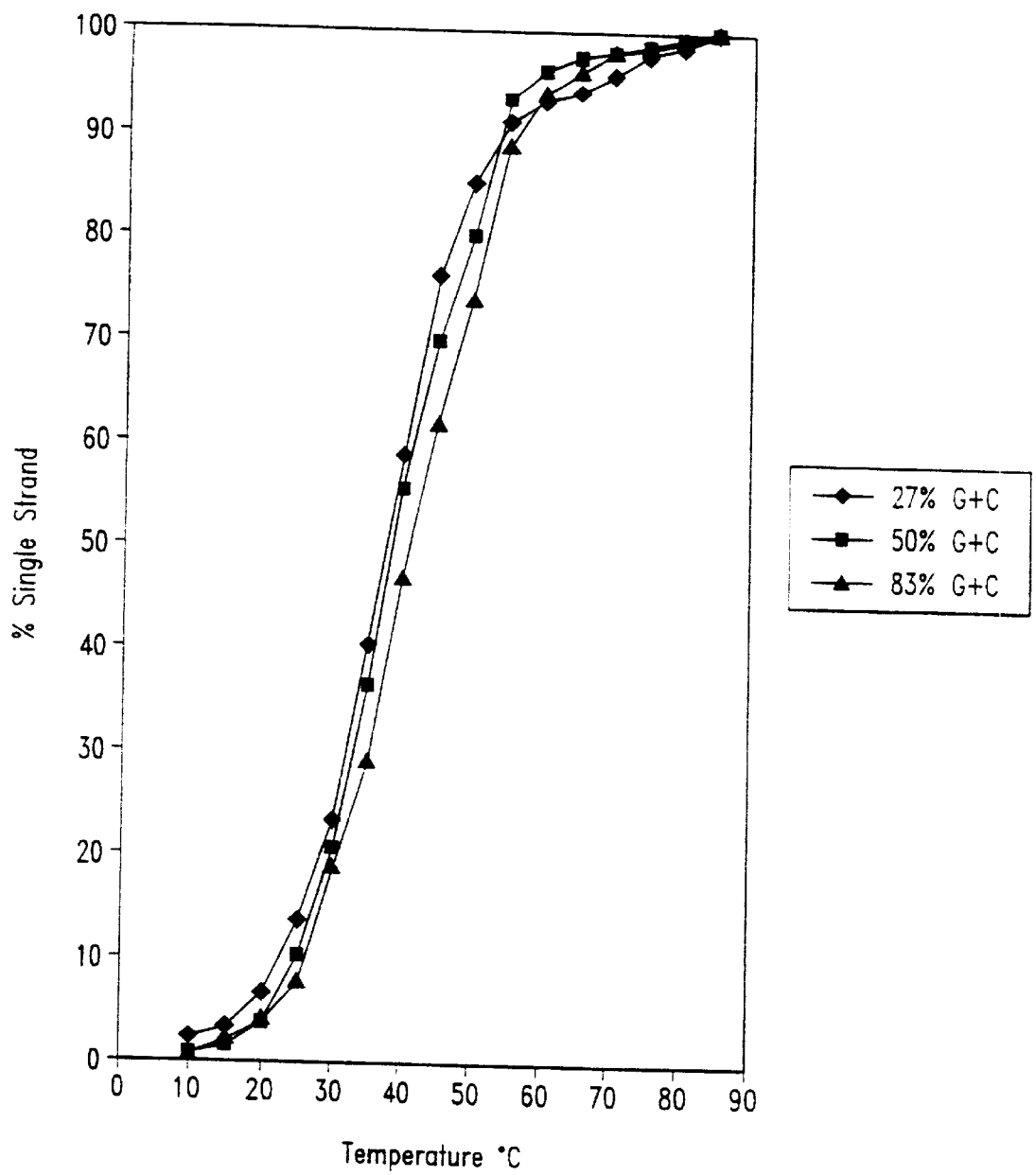
FIG. 15 is a graph showing the difference in $T_d$ between three duplexes, that vary in G+C content from 27% to 83%. The percentage of single strand DNA (y-axis) is plotted versus temperature (° C.; x-axis). The melting solution was 100 mM diisobutylamine acetate.

FIG. 14 is a graph showing the difference in T$_d$ between three duplexes, that vary in G+C content from 27% to 83%. The capture oligonucleotide is a 36-mer (DMO-GC36cap: 5'-hexylamine-GCAGCCTCGCGGAGGCGGATGATCG-TCATTAGTATT-3' SEQ ID NO: 6) and three complementary oligos which are labeled with the fluorochrome are DMO-83GC: 5'-Texas Red-CCGCCTCCGCGAGGCT5C-3'; DMO-50GC: 5'-Texas Red-AATGACGATCATCCGCCT-3' (SEQ ID NO: 7); DMO-27GC: -Texas Red-AATACTAATGACGATCAT-3'(SEQ ID NO: 8). The temperature difference between any two T$_d$s at α=0.5 is defined as the ΔT$_d$. The percentage of single strand DNA (y-axis) is plotted versus temperature (° C.; x-axis). The melting solution was 100 mM 2-methoxyethylamine trifluoroacetate. The maximum difference between the 3 melting curves in the T$_d$ was 6° C. The helical coil transition of the 27% G+C content was 21° C., 50% G+C was 33° C. and for the 83% G+C duplex was 29° C. Note that the helical coil transitions (HCTs) of the 3 different G+C content oligonucleotides is different. This is in contrast to the case with diisobutylamine as shown in FIG. 15. FIG. 15 is a graph showing the difference in T$_d$ between three duplexes, that vary in G+C content from 27% to 83% (the same system as described in FIG. 14. The temperature difference between any two $T_d$s at $\alpha=0.5$ is defined as the $\Delta T_d$. The percentage of single strand DNA (y-axis) is plotted versus temperature (° C.; x-axis). The melting solution was 100 mM diisobutylamine acetate. The maximum difference between the 3 melting curves in the $T_d$ was 5° C. The helical coil transition of the 27% G+C content was 22° C., 50% G+C was 26° C. and for the 83% G+C duplex was 25° C. The helical coil transitions for the three oligonucleotide duplexes are very similar. This is the behavior that is preferred for use in array hybridizations or polymerase chain reactions, or with use of any enzymatic based assay.

Figure 16:
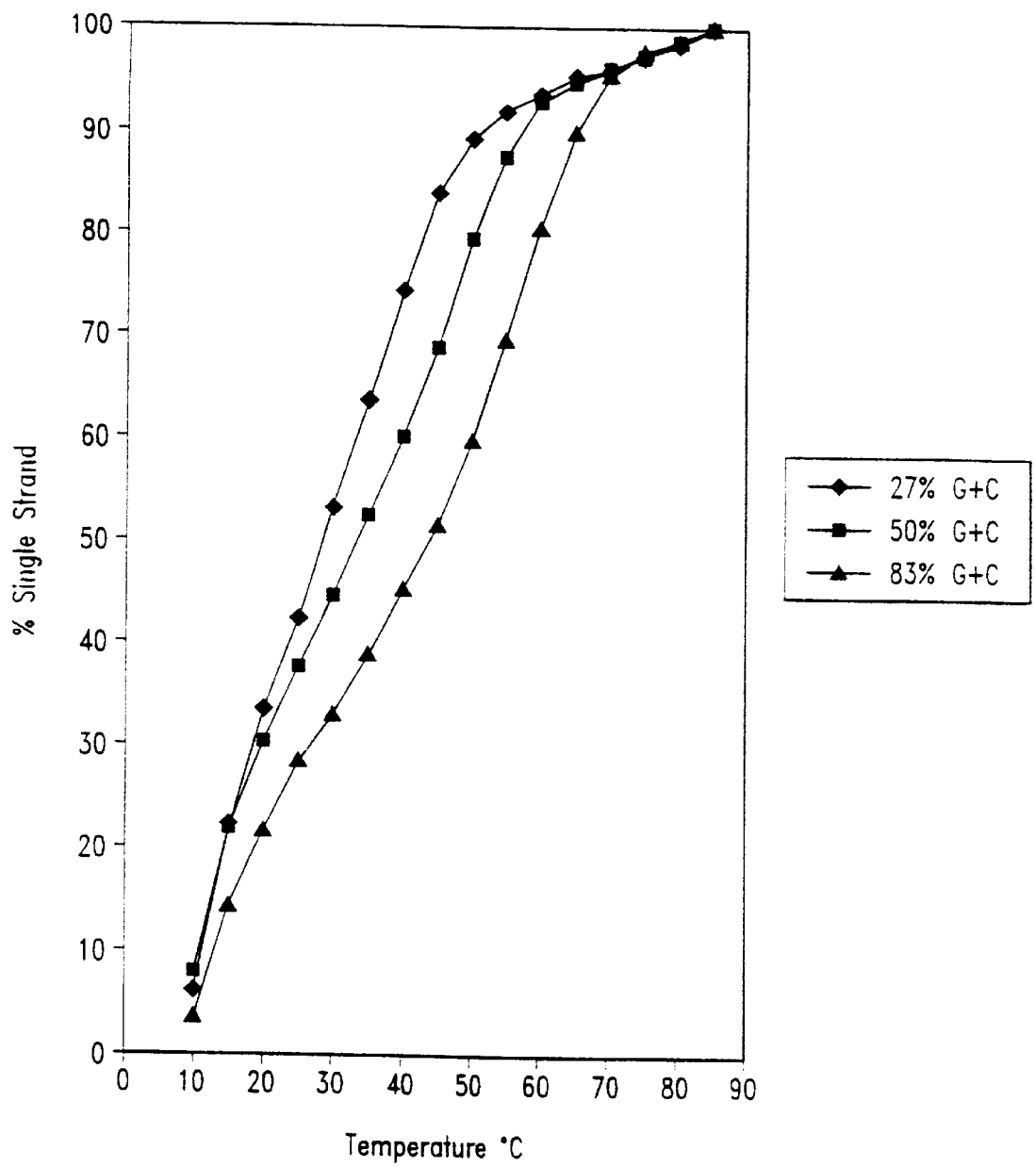
FIG. 16 is a graph showing the difference in $T_d$ between three duplexes, that vary in G+C content from 27% to 83%. The percentage of single strand DNA (y-axis) is plotted versus temperature (° C.; x-axis). The melting solution was 2 M guanidinium thiocyanate.

In FIG. 16 the inability of GuSCN to neutralize G+C content is shown. FIG. 16 is a graph showing the difference in $T_d$ between three duplexes, that vary in G+C content from 27% to 83% (the same capture and probe oligonucleotides as described in FIG. 14). The temperature difference between any two $T_d$s at $\alpha=0.5$ is defined as the $\Delta T_d$. The percentage of single strand DNA (y-axis) is plotted versus temperature (° C.; x-axis). The melting solution was 2 M guanidinium thiocyanate. The maximum difference between the 3 melting curves in the $T_d$ was 16° C. The helical coil transition of the 27% G+C content was 28° C., for the 50% G+C duplex was 30° C. and for the 83% G+C duplex was 32° C. Similar results were obtained with 1×PCR buffer (FIG. 17) and 1×SSC buffer (FIG. 18). There was also no neutralization of G+C content with 20% formamide (FIG. 19) and 1×SSC buffer.

Figure 18:
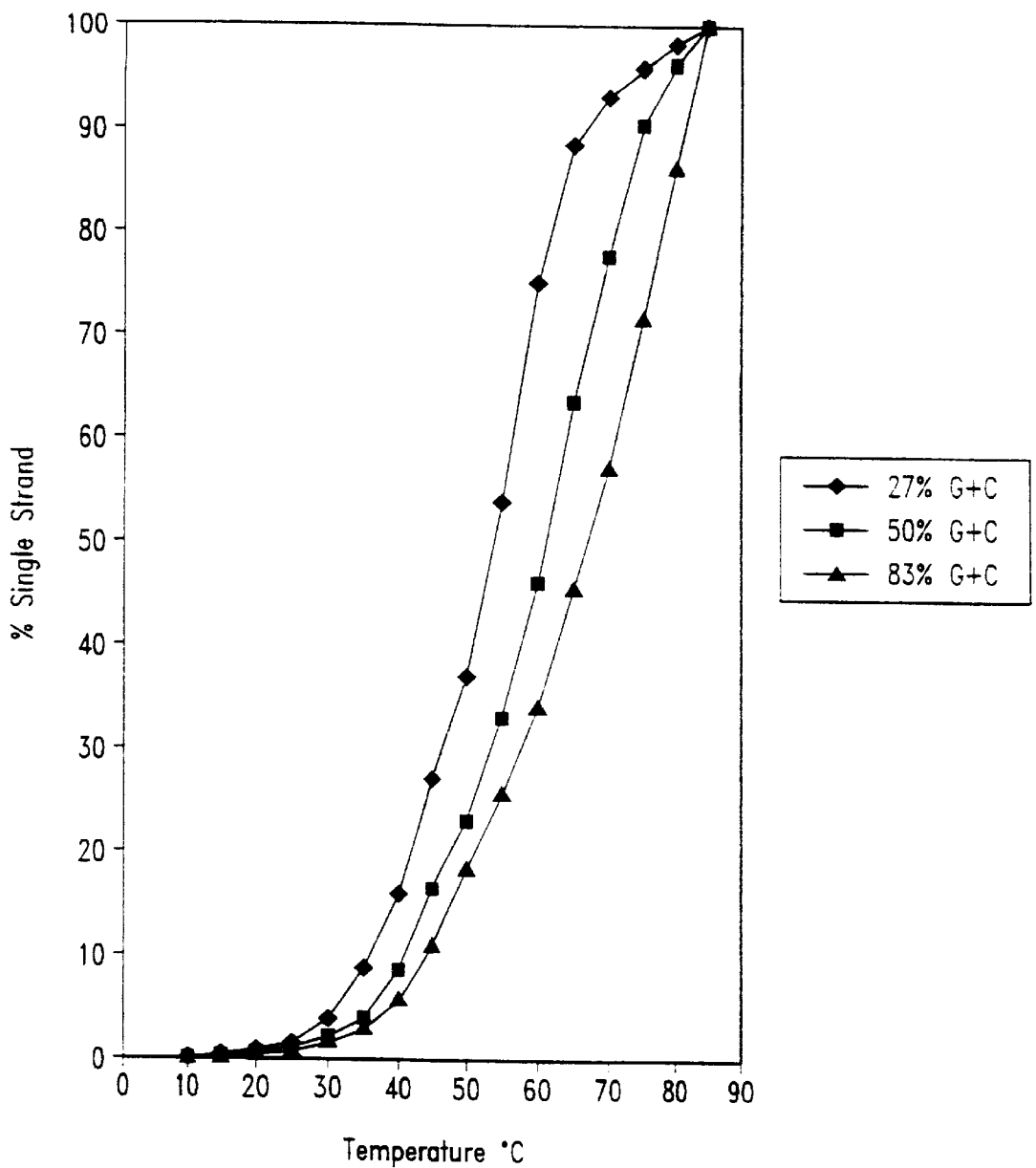
FIG. 18 is a graph showing the difference in $T_d$ between three duplexes, that vary in G+C content from 27% to 83%. The percentage of single strand DNA (y-axis) is plotted versus temperature (° C.; x-axis). The melting solution was 1×SSC.
Figure 19:
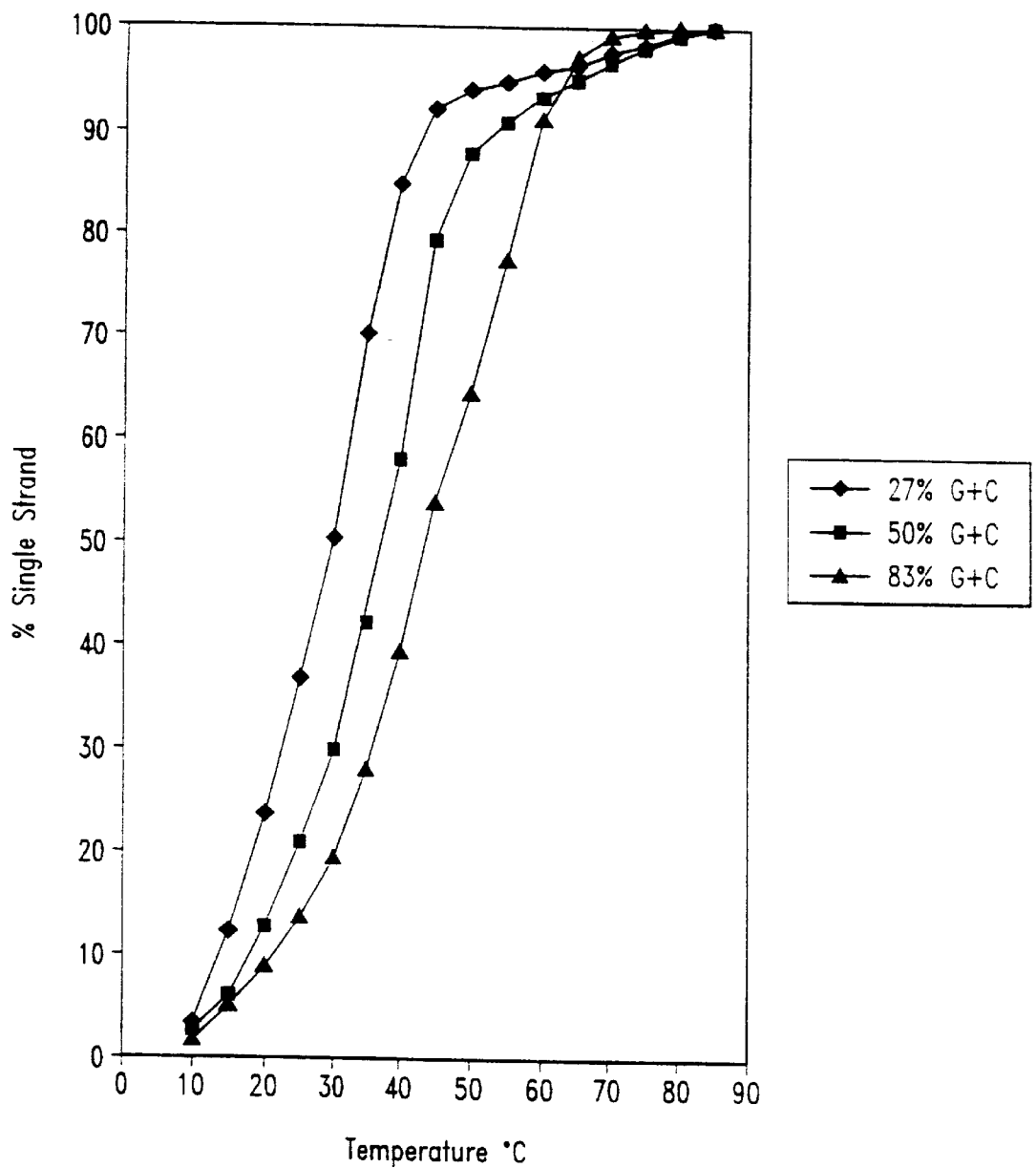
FIG. 19 is a graph showing the difference in $T_d$ between three duplexes, that vary in G+C content from 27% to 83%. The percentage of single strand DNA (y-axis) is plotted versus temperature (° C.; x-axis). The melting solution was 20% formamide, 10 mM Tris pH 7.6, and 5 mM EDTA with 0.1% sarkosyl.
Figure 20:
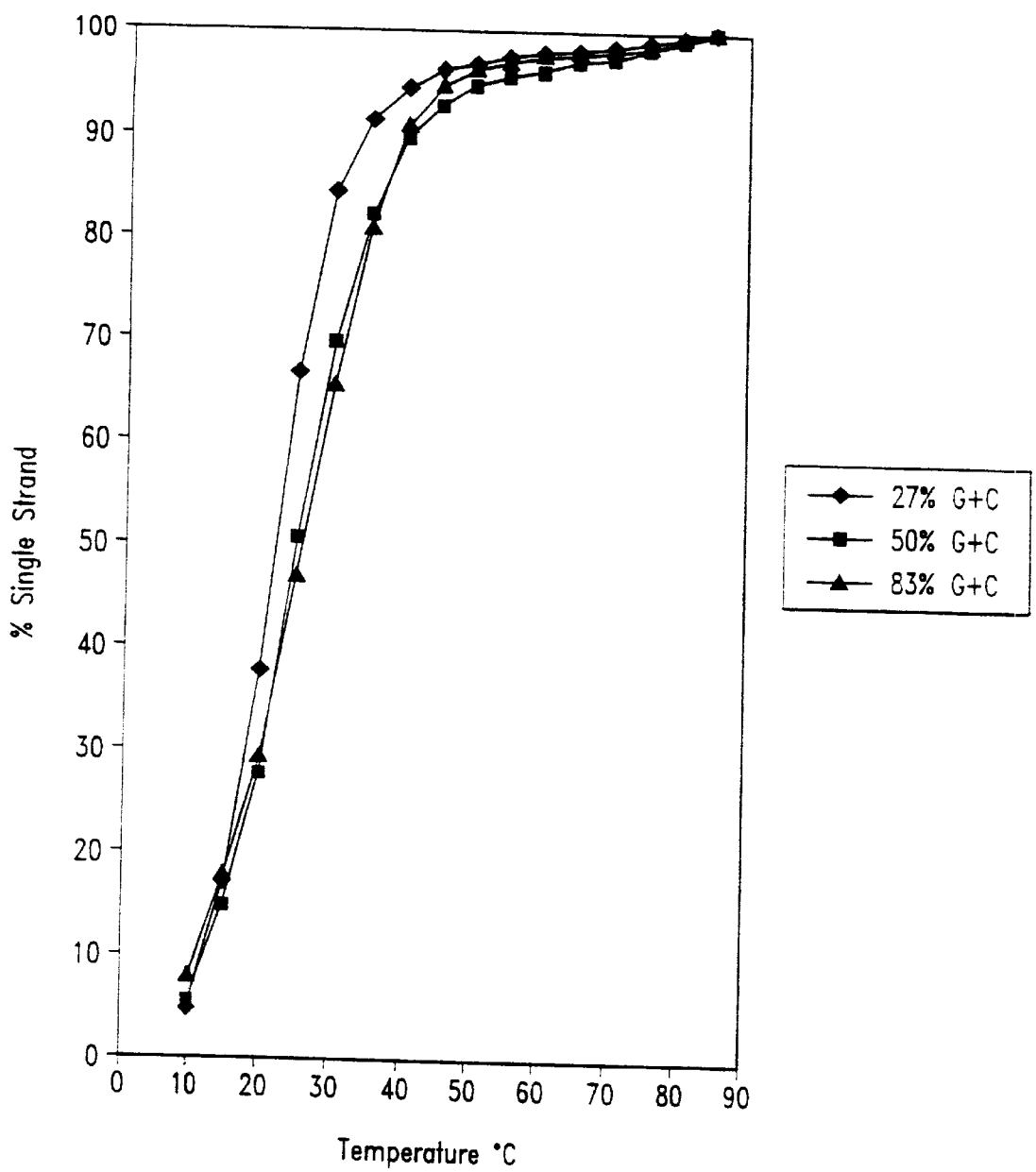
FIG. 20 is a graph showing the difference in $T_d$ between three duplexes, that vary in G+C content from 27% to 83%. The percentage of single strand DNA (y-axis) is plotted versus temperature (° C.; x-axis). The melting solution was 1 M dicyclohexylammonium acetate.

In contrast to the situation in FIGS. 17, 18 and 19, FIG. 20 shows the melting behavior of the 3 different G+C oligonucleotide duplexes in 1 M dicyclohexylamine acetate. FIG. 20 is a graph showing the difference in $T_d$ between three duplexes, that vary in G+C content from 27% to 83% (same duplexes as described in FIG. 14). The temperature difference between any two $T_d$s at $\alpha=0.5$ is defined as the $\Delta T_d$. The percentage of single strand DNA (y-axis) is plotted versus temperature (° C.; x-axis). The melting solution was 1 M dicyclohexylamine acetate. The maximum difference between the 3 melting curves in the $T_d$ or $T_m$ is 3° C. The helical coil transition of the 27% G+C content was 13° C., for the 50% G+C duplex was 17° C. and for the 83% G+C duplex was 19° C. This is an ideal profile for a hybotrope. In contrast the narrow helical coil transition observed in FIG. 20, a much wider HCT is observed with 500 mM n-ethylbutylamine acetate.

Figure 21:
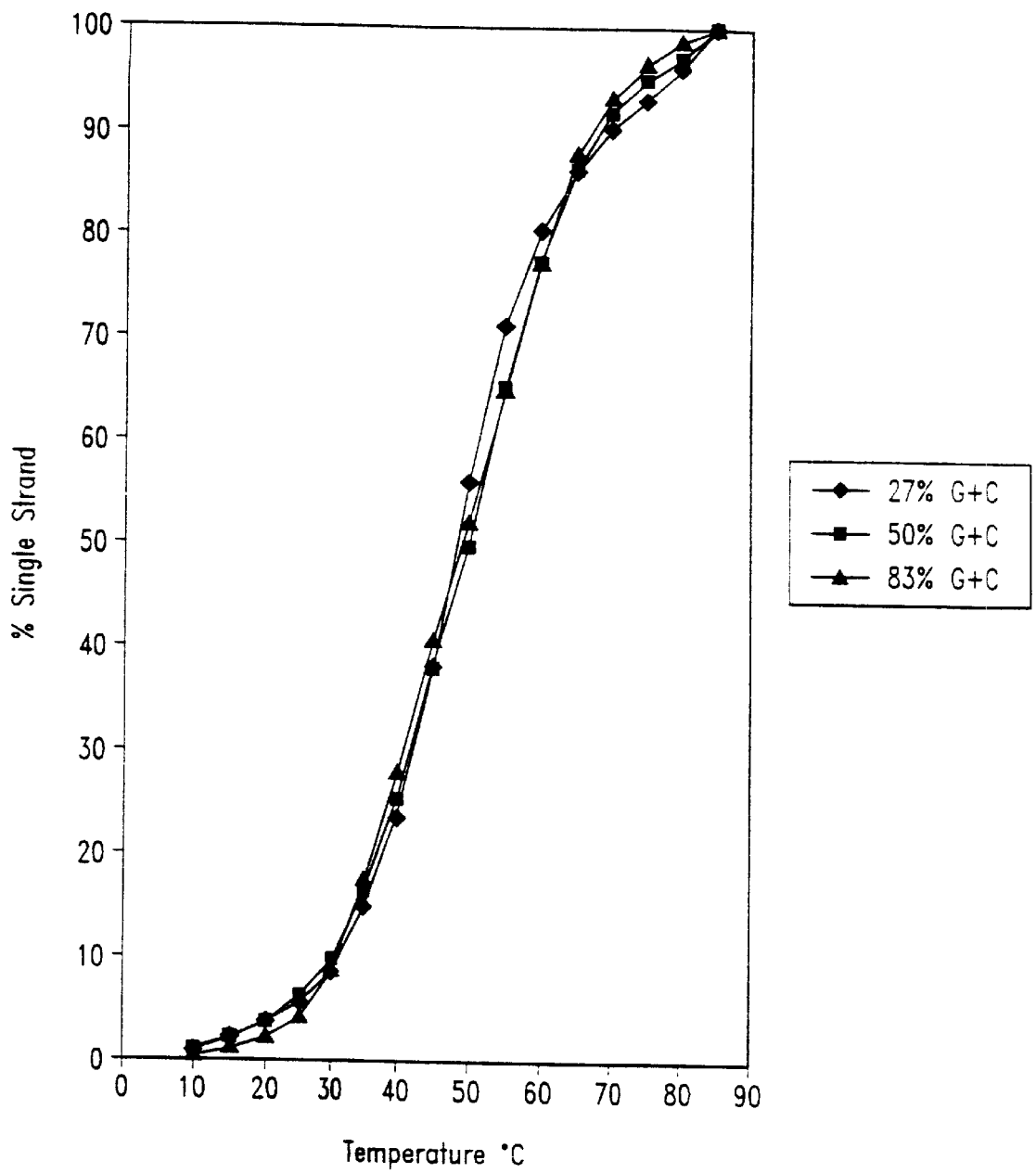
FIG. 21 is a graph showing the difference in $T_d$ between three duplexes, that vary in G+C content from 27% to 83%. The percentage of single strand DNA (y-axis) is plotted versus temperature (° C.; x-axis). The melting solution was 500 mM n-ethylbutylammmonium acetate.

FIG. 21 is a graph showing the difference in $T_d$ between three duplexes, that vary in G+C content from 27% to 83% (the identical duplex system as described in FIG. 14). The temperature difference between any two $T_d$s at $\alpha=0.5$ is defined as the $\Delta T_d$. The percentage of single strand DNA (y-axis) is plotted versus temperature (° C.; x-axis). The melting solution was 500 mM n-ethylbutylamine acetate. The maximum difference between the 3 melting curves in the $T_d$ is 1° C. The helical coil transition of the 27% G+C content was 22° C., for the 50% G+C duplex was 22° C. and for the 83% G+C duplex was 26° C.

Figure 22:
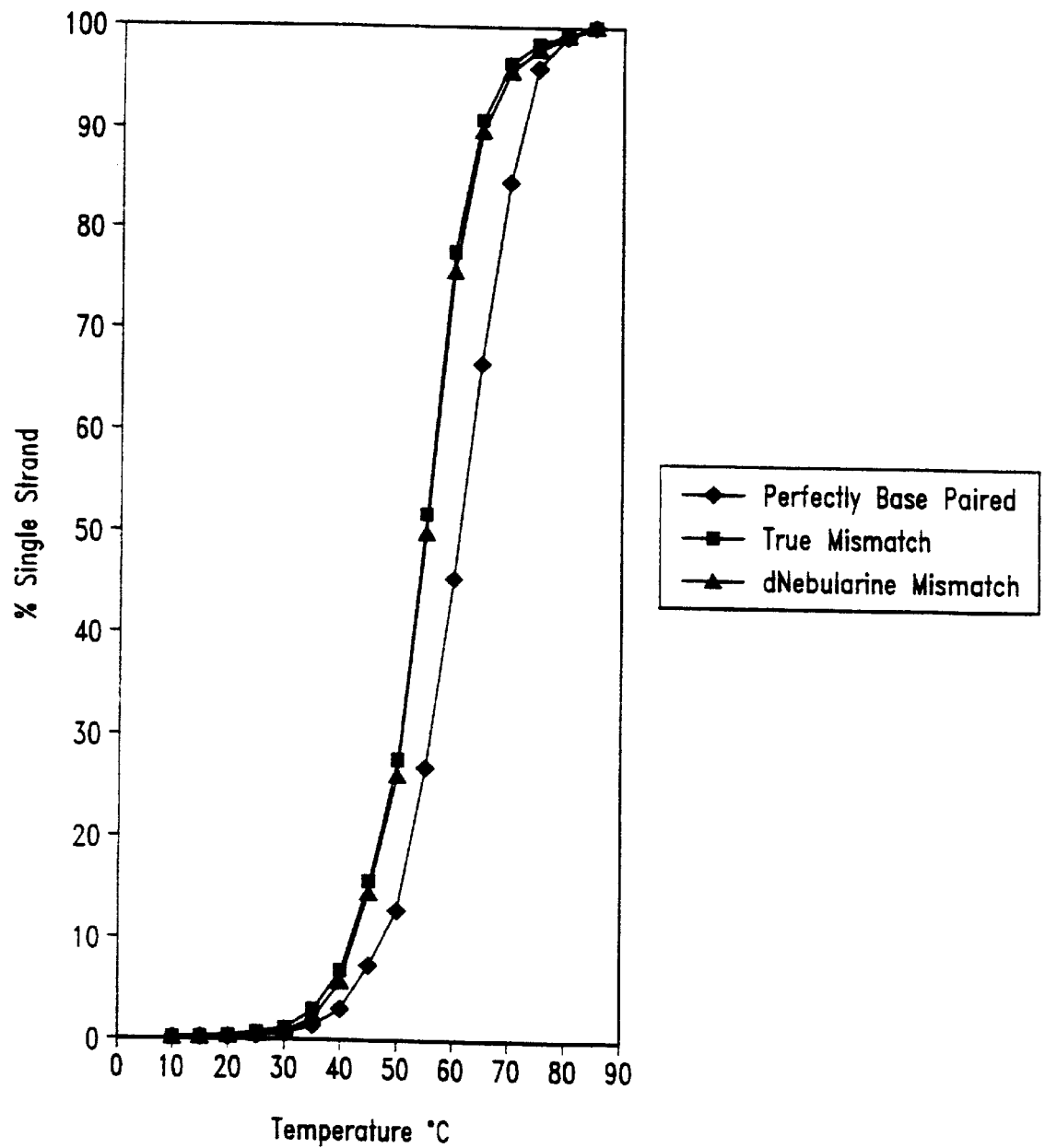
FIG. 22 is a graph showing the difference in $T_d$ between three duplexes, one that is perfectly based-paired and the other two that contains a mismatch or a deoxyNebularine substitution. The percentage of single strand DNA (y-axis) is plotted versus temperature (° C.; x-axis). DMO-2060: 5'-hexylamine-GTCATACTCCTGCTTGCTGATCCACATCTG-3' (oligonucleotide SEQ ID NO: 1; immobilized on the nylon bead.; DMO-2055: 5'-Texas Red-TGTGGATCAGCAAGCAGGAGTATG-3' (perfect complement SEQ ID NO: 2); DMO-2058; 5'-Texas Red-TGTGGATCAGGAAGCAGGAGTATG-3' (mismatch complement SEQ ID NO: 3); and DMO-2058-dN: 5'-Texas Red-TGTGGATCAG(deoxyNebularine)AAGCAGGAGTATG-3' (deoxyNebularine mismatch complement SEQ ID NO: 4). The melting solution was 1 M diisopropylamine acetate. The maximum difference between the 3 melting curves in the $T_d$ or $T_m$ is 6° C. The helical coil transition (HCT) of the true mismatch was 14° C.; the HCT for the deoxyNebularine mismatch duplex was 14° C. and the HCT for the perfectly based paired duplex was 16° C.

The ability of some of the G+C neutralizing buffer to act as hybotropes is illustrated in FIG. 22. FIG. 22 is a graph showing the difference in $T_d$ between three duplexes, one that is perfectly based-paired and the other two that contains a mismatch or a deoxynebularine substitution. The temperature difference between any two $T_d$s at $\alpha=0.5$ is defined as the $\Delta T_d$. The percentage of single strand DNA (y-axis) is plotted versus temperature (° C.; x-axis). DMO-2060: 5'-hexylamine-GTCATACTCCTGCTTGCTGATCCACATCTG-3' (oligonucleotide immobilized on the nylon bead. SEQ ID NO: 1); DMO-2055: 5'-Texas Red-TGTGGATCAGCAAGCAGGAGTATG-3' (perfect complement) SEQ ID NO: 2; DMO-2058; 5'-Texas Red-TGTGGATCAGGAAGCAGGAGTATG-3' (mismatch complement) SEQ ID NO: 3; and DMO-2058-dN: 5'-Texas Red-TGTGGATCAG(deoxynebularine)AAGCAGGAGTATG-3' (deoxynebularine mismatch complement). The melting solution was 1 M diisopropylamine acetate. The maximum difference between the 3 melting curves in the $T_d$ is 6° C. The helical coil transition (HCT) of the true mismatch was 14° C.; the HCT for the deoxyNebularine mismatch duplex was 14° C. and the HCT for the perfectly based paired duplex was 16° C. The same situation was observed for 1 M diisopropylamine acetate (FIG. 22), 1 M N,N-dimethylcyclohexylamine acetate (FIG. 23) and 1 M dicyclohexylamine acetate (FIG. 24) and N,N-dimethylhexylamine acetate (FIG. 25).

d. Effect of Hybotrope Concentration on Discrimination

As shown herein, the discrimination between mismatched oligonucleotides (mutant abbreviated as "mt") and perfectly based-paired oligonucleotides (abbreviated as "wt") is not a function of concentration of a particular hybotrope but rather a function of hybotrope type. Surprisingly, the HCT for the hybotropes LiTCA, GuSCN, GuHCl, and NaClO$_4$ does not change over about the range of about 0.5 M to about 6.0 M. Moreover, the slope of the mt duplex is always observed to be greater than for wt duplexes (see FIG. 9). Furthermore, the difference between the $T_m$ of the wt duplex and the mutant duplex ($\Delta T_d$) is not affected by the concentration of the hybotrope. However, the $T_d$ is directly related to concentration. Because $\Delta T_d$ does not change over a wide concentration range for the hybotropic solutions, a wide temperature range can be employed for conducting oligonucleotide-based assays (e.g., 20° C. to 80° C.). Second, relatively low concentrations (e.g., 0.5 M) of hybotrope may be employed in hybridization and enzymatic-based assays, including polymerase catalyzed reactions.

The approximate concentration range at which a solution of a compound (such as dimethylcyclohexylammonium acetate) exhibits the characteristics of a hybotropic solution is approximately 0.05 to 1.0 M.

e. Effect of Length of Duplex

The length of an oligonucleotide probe (i.e., resultant duplex) has the effect of increasing the $T_m$ as length increases. Due to this relationship, discrimination using a hybotrope is effectively limited to hybridization lengths of 4–40 bases and preferably 4–30 bases.

f. Assays for Determining if a Compound is Hybotropic

As discussed above, a hybotrope is a chemical that can increase the enthalpy of a nucleic acid duplex by 20% or more when referenced to a standard salt solution. A convenient assay for measuring this increased enthalpy is a thermal transition assay. A hybotrope may be identified as any chemical or any mixture of a chemical in an aqueous or organic environment with buffers, chelators, salts and/or detergents that can decrease the enthalpy of a nucleic acid duplex by 20% when referenced to a standard salt solution (0.165 M NaCl, 0.01 M Tris pH 7.2, 5 mM EDTA and 0.1% SDS) when the hybotrope is present in the environment within a molarity range of 0.1 M to 10 M. Although a hybotrope of the present invention may achieve the described effect on the enthalpy of a nucleic acid duplex, the present invention does not require that the hybotrope be present within a concentration range of 0.1 M to 10 M in the methods of the present invention. Indeed, lower hybotrope concentrations (i.e., lower than 0.1 M) may be advantageously employed in methods of the present invention. The reference oligonucleotide is 5'-GTCATACTCCTGCTTGCTGATCCACATCTG-3' (SEQ ID NO: 1) as the immobilized oligonucleotide and 5'-TGTGGATCAGCAAGCAGGAGTATG-3' (SEQ ID NO: 2) as the solution nucleotide which is typically labeled at the 5'-end with a fluorochrome such as Texas Red. The oligonucleotide duplex (24 nucleotides in length) has a helical to coil transition (HCT) of 25° C. or less." Moreover, a suitable hybotrope is soluble in water, other protic solvent or aprotic solvent. Although not required, a hybotrope preferably does not inactivate polymerases when in they are with polymerases and the like in PCR reactions (and the like). Assays for these properties are briefly discussed below.

HCT of an 18–24 mer with a 50% G+C content are readily measured for a given solution. Briefly, an 18–24 mer oligonucleotide and its complement with a 50% G+C are synthesized. The oligonucleotides are dissolved to 2 μM in the candidate hybotrope solution. The mixture is heated to 85° C. (at 0.5° C./min) and then cooled to 10–15° C. to allow hybridization. Absorbance versus time is recorded at 260 nm by a UV-VIS spectrophotometer equipped with a thermal programmer. The HCT is determined from a plot of normalized absorbance values (fully annealed=0% single strand; fully denatured=100% single strand) versus temperature. A solution in which the temperature difference between 80% and 20% single stranded (HCT) is $\leq 35°$ C. is a preferred hybotropic solution within the context of this invention.

HCT values may be determined in a high-throughput manner using nucleic acid molecules affixed to an array of pins. A plurality of pins arranged in an array are simultaneously submerged into a complementary plurality of solutions also arranged in the array and containing nucleic acid molecules which may hybridize to the nucleic acid molecules affixed to the pin. The pins are removed from the solutions, washed to remove unhybridized nucleic acid molecules, and then immersed into a series of increasing warm buffer solutions ("dehybridization solutions") each member of the series consisting of an array of solutions where none of the solutions contain nucleic acid. At some temperature, the nucleic acid molecule hybridized to a pin will melt away from the pin and into the dehybridization solution. The series of dehybridization solutions are analyzed for nucleic acid content, and this information allows a melting temperature for the hybridization at each pin to be determined.

Figure 27:
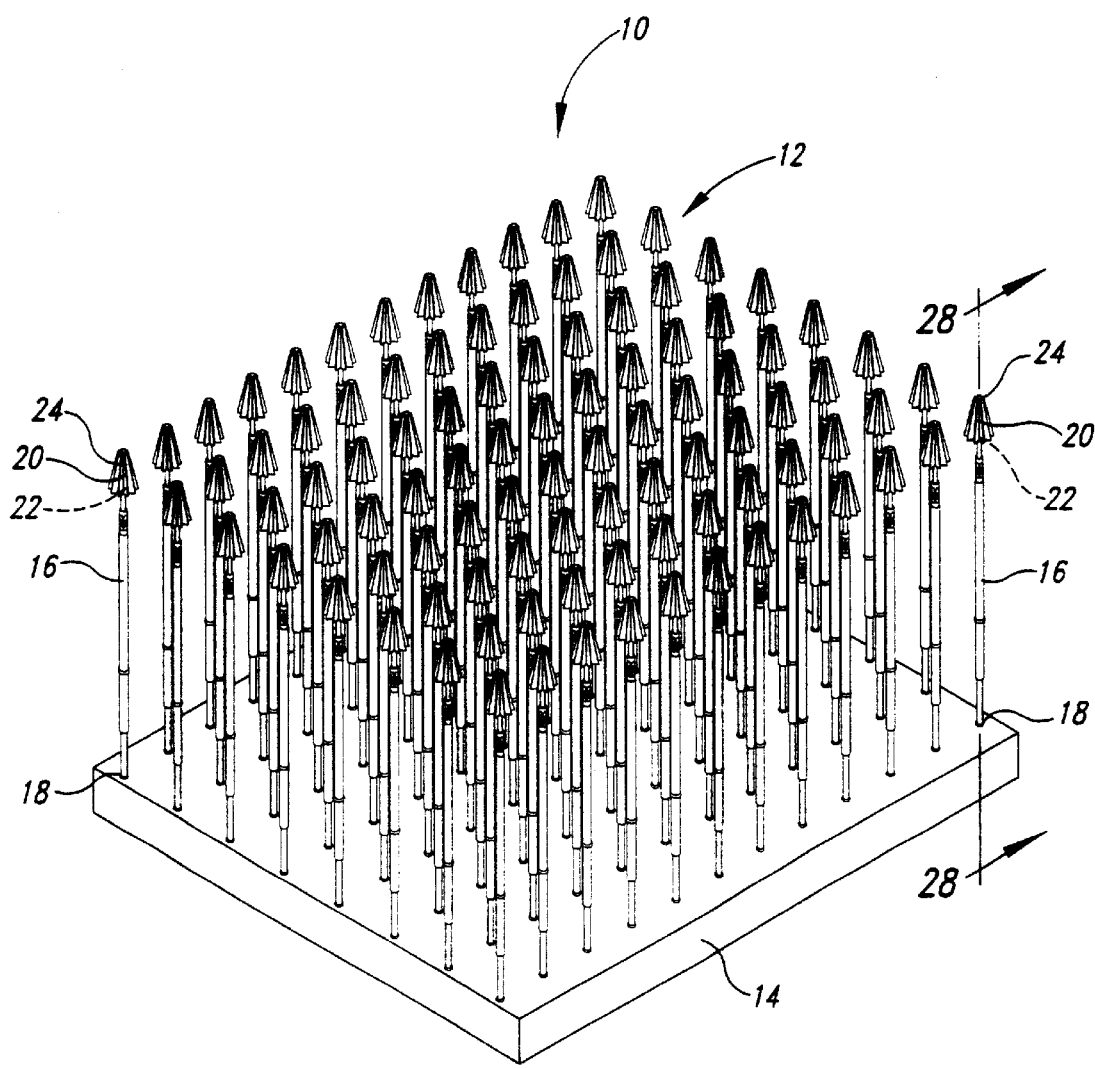
FIG. 27 is an isometric view of an array of solid-phase sample-retaining assemblies which may be used to perform thermodynamic measurements as described herein.

Such an array of pins is illustrated in FIGS. 27 through 32. An array 10 of solid-phase sample-retaining assemblies 12 is best seen in FIG. 27, where the array 10 includes a plurality of sample-retaining assemblies 12 attached to a base structure 14. Each sample-retaining assembly 12 includes a support pin 16 securely fixed at one end 18 to the base 14, and a sample-retaining tip structure 20 is attached to the other end 22 of the support pin 16. Each tip structure 20 in the exemplary embodiment is a Nylon 6/6 solid support structure, and the Nylon 6/6 is coated with a poly(ethyleneinine) (PEI) layer 24 or other selected chemical layer. The PEI layer 24 or other selected chemical layer is adapted to bind to a selected biomolecule to form a solid phase sample which may be used in making thermodynamic measurements, such as determining melting temperatures.

The array 10 includes, for example, eight substantially parallel rows of twelve sample-retaining assemblies 12 to define an array with ninety-six sample-retaining assemblies equally spaced along the base structure 14. Each sample-retaining assembly 12 has approximately the same length so the tip structures 20 are equally spaced from the base, thereby defining a substantially coplanar array of solid-phase sample-retaining tip structures. The tip structures 20 are spaced apart to mate with a conventional 96-well Cetus plate or microtiter plate that is adapted to receive and retain selected liquid samples of biomolecules or nucleic acids. While the exemplary embodiment has an 8×12 array of sample-retaining assemblies 12, alternate embodiments have other configurations, including a 1×8 array, a 1×12 array, and a 4×12 array.

In the exemplary embodiment, the ninety-six tip structures 20 are adapted to be dipped into the wells of the Cetus plate with the biomolecules therein such that the biomolecules chemically bind to the PEI layer 24. When the tip structures 20 are removed from the sample, the biomolecules are adhered to the PEI layer, thereby forming the solid-phase sample of the biomolecule. The tip structures 20 with the solid phase sample thereon can then be used in synthesizing or analyzing procedures, such as a solid-phase nucleic acid assay and detection process for measuring melting temperatures of duplex oligonucleotides.

The array 10 may be installed in a robotic or automatic actuator so the base 14 is clamped into the actuator and the sample-retaining assemblies 12 project away from the base. The actuator quickly and accurately moves the array 10 during automated testing to selected controlled positions or stations in accordance with a predetermined testing, synthesizing, or analyzing process. Such automated testing with the array 10 and the ninety-six solid phase samples allows for substantially faster testing, synthesizing, or analyzing procedures.

Figure 28A:
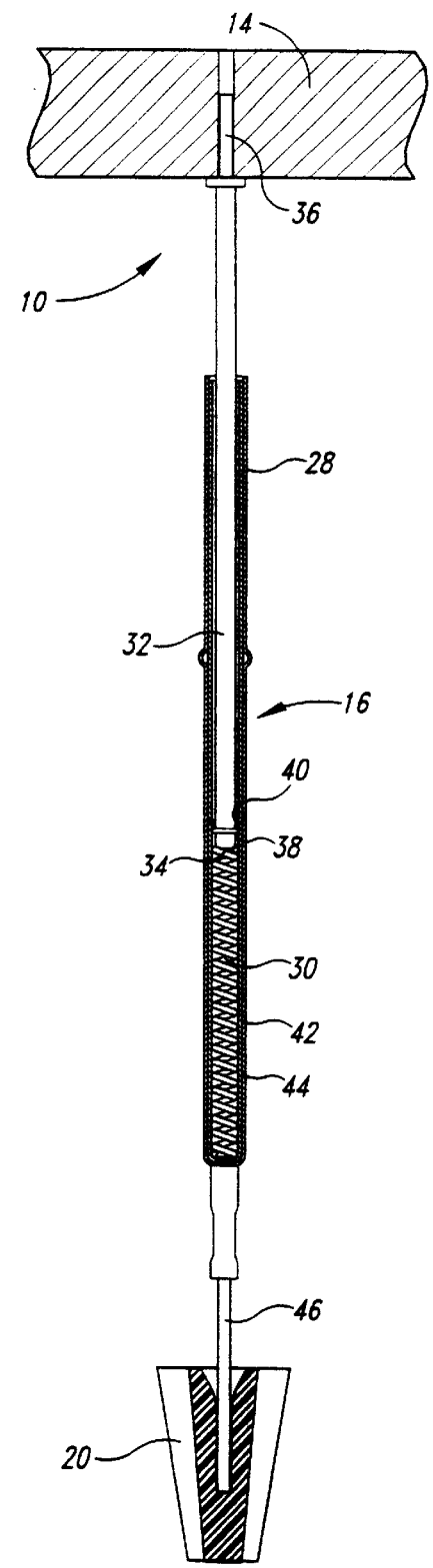
FIG. 28A is an enlarged cross-sectional view of a solid-phase sample-retaining assembly taken substantially along line 2—2 of FIG. 27.

The array 10 is well suited for such automated processing, in part, because of the support pins 16 of the sample-retaining assemblies 12. As best seen in FIG. 28A, each support pin 16 is a spring probe that is typically used for construction and testing of electronic components, but has been adapted for use in the present invention. The spring probe generally includes a housing 28 encasing a biasing member 30. A plunger 32 extends into the housing 28 so a first end 34 of the plunger is within the housing 28 adjacent to the biasing member and a second end 36 is exterior of the housing. The biasing member 30 in the exemplary embodiment is a compression spring that pushes axially against the plunger 32 toward the base 14. The plunger's first end 34 has a shoulder 38 that engages a stop 40 projecting radially inwardly from the housing 28 to limit the maximum extension of the plunger 32 with respect to the housing. The plunger's second end 36 is fixedly attached to the base 14, and the plunger 32 projects substantially perpendicularly away from the base.

In the exemplary embodiment, the housing 28 includes concentric inner and outer tubular barrels 42 and 44, wherein the biasing member 30 and the plunger's first end 34 are contained within the inner barrel. The outer barrel 44 removably receives the inner barrel 42 therein and frictionally engages the inner barrel such that the inner and outer barrels are removably attached to each other. The outer barrel 44 terminates at a distal end portion 46 that is spaced away from the base 14 and that connects to the tip structure 20. Accordingly, the housing's outer barrel 44 and the tip structure 20 are removable as a unit from the inner barrel 42 and plunger 32, which remain fixed to the base 14. Thus, an outer barrel 44 and tip structure 20 can be easily and quickly replaced as a unit without having to replace the entire spring probe. Suitable spring probes are available from Everett Charles (Pomona, Calif.), Interconnect Devices, Inc. (Kansas City, Kans.), Test Connections, Inc. (Upland, Calif.), and other manufacturers. While the exemplary embodiment utilizes spring probes as the support pins 16, other support pins, including biased or unbiased support pins, may also be employed.

Figure 28B:
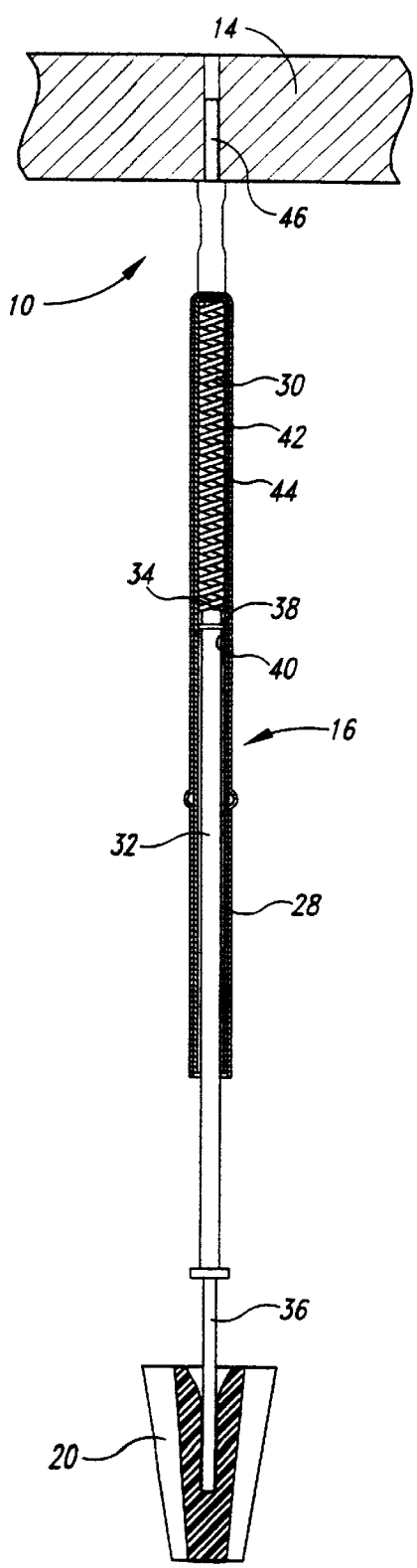
FIG. 28B is a cross-sectional view of a solid-phase sample-retaining assembly of an alternate embodiment.

As best seen in FIG. 28B, an alternate approach includes the spring probe as the support pin 16, but the spring probe is oriented 180° from the embodiment described above and illustrated in FIG. 28A. For example, the distal end portion 46 of the outer barrel 44 is fixedly attached to the base 14 and the second end 36 of the plunger 32 is spaced away from the base and connected to the tip structure 20. This spring probe configuration in the alternate embodiment is similar to the spring probe configuration described in co-pending U.S. Provisional Patent Application No. 60/053,435, entitled "Apparatus and Methods for Arraying Solution onto a Solid Support", which is hereby incorporated by reference in its entirety.

The spring probes provide a safety feature that protects the array 10 from being damaged during operation. During a sampling or analyzing process, for example, wherein the array 10 is moved to selected positions and the tip structures 20 are dipped into Cetus plate wells or the like, and if the support pins 16 or tip structures inadvertently impacts a surface or other object, the spring probe will compress axially to absorb the impact and then return to the uncompressed position.

Figure 29:
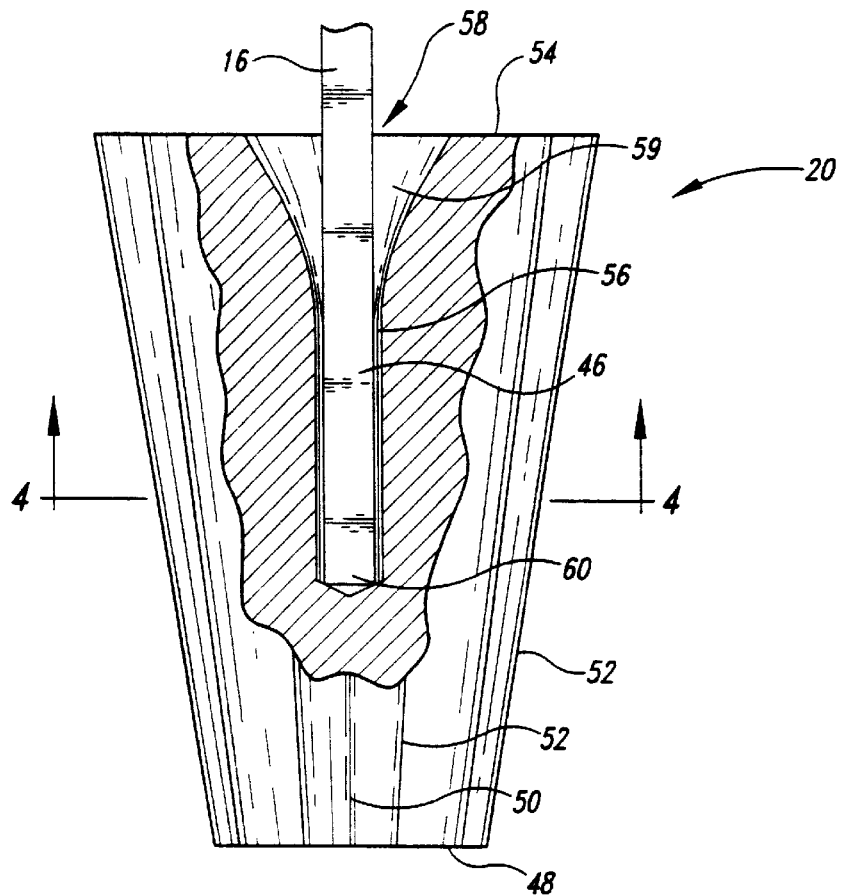
FIG. 29 is an enlarged partially cut away view of a tip structure of a sample-retaining assembly of FIG. 27.

As best seen in FIG. 29, the tip structure 20 of the exemplary embodiment has a truncated-conical shape with a plurality of channels or flutes 50 formed therein. The flutes 50 are V-shaped flutes that extend axially between a flat distal face 48 and a flat proximal face 54. The flutes 50 have veins or ridges 52 that converge from the proximal face 54 toward the distal face 48 at a selected angle. The truncated conical shape of the tip structure 20 is selected so it virtually identically matches the lower cross-sectional shape of a Cetus plate well. Accordingly, the tip structure 20 is shaped and sized to fit in a very precise position within the Cetus plate well.

The tip structure 20 includes a pin-receiving aperture 56 with an open proximal end 58 in the proximal face 54 and a closed distal end 60 at a mid-portion between the tip structure's proximal and distal faces 54 and 48, respectively. The pin-receiving aperture 56 is shaped and sized to removably receive the support pin's distal end portion 46. Accordingly, the tip structure 20 is removably connected to the support pin 16.

As shown in the Figures, the pin-receiving aperture 56 is coaxially aligned with the tip structure's longitudinal axis. The aperture's proximal portion 59 is generally funnel-shaped such that the aperture's open proximal end 58 has a larger diameter than the closed distal end 60. The funnel-shaped proximal portion 59 is adapted to receive the support pin's distal end portion 46 therein. In the event the support pin is slightly misaligned relative to the aperture 56 during an installation procedure, the funnel-shaped proximal portion 59 will receive and direct the support pin 16 into a position such that the spring probe is coaxially aligned with the tip structure 20.

Figure 30:
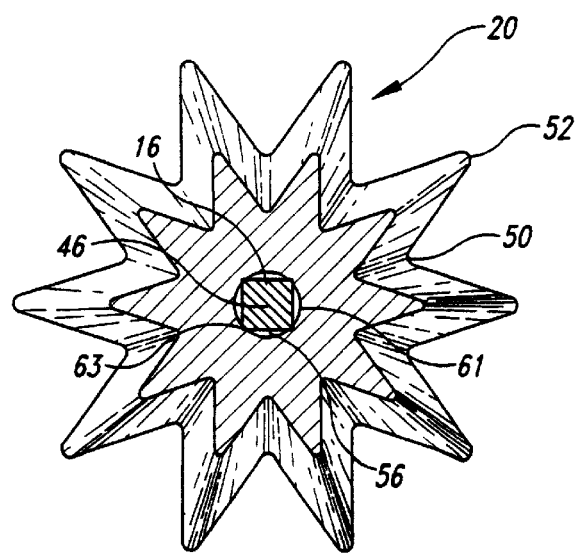
FIG. 30 is an enlarged cross-sectional view of the tip structure taken substantially along line 4—4 of FIG. 29.

As best seen in FIG. 30, the aperture 56 in is defined by an axial interior wall 61 of the tip structure 20 and has a substantially circular cross-sectional shape. The spring probe's distal end portion 46, however, has a substantially square cross-sectional shape with four corners 63. The spring probe's distal end portion 46 is sized such that the corners 63 frictionally engage the tip structure's interior wall 61 so as to frictionally retain the tip structure 20 on the support pin 16.

In an alternate approach, the end portion has a polygonal-shaped cross-sectional area with a plurality of corners that engage the tip structure's interior wall 61. As an example, an octagonal-shaped cross-sectional area having the eight corners that frictionally engage the interior wall 61. In another alternate approach, the support pin's distal end portion has a circular cross-sectional shape that substantially corresponds to the circular cross-sectional area of the pin-receiving aperture 56 such that the tip structure 20 is press-fit onto the spring probe's distal end portion 46 and is frictionally retained thereon. In another approach, the tip structure 20 is adhered to the distal end portion 46 with a conventional adhesive such that the tip structure is permanently affixed to the support pin 16.

As best seen in FIG. 30, the flutes 50 and ridges 52 define the truncated conical-shaped tip structure 20 with a generally star-shaped cross-sectional area. As a result, the tip structure 20 has an enlarged exterior surface 62 so a greater amount of biomolecules can attach to the PEI layer 24 during formation of the solid-phase sample. In the Figure, the flutes 50, ridges, distal face 48 and proximal face 54 of the tip structure 20 define a high-surface area, Nylon 6/6 solid support that is covalently bonded to the PEI layer 24. In alternate approaches, the tip structure 20 is made of a solid substrate, such as glass or silicon and the PEI layer 24 is covalently bound to the solid substrate using silylating chemistry.

In an alternate approach, the exterior surface 62 of the tip structure 20 along the flutes 50 and ridges 52 is dimpled so as to provide a further increased surface area along which the PEI layer 24 will bind. In one embodiment, the dimples are generally microscopic, and in an alternate embodiment, the dimples are macroscopic. Accordingly, the dimpled tip structure 20 provides a larger reaction surface for greater efficiency in the thermodynamic measurements.

During a typical thermodynamic measurement, the tip structure 20 is thermocycled, wherein the tip structure 20 is cycled between high and low temperatures. The ridges 52 of the tip structure 20 form a plurality of heat exchange fins 64 that allow for faster temperature change of the tip structure during the thermocycling. As a result, the thermocycling can be done faster and more efficiently.

Figure 31:
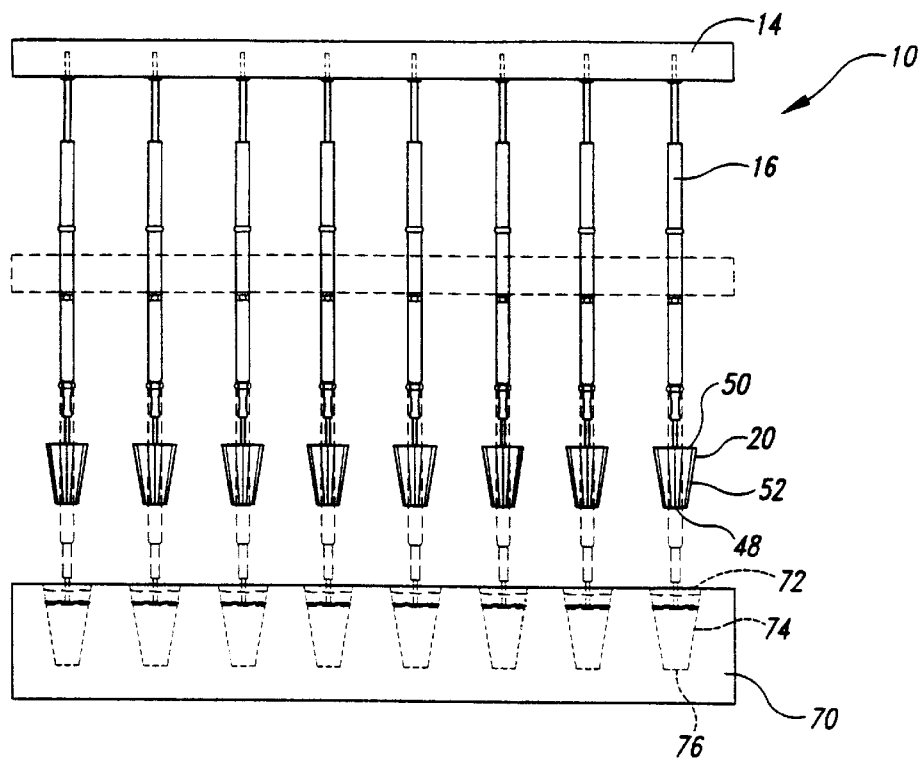
FIG. 31 is a side elevational view of the array of FIG. 27 shown in solid lines positioned above a microtiter plate with a plurality of wells with liquid biomolecule samples therein, and shown in phantom lines in lowered position with the tip structures positioned within the wells.

As best seen in FIG. 31, the array 10 is adapted to be combined and used with a Cetus or microtiter plate 70 having a plurality of wells 72 therein. As discussed above, the shape of a portion of the well 72 substantially matches the truncated conical shape of the tip structure 20. Accordingly, the ridges 52 substantially engage sidewalls 74 of the well 72 and the tip structure's flat distal face 48 is positioned against the bottom 76 of the well. In a preferred method, the microtiter plate 70 has an array of wells formed by eight substantially parallel rows of twelve wells 72 to form the ninety-six well configuration that mates with the tip structures of the array 10. In other embodiments, the microtiter plates 70 have arrays of 1×8 wells, 1×12 wells, and 4×12 wells.

During use of the array 10, the array can be automatically or manually moved from a raised position, shown in solid lines in FIG. 31 with the tip structures 20 being out of the wells 72, to a lowered position, shown in phantom lines with the tip structures being positioned within the wells 72. The wells 72, in one example, contain a liquid sample with the selected biomolecules therein. When the array 10 is in the lowered position and the tip structures 20 are in the liquid sample, the chemical reaction occurs between the PEI layer 24 and the biomolecule, so as to form the selected solid-phase sample of the biomolecule. In the exemplary embodiment, the well 72 has a depth that is approximately 33% larger than that of the tip structure 20, so when the tip structure is dunked into the well, the liquid sample flows over the entire tip structure to bind as much of the biomolecule as possible.

Figure 32:
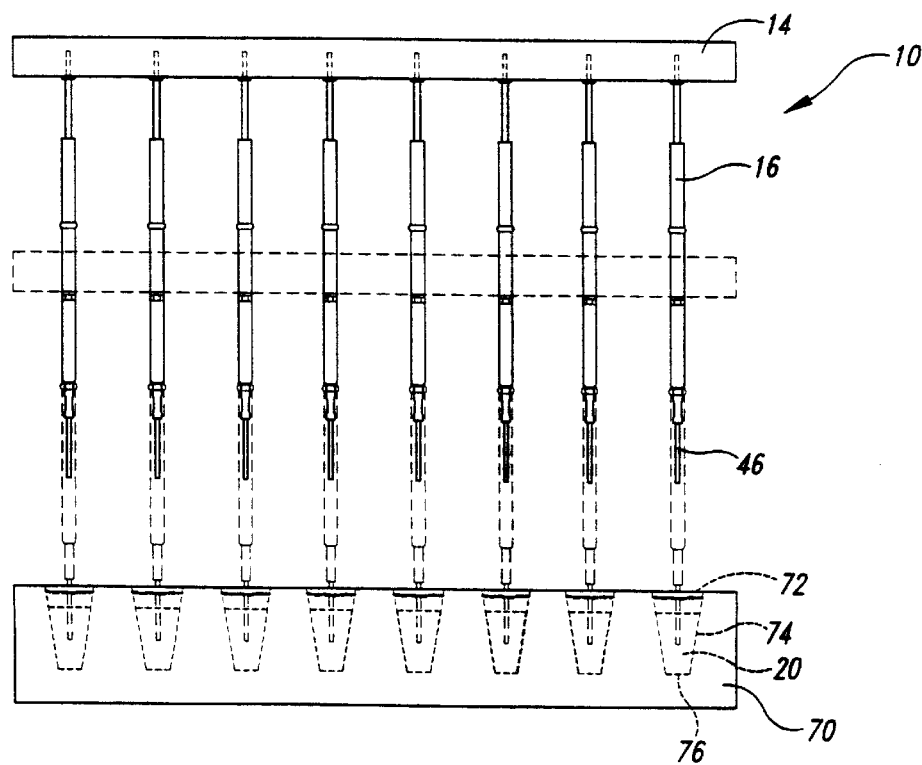
FIG. 32 is an enlarged side elevation view of the array of FIG. 27 shown with a plurality of the tip structure positioned in the wells of a microtiter plate.

As best seen in FIG. 32, the array 10 of sample-retaining assemblies 12 is also usable by positioning the tip structures 20 within the wells 72 and separating the tip structures from the support pins 16, as shown in solid lines, so the tip structures remain in the wells. The base 14 and support pins 16 are then moved as a unit away from the microtiter plate 70. As a result, the microtiter plate 70 with the ninety-six tip structures 20 retained or stored within the wells 72 can be moved as a unit and, as an example, placed in cold storage or other suitable storage locations until the solid-phase samples are needed for a selected synthesizing or analyzing procedure, such as a thermodynamic measurement.

In the illustrated embodiment, the wells 72 retain the tip structures 20 in a very precise location relative to the microtiter plate 70 so the tip structures can be easily and substantially simultaneously installed onto the support pins 16. As an example, the microtiter plate 70 is held in a known and fixed location, and the base 14 and support pins 16 are moved as a unit, either automatically or manually to a selected position above the wells 72 such that the support pins substantially coaxially align with the pin-receiving aperture 56 in the tip structures. The base 14 and support pins 16 are then moved toward the microtiter plate 70 such that the support pins 16 are pressed into the apertures in the tip structures, thereby releasably connecting the tip structures to the support pins. The base 14, support pins 16, and tip structures 20 are then moved as a unit away from the microtiter plate 70, thereby removing the tip structures 20 from the wells 72. The sample-retaining tip assemblies 12 with solid phase samples thereon can be moved to a predetermined location and subjected to selected solid-phase procedures for analyzing or synthesizing a nucleic acid.

The solid supports as described herein can be used in parallel and are preferentially configured in a 96-well or 384-well format. The solid supports can be attached to pegs, stems, or rods in a 96-well or 384-well configuration, the solid supports either being detachable or alternatively integral to the particular configuration. The particular configuration of the sold supports is not of critical importance to the functioning of the assay, but rather, affects the ease of adapting the assays to automated systems.

B. Specificity Spacers

The invention provides an oligonucleotide comprising a plurality of fragments, each fragment shown schematically by structure (1)

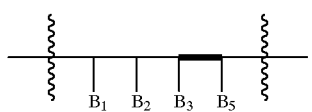

(1)

wherein,

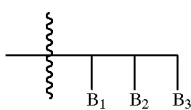

represents a sequence of at least three nucleotides as found in wild-type DNA, where "B" represents a base independently selected at each location;—— represents a series of covalent chemical bonds termed a "specificity spacer," which separates and connects two bases $B_3$ $_{and\ B5}$;

the specificity spacer having steric and chemical properties such that (a) it does not disrupt the Watson-Crick hydrogen bonding that occurs between adjacent bases B in an oligonucleotide incorporating a fragment of structure (1) and an oligonucleotide fragment having a complementary base sequence, as shown schematically as structure (2)

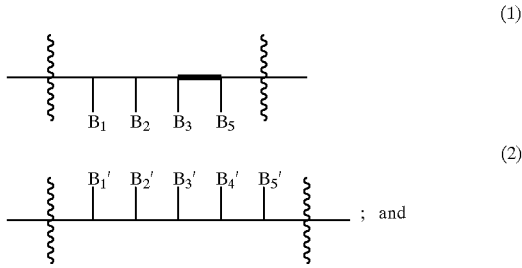

; and and (b) it cannot enter into hydrogen bonding with a base positioned opposite itself in a hybridized complementary base sequence of structure (2).

While the specificity spacer does not have any of an adenine, guanine, cytosine, uracil or thymine in a position which can form Watson-Crick hydrogen bonds with a base in a complementary position of a hybridized oligonucleotide, the specificity may or may not have an analog to one of an adenine, guanine, cytosine, uracil or thymine base such that a polymerase will read through the analog and continue transcription. When the specificity spacer contains such a base analog bonded through a ribose sugar, the spacer will be referred to herein as having a base analog residue. An "abasic residue" as used herein does not have such a base analog, and thus the presence of an "abasic residue" in an oligonucleotide will stop polymerase transcription.

The specificity spacer may have the structure (3)

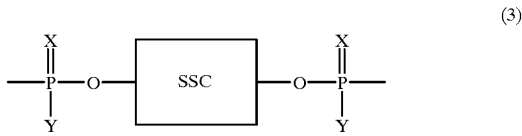

(3)

wherein X is sulfur (S) or oxygen (O); Y is selected from oxygen, sulfur, methyl and amino when X is oxygen, or Y is selected from oxygen and sulfur when X is sulfur; and SSC represents a specificity spacer component having a chain of 2–5 carbons shown in the structure (4)

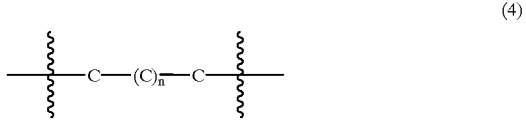

(4)

wherein n is 0, 1, 2 or 3, and each of the shown 2–5 carbons of the specificity spacer component may be independently substituted with $C_1$–$C_{10}$-hydrocarbyl or $C_1$–$C_{10}$ hydrocarbyloxy, and any two of the shown 2–5 carbon atoms which are bonded directly to one another may form a carbocyclic or heterocyclic 5–6 membered ring. If the specificity spacer component (SSC) contains a base analog that can be read by a polymerase attached through a ribose or deoxyribose, then the specificity spacer provides a base analog residue. However, if the SSC does not contain a base analog that can be read by a polymerase, then the specificity spacer provides an abasic residue.

A preferred specificity spacer component has the structure (5)

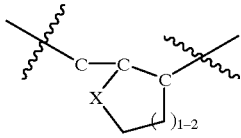
(5)

wherein n is 1 and X is selected from carbon, oxygen and sulfur, such that any carbon shown in the structure (5), including X when it is carbon, may be substituted with hydrogen, $C_1$–$C_5$hydrocarbyl, $C_1$–$C_5$hydrocarbyloxy, a non-hydrogen bonding purine base analog or a non-hydrogen bonding pyrimidine base analog. When the structure (5) contains a non-hydrogen bonding purine base analog or a non-hydrogen bonding pyrimidine base analog, then the specificity spacer provides a base analog residue.

Another preferred specificity spacer component has the structure (6)

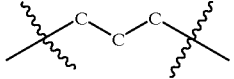
(6)

wherein each of the three shown carbons may be substituted with hydrogen, $C_1$–$C_{10}$hydrocarbyl or $C_1$–$C_{10}$hydrocarbyloxy. This, this specificity spacer provides an abasic residue.

Preferred compositions of the invention have, and preferred methods of the invention employ, oligonucleotide having a plurality of specificity spacers. No two specificity spacers should be adjacent to one another. In fact, it is preferred that all nearest specificity spacers are separated by 4–14 nucleotides having a wild-type sequence. That is, at least 4 wild-type (also referred to as "native") nucleotides (AMP, GMP, CMP, UMP, dAMP, dGMP, dCMP, dTMP) are preferably situated between any two specificity spacers. Furthermore, it is also preferred that when a plurality of specificity spacers are present in an oligonucleotide, there are no more than about 14 wild-type nucleotides separating any two closest specificity spacers. In one embodiment of the invention, all nearest specificity spacers in the oligonucleotide are separated by 5–6 wild-type nucleotides. In another embodiment, all nearest specificity spacers are separated by 8–12 wild-type nucleotides.

It is preferred that specificity spacers constitute 15–60% of the total positions occupied by the specificity spacers and the nucleotides having a wild-type sequence which constitute the oligonucleotide. When the oligonucleotide contains less than about 15% specificity spacer, then the desirable effects of specificity spacers on HCT is less apparent. When the oligonucleotide contains more than about 60% specificity spacer, then there are not enough positions devoted to wild-type nucleotides to provide meaningful information.

A preferred specificity spacer is deoxyNebularine, which has essentially the same size and shape features of a wild-type nucleotide (i.e., AMP, GMP, CMP, UMP, dAMP, dGMP, dCMP or dTMP) however does not enter into the standard Watson-Crick hydrogen bonding with any of adenine, guanine, cytosine, uracil or thymine. Another example is the difluorotoluene nucleoside described in Moran, S. et al. *J.A.C.S.* 119, 2056–2057 (1997) which codes for adenine in DNA replication with a polymerase enzyme, however does form paired complexes with any wild-type nucleotide. Such base-isosteres of wild-type nucleotides provide base analog residues in a nucleic acid molecule of compositions of the invention.

As described herein, an increase in specificity of priming or probing when using synthetic oligonucleotides is accomplished by minimizing the helical coil transition of the respective primer duplex, thereby increasing the stringency factor of the respective sequence. An increased stringency factor of an oligonucleotide decreases the stability of a mismatch and therefore promotes a high fidelity hybridization. Furthermore, increasing the stringency factor or decreasing HCT may also result in an increase in the specificity of priming. One way to increase stringency is to introduce one or more abasic residues or base analog residues (e.g., deoxynebularine residues) into one strand of a duplex. Thus, introducing one of these abasic residues or base analog residues (collectively "residues") leads to a "base pair" that is not strongly hydrogen bonded. In effect, this is analogous to a mismatch and will decrease the $T_d$ and HCT of the respective derived oligonucleotide compared to a perfectly base-paired oligonucleotide that has the same sequence. Although, for the sake of simplicity, the oligonucleotides in the examples below incorporate only one type of these residues (abasic residues or base analog residues) at a time, combinations such as an abasic residue and base analog residue may be utilized.

As noted above, an abasic residue is a molecular fragment that approximates the length of a ribofuranose sugar, is covalently attached to neighboring bases and is not substituted at the beta anomeric carbon with a group that interacts (ie., hydrogen bonds) with the base on the opposite strand of a duplex. Abasic residues in oligonucleotides can be introduced by the chemical or enzymatic hydrolysis of the glycosidic bond. The resulting structure is apurinic or apyrimidinic, lacks coding information, and fails to base pair. Precursors to abasic residues may be obtained commercially. For example, the CE phosphoramidite of the tetrahydrofuran derivative is commercially available as dSPACER™ Glenn Research, Sterling, Va.) as are other "spacer" phosphoramidites (Glenn Research, Sterling, Va.). Alternatively, an specificity spacer may comprise a backbone of N-(2-aminoethyl)-glycine linked by amide bonds. Unlike native DNA or RNA backbone, this specificity spacer has no deoxyribose or phosphate groups.

The typical placement of the specificity spacer site (e.g., abasic residue site or base analog residue site) is approximately in the middle of the oligonucleotide. A typical primer has the following configuration: 5'-$N_{10}$-spacer-$N_{10}$-3'. However, multiple specificity spacer sites may be placed in the oligonucleotide(s) at regular or irregular intervals, depending on the value of HCT to be achieved. Generally, a primer ranges in length from 6 to 40 or from 16 to 30 nucleotides (nt) in length and may contain from 1 to 5 specificity spacer sites. Thus, specificity spacer sites can be incorporated at a spacing of 3, 4, 5, 6, or 8 nucleotides or incorporated in any combination of nucleotides (or analogues) that base-pair with specificity spacer sites. For example, a 6-mer may have one 1 specificity spacer site, an 18-mer, 2 specificity spacer sites, a 24-mer has 3 sites, etc.

As a general guideline, when an oligonucleotide is used to detect a mutation, the specificity spacer site is preferably not located at the site of the mutation. However, specificity spacer sites may be placed at the site of mutations that are not of interest (e.g., a polymorphism that does not result in a phenotype).

As shown in Table 4 A, introduction of an abasic residue into 5'-hexylamine-TGTGGATCAGCA-spacer-GCAGGAGTATG-3' (SEQ ID NO: 9), wherein the spacer is either the C3-spacerTmor dSPACER™ from Glenn Research (Sterling, Va., where these two chemicals have the same effect but are chemically distinct), lowers the HCT from 2.5° C. to 6° C. compared to a normal oligonucleotide, depending on the solution used.

TABLE 4A

| Buffer Type Factor | Oligo Type | HCT (° C.) | $T_d$ (° C.) | Stringency factor |
|---|---|---|---|---|
| 1X PCR buffer | normal | 18 | 65 | na |
| 1X PCR buffer | deoxynebularine | 12 | 58 | na |
| 0.5 M EP | normal | 28 | 68 | na |
| 0.5 M EP | deoxynebularine | 20 | 60 | na |
| 1X PCR buffer | normal | 18 | | |
| 1X PCR buffer | abasic (dSPACER) | 12 | | |
| 1X PCR buffer | abasic (C3 spacer) | 12 | | |
| 0.5 M TMATCA | normal | 14 | | |
| 0.5 M TMATCA | abasic (dSPACER) | 8 | | |
| 0.5 M TMATCA | abasic (C3 spacer) | 8 | | |
| 2.0 M LiTCA | normal | 12.5 | 44.5 | 4.97 |
| 2.0 M LiTCA | abasic (dSPACER) | 10 | 39 | 6.37 |
| 2.0 M LiTCA | abasic (C3 spacer) | 10 | 39 | 6.25 |
| 3.0 M GuSCN | normal | 16 | 35.5 | 3.85 |
| 3.0 M GuSCN | abasic (dSPACER) | 12.5 | 32 | 5.24 |
| 3.0 M GuSCN | abasic (C3 spacer) | 12.5 | 31 | 5.31 |

Base analogs, which likewise are incorporated into an oligonucleotide and maintain essentially the "natural" separation between adjacent nucleotides, have a moiety with approximately the same spatial requirements of a G, C, A, or T base. However, this moiety cannot hydrogen bond to a complementary strand, but provides sufficient structural similarity to a native purine or pyrimidine base that a polymerase will read through it and continue preparing a complementary strand. An example of such a base analog is deoxyNebularine (dN). The base analog can also be used to increase the enthalpy of an oligonucleotide duplex. Preferably, the base analog replaces a G, C, or T base in a probe or primer. Multiple base analog sites may be placed in the oligonucleotide(s) at regular or irregular intervals, depending on the value of HCT to be achieved. Generally, a primer ranges in length from 6 to 40, preferably from 16 to 30 bases and contains from 1 to 5 base analog sites. A typical primer has the following configuration: 5'-$N_{10}$-base analog-$N_{10}$-3'. As shown in Table 4B, introduction of a deoxyNebularine residue into 5'-hexylamine-TGTGGATCAGCA-dN-GCAGGAGTATG-3'(SEQ ID NO: 9) lowers the HCT from 2.5° C. to 6° C., depending on the hybridization solution or hybotrope used.

TABLE 4B

| Buffer Type | Oligo Type | HCT* | $T_d$* | Stringency Factor |
|---|---|---|---|---|
| 1X PCR buffer | normal | 18 | | |
| 1X PCR buffer | deoxyNebularine | 12 | | |
| 1X PCR buffer | deoxyNebularine | 12 | | |
| 0.5 M TMATCA | normal | 14 | | |
| 0.5 M TMATCA | deoxyNebularine | 8 | | |

TABLE 4B-continued

| Buffer Type | Oligo Type | HCT* | $T_d$* | Stringency Factor |
|---|---|---|---|---|
| 0.5 M TMATCA | deoxyNebularine | 8 | | |
| 2.0 M LiTCA | normal | 12 | 44 | 5.0 |
| 2.0 M LiTCA | deoxyNebularine | 10 | 39 | 6.3 |
| 2.0 M LiTCA | deoxyNebularine | 10 | 39 | 6.3 |
| 3.0 M GuSCN | normal | 16 | 35 | 3.9 |
| 3.0 M GuSCN | deoxyNebularine | 12.5 | 32 | 5.2 |
| 3.0 M GuSCN | deoxyNebularine | 12.5 | 31 | 5.3 |

*= ° C.

C. Methods of Using Hybotropes and Nucleic Acid Molecules Containing SPECIFICITY SPACERS.

1. Molecule of Interest (MOI)

Examples of MOIs include nucleic acids or nucleic acid analogues (e.g., PNA), fragments of nucleic acids (i.e., nucleic acid fragments), synthetic nucleic acids or fragments, oligonucleotides (e.g., DNA or RNA), proteins, peptides, antibodies or antibody fragments, receptors, receptor ligands, members of a ligand pair, cytokines, hormones, oligosaccharides, synthetic organic molecules, drugs, and combinations thereof.

Preferred MOIs include nucleic acid fragments. Preferred nucleic acid fragments are primer sequences that are complementary to sequences present in vectors, where the vectors are used for base sequencing. Preferably a nucleic acid fragment is attached directly or indirectly to a tag at other than the 3' end of the fragment; and most preferably at the 5' end of the fragment. Nucleic acid fragments may be purchased or prepared based upon genetic databases (e.g., Dib et al., Nature 380:152–154, 1996 and CEPH Genotype Database, http://www.cephb.fr) and commercial vendors (e.g., Promega, Madison, Wis.).

As used herein, MOI includes derivatives of an MOI that contain functionality useful in joining the MOI to a T-L-$L_h$ compound. For example, a nucleic acid fragment that has a phosphodiester at the 5' end, where the phosphodiester is also bonded to an alkyleneamine, is an MOI. Such an MOI is described in, e.g., U.S. Pat. No. 4,762,779 that is incorporated herein by reference. A nucleic acid fragment with an internal modification is also an MOI. An exemplary internal modification of a nucleic acid fragment is where the base (e.g., adenine, guanine, cytosine, thymidine, uracil) has been modified to add a reactive functional group. Such internally modified nucleic acid fragments are commercially available from, e.g., Glen Research, Herndon, Va. Another exemplary internal modification of a nucleic acid fragment is where an deoxynebularine phosphoramidate is used to synthesize a modified phosphodiester that is interposed between a sugar and phosphate group of a nucleic acid fragment. The deoxynebularine phosphoramidate contains a reactive group that allows a nucleic acid fragment that contains this phosphoramidate-derived moiety to be joined to another moiety, e.g., a T-L-$L_h$ compound. Such deoxynebularine phosphoramidates are commercially available from, e.g., Clonetech Laboratories, Inc., Palo Alto, Calif.

As noted herein, a hybotrope, an oligonucleotide containing one or more specificity spacers, an oligonucleotide containing one or more abasic residues, an oligonucleotide containing one or more base analog residues, or combinations thereof, may be used in essentially any reaction involving hybridization of a duplex in which the annealed region is from about 6 to about 40 base pairs long. Such reactions include screening for one or few base changes (e.g., genetic screen), DNA sequence analysis by random oligonucleotide hybridization, amplification reactions, RTase mediated polymerization, such as for synthesis of cDNA, differential amplification, and the like.

As used herein, a "discrimination temperature" is a temperature at which a hybridization reaction is performed that allows discrimination between a mismatched duplex and a perfectly matched duplex. As shown herein, a range of temperatures satisfy criteria of a discrimination temperature. The discrimination temperature ranges from the temperature at which an α value (fraction of single stranded nucleic acid) is 0.2 for a given oligonucleotide duplex (or nucleic acid duplex) containing a mismatch at any place in the duplex, to the temperature at which a value for α equals 0.8 for the same given oligonucleotide duplex (or nucleic acid duplex), but which does not contain a mismatch at any place in the duplex. An α value is the fraction of single stranded nucleic acid at any given temperature generated during the thermal transition of a DNA strand from a double-stranded to a single stranded form. In determining α, the mismatch can be due to any type of modified nucleotide, nucleoside, or derivative thereof. A discrimination temperature is applicable to any given duplex 6 nt to 250 nt in length, of any given G+C content, containing modified or substituted nucleotides or nucleosides, and in which the duplex is composed of deoxyribonucleotides, ribonucleotides, or mixtures of different types of strands. As an example, for an oligonucleotide duplex of 18 nucleotides in length, the critical discrimination temperature (range) is from 10 to 15° C. The lowest temperature of the discrimination temperature range will depend at least in part on the concentration and type of hybotrope used or abasic residue-containing or base analog-containing oligonucleotide, and can range from 0 to 80° C., preferably from 20 to 50° C.

2. Amplification Based Assays a. AFLP (Amplified Fragment Length Polymorphism)

Genomic DNA is digested with restriction endonucleases (e.g. EcoR I and Mse I). Adaptors (e.g. EcoR I and Mse I) are ligated to the restricted DNA. PCR is performed using degenerate primers that are complementary to the adaptors and contain 2–3 nucleotides (chosen at random) at the 3' end. Only primers that anneal to the adaptors and complement 2–3 nucleotides of the target genomic DNA will yield product. Consequently a subset of the fragments is amplified and can be separated by gel electrophoresis to generate a "fingerprint" of the genomic DNA. (Valsangiacomo, C. et al., *J. Clin. Microbiol.* 33:1716, 1995).

b. Alu-PCR

Amplification using primers specific for human Alu repeat elements. (Nelson, D. L. et al., *Proc. Natl. Acad. Sci. USA* 86:6686, 1989.)

c. AMP-FLP (Amplified Fragment Length Polymorphism)

PCR amplification of variable number tandem repeat (VNTR) loci. The PCR product size is highly variable among individuals and can be used in forensics and paternity analysis. Amplified products are separated by polyacrylamide gel electrophoresis and detected by silver staining or fluorescence. (Budowle, B. et al., *Am. J. Hum. Genet.* 48:137,1991.)

d. A-PCR (Anchor Polymerase Chain Reaction)

Anchor sequences serve as a substitute for unknown sequence in a PCR reaction. For example, first strand cDNA can be tailed with dGTP and terminal transferase. Second strand cDNA is primed with oligo(dC). Subsequent amplification is then performed with oligo(dC) and the gene specific primer used for first strand cDNA synthesis. (Loh, E. Y. et al., *Science* 243:217, 1989.)

e. AP-PCR (Arbitrarily Primed Polymerase Chain Reaction)

Methods for creating genomic fingerprints from samples for which little is known about the target sequence to be amplified. Performing the first few PCR cycles at low stringency using short arbitrary oligonucleotides (typically 10–20 bp) generates strain-specific arrays of DNA fragments (fingerprints). After completion of these early cycles, some of the PCR products will have ends complementary to the primers. The PCR cycles are then completed at higher stringency. DNA amplified in this manner can be used to determine the relatedness of species or for analysis of Restriction Fragment Length Polymorphisms (RFLPs). (Welsh, J. and McClelland, M., *Nucl. Acids Res.* 18:7213, 1990.)

f. aRNA (Antisense RNA)

RNA amplification system that avoids the bias commonly observed with PCR amplification. First strand cDNA synthesis of the RNA preparation is primed with oligo(dT) containing a T7 RNA promoter sequence at the 5' end. Second strand cDNA synthesis is catalyzed with *E. coli* DNA Polymerase I and RNase H. The resulting double stranded cDNA is treated with T4 DNA Polymerase to generate blunt ends. Amplified antisense RNA (aRNA) is synthesized with T7 RNA Polymerase. (Van-Gelder, R. N. et al., *Proc. Natl. Acad. Sci. USA* 87:1663, 1990.)

g. ASPCR (Allele-Specific Polymerase Chain Reaction)

Mutation detection using ASO primers (Allele-Specific Oligonucleotide) in a PCR reaction. PCR product is only generated if there is no mismatch between the primers and target sequence of interest. (Saiki, R. K. et al., *Nature* (London) 324:163, 1986; Wu, D. Y. et al., *Proc. Natl. Acad. Sci. USA* 86:2757, 1989.)

h. ASRA (Allele Specific Restriction Assay)

Amplification of genomic DNA using primers that introduce a restriction recognition sequence in normal alleles, but not in mutant alleles. (Todd, A. V. et al., *Am. J. Hematol.* 38:207, 1991.)

i. Asymmetric PCR

Technique for generating predominately single stranded DNA using PCR amplification. The reaction is performed with one of the amplification primers present in a 100-fold molar excess. (Gyllensten, U. B. and Erlich, H. A., *Proc. Natl. Acad Sci. USA* 85:7652, 1988.)

j. Competitive PCR

"Quantitative PCR" employing the co-amplification of competitor and unknown target nucleic acids. The competitor fragment typically differs from the unknown target by the presence of a small insert/deletion or mutated restriction endonuclease site. Consequently, the amplification product derived from the added competitor can be distinguished from the sample nucleic acid of interest. Because the competitor and target are amplified in the same reaction, with the same primers, the process is more quantitative than amplifying an unrelated control target. (Wang, A. M., Doyle, M. V. and Mark, D. F., *Proc. Natl. Acad. Sci. USA* 86:9717, 1989 and Gilliland, G. et al. *Proc. Natl. Acad. Sci. USA* 87:2725, 1990.)

k. COP (Competitive Oligonucleotide Priming)

Process for the detection of mutant alleles by PCR. The process is based upon the observation that primers that are completely complementary to the target sequence are extended more efficiently than primers with a single base mismatch (100:1), under low stringency conditions. By differentially labeling the primers, the genotype of the allele can be determined. Note that this process is distinct from ARMS. The mismatch occurs within the oligonucleotide, not at the 3' end. (Gibbs, R. A., Nguyen, P. N. and Caskey, C. T., *Nucl. Acids Res.* 17:2437, 1989.)

l. DAF (DNA Amplification Fingerprinting)

PCR amplification using a single arbitrary primer. The amplification products are separated on a polyacrylamide gel and detected by silver staining. The electrophoresis pattern can be used to "fingerprint" the sample. (Caetano-Anolles, G., Bassam, B. J. and Gresshoff, P. M., *Bio/Technology* 9:553, 1991.)

m. DARTT (DNA Amplification-Restricted Transcription-Translation)

PCR amplification using primers that: 1) add transcription/translation initiation signals onto the amplified product; and 2) generate a truncated product. The PCR product is transcribed and translated in vitro. The truncated protein products are used to define functional sites on the molecule. (Mackow, E. R. et al., *Proc. Natl. Acad. Sci. USA* 87:518, 1990 [published erratum in *Proc. Natl. Acad Sci. USA* 87:4411, 1990.])

n. DD-PCR (Differential Display Polymerase Chain Reaction)

Process for comparing the gene expression profile from two different tissue/cell samples (e.g., normal versus tumor). First strand cDNA synthesis is performed with an oligo(dT) primer that contains a few defined nucleotides at the 3' position (e.g., (T)15GC or (T)15CA). Second strand cDNA synthesis is primed with a short (9–10mer) arbitrary primer. The double stranded cDNA that is produced is amplified by PCR and separated on a polyacrylamide gel. Primer extension will only occur from a subset of the total RNA population (polymerases do not efficiently extend 3' mismatches). The banding patterns of the two different samples are compared to identify differences in gene expression. (Liang, P. and Pardee, A. B., *Science* 257:967, 1992.)

o. DD-RTPCR (Differential Display Reverse Transcription and Polymerase Chain Reaction).

p. See DD-PCR.

q. DNA Cycle Sequencing

Sequencing reaction consisting of multiple cycles of denaturation, annealing and primer extension. This cycling reduces the amount of template required for DNA sequencing. (Murray, V. *Nucl. Acids Res.* 17:8889, 1989.)

r. DOP-PCR (Degenerate Oligonucleotide Primed Polymerase Chain Reaction)

Amplification of a portion of the genome using degenerate primers. Typically, the first few cycles are performed at low temperatures to facilitate primer annealing to multiple positions on the target genome. In later cycles, the annealing temperature is increased to favor amplification of material synthesized in the early cycles. (Telenius, H. et al. *Genomics* 13:718, 1992.)

s. EC-PCR (Expression Cassette Polymerase Chain Reaction)

Method for the site-specific replacement of 5' and 3' gene sequences to facilitate cloning and expression in *E. coli*. Replacement sequences may include translation start and end signals and restriction endonuclease sites. The protocol can also be used to characterize protein domains. (MacFerrin, K. D. et al. *Proc. Natl. Acad. Sci. USA* 87:1937, 1990.) Also see DARTT.

t. GAWTS (Genomic Amplification with Transcript Sequencing)

Method used to determine the sequence of DNA from an individual when partial sequence information is available. A phage RNA polymerase promoter sequence (T7, T3, or SP6) is attached to the 5'-end of one or both PCR primers. The phage promoter sequence allows the PCR product to be transcribed into RNA. The RNA is then sequenced using a reverse transcriptase. (Stoflet, E. S. et al. *Science* 239:491, 1988.)

U. In Situ PCR

Method for conducting PCR amplification within individual cells. This technique combines the high sensitivity of PCR with the cytological localization of sequences provided by In Situ Hybridization (ISH). (Haase, A. T., Retzel, E. F. and Staskus, K. A., *Proc. Natl. Acad. Sci. USA* 87:4971, 1990.)

v. In Situ RT-PCR

Used for the detection of low copy RNA sequences, an intracellular reverse transcription step is added as a preliminary step to In Situ PCR to generate cDNA from RNA templates. (Komminoth, P., Adams, V., Long, A. A., Roth, J., Saremaslani, P., Flury, R., Schmid, M., Heitz, P. U., *Path. Res. Pract.* 190:1017, 1994.)

w. IPCR (Inverse Polymerase Chain Reaction)

Protocol for amplifying target sequences that lie outside the region of known sequence information. The target DNA is restricted with an endonuclease that cleaves on both sides of the known region. The DNA is then ligated and cleaved with a restriction endonuclease that cleaves within the region of known sequence. The process generates a linear fragment with known priming sequences that are opposing each other and useful for amplification. This is in contrast to the starting material where the primers "pointed" away from each other, hence the designation inverse PCR. (Triglia, T., Peterson, M. G. and Kemp, D. J., *Nucl. Acids Res.* 16:8186, 1988.)

x. IRS-PCR (Interspersed Repetitive Sequence Polymerase Chain Reaction)

Amplification using primers specific for human long interspersed repeat elements (LINE). Can be combined with Alu specific primers (Alu-PCR). (Ledbetter, S. A. et al., *Genomics* 6:475, 1990.)

y. LA-PCR (Long and Accurate Polymerase Chain Reaction)

An adaptation of the PCR reaction that permits amplification of large fragments (>6 kb). The reaction is performed with a blend of thermal stable polymerases. The predominate polymerase (e.g., KlenTaq or Taq) lacks a 3'→5' exonucleae (proofreading) activity. The second polymerase (e.g., Tli or Pfu) exhibits proofreading activity. Misincorporated nucleotides added by the predominate enzyme are removed by the proofreading activity of the second polymerase. Consequently, the repaired molecule is a substrate for continued extension by the predominate polymerase. (Barnes, W. M. *Proc. Natl. Acad. Sci. USA* 91:2216, 1994.)

z. LAR (Ligation Amplification Reaction)

Amplification reaction based upon the ability of a DNA ligase to covalently attach (ligate) two oligonucleotides that anneal adjacent to one another on a target template molecule. Oligonucleotides that contain mismatches at the termini are inefficient substrates for the ligase. Two additional oligonucleotides, complementary to the product of the first ligation reaction facilitate exponential amplification of the reaction. (Wu, D. Y. and Wallace, R. B., *Genomics* 4:560, 1989.)

aa. LCR (Ligase Chain Reaction)

LAR using a thermal stable DNA ligase. (Barany, F., *Proc. Natl. Acad. Sci. USA.* 88:189, 1991.)

bb. LDR (Ligase Detection Reaction)

Related to LCR, except the reaction only uses two adjacent primers that are complementary to one strand of the target molecule. Consequently, the reaction provides for linear amplification (detection) of the target molecule, as opposed to the exponential amplification achieved by LCR. (Barany, F., *Proc. Natl. Acad. Sci. USA*. 88:189, 1991.)

cc. LM-PCR (Ligation-Mediated Polymerase Chain Reaction)

Method for footprinting or sequencing DNA. Genomic DNA is subjected to chemical modification to cleave the DNA [Maxam, A. M. and Gilbert, W., *Meth. Enzymol.* 65:499, 1980.] A gene-specific primer is annealed to the cleaved fragments and extended by a DNA polymerase. Primer extension creates a blunt-end fragment. A linker is ligated to the blunt end molecules, serving as an anchor for subsequent amplification. The PCR products generated using the anchor and gene specific primers are resolved on a polyacrylamide/urea gel, transferred onto a solid support and detected with a gene-specific probe. (Mueller, P. R. and Wold, B., *Science* 246:780, 1989 [erratum *Science* 248:802, 1990]; Pfeifer, G. P. et al., *Science* 246:810, 1989.)

dd. Long (Long Range) PCR

See LA-PCR above.

ee. MOPAC (Mixed Oligonucleotide Primed Amplification of cDNA)

Method for cloning a cDNA homolog based upon amino acid similarity to a known gene. Degenerate oligonucleotides are derived from the amino acid sequence of the known gene. The population of degenerate oligonucleotides is used to amplify the related gene from the desired organism. (Lee, C. C. et al., *Science* 239:1288, 1988.)

ff. Multiplex PCR

Simultaneous amplification of multiple gene products within the same reaction. This technique is usually used to detect well characterized gene deletions/insertions and to detect expression of genes. (Chamberlain, J. S. et al. *Nucl. Acids Res.* 16:11141, 1988; *Andrologia* 26:97, 1994 and *Biotechniques* 23:504, 1997.)

gg. NASBA (Nucleic Acid Sequence Based Amplification)

See 3SR. Compton, J., *Nature* 350:91, 1991.

hh. Nested PCR

Two-stage amplification reaction. Primers that complement regions of the first stage amplification product are used to amplify a portion of the original PCR product. The use of nested primer pairs significantly increases amplification specificity. (Porter-Jordan, K. et al., *J. Med. Virol.* 30:85, 1990.)

ii. Panhandle PCR

Method for amplifying unknown flanking DNA sequences. Genomic DNA is digested with a restriction endonuclease that yields a 5' overhang. An oligonucleotide that is complementary to a portion of the known sequence is ligated onto the digested DNA, yielding sequences that are complementary to portions of the known sequence on both ends of the molecule. Upon denaturing and annealing at low concentrations, the products form an intrastrand stem-loop structure with a recessed 3' end. The 3' end is extended with Taq DNA Polymerase, yielding a short stretch of defined sequence that can be used to amplify the unknown region. (Jones, D. H. and Winistorfer, S. C., *Nucl. Acids Res.* 20:595, 1992.)

jj. PASA (Polymerase Chain Reaction Amplification of Specific Alleles)

See ARMS. Sommer, S. S. et al., *Mayo Clin. Proc.* 64:1361,1989.

kk. PCR (Polymerase Chain Reaction)

Amplification of a specific fragment of DNA using polymerase extension of two specific oligonucleotides complementary to the region of interest. (Saiki, R. K. et al., *Science* 230:1350, 1985.)

ll. PCR-ELISA

Control DNA is added to every PCR mix as an internal amplification control. After completion of the competitive PCR, the target DNA and the control DAN are detected by calorimetric reaction in a microtiter plate.

mm. PCR-SSCP (Polymerase Chain Reaction and Single-Strand Conformation Polymorphism)

A mutation detection protocol that combines PCR amplification with SSCP. The PCR reaction is performed with a labeled primer, circumventing the need for transfer of the DNA onto a solid support and subsequent hybridization. The labeled PCR products are denatured and separated on a polyacrylamide gel. (Orita, M. et al., *Genomics* 5:874, 1989.)

nn. PTT (Protein Truncation Test)

Coupled PCR (or RT-PCR) and in vitro transcription/translation. One of the amplification primers contains a phage RNA polymerase promoter sequence that permits transcription and translation of the amplification products. The technique is used to quickly identify nonsense mutations that result in truncated gene products. (Roest, P. A. et al., *Hum. Mol. Genet.* 2:1719, 1993.)

oo. Qb (Q-beta Replicase)

A bacteriophage RNA polymerase that is capable of exponential amplification of Qb phage RNA sequences. Midivariant constructs have been designed that contain chimeric phage and probe sequences. After hybridization and extensive washing, the probe (versus target) sequences can be rapidly and exponentially amplified. (Lizardi, P. M. et al., *BioTechnology* 6:1197, 1988.)

pp. QC-PCR (Quantitative Competitive Polymerase Chain Reaction)

See Competitive PCR. (Becker-Andre, M., *Meth. Mol. Cell. Biol.* 2:189, 1991.)

qq. QPCR (Quantitative Polymerase Chain Reaction)

Estimation of the amount of starting, target template DNA. Typically requires the use of an internal standard. See Competitive PCR and TaqManä.

rr. RACE (Rapid Amplification of cDNA Ends)

Protocols developed to facilitate the cloning of the 5' (5'-RACE) or 3' (3'-RACE) ends of a cDNA using information obtained from an incomplete cDNA clone. (Frohman, M. A., Dush, M. K. and Martin, G. R., *Proc. Natl. Acad. Sci. USA* 85:8998, 1988.)

ss. RAPD (Randomly Amplified Polymorphic DNA)

See AP-PCR. (Williams, J. G. et al., *Nucl. Acids Res.* 18:6531, 1990.)

tt. RAP-PCR (RNA Arbitrarily Primed Polymerase Chain Reaction)

RNA fingerprinting protocol that uses an arbitrary oligonucleotide to prime first strand cDNA synthesis. Second strand cDNA synthesis and amplification is primed with the same oligonucleotide. The amplification products are resolved by gel electrophoresis. (Ralph, D., McClelland, M. and Welsh, J., *Proc. Natl. Acad. Sci. USA* 90:10710, 1993; Welsh, J. et al., *Nucl. Acids Res.* 20:4965, 1992.) Similar to DD-PCR.

uu. RAWTS (RNA Amplification with Transcript Screening)

Similar to GAWTS, except the starting template is RNA. After reverse transcription, the cDNA target is subjected to GAWTS. (Sarkar, G. and Sommer, S. S., *Nucl. Acids Res.* 16:5197,1988.)

vv. RFLP (Restriction Fragment Length Polymorphism)

Method for mapping highly variable regions within a genome that give rise to alternate restriction digestion patterns. Genomic DNA is digested with restriction endonucleases, separated by gel electrophoresis and transferred to a solid support. The immobilized DNA is hybridized with a labeled probe to reveal the digestion pattern of the region of interest. (Kiko, H., Niggemann, E. and Ruger, W., *Mol. Gen. Genet.* 172:303, 1979; Wyman, A. R. and White, R., *Proc. Natl. Acad. Sci. USA* 77:6754, 1980.)

ww. RLM-RACE (RNA Ligase-Mediated Rapid Amplification of cDNA Ends)

RACE procedure that employs T4 RNA Ligase to attach an oligonucleotide onto the 5' or 3' end of an RNA transcript prior to cDNA synthesis and amplification. (Liu, X. and Gorovsky, M. A., *Nucl. Acids Res.* 21:4954, 1993.)

xx. RL-PCR (Reverse Ligation-Mediated Polymerase Chain Reaction)

Method for RNA footprinting. The RNA sample is treated with a ribonuclease under conditions that favor a single cleavage event per molecule, but do not disrupt RNA-RNA or RNA-protein complexes. A linker of defined sequence is ligated onto the cleaved RNA with T4 RNA Ligase. First strand cDNA synthesis is primed with a gene specific primer. Several cycles of PCR amplification are performed with the gene specific primer and the linker oligonucleotide. Subsequent cycles of amplification are performed with a radiolabeled primer and the products are resolved by polyacrylamide gel electrophoresis. (Bertrand, E. et al., *Proc. Natl. Acad. Sci. USA* 90:3496, 1993.)

yy. RT-PCR (Reverse Transcription and Polymerase Chain Reaction)

Coupled reverse transcription, second strand cDNA synthesis and PCR amplification.

zz. Sexual PCR

Process for generating hybrid or mutated genes. The PCR product encoding a gene of interest is treated with DNase I to generate a pool of random fragments. The fragments (approx. 50 bp) are gel purified and reamplified without any exogenous primer. This results in fragment annealing and extension by Taq DNA Polymerase. The resulting products are then subjected to amplification with the primers used to generate the initial PCR product. This process can be used to generate mutant versions of the target, or chimeras of related genes. (Stemmer, W. P. C., *Nature* 370:389, 1994; Stemmer, W. P. C., *Proc. Natl. Acad. Sci. USA* 91:10747, 1994.)

aaa. SISPA (Sequence Independent Single Primer Amplification)

Nonspecific amplification of DNA achieved by the directional ligation of asymmetric linkers onto the termini of blunt end target nucleic acid. A primer, complementary to the linker sequences is used to amplify the total DNA population. (Reyes, G. R. and Kim, J. P., *Mol. Cell. Probes* 5:473, 1991.)

bbb. SLIC (Single Stranded Ligation to single stranded cDNA)

Method for cloning the 5' end of cDNAs. Total RNA is reverse transcribed with a primer containing an oligo(dT) tail or a gene-specific primer. An oligodeoxyribonucleotide anchor primer is ligated onto the first strand cDNA with T4 DNA Ligase. PCR amplification is performed using the anchor and first strand cDNA synthesis primers. (Edwards, J. B. D. M., Delort, J. and Mallet, J., *Nucl. Acids Res.* 19:5227, 1991.)

ccc. SnuPE (Single nucleotide Primer Extension)

Technique for mutation detection based upon the inefficient extension of 3' mismatches by Taq DNA Polymerase. A primer is annealed immediately adjacent to the suspected mutation in the target PCR amplification product and incubated with Taq DNA Polymerase in the presence of a single radiolabeled nucleotide. Primer extension (incorporation of the radiolabeled nucleotide) is indicative of wild type sequences. A single base mismatch will not be efficiently extended. (Kuppuswamy, M. N. et al., *Proc. Natl. Acad. Sci. USA* 88:1143, 1991.)

ddd. SSP-PCR (Single Specific Primer Polymerase Chain Reaction)

Protocol for the amplification of target nucleic acid when sequence information is only available for one extremity. Genomic DNA is digested with a restriction endonuclease and ligated onto a linearized plasmid vector. PCR amplification is performed with primers complementary to the vector and known regions of the target of interest. (Shyamala, V. and Ames, G. F.-L., *Gene* 84:1, 1989; Shyamala, V. and Ames, G. F.-L., *Methods Enzymol.* 217:436, 1993.)

eee. Suppression PCR

This method suppresses nonspecific amplification during PCR. cDNA adaptors are engineered on the ends of some cDNA strands. Suppression occurs when complementary sequences are present on each end of a single-stranded cDNA. During each primer annealing step, the hybridization kinetics strongly favor self-hybridization between the engineered ends of the cDNA over annealing with shorter primers. (Sieber, P. D., et al., *Nucleic Acids Res.* 23:1087, 1995; Siebert, P. D., et al., *Proc. Natl. Acad. Sci. USA* 93:6025.)

fff. TaqMan™

Real time (kinetic) quantitation of PCR products using a target-specific, energy transfer probe. The assay is based upon the 5' exonuclease activity of Taq DNA Polymerase (Holland, P. M. et al., *Proc. Natl. Acad. Sci. USA* 88:7276, 1991). Cleavage of the TaqMan™ probe occurs upon hybridization to the target PCR product, liberating a fluorescent fragment. The fluorescent signal is dependent upon the concentration of the PCR product. (Heid, C. A. et al., *Genome Res.* 6:986, 1996.)

ggg. TAS (Transcription-based Amplification System)

Reverse transcription is primed with an oligonucleotide that contains a phage RNA polymerase promoter sequence. After second strand cDNA synthesis, the cDNA is transcribed with a phage RNA polymerase. The reaction can be amplified by multiple cycles of cDNA synthesis and transcription. (Kwoh, D. Y. et al., *Proc. Natl. Acad. Sci. USA* 86:1173, 1989.)

hhh. TMA (Transcription Mediated Amplification)

cDNA synthesis is primed with an oligonucleotide that contains a phage (T7) RNA Polymerase promoter. Multiple RNA copies are synthesized with T7 RNA Polymerase. The resultant RNA copies are substrates for AMV Reverse Transcriptase, consequently the cycle repeats itself. This cycling of reverse transcription and transcription reactions (in the presence of the third enzyme, RNase H) can result in a 107-fold amplification within 1–2 hours. Since the reaction is isothermal, potential damage to surrounding tissues by the high temperatures required for PCR amplification is avoided. (Zehbe I. et al., *Cell Vision* 1:46, 1994.)

iii. Touchdown PCR

Method for reducing mispriming events in PCR amplification. The annealing temperature is gradually reduced with increasing cycle number (e.g., 1° C. every second cycle) until the desired "touchdown" annealing temperature is achieved. Amplification is then continued for a number of cycles using the "touchdown" annealing temperature. (Don, R. H. et al., *Nucl. Acids Res.* 19:4008, 1991.)

jjj. 3SR (Self-Sustained Sequence Replication)

An isothermal, continuous process of reverse transcription and RNA transcription that yields exponential amplification of the desired target sequences. mRNA is converted to double stranded cDNA using AMV Reverse Transcriptase, RNase H and oligonucleotides that contain a T7 RNA Polymerase promoter sequence. The double stranded cDNA is a substrate for T7 RNA Polymerase. The antisense RNA produced from the transcription reaction is a substrate for double stranded cDNA synthesis, as described above. The resulting cDNA can then serve as substrate for both sense and antisense RNA transcription by T7 RNA Polymerase. (Guatelli, J. C. et al., *Proc. Natl. Acad. Sci. USA* 87:1874, 1990.)

3. Detection of a Mutation

Mutations involving a single nucleotide can be identified in a sample by physical, chemical, or enzymatic means. Generally, methods for mutation detection may be divided into scanning techniques, which are suitable to identify previously unknown mutations, and techniques designed to detect, distinguish, or quantitate known sequence variants.

Several scanning techniques for mutation detection have been developed in heteroduplexes of mismatched complementary DNA strands, derived from wild-type and mutant sequences, that exhibit an abnormal behavior especially when denatured. This phenomenon is exploited in denaturing and temperature gradient gel electrophoresis (DGGE and TGGE, respectively) methods. Duplexes mismatched in even a single nucleotide position can partially denature, resulting in retarded migration, when electrophoresed in an increasingly denaturing gradient gel (Myers et al., *Nature* 313:495, 1985; Abrams et al., *Genomics* 7:463, 1990; Henco et al., *Nucl. Acids Res.* 18:6733, 1990). Although mutations may be detected, no information is obtained regarding the precise location of a mutation. Mutant forms must be further isolated and subjected to DNA sequence analysis.

Alternatively, a heteroduplex of an RNA probe and a target strand may be cleaved by RNase A at a position where the two strands are not properly paired. The site of cleavage can then be determined by electrophoresis of the denatured probe. However, some mutations may escape detection because not all mismatches are efficiently cleaved by RNase A.

Mismatched bases in a duplex are also susceptible to chemical modification. Such modification can render the strands susceptible to cleavage at the site of the mismatch or cause a polymerase to stop in a subsequent extension reaction. The chemical cleavage technique allows identification of a mutation in target sequences of up to 2 kb and it provides information on the approximate location of mismatched nucleotide(s) (Cotton et al., *PNAS USA* 85:4397, 1988; Ganguly et al., *Nucl. Acids Res.* 18:3933, 1991). However, this technique is labor intensive and may not identify the precise location of the mutation.

An alternative strategy for detecting a mutation in a DNA strand is by substituting (during synthesis) one of the normal nucleotides with a modified nucleotide, altering the molecular weight or other physical parameter of the product. A strand with an increased or decreased number of this modified nucleotide relative to the wild-type sequence exhibits altered electrophoretic mobility (Naylor et al., *Lancet* 337:635, 1991). This technique detects the presence of a mutation, but does not provide the location.

Two other strategies visualize mutations in a DNA segment by altered gel migration. In the single-strand conformation polymorphism technique (SSCP), mutations cause denatured strands to adopt different secondary structures, thereby influencing mobility during native gel electrophoresis. Heteroduplex DNA molecules, containing internal mismatches, can also be separated from correctly matched molecules by electrophoresis (Orita, *Genomics* 5:874, 1989; Keen, *Trends Genet.* 7:5, 1991). As with the techniques discussed above, the presence of a mutation may be determined but not the location. As well, many of these techniques do not distinguish between a single and multiple mutations.

All of the above-mentioned techniques indicate the presence of a mutation in a limited segment of DNA and some of them allow approximate localization within the segment. However, sequence analysis is still required to unravel the effect of the mutation on the coding potential of the segment. Sequence analysis is very powerful, allowing, for example, screening for the same mutation in other individuals of an affected family, monitoring disease progression in the case of malignant disease or for detecting residual malignant cells in the bone marrow before autologous transplantation. Despite these advantages, the procedure is unlikely to be adopted as a routine diagnostic method because of the high expense involved.

A large number of other techniques have been developed to analyze known sequence variants. Automation and economy are very important considerations for these types of analyses that may be applied, for screening individuals and the general population. None of the techniques discussed below combine economy, automation with the required specificity.

Mutations may be identified via their destabilizing effects on the hybridization of short oligonucleotide probes to a target sequence (see Wetmur, *Crit. Rev. Biochem. Mol. Biol.*, 26:227, 1991). Generally, this technique, allele-specific oligonucleotide hybridization involves amplification of target sequences and subsequent hybridization with short oligonucleotide probes. An amplified product can thus be scanned for many possible sequence variants by determining its hybridization pattern to an array of immobilized oligonucleotide probes.

However, establishing conditions that distinguish a number of other strategies for nucleotide sequence distinction all depend on enzymes to identify sequence differences (Saiki, *PNAS USA* 86:6230, 1989; Zhang, *Nucl. Acids Res.* 19:3929, 1991).

For example, restriction enzymes recognize sequences of about 4–8 nucleotides. Based on an average G+C content, approximately half of the nucleotide positions in a DNA segment can be monitored with a panel of 100 restriction enzymes. As an alternative, artificial restriction enzyme recognition sequences may be created around a variable position by using partially mismatched PCR primers. With this technique, either the mutant or the wild-type sequence alone may be recognized and cleaved by a restriction enzyme after amplification (Chen et al., *Anal. Biochem.* 195:51, 1991; Levi et al., *Cancer Res.* 51:3497, 1991).

Another method exploits the property that an oligonucleotide primer that is mismatched to a target sequence at the 3' penultimate position exhibits a reduced capacity to serve as a primer in PCR. However, some 3' mismatches, notably G-T, are less inhibitory than others limiting its usefulness. In attempts to improve this technique, additional mismatches are incorporated into the primer at the third position from the 3' end. This results in two mismatched positions in the three 3' nucleotides of the primer ybridizing with one allelic variant, and one mismatch in the third position in from the 3' end when the primer hybridizes to the other allelic variant (Newton et al., *Nucl. Acids Res.* 17:2503, 1989). It is necessary to define amplification conditions that significantly favor amplification of a 1 bp mismatch.

DNA polymerases have also been used to distinguish allelic sequence variants by determining which nucleotide is added to an oligonucleotide primer immediately upstream of a variable position in the target strand.

A ligation assay has been developed. In this method, two oligonucleotide probes hybridizing in immediate juxtaposition on a target strand are joined by a DNA ligase. Ligation is inhibited if there is a mismatch where the two oligonucleotide probes abut.

Other highly sensitive hybridization protocols may be used. The methods of the present invention enable one to readily assay for a nucleic acid containing a mutation suspected of being present in cells, samples, etc., i.e., a target nucleic acid. The "target nucleic acid" contains the nucleotide sequence of deoxyribonucleic acid (DNA) or ribonucleic acid (RNA) whose presence is of interest, and whose presence or absence is to be detected for in the hybridization assay. The hybridization methods of the present invention may also be applied to a complex biological mixture of nucleic acid (RNA and/or DNA). Such a complex biological mixture includes a wide range of eucaryotic and procaryotic cells, including protoplasts; and/or other biological materials which harbor polynucleotide nucleic acid. The method is thus applicable to tissue culture cells, animal cells, animal tissue, blood cells (e.g., reticulocytes, lymphocytes), plant cells, bacteria, yeasts, viruses, mycoplasmas, protozoa, fungi and the like. By detecting a specific hybridization between nucleic acid probes of a known source, the specific presence of a target nucleic acid can be established.

A typical hybridization assay protocol for detecting a target nucleic acid in a complex population of nucleic acids is as follows: Target nucleic acids are separated by size on a gel matrix (electrophoresis), cloned and isolated, subdivided into pools, or left as a complex population. The target nucleic acids are transferred, spotted, or immobilized onto a solid support such as a nylon membrane or nitrocellulose membrane. (This "immobilization" is also referred to as "arraying"). The immobilized nucleic acids are then subjected to a heating step or UV radiation, which irreversibly immobilizes the nucleic acid. The membranes are then immersed in "blocking agents" which include Dendhart's reagent (Dendhart, *Biochem. Biophys. Res. Comm.* 23:641, 1966), heparin (Singh and Jones, *Nucleic Acids Res.* 12:5627, 1984), and non-fat dried milk (Jones et al., *Gene Anal. Tech.* 1:3, 1984). Blocking agents are generally included in both the prehybridization step and hybridization steps when nitrocellulose is used. The target nucleic acids are then probed with labeled oligonucleotide probes under conditions described above in hybotrope-based solutions. Probes may be detected by a conjugated enzyme. Unbound enzyme is then washed away and the membrane is immersed in a substrate solution. Signal is then detected by calorimetric means, by fluorescence or by chemiluminescence, depending on substrate type. Alternatively, the probe is directly labeled (e.g., radioactive isotope, fluorescent molecule, mass-spectrometry tags; see WO 97/27331; WO 97/27325; and WO 97/27327).

Although the assay descriptions above are illustrated using a hybotropic solution, the assays may be performed with oligonucleotides containing specificity spacers such as abasic residues or base analog residues as described herein. With such reagents, the abasic residue(s) or analog(s) should be positioned at a position other than the mutation site of interest. As described herein, the combination of such oligonucleotides with a hybotrope can further improve discrimination.

Single base mutations may also be detected in primer extension assays. In this strategy, an oligonucleotide primer is designed so that when hybridized to a template, the 3' most base will coincide with a mutation site of interest. For this assay, at least two primers are preferably used, one has the wild type base at the 3' end, the other(s) has a base that mismatches. Optionally, the oligonucleotide primer may also contain one or more nucleoside analogues. Enzyme is added to the template, and rimer in an appropriate buffer and hybotrope and synthesis allowed to proceed. although an extension product may be detected from this single round of synthesis, sensitivity can be increased by multiple rounds of synthesis, such as in amplification reactions. Thus, if there is a mismatch at the 3' end of the primer, neither extension or amplification products will be formed, or formed to a detectable level. (Newton et al., *Nucl. Acids Res.* 17: 2503, 1989).

The amplification reactions are performed essentially as described below in a buffer containing an amine-base salt. Such salts include ethylbutylamine acetate, bis-methoxyamine acetate, dipropylamine acetate, diisoproylamine acetate and preferably ethyl piperidine. Other amino salts that support polymerase activity may also be used. A reduction in activity, although not preferable, may be tolerated. The amine-based salts can be used at a concentration ranging from about 5 mM to about 6 M, preferably from about 50 mM to about 2.5 M.

In addition, the oligonucleotide primer may contain one or more nucleoside analogues, such as those described herein. The analogue, such as deoxynebularine, will generally be positioned around the middle of the sequence, but can be located anywhere other than the 3' most base.

4. DNA Sequence Analysis

DNA sequence analysis is conventionally performed by hybridizing a primer to target DNA and performing chain extensions using a polymerase. Specific stops are controlled by the inclusion of a dideoxynucleotide. The specificity of priming in this type of analysis can be increased by including a hybotrope in the annealing buffer and/or incorporating an abasic residue in the primer and annealing at a discriminating temperature.

Other sequence analysis methods involve hybridization of the target with an assortment of random, short oligonucleotides. The sequence is constructed by overlap hybridization analysis. In this technique, precise hybridization is essential. Use of hybotropes or abasic residues and annealing at a discriminating temperature is beneficial for this technique to reduce or eliminate mismatched hybridization. The goal is to develop automated hybridization methods in order to probe large arrays of oligonucleotide probes or large arrays of nucleic acid samples. Application of such technologies include gene mapping, clone characterization, medical genetics and gene discovery, DNA sequence analysis by hybridization, and finally, sequencing verification.

Many parameters must be controlled in order to automate or multiplex oligonucleotide probes. The stability of the respective probes must be similar, the degree of mismatch with the target nucleic acid, the temperature, ionic strength, the A+T content of the probe (or target), as well as other parameters when the probe is short (i.e., 6 to 50 nucleotides) should be similar. Usually, the conditions of the experiment and the sequence of the probe are adjusted until the formation of the perfectly based paired probe is thermodynamically favored over the any duplex that contains a mismatch. Very large scale applications of probes such as sequencing by hybridization (SBH), or testing highly polymorphic loci such as the cystic fibrosis trans-membrane protein locus require a more stringent level of control of multiplexed probes. William Bains (*GATA* 11:49, 1994), has ascertained that the ability to use multiplexed oligonucleotide probes is generally much more difficult to implement than is suggested by theory. Hybotropes and specificity spacers will essentially overcome the limitations in the use of multiplexed probes as presented by Bains.

The actual required length of an oligonucleotide probe to uniquely prime any natural nucleic acid target is far longer than is predicted by theory. In general, the probability that a given probe is unique is related to the length. Theoretically, the length is 12 to 15 nucleotides when the target is 520 kilobases in length. However, it is shown that a probe needs to be 24 nucleotides in order to possess a 90% probability of being unique. Therefore, using longer "short" probes (i.e., 24–36 nucleotide lengths) in hybridization assays that need to be specific is highly desirable. The methods and compositions presented here substantially aid in the use of long oligonucleotide probes (i.e., 24–36 nucleotide lengths) in terms of discrimination.

5. Use of Hybotropes in Amplification-Based Assays

The observation that $\Delta T_d$ does not change as a function of concentration of hybotrope has substantial utility for use in DNA, RNA or nucleic acid amplifications based on primer extension by a polymerase (e.g., polymerase chain reaction, see U.S. Pat. Nos. 4,683,195; 4,683,202; and 4,800,159, cycling probe technology, NASBA), ligation (LCR, ligation chain reaction), and RNA amplification (see Lizardi et al., Bio/Technology 6:1197, 1988; Kramer et al., Nature 339:401, 1989; Lomeli et al., Clin. Chem. 35:1826, 1989; U.S. Pat. No. 3,786,600). For example, PCR buffer is optimized for the polymerase rather than for specific priming. The current practice is to employ conditions that favor performance of the polymerase over specificity of priming with oligonucleotides. Thus, PCR buffer as currently commercially available does not provide or support a high level of stringency of hybridization of PCR primers.

Commercially available PCR buffers are examined with respect to the melting behavior of 24-mer oligonucleotides in both the wild-type (wt) and mutant (mt) forms. In Table 5, the level of discrimination achieved in PCR buffer versus a low molarity concentration of hybotrope is shown.

TABLE 5

$\Delta T_d$ for PCR buffers and low molarity hybotropes

| Solution | Conc. | Oligo Length | HCT* | $\Delta T_d$* | $T_d$* |
|---|---|---|---|---|---|
| PCR buffer | 1x | 24-mer wt | 25 |  | 61 |
| PCR buffer | 1x | 24-mer mt | 24 | 1 | 60 |
| PCR buffer | 1x | 24-mer mt | 14 | 1 | 60 |
| DMCHAA | 0.5 M | 24-mer wt | 18 |  | 30.5 |
| DMCHAA | 0.5 M | 24-mer mt | 12 | 5 | 25.5 |
| LiTCA | 0.1 M | 24-mer wt | 12 |  | 65.5 |
| LiTCA | 0.1 M | 24-mer mt | 8 | 4 | 61.5 |

*= ° C.

As shown, the HCT for standard PCR buffer is about 15° C., whereas the HCT for 0.5 M DMCHAA is about 18° C. (for a 66% G+C content oligonucleotide duplex). The $\Delta T_d$ for the 1xPCR buffer is only 1° C. for the 24-mer, whereas the $\Delta T_d$ for 0.5 M DMCHAA is 5° C. Therefore, priming specificity is significantly improved in 0.5 M DMCHAA versus 1xPCR buffer. Higher concentrations of hybridization solutions may also be used (0.5 M to 3.0 M DMCHAA), but in general PCR conditions can accommodate 5 mM to 150 mM concentrations of hybotrope or amine-based salts.

Alternatively, priming is performed in a hybotrope solution and chain extension is performed in a separate buffer that supports the polymerase. For example, a solid phase PCR could be employed where the solid phase is moved through two solutions. Priming would occur in some appropriate concentration of LiTCA or amine-based salt and then the polymerase chain reaction would take place in a different PCR buffer containing the polymerase. It is also possible to conduct the first few rounds in the amplification in a hybotrope based hybridization solution and conducting the remaining rounds on normal PCR buffer (generally, only the first few rounds are important for specificity).

The use of deoxyNebularine modified oligonucleotides will also increase the specificity of priming in the PCR. One deoxyNebularine substitution incorporated into an oligonucleotide reduces the HCT by 2.5° C. Two oligonucleotides probes containing 3 deoxyNebularine sites per 24-mer decrease HCT by 8° C. relative to the unsubstituted control. This decrease in the HCT dramatically increases the level of specificity of priming in an amplification reaction (e.g., polymerase chain reaction). This is likely due to the reduction of false or mis-priming during the first few (e.g., 10) cycles of PCR. That is, the enthalpy of the deoxyNebularine substituted oligonucleotide increases relative to the unsubstituted primer, thus increasing the specificity of priming. Within the context of this invention, the primer is preferably 6 to 36 bases in length and contains 1 to 6 deoxyNebularine sites. The sites are preferably separated by 4, 5, 6, 7 or 8 nucleotides and may be separated by up to 12 to 24 nucleotides. The substitutions are also preferably clustered at the 3' end of the primer to ensure specificity of primer extension by nucleic acid polymerases, which may be, for example, DNA or RNA primers. Moreover, the temperature range over which priming occurs is dramatically reduced when deoxyNebularine-substituted primers are used.

The results also indicate that the dSpacer™ substitution prevents the polymerase from "reading through" the abasic site. When the polymerase encounters an abasic residue, chain extension is terminated. However, unlike abasic residues, a deoxyNebularine residue does not terminate chain extension, although, as noted above, the temperature range over which amplification occurs is much reduced compared to non-substituted oligonucleotides. Therefore, deoxyNebularine substituted primers, and other primers having base analog residue substitutions can substantially increase the specificity of a DNA polymerase chain reaction.

Furthermore, the combination of an deoxyNebularine or other base analog residue site in an amplification PCR primer and a hybotrope salt solution, which promotes a high enthalpy value for the primer duplex, significantly lowers the HCT of the primer duplex. As discussed above, when the HCT decreases, the stringency factor increases and high-discrimination priming of the polymerase chain reaction can take place. These are conditions required for favorable multiplexing PCRs. The term multiplexing refers to the ability to use more than one set of primers in a PCR reaction and generate multiple products or the ability to use more than one target nucleic acid per set of PCR primers.

The use of the hybotropic amine-based salts is of particular utility because the dependence of G+C content on $T_d$ (stability) is neutralized. However, other hybotropes of the present invention which may be used in the polymerase chain reaction include, without limitation, bis(2-methoxyethyl)amine acetate, 1-ethylpiperidine acetate, 1-ethylpiperidine trichloroacetate, 1-ethylpiperidine trifluoroacetate, 1-methylimidizole acetate, 1-methylpiperidine acetate, 1-methylpiperidine trichloroacetate, 1-methylpyrrolidine acetate, 1-methylpyrrolidine trichloroacetate, 1-methylpyrrolidine trifluoroacetate, 2-methoxyethylamine acetate, N,N-dimethylcyclohexylamine acetate, N,N-dimethylcyclohexylamine trifluoroacetate, N,N- dimethylcyclohexylamine, N,N-dimethylheptylamine acetate, N,N-dimethylheptylamine acetate, N,N-dimethylhexylamine acetate, N,N-dimethylhexylamine acetate, N,N-dimethylisopropylamine acetate, N-ethylbutylamine acetate, N-ethylbutylamine trifluoroacetate, N,N-dimethylaminobutane trichloroacetate, N,N-dimethylisopropylamine trichloroacetate, triethanolamine acetate, triethylamine acetate, triethylamine trichloroacetate, tripropylamine acetate, tetraethylammonium acetate. These compounds or chemicals can be combined in amplification reaction with divalent cations such as $Mg^{++}$, buffers, detergents, co-factors, nucleotides and their analogs, polymerases and/or ligases. The compounds listed above can be used in concentration ranging from about 5 mM to about 6 M, preferably from about 10 mM to about 0.150 M.

The following are preferred steps in an extension assay for detecting single nucleotide polymorphisms according to the present invention. The 3' end of the primer is placed directly over the single nucleotide polymorphism. If the 3' end is mismatched, extension will not (or will only negligibly) occur, however it the 3' end is perfectly base-paired, extension will take place, so long as the extension reaction is conducted in a hybotrope-containing media as described herein. Preferably, the hybotrope-containing media contains a primary, secondary or tertiary amine salt of acetate, halogenated acetate, propionate or halogenated propionate.

In this format, the label is on the primer and the label or tag identifies whether the primer possesses the wildtype or mutant sequence (at the 3' end). The length of the primer after the extension reaction has been allowed to occur then determines whether the target nucleic acid possesses the wildtype or mutant sequence. The primer may hybridize to the target such that the primer extends 1, 2, 3, 4, or 5 nucleotides past the site of the polymorphism. Preferably, the primer is 1–2 nucleotides past the site of the mutation or polymorphism. The primer may contain one or more specificity spacers are defined herein.

More specifically, the above-described assay may be performed with primers labeled at their 5' end with fluorochromes. The wildtype primer may be labeled with, for example, fluorescein, while the mutant primer is labeled with something other than fluorescein, such as Texas Red. Both primers are then added to a PCR and amplification is allowed to occur in the presence of a hybotrope of the invention, and preferably with the amine based hybotrope salts described herein (preferably primary, secondary or tertiary ammonium salts of acetate, halogenated acetate, propionate or halogenated propionate). If the wildtype allele is present, then the wildtype primer will extend, and if the mutant target is present then the mutant primer will extend. If the wildtype allele is not present, then the wildtype primer will not extend, and if the mutant target is not present then the mutant primer will not extend. It is possible that both alleles are present and both the wildtype and mutant primers will extend. The extended PCR primer products are then separated from the non-extended primers (by using a molecular weight cutoff filter, a size exclusion gel, etc.). A solution containing the extended products is then read using a fluorometer. The solution is scanned twice, once at the fluorescein emission and once at the Texas Red emission (or scanned simultaneously using a diode array fluorometer). The ratio of green to red is then calculated. If the ratio is about >5/1 green to red both alleles are wildtype, if the ratio is about <0.2/1 green to red, then both alleles are mutant, and if the ratio is about 1/1, both alleles are present.

Alternatively, the above-described assay may be performed with primers that are labeled with unique tags that may be distinguished by mass spectrometry, and which may be referred to herein as "CMSTs". Suitable tags for mass spectrometry are described in U.S. patent application Ser. No. 08/898,180 filed Jul. 22, 1997, the disclosure of which is incorporated herein by reference.

According to this approach, two primers are provided, each labeled at the 5' end with different CMSTs. The wildtype primer is labeled with, for example, a mw 483 tag, and the mutant primer is labeled with mw 495 tag. Both primers are then added to a PCR and amplification is allowed to occur in the presence of the hybotrope (preferably a primary, secondary or tertiary amine salt of acetate, halogenated acetate, propionate, and halogenated propionate, such as 1-ethyl-pipendine, diisopropylammonium acetate, etc.). If the wildtype allele is present, then the wildtype primer will extend, and if the mutant target is present then the mutant primer will extend. If the wildtype allele is not present, then the wildtype primer will not extend, and if the mutant target is not present then the mutant primer will not extend. It is possible that both alleles are present and both the wildtype and mutant primers will both extend. The extended PCR primer products are then separated from the non-extended primers (by using a molecular weight cutoff filter, a size exclusion gel, etc.). A solution containing the extended products is then injected into the mass spectrometer, the tags are cleaved in flow, and the tag mass is determined by the mass spectrometer. The ratio of tags is then calculated. If the ratio is about >5/1 483/495 then both alleles are wildtype, if the ratio is about <0.2/1 483/495, then both alleles are mutant, if the ratio is about 1/1, both alleles are present. The CMST tagging approach permits the multiplexing of many primers and alleles.

Thus, the present invention provides a method of performing a single nucleotide polymorphism assay to detect the presence or absence of a non-wild-type nucleotide in a target oligonucleotide. The method includes the steps:

(a) providing a single-stranded target oligonucleotide, a first primer comprising a first label and a first nucleotide sequence, and a second primer comprising a second label and a second nucleotide sequence, where the first and second labels are non-identical, and the first and second nucleotide sequences are identical except that the first primer contains a wild-type nucleotide at a distance of "x" nucleotides from the 3'-most end of the first nucleotide sequence, and the second primer contains a non-wild-type nucleotide at a distance of "x" nucleotides from the 3'-most end of the second nucleotide sequence, where "x" is an integer ranging from 1 to 5 and the wild-type and non-wild-type nucleotides are non-identical, and where the target comprises an oligonucleotide sequence that defines a priming sequence, and the priming sequence is capable of hybridizing to at least one of the first and second primers in a manner effective to allow a polymerase to extend the primer of a hybridized primer and target;

(b) mixing the target, the first primer, the second primer, a polymerase and a hybotrope under conditions that allow the target to hybridize to at least one of the first and second primers in a manner that allows the polymerase to extend a primer that hybridizes to a target;

(c) separating primers that have been extended from any primers that have not been extended; and (d) determining the relative amounts of first and second labels in the primers that have been extended.

Another assay that may be advantageously performed with hybotropes of the invention are single nucleotide extension assays. In this assay format the 3' end of the primer is placed 1 nucleotide behind the single nucleotide polymorphism. In this format the label is in the dideoxy-terminator (ddNTP) and the label or tag identifies whether the reaction product possesses the wildtype or mutant sequence (at the 3' end). The length of the primer after the extension reaction is one nucleotide longer than the non-extended product.

Such an assay may be run as follows. Start with ddNTPs labelled with fluorochromes. The wildtype ddNTP is labelled with, for example, fluorescein, while the mutant ddNTP is labeled with something other than fluorescein, for example, Texas Red. Both primers are then added to a PCR and amplification is allowed to occur in the presence of a hybotrope of the invention, where the hybotrope is preferably a primary, secondary or tertiary amine salt of acetate, halogenated aceate, propionate or halogenated propionate. If the wildtype allele is present, then the wildtype primer will extend, and if the mutant target is present then the mutant primer will extend. If the wildtype allele is not present, then the wildtype primer will not extend, and if the mutant target is not present then the mutant primer will not extend. It is possible that both alleles are present and both the wildtype and mutant primers will both extend. The extended PCR primer products are then separated from the non-extended primers (by using a molecular weight cutoff filter, a size exclusion gel, etc.). A solution containing the extended products is then read using a fluorometer. The solution is scanned twice, once at the fluorescein emission and once at the Texas Red emission (or scanned simultaneously using a diode array fluorometer). The ratio of green to red is then calculated. If the ratio is about >5/1 green to red then both alleles are wildtype, if the ratio is about <0.2/1 green to red then both alleles are mutant, if the ratio is about 1/1 then both alleles are present. While this assay might be run with CMST-labeled dideoxynucleotides, the CMST tag must be carefully selected and positioned so as not to interfere with the action of the polymerase.

6. cDNAs as Representative Populations of mRNAs and use as Probes

Most mRNAs are transcribed from single copy sequences. Another property of cDNAs is that they represent a longer region of the genome because of the introns present in the chromosomal version of most genes. The representation varies from one gene to another but can be very significant as many genes cover more than 100 kb in genomic DNA, represented in a single cDNA. One possible use of molecular hybridization is the use of probes from one species to find clones made from another species. Sequence divergence between the mRNAs of mouse and man permits specific cross-reassociation of long sequences, but except for the most highly conserved regions, prevents cross-hybridization of PCR primers.

Differential screening in complex biological samples such as developing nervous system using cDNA probes prepared from single cells is now possible due to the development of PCR-based and cRNA-based amplification techniques. Several groups reported previously the generation of cDNA libraries from small amounts of poly (A)+RNA (1 ng or less) prepared from 10–50 cells (Belyav et al., *Nuc. Acids Res.* 17:2919, 1989). Although the libraries were sufficiently representative of mRNA complexity, the average cDNA insert size of these libraries was quite small (<2 kb).

More recently, methodologies have been combined to generate both PCR-based (Lambolez et al., *Neuron* 9:247, 1992) and cRNA-based (Van Gelder et al., *Proc. Natl. Acad. Sci. USA* 87:1663, 1990) probes from single cells. After electrical recordings, the cytoplasmic contents of a single cell were aspirated with patch-clamp microelectrodes for in situ cDNA synthesis and amplification. PCR was used to amplify cDNA of selective glutamate receptor mRNAs from single Purkinje cells and GFAP mRNA from single glia in organotypic cerebellar culture (Lambolez et al., *Neuron* 9:247, 1992). In the case of cRNA amplification, transcription promoter sequences were designed into primers for cDNA synthesis and complex antisense cRNAs were generated by in vitro transcription with bacteriophage RNA polymerases.

Thus, within one embodiment of the invention, tagged cRNAs can be utilized as tagged probes to screen cDNA libraries randomly or in "expression profiling" experiments to screen Southern blots containing cDNA fragments of interest (receptors, growth factors, ion channels etc.). It appears that the lack of linearity of amplification, often encountered with PCR-based approaches, is minimized with cRNA-based methods.

7. Oligonucleotide-Ligation Assay

Oligonucleotide-ligation assay is an extension of PCR-based screening that uses an ELISA-based assay (OLA, Nickerson et al., *Proc. Natl. Acad. Sci. USA* 87:8923, 1990) to detect the PCR products that contain the target sequence. Thus, both gel electrophoresis and colony hybridization are eliminated. Briefly, the OLA employs two adjacent oligonucleotides: a "reporter" probe (tagged at the 5' end) and a 5'-phosphorylated/3'-biotinylated "anchor" probe. The two oligonucleotides, which are complementary to sequences internal to the PCR primers, are annealed to target DNA and, if there is perfect complementarity, the two probes are ligated by T4 DNA ligase. Capture of the biotinylated anchor probe on immobilized streptavidin and analysis for the covalently linked reporter probe test for the presence or absence of the target sequences among the PCR products.

8. Application of Hybridization Techniques a. Forensics

The identification of individuals at the level of DNA sequence variation offers a number of practical advantages over such conventional criteria as fingerprints, blood type, or physical characteristics. In contrast to most phenotypic markers, DNA analysis readily permits the deduction of relatedness between individuals such as is required in paternity testing. Genetic analysis has proven highly useful in bone marrow transplantation, where it is necessary to distinguish between closely related donor and recipient cells. Two types of probes are now in use for DNA fingerprinting by DNA blots. Polymorphic minisatellite DNA probes identify multiple DNA sequences, each present in variable forms in different individuals, thus generating patterns that are complex and highly variable between individuals. VNTR probes identify single sequences in the genome, but these sequences may be present in up to 30 different forms in the human population as distinguished by the size of the identified fragments. The probability that unrelated individuals will have identical hybridization patterns for multiple VNTR or minisatellite probes is very low. Much less tissue than that required for DNA blots, even single hairs, provides sufficient DNA for a PCR-based analysis of genetic markers. Also, partially degraded tissue may be used for analysis since only small DNA fragments are needed. Forensic DNA analyses will eventually be carried out with polymorphic DNA sequences that can be studied by simple automatable assays such as OLA. For example, the analysis of 22 separate gene sequences, each one present in two different forms in the population, could generate 1010 different outcomes, permitting the unique identification of human individuals.

b. Tumor Diagnostics

The detection of viral or cellular oncogenes is another important field of application of nucleic acid diagnostics. Viral oncogenes (v-oncogenes) are transmitted by retroviruses while their cellular counterparts (c-oncogenes) are already present in normal cells. The cellular oncogenes can, however, be activated by specific modifications such s point mutations (as in the c-K-ras oncogene in bladder carcinoma and in colorectal tumors), promoter induction, gene amplification (as in the N-myc oncogene in the case of neuroblastoma) or the rearrangement of chromosomes (as in the translocation of the c-abl oncogene from chromosome 9 to chromosome 22 in the case of chronic myeloid leukemia). Each of the activation processes leads, in conjunction with additional degenerative processes, to an increased and uncontrolled cell growth. The so-called "recessive oncogenes" which must be inactivated for the formation of a tumor (as in the retinoblastoma (Rb gene and the osteosarcoma can also be detected with the help of DNA probes. Using probes against immunoglobulin genes and against T-cell receptor genes, the detection of B-cell lymphomas and lymphoblastic leukemia is possible.

C. Transplantation Analyses

The rejection reaction of transplanted tissue is decisively controlled by a specific class of histocompatibility antigens (HLA). They are expressed on the surface of antigen-presenting blood cells, e.g., macrophages. The complex between the HLA and the foreign antigen is recognized by T-helper cells through corresponding T-cell receptors on the cell surface. The interaction between HLA, antigen and T-cell receptor triggers a complex defense reaction which leads to a cascade-like immune response on the body.

The recognition of different foreign antigens is mediated by variable, antigen-specific regions of the T-cell receptor—analogous to the antibody reaction. In a graft rejection, the T-cells expressing a specific T-cell receptor which fits to the foreign antigen, could therefore be eliminated from the T-cell pool. Such analyses are possible by the identification of antigen-specific variable DNA sequences which are amplified by PCR and hence selectively increased. The specific amplification reaction permits the single cell-specific identification of a specific T-cell receptor.

Similar analyses are presently performed for the identification of auto-immune disease like juvenile diabetes, arteriosclerosis, multiple sclerosis, rheumatoid arthritis, or encephalomyelitis.

d. Genome Diagnostics

Four percent of all newborns are born with genetic defects; of the 3,500 hereditary diseases described which are caused by the modification of only a single gene, the primary molecular defects are only known for about 400 of them.

Hereditary diseases have long since been diagnosed by phenotypic analyses (anamneses, e.g., deficiency of blood: thalassemias), chromosome analyses (karyotype, e.g., mongolism: trisomy 21) or gene product analyses (modified proteins, e.g., phenylketonuria: deficiency of the phenylalanine hydroxylase enzyme resulting in enhanced levels of phenylpyruvic acid). The additional use of nucleic acid detection methods considerably increases the range of genome diagnostics.

In the case of certain genetic diseases, the modification of just one of the two alleles is sufficient for disease (dominantly transmitted monogenic defects); in many cases, both alleles must be modified (recessively transmitted monogenic defects). In a third type of genetic defect, the outbreak of the disease is not only determined by the gene modification but also by factors such as eating habits (in the case of diabetes or arteriosclerosis) or the lifestyle (in the case of cancer). Very frequently, these diseases occur in advanced age. Diseases such as schizophrenia, manic depression or epilepsy should also be mentioned in this context; it is under investigation if the outbreak of the disease in these cases is dependent upon environmental factors as well as on the modification of several genes in different chromosome locations.

Using direct and indirect DNA analysis, the diagnosis of a series of genetic diseases has become possible: sickle-cell anemia, thalassemias, al-antitrypsin deficiency, Lesch-Nyhan syndrome, cystic fibrosis/mucoviscidosis, Duchenne/Becker muscular dystrophy, Alzheimer's disease, X-chromosome-dependent mental deficiency, Huntington's chorea.

e. Infectious Disease

The application of recombinant DNA methods for diagnosis of infectious diseases has been most extensively explored for viral infections where current methods are cumbersome and results are delayed. In situ hybridization of tissues or cultured cells has made diagnosis of acute and chronic herpes infection possible. Fresh and fomalin-fixed tissues have been reported to be suitable for detection of papillomavirus in invasive cervical carcinoma and in the detection of HIV, while cultured cells have been used for the detection of cytomegalovirus and Epstein-Barr virus. The application of recombinant DNA methods to the diagnosis of microbial diseases has the potential to replace current microbial growth methods if cost-effectiveness, speed, and precision requirements can be met. Clinical situations where recombinant DNA procedures have begun to be applied include the identification of penicillin-resistant Neisseria gonorrhoeae by the presence of a transposon, the fastidiously growing chlamydia, microbes in foods; and simple means of following the spread of an infection through a population. The worldwide epidemiological challenge of diseases involving such parasites as leishmania and plasmodia is already being met by recombinant methods.

9. Gene Expression Analysis

Within a particularly preferred embodiment of the invention, assays or methods are provided which are described as follows: RNA from a target source is bound to a solid support through a specific hybridization step (i.e., capture of poly(A) mRNA by a tethered oligo(dT) capture probe). The solid support is then washed and cDNA is synthesized on the solid support using standard methods (i.e., reverse transcriptase). The RNA strand is then removed via hydrolysis. The result is the generation of a DNA population which is covalently immobilized to the solid support which reflects the diversity, abundance, and complexity of the RNA from which the cDNA was synthesized. The solid support then interrogated (hybridized) with 1 to several thousand probes that are complementary to a gene sequence of interest. Each probe type is labeled with a cleavable mass spectrometry tag or other type of cleavable tag. After the interrogation step, excess or unhybridized probe is washed away, the solid support is placed (for example) in the well of a microtiter plate and the mass spectrometry tag is cleaved from the solid support. The solid support is removed from the well of sample container, and the contents of the well are measured with a mass spectrometer. The appearance of specific mass spectrometer tags indicate the presence of RNA in the sample and evidence that a specific gene is expressed in a given biological sample. The method can also be quantifiable.

The compositions and methods for the rapid measurement of gene expression using cleavable tags can be described in detail as follows. Briefly, tissue (liver, muscle, etc.), primary or transformed cell lines, isolated or purified cell types or any other source of biological material in which determining genetic expression is useful can be used as a source of RNA. In the preferred method, the biological source material is lysed in the presence of a chaotrope in order to suppress nucleases and proteases and support stringent hybridization of target nucleic acid to the solid support. Tissues, cells and biological sources can be effectively lysed in 1 to 6 molar chaotropic salts (guanidine hydrochloride, guanidine thiocyanate, sodium perchlorate, etc.). After the source biological sample is lysed, the solution is mixed with a solid support to effect capture of target nucleic acid present in the lysate. In one permutation of the method, RNA is captured using a tethered oligo(dT) capture probe. Solid supports can include nylon beads, polystyrene microbeads, glass beads and glass surfaces or any other type of solid support to which oligonucleotides can be covalently attached. The solid supports are preferentially coated with an amine-polymer such as polyethylene(imine), acrylamide, amine-dendrimers, etc. The amines on the polymers are used to covalently immobilize oligonucleotides. Oligonucleotides are preferentially synthesized with a 5'-amine (generally a hexylamine which is includes a six carbon spacer-arm and a distal amine). Oligonucleotides can be 15 to 50 nucleotides in length. Oligonucleotides are activated with homo-bifunctional or hetero-bifunctional cross-linking reagents such as cyanuric chloride. The activated oligonucleotides are purified from excess cross-linking reagent (i. e., cyanuric chloride) by exclusion chromatography. The activated oligonucleotide are then mixed with the solid supports to effect covalent attachment. After covalent attachment of the oligonucleotides, the unreacted amines of the solid support are capped (i.e., with succinic anhydride) to eliminate the positive charge of the solid support.

The solid supports can be used in parallel and are preferentially configured in a 96-well or 384-well format. The solid supports can be attached to pegs, stems, or rods in a 96-well or 384-well configuration, the solid supports either being detachable or alternatively integral to the particular configuration. The particular configuration of the sold supports is not of critical importance to the functioning of the assay, but rather, affects the ability of the assay to be adapted to automation.

The solid supports are mixed with the lysate for 15 minutes to several hours to effect capture of the target nucleic acid onto the solid support. In general, the "capture" of the target nucleic acid is through complementary base pairing of target RNA and the capture probe immobilized on the solid support. One permutation utilizes the 3' poly(A) stretch found on most eucaryotic messengers RNAs to hybridize to a tethered oligo(dT) on the solid support. Another permutation is to utilize a specific oligonucleotide or long probes (greater than 50 bases) to capture an RNA containing a defined sequence. Another possibility is to employ degenerate primers (oligonucleotides) that would effect the capture of numerous related sequences in the target RNA population. Hybridization times are guided by the sequence complexity of the RNA population and the type of capture probe employed. The lysate is preferentially agitated with the solid support continually to effect diffusion of the target RNA. Once the step of capturing the target nucleic acid is accomplished, the lysate is washed from the solid support and all chaotrope or hybridization solution is removed. The solid support is preferentially washed with solutions containing ionic or non-ionic detergents, buffers and salts. The next step is the synthesis of DNA complementary to the captured RNA. In this step, the tethered capture oligonucleotide serves as the extension primer for reverse transcriptase. The reaction is generally performed at 25 to 37° C. and preferably agitated during the polymerization reaction. After the cDNA is synthesized, it becomes covalently attached to the solid support since the capture oligonucleotide serves as the extension primer. The RNA is then hydrolyzed from the cDNA/RNA duplex. The step can be effected by the use of heat which denatures the duplex or the use of base (i.e., 0.1 N NaOH) to chemically hydrolyze the RNA. The key result at this step is to make the cDNA available for subsequent hybridization with defined probes. The solid support or set of solid supports are then further washed to remove RNA or RNA fragments. At this point the solid support contains a approximate representative population of cDNA molecules that represents the RNA population in terms of sequence abundance, complexity, and diversity.

The next step is to hybridize selected probes to the solid support to identify the presence or absence and the relative abundance specific cDNA sequences. Probes are preferentially oligonucleotides in length of 15 to 50 nucleotides. The sequence of the probes is dictated by the end-user of the assay. For example, if the end-user intended to study gene expression in an inflammatory response in a tissue, probes would be selected to be complementary to numerous cytokine mRNAs, RNAs that encode enzymes that modulate lipids, RNAs that encode factors that regulate cells involved in an inflammatory response, etc. Once a set of defined sequences are defined for study, each sequence is made into an oligonucleotide probe. The tag(s) is then attached to the respective oligonucleotide(s). The oligonucleotide(s) are then hybridized to the cDNA on the solid support under appropriate hybridization conditions. After completion of the hybridization step, the solid support is washed to remove any unhybridized probe. The presence (and abundance) or absence of an expressed mRNA is then determined.

10. Single Nucleotide Extension Assay

The primer extension technique may be used for the detection of single nucleotide changes in a nucleic acid template (Sokolov, *Nucleic Acids Res.,* 18:3671, 1989). The technique is generally applicable to detection of any single base mutation (Kuppuswamy et al., *Proc. Natl. Acad. Sci. USA,* 88:1143–1147, 1991). Briefly, this method first hybridizes a primer to a sequence adjacent to a known single nucleotide polymorphism. The primed DNA is then subjected to conditions in which a DNA polymerase adds a labeled dNTP, typically a ddNTP, if the next base in the template is complementary to the labeled nucleotide in the reaction mixture. In a modification, cDNA is first amplified for a sequence of interest containing a single-base difference between two alleles. Each amplified product is then analyzed for the presence, absence, or relative amounts of each allele by annealing a primer that is 1 base 5' to the polymorphism and extending by one labeled base (generally a dideoxynucleotide). Only when the correct base is available in the reaction will a base to incorporated at the 3'-end of the primer. Extension products are then analyzed by hybridization to an array of oligonucleotides such that a non-extended product will not hybridize.

Briefly, in the present invention, each dideoxynucleotide is labeled with a unique tag. Of the four reaction mixtures, only one will add a dideoxy-terminator on to the primer sequence. If the mutation is present, it will be detected through the unique tag on the dideoxynucleotide after hybridization to the array. Multiple mutations can be simultaneously determined by tagging the DNA primer with a unique tag as well. Thus, the DNA fragments are reacted in four separate reactions each including a different tagged dideoxyterminator, wherein the tag is correlative with a particular dideoxynucleotide and detectable by non-fluorescent spectrometry, or potentiometry. The DNA fragments are hybridized to an array and non-hybridized material is washed away. The tags are detected by the respective detection technology (e.g., fluorescence, infrared spectrometry, potentiostatic amperometry or UV/visible spectrophotometry). The tags detected can be correlated to the particular DNA fragment under investigation as well as the identity of the mutant nucleotide.

11. Other Assays

The methods described herein may also be used to genotype or identification of viruses or microbes. For example, F+RNA coliphages may be useful candidates as indicators for enteric virus contamination. Genotyping by nucleic acid amplification and hybridization methods are reliable, rapid, simple, and inexpensive alternatives to serotyping (Kafatos et. al., *Nucleic Acids Res.* 7:1541, 1979). Amplification techniques and nucleic aid hybridization techniques have been successfully used to classify a variety of microorganisms including *E. coli* (Feng, Mol. *Cell Probes* 7:151, 1993), rotavirus (Sethabutr et. al., *J. Med Virol.* 37:192, 1992), hepatitis C virus (Stuyver et. al., *J. Gen Virol.* 74:1093, 1993), and herpes simplex virus (Matsumoto et. al., *J. Virol. Methods* 40:119, 1992).

Genetic alterations have been described in a variety of experimental mammalian and human neoplasms and represent the morphological basis for the sequence of morphological alterations observed in carcinogenesis (Vogelstein et al., *NEJM* 319:525, 1988). In recent years with the advent of molecular biology techniques, allelic losses on certain chromosomes or mutation of tumor suppressor genes as well as mutations in several oncogenes (e.g., c-myc, c-jun, and the ras family) have been the most studied entities. Previous work (Finkelstein et al., *Arch Surg.* 128:526, 1993) has identified a correlation between specific types of point mutations in the K-ras oncogene and the stage at diagnosis in colorectal carcinoma. The results suggested that mutational analysis could provide important information of tumor aggressiveness, including the pattern and spread of metastasis. The prognostic value of TP53 and K-ras-2 mutational analysis in stage III carconoma [carcinoma???] of the colon has more recently been demonstrated (Pricolo et al., *Am. J. Surg.* 171:41, 1996). It is therefore apparent that genotyping of tumors and pre-cancerous cells, and specific mutation detection will become increasingly important in the treatment of cancers in humans.

D. Hybotropes and Nucleic Acid Molecules in Arrays

In the fields of molecular biology and microbiology, it has long been common to employ solid supports having biomolecules immobilized thereon. Immobilization provides various advantages, such as, allowing for multiplexing of samples and ready measurements of tags employed in a large number of signal systems.

Recently, intense attention has focused on creating arrays of biomolecules, and particularly polynucleotides, on a flat solid support. The advent of large scale genomic projects and the increasing medical use of molecular diagnostics, has prompted the development of large volume throughput methods for screening recombinant DNA libraries representing entire genomes, the performance of large scale DNA sequencing projects, and executing replicative immunological assays, nucleic acid hybridization assays, or polymerase chain reaction assays. The following publications (and the references cited therein), which are exemplary only, provide general and specific overviews of large throughput methods that rely on biomolecular arrays, as well as methods of preparing such arrays: M. D. Eggers et al., *Advances in DNA Sequencing Technology, SPIE* 1891:113–126, 1993; A. B. Chetverin et al., *BioTechnology* 12:1093–1099, 1994; E. M. Southern, *Nucleic Acids Research* 22:1368–1373, 1994; R. J. Lipshutz et al., *BioTechniques* 19:442–447, 1995; M. Schena *BioEssays* 18:427–431, 1996; A. P. Blanchard et al., *Biosensors & Bioelectronics* 11:687–690, 1996; M. J. O'Donnell-Maloney et al., *Genetic Analysis: Biomolecular Engineering* 13:151–157, 1996; A. Regalado, *Start-Up* 24–30, October 1996; and D. Stipp, *Fortune* 30–41, Mar. 31, 1997.

The need for high throughput methodology has led, in some cases, to a change from a 96-well microtiter dish format, to a 384-well (Maier et al., *J. Biotechnology* 35:191, 1994) or 864-well (Drmanac et al., *Electrophoresis* 13:120, 1992) format, which can also be used in conjunction with robotic devises (see, e.g., Belgrader et al., *BioTechniques* 19:426, 1995; Wilke et al., *Diagnostic Microbiology and Infect. Disease* 21:181, 1995). However, all of these automated techniques require the use of a robotic pin-tool devise that is capable of reproducibly transferring equal volumes of liquid from one arrayed configuration (i.e., 96-well microtiter plate) to another (i.e., 96-spot array on a hybridization filter membrane).

Recently, methods have also been developed to synthesize large arrays of short oligodeoxynucleotides (ODNs) bound to a glass surface that represent all, or a subset of all, possible nucleotide sequences (Maskos and Southern, *Nucl. Acids Res.* 20:1675, 1992, incorporated herein by reference). Once such an ODN array has been made it may be used to perform DNA sequencing by hybridization (Southern et al., *Genomics* 13:1008, 1992; Drmanac et al., *Science* 260:1649, 1993, incorporated herein by reference). The utility of this method of DNA sequencing would be greatly improved if better methods existed for the transfer and arraying of the precise amounts of the biochemical reagents required for the synthesis of large sets ODNs bound to hybridizable surfaces. This would enable greater equality of ODN yield at each position within the array and also increase the nucleotide chain length it is possible to synthesize.

The polymerase chain reaction (PCR) has found wide application to many different biological problems. Two major limitations to the commercial utilization of PCR are the high cost of the reagents and the inability to automate the performance of the process. Reagent costs can be lowered if the total volume of each reaction can be decreased, allowing a concomitant decrease in DNA polymerase and nucleotides. An accurate and reliable means to array small volumes of reagents using a robotically controlled pin tool could help solve both of these PCR problems.

The combination of hybotropes and modified oligonucleotide probes described in this application will permit the useful multiplexing of probes and "capture" oligonucleotides in the array format. As stated above, the present invention provides (a) a composition that includes a nucleic acid molecule, preferably having 6–100 nucleotides, and a hybotrope salt; (b) a non-flowing composition that includes a nucleic acid molecule of 6–100 nucleotides and a hybotrope salt; (c) a composition which is free from organic solvent, and includes a nucleic acid molecule of 6–100 nucleotides and a hybotrope salt. In one embodiment, the nucleic acid molecule is DNA. In another embodiment, the nucleic acid molecule is RNA. In yet another embodiment, the nucleic acid molecule is cDNA.

The nucleic acid molecule in these compositions may be immobilized (affixed) on a solid support, and in fact may be arranged in an array on a solid support. The nucleic acid molecule may be immobilized by any of the immobilization techniques known in the art, and mentioned above. The nucleic acid may be immobilized by contacting the nucleic acid with a solid support having a coating of poly (ethyleneimine) (PEI). The solid support may be organic or inorganic, where organic solid supports include plastics such as nylon-6,6, nylon and polystyrene, while inorganic solid supports include quartz, gold, glass and silicon. Preferred solid supports are a glass plate and a silicon wafer. The PEI coating may be applied by the methods disclosed in Van Ness, et al. *Nucleic Acids Res.* 19:3345, 1991, and international publication No. WO 94/00600, both of which are incorporated herein by reference. Suitable methods of applying a layer of PEI to solid supports of glass or silicon are described, for example, by Wasserman, *Biotechnology and Bioengineering* XXII:271, 1980, and by D'Souza, *Biotechnology Letters* 8:643, 1986. The preparation of biomolecule arrays using a PEI coating on a flat surface is described in our co-pending U.S. Patent Application No. 60/053,435 which is hereby incorporated by reference.

When in an array format, the nucleic acid molecules are preferably arranged in separated domains which form the array, where the number of domains present in an array is selected from the ranges 10 to 50, 50 to 400, and 400 to 800. Typically, the domains are substantially circular, where the circles have an average diameter of about 10 microns to 200 microns. In the array, the nucleic acid molecules represent a plurality of sequences, such that each domain may have a unique sequence of native nucleotides (i.e., adenosine/deoxyadenosine 5' phosphate, (AMP and dAMP), guanosine/deoxyguanosine 5' phosphate (GMP and dGMP)), cytidine/deoxycytidine 5' phosphate (CMP and dCMP), uridine 5' phosphate (UMP), and deoxythymidine 5' phosphate (dTMP)) and specificity spaces, or wherein each domain may contain nucleic acid molecules having differing sequences of native nucleotides and specificity spacers.

In one embodiment, the invention provides an array containing a plurality of oligonucleotides immobilized in an array format to a solid support. Each oligonucleotide of the plurality includes a plurality of fragments, where each fragment is shown schematically by structure (1)

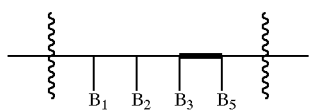

(1)

wherein

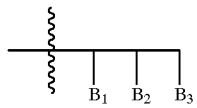

represents a sequence of at least three nucleotides as found in wild-type DNA, where "B" represents a base (adenine, guanine, cytosine, thymine or uracil) independently selected at each location; —— represents a series of covalent chemical bonds termed a "specificity spacer," which separates and connects two bases $B_3$ and $B_5$. The specificity spacer has steric and chemical properties such that (a) it does not prevent hybridization between a fragment of structure (1) and an oligonucleotide fragment having a complementary base sequence, as shown schematically as structure (2)

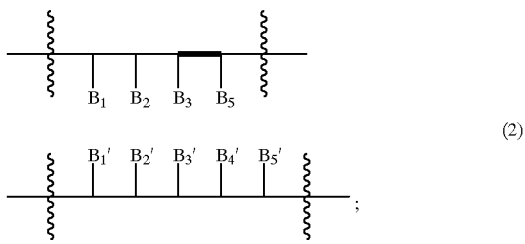

and (b) it cannot enter into hydrogen bonding with a base positioned opposite itself in a hybridized complementary base sequence of structure (2).

In the array, the specificity spacer may have the formula

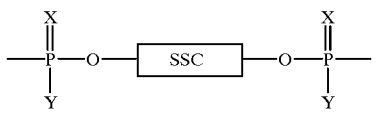

wherein X is oxygen (O) or sulfur (S), Y is selected from oxygen, sulfur, methyl and amino when X is oxygen, or Y is selected from oxygen and sulfur when X is sulfur; and SSC represents a specificity spacer component having a chain of 2–5 carbon atoms shown in the structure (4)

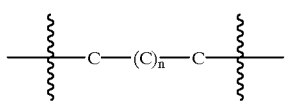

(4)

wherein n is 0, 1, 2 or 3, and each of the shown 2–5 carbon atoms of the specificity spacer component may be independently substituted with $C_1$–$C_{10}$hydrocarbyl or $C_1$–$C_{10}$hydrocarbyloxy, and any two of the shown 2–5 carbon atoms which are bonded directly to one another may form a carbocyclic or heterocyclic 5–6 membered ring.

In the array, the specificity spacer component may have the formula (5)

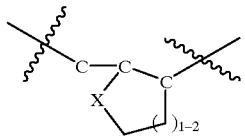

(5)

wherein n is 1 and X is selected from carbon, oxygen and sulfur, such that any carbon shown in formula (5), including X when it is carbon, may be substituted with hydrogen, $C_1$–$C_5$hydrocarbyl, $C_1$–$C_5$hydrocarbyloxy, a non-hydrogen bonding purine base analog or non-hydrogen bonding pyrimidine base analog.

In the array, the specificity spacer component may have the structure (6)

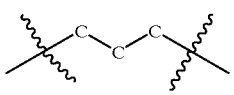

(6)

wherein each of the three shown carbons may be substituted with hydrogen, $C_1$–$C_{10}$ hydrocarbyl or $C_1$–$C_{10}$ hydrocarbyloxy.

In a preferred array, each of the plurality of oligonucleotides has a plurality of specificity spacers, where no two specificity spacers are adjacent to one another. In fact, preferably all nearest specificity spacers are separated by 4–14 nucleotides having wild-type sequence. The oligonucleotides affixed in the array format contain specificity spacers such that nearest specificity spacers are preferably separated by 5–6 nucleotides having wild-type sequence. In another embodiment, all nearest specificity spacers in the affixed oligonucleotides are separated by 8–12 nucleotides having wild-type sequence. Furthermore, it is preferred that specificity spacers constitute 15–60% of the positions occupied by the total of specificity spacers and nucleotides having wild-type sequence.

Hybotropes that neutralize the G+C content effect on $T_m$ or $T_d$ are especially useful in the application and use of array technology. In traditional hybridization solutions the difference in $T_m$ or $T_d$ when the G+C content is varied from 20% to 80% is generally 12 to 16° C. Therefore is it impossible to maintain the ideal hybridization temperature which is 1 to 8 degrees below the $T_m$ of the respective oligonucleotide duplex as the G+C content is varied. Solutions (hybotropes) which neutralize the effect of G+C on $T_m$ or $T_d$ permit the useful multiplexing of probes. Hybotropes such as bis(2-methoxyethyl)amine acetate, 1-ethylpiperidine acetate, 1-ethylpiperidine trichloroacetate, 1-ethylpiperidine trifluoroacetate, 1-methylimidizole acetate, 1-methylpiperidine acetate, 1-methylpiperidine trichloroacetate, 1-methylpyrrolidine acetate, 1-methylpyrrolidine trichloroacetate, 1-methylpyrrolidine trifluoroacetate, 2-methoxyethylamine acetate, N,N-dimethylcyclohexylamine acetate, N,N-dimethylcyclohexylamine trifluoroacetate, N,N-dimethylcyclohexylamine, N,N-dimethylheptylamine acetate, N,N-dimethylheptylamine acetate, N,N-dimethylhexylamine acetate, N,N-dimethylhexylamine acetate, N,N-dimethylisopropylamine acetate, N-ethylbutylamine acetate, N-ethylbutylamine trifluoroacetate, N,N-dimethylaminobutane trichloroacetate, N,N-dimethylisopropylamine trichloroacetate, triethanolamine acetate, triethylamine acetate, triethylamine trichloroacetate, tripropylamine acetate, tetraethylammonium acetate are useful in array formats.

A number of genetic diseases are caused by single, or a limited set, of mutations due to founder effects or advantages to heterozygous carriers. There is an increasing clinical interest in monitoring sequence variants associated with, for example, altered metabolism of drugs or serving as genetic markers in forensic medicine, and in the diagnosis of infectious disease, identification of drug-resistant variant strains may require distinction between similar sequence variants.

The solutions described herein are used to increase the specificity of priming in the PCR. There are several options in terms of a mechanism in which the specificity of the priming step can be improved. The first is a through the use of a solid support to which one of the PCR primers is (covalently) attached. The solid support can take many forms such as beads, membranes, etc. The priming step can take place in the hybotrope and then the solid support can be washed and moved into a solution that supports the polymerase chain extension. The solid support is then moved back into the nesstrope for the priming reaction and the cycle is repeated. The cycling of the solid support between the two different solutions only has to occur to a limited number of times (1–15 cycles) after which time the traditional amplification cycle in a standardized PCR buffer can be allowed proceed. Alternatively, the target nucleic acids of interest are moved between the priming solution and the polymerase extension reaction solution using electric fields (i.e., electrophoresis).

The use of hybotropes and/or specificity spacer-containing (including abasic residue-containing or base analog residue-containing) oligonucleotide probes can be used to increase the specificity and efficiency of isothermal applications of polymerases to the amplification of nucleic acid sequences. Applications of isothermal conditions for using nucleic acid polymerases include nucleic acid sequencing, genotyping, mutation detection, oligonucleotide ligation assays, mutation detection, and the like.

Within the context of the present invention it should be understood that "biological samples" include not only samples obtained from living organisms (e.g., mammals, fish, bacteria, parasites, viruses, fungi and the like) or from the environment (e.g., air, water or solid samples), but biological materials which may be artificially or synthetically produced (e.g., phage libraries, organic molecule libraries, pools of genomic clones and the like). Representative examples of biological samples include biological fluids (e.g., blood, semen, cerebral spinal fluid, urine), biological cells (e.g., stem cells, B or T cells, liver cells, fibroblasts and the like), and biological tissues.

Within various embodiments of the above-described methods, the nucleic acid probes and or molecules of the present invention may be generated by, for example, a ligation, cleavage or extension (e.g., PCR) reaction. Within other related aspects the nucleic acid probes or molecules may be tagged at their 5'-end, and the so-tagged molecules function as oligonucleotide primers or dideoxynucleotide terminators.

The following examples are offered by way of illustration, and not by way of limitation.

EXAMPLES

Example 1

Preparation, Properties, and Uses of Novel Hybotropes

A novel hybotrope is synthesized which demonstrates properties not previously described for a salt solution. The amine-based compounds are synthesized into acetate salts, trichloroacetate salts, trifluoroacetate salts and the like by neutralization of the base with acetic acid, trichloroacetic acid, or trifluoroacetic acid. Stock solutions of 1–6 M were prepared. In some cases the base amine was re-distilled prior to use. In some cases the resulting salt solution is then dried under vacuum to complete dryness and the mass is determined. The salt is then dissolved in water to a final concentration of 0.5 to 3.0 M. In some cases the resulting salt solution is then buffered with a buffer such as Tris-HCl, pH 7.0–8.5, and detergents, such as sarkosyl, are added to about 0.1%, and optionally EDTA is added to 0.5 to 5 mM.

Tetramethyl ammonium- and tetraethyl ammonium-trichloroacetate are synthesized by neutralizing tetramethyl ammonium- and tetraethyl ammonium-hydroxide with trichloroacetate to pH 7.0 to pH 8.5, depending upon the application. The resulting salt solution is then dried under vacuum to complete dryness and the mass is determined. The salt is then dissolved in water to a final concentration of 0.5 to 3.0 M. The resulting salt solution is then buffered with a buffer such as Tris-HCl, pH 7.0–8.5, and detergents, such as sarkosyl, are added to about 0.1%, and optionally EDTA is added to 0.5 to 5 mM.

These hybotropes possess the property of neutralizing the differences in G+C and A+T base-pairing strength while simultaneously lowering the $T_d$ and $\Delta AT_d$, increasing $\Delta T_d$. In Table 6, the characteristics of the novel hybotropes are set forth.

25% G+C content: 5'-AAATAATTCAGGGTCAAAA-3' (SEQ ID NO:10)
36% G+C content: 5'-CTGTCGTAGGTAAATAACT-3' (SEQ ID NO:11)
42% G+C content: 5'-AAAAAGTGGGGAAGTGAGT-3' (SEQ ID NO:12)
57% G+C content: 5'-GTGTTAACTTCCGCTCCTC-3' (SEQ ID NO:13)
63% G+C content: 5'-GGCGTAGGTCTGTCGTGCT-3' (SEQ ID NO:14)
73% G+C content: 5'-GGTGTGGGTCCGTCGTGCC-3' (SEQ ID NO:15)

The following $T_d$s are obtained in the hybridizations described below:

TABLE 6

| Solution Type | Length of Probe | G + C Content | $T_d$ | HCT |
|---|---|---|---|---|
| 0.5 M DMCHAA | 19-mer | 25% | 35.0 | 18 |
| 0.5 M DMCHAA | 19-mer | 36% | 36.5 | 18 |
| 0.5 M DMCHAA | 19-mer | 42% | 36.5 | 18 |
| 0.5 M DMCHAA | 19-mer | 57% | 36.0 | 18.5 |
| 0.5 M DMCHAA | 19-mer | 63% | 37 | 19 |
| 0.5 M DMCHAA | 19-mer | 73% | 37 | 19 |
| 3 M TEATCA | 19-mer | 25% | 38.0 | 7.5 |
| 3 M TEATCA | 19-mer | 36% | 38.5 | 10 |
| 3 M TEATCA | 19-mer | 42% | 39 | 11.5 |
| 3 M TEATCA | 19-mer | 57% | 40 | 12 |
| 3 M TEATCA | 19-mer | 63% | 41 | 13 |
| 3 M TEATCA | 19-mer | 73% | 42 | 14 |
| 3 M TMACl | 19-mer | 25% | 37 | 12.5 |
| 3 M TMACl | 19-mer | 36% | 62 | 14 |
| 3 M TMACl | 19-mer | 42% | 60 | 15.5 |
| 3 M TMACl | 19-mer | 57% | 65 | 17 |
| 3 M TMACl | 19-mer | 63% | 59 | 17.5 |
| 3 M TMACl | 19-mer | 73% | 59 | 17.5 |
| 0.5 M EP | 19-mer | 25% | 56.5 | 25 |
| 0.5 M EP | 19-mer | 36% | 56.5 | 25 |
| 0.5 M EP | 19-mer | 42% | 57 | 25.5 |
| 0.5 M EP | 19-mer | 57% | 57 | 25.5 |
| 0.5 M EP | 19-mer | 63% | 58 | 26 |
| 0.5 M EP | 19-mer | 73% | 58.5 | 26.5 |
| 3 M TMATCA | 19-mer | 25% | 44.5 | 8 |
| 3 M TMATCA | 19-mer | 36% | 45.5 | 10 |
| 3 M TMATCA | 19-mer | 42% | 43 | 11.5 |
| 3 M TMATCA | 19-mer | 57% | 48.5 | 12 |
| 3 M TMATCA | 19-mer | 63% | 47 | 13 |
| 3 M TMATCA | 19-mer | 73% | 48.5 | 14 |
| 2 M TMATCA | 19-mer | 25% | 43 | 15 |
| 2 M TMATCA | 19-mer | 36% | 44.5 | 17 |
| 2 M TMATCA | 19-mer | 42% | 44.5 | 18 |
| 2 M TMATCA | 19-mer | 57% | 53 | 19.5 |
| 2 M TMATCA | 19-mer | 63% | 48 | 19.5 |
| 2 M TMATCA | 19-mer | 73% | 52 | 19 |
| 30% formamide | 19-mer | 25% | 25 | 20 |
| 30% formamide | 19-mer | 36% | 27.5 | 20 |
| 30% formamide | 19-mer | 42% | 29 | 20 |
| 30% formamide | 19-mer | 57% | 40 | 21 |
| 30% formamide | 19-mer | 63% | 37.5 | 22 |
| 30% formamide | 19-mer | 73% | 40 | 23 |

TABLE 6-continued

The data in Table 6 clearly indicate a decrease in the helical coil transition in solutions containing 3 M TMATCA or 3 M TEACl compared to the control solution which is TMACl. An average decrease of 3.5° C. is observed for solutions containing 3 M TMATCA or 3 M TEACl compared to the control solution which iss TMACl. Also, formamide has a surprisingly high value for the helical coil transition, which ranges from 20 to 23° C. depending on the G+C value. Also shown is the concentration dependence of the ability of a TMATCA solution to neutralize G+C content. At 2 M, TMATCA is neither able to neutralize G+C content or reduce the HCT. The data of Table 6 clearly indicates an excellent G+C neutralization effect on low molarity solutions (0.5 M) of EP and DMCHAA.

Example 2

Determintion of the Melting Temperature of Oligonucleotide Duplexes in Various Hybotrope and Non-Hybotrope Based Hybridization Solutions This example describes the determination of the $T_d$ of wild type and mutant oligonucleotides when hybridized to a target nucleic acid. It is shown that hybotrope based hybridization solutions allow the detection of single base pair mutations in a nucleic acid target with a probe up to a 30 nucleotides in length.

Solutions and Reagents

Filter wash (FW) is 0.09 M NaCl, 540 mM Tris pH 7.6, 25 mM EDTA. SDS/FW is FW with 0.1% sodium dodecyl sulfate (SDS). Hybridization solutions contain the text specified concentration of hybotrope 2% N-lauroylsarcosine (sarcosyl), 50 mM Tris pH 7.6 and 25 mM EDTA. Formamide hybridization solution contains 30% formamide, 0.09 M NaCl, 40 mM Tris-HCl pH 7.6, 5 mM EDTA and 0.1% SDS. GuSCN is purchased from Kodak (Rochester, N.Y.). GuCl, lithium hydroxide, trichloroacetic acid, NaSCN, $NaClO_4$ and KI, are purchased from Sigma (St. Louis, Mo). Rubidium hydroxide is purchased from CFS Chemicals (Columbus, Ohio). CsTFA is purchased from Pharmacia (Piscataway, N.J.).

Preparation of LiTCA, TMATCA and TEATCA

LiTCA and TMATCA, and TEATCA are prepared by the dropwise titration of a 3 N solution of LiOH, TEAOH and TMAOH respectively, with trichloroacetic acid (100% w/v, 6.1 N) to pH 7.0 on ice with constant stirring. The salt is evaporated to dryness under vacuum, washed once with ether and dried. In general, the amine-based compounds are synthesized into acetate salts, trichloroacetate salts, trifluoroacetate salts and the like by neutralization of the base with acetic acid, trichloroacetic acid, or trifluoroacetic acid. Stock solutions of 1–6 M were prepared. In some cases the base amine was re-distilled prior to use. In some cases the resulting salt solution is then dried under vacuum to complete dryness and the mass is determined. The salt is then dissolved in water to a final concentration of 0.5 to 3.0 M. In some cases the resulting salt solution is then buffered with a buffer such as Tris-HCl, pH 7.0–8.5, and detergents, such as sarkosyl, are added to about 0.1%, and optionally EDTA is added to 0.5 to 5 mM.

Tetramethyl ammonium- and tetraethyl ammonium-trichloroacetate are synthesized by neutralizing tetramethyl ammonium- and tetraethyl ammonium-hydroxide with trichloroacetate to pH 7.0 to pH 8.5, depending upon the application. The resulting salt solution is then dried under vacuum to complete dryness and the mass is determined. The salt is then dissolved in water to a final concentration of 0.5 to 3.0 M. The resulting salt solution is then buffered with a buffer such as Tris-HCl, pH 7.0–8.5, and detergents, such as sarkosyl, are added to about 0.1%, and optionally EDTA is added to 0.5 to 5 mM.

Oligonucleotide Synthesis

Oligonucleotides are synthesized on a commercial synthesizer using standard cyanoethyl-N,N-diisopropylaminophosphoramidite (CED-phosphoramidite) chemistry. Amine tails are incorporated onto the 5'-end using the commercially available N-monomethoxytritylaminohex-6-yloxy-CED-phosphoramidite. Alternatively, oligonucleotides are commercially purchased (Midland Certified Reagents, Midland, Tex.).

Oligonucleotides

The following oligonucleotides are used to measure the difference in $T_d$ between a wild type oligonucleotide and a mutant oligonucleotide. The wild type oligonucleotide represents fully and perfectly base-paired duplex and a mutant oligonucleotide represents a single base pair mismatch (generally in the middle of the oligonucleotide).

The sequence of the "capture" oligonucleotide is 5'-GTCATACTCCTGCTTGCTGATCCACATCTG-3' (SEQ ID NO: 1). The sequence of the wild type 30-mer is 5'-CAGATGGGTATCAGCAAGCAGGAGTATGAC-3' (SEQ ID NO:16), the sequence for the wild type 24-mer 5'-ATGGGTATCAGCAAGCAGGAGTAT-3' (SEQ ID NO: 17), the sequence for the wild type 18-mer 5'-GGTATCAGCAAGCAGGAG-3' (SEQ ID NO: 18). The sequence of the mutant 30-mer is 5'-CAGATGGGTATCAGGAAGCAGGAGTATGAC-3' (SEQ ID NO: 19), the sequence for the mutant 24-mer 5'-ATGGGTATCAGGAAGCAGGAGTAT-3' (SEQ ID NO: 20), the sequence for the mutant 18-mer 5'-GGTATCAGGAAGCAGGAG-3'(SEQ ID NO:21).

Melting temperature measurements can be performed using either beads or tips, to which oligonucleotide is bound. Each of these methods is described below. The use of tips is generally preferred as it affords a high throughput method for the measurement of the thermodynamic properties of oligonucleotide duplexes.

Preparation and Use of Nylon Bead Supports (ODN-Bead)

ODN (oligonucleotide)-beads (3/32nd inch diameter) are prepared as previously described (Van Ness et al., *Nucl. Acids Res.* 19:3345, 1991). The ODN-beads contain 0.01 to 1.2 mg/bead of covalently immobilized ODN.

$T_d$ and $T_{opt}$ values may be determined using the ODN-Beads in various hybridization solutions containing hybotropic salts. Amine ODNs are labeled by reaction with amine-reactive fluorochromes. The derived ODN preparation is divided into 3 portions and each portion is reacted with (a) 20-fold molar excess of Texas Red sulfonyl chloride (Molecular Probes, Eugene, Oreg.); (b) 20-fold molar excess of Lissamine sulfonyl chloride (Molecular Probes, Eugene, Oreg.); or (c) 20-fold molar excess of fluorescein isothiocyanate. The final reaction conditions consist of 0.15 M sodium borate at pH 8.3 for 1 hour at room temperature. The unreacted fluorochromes are removed by size exclusion chromatography on a G-50 Sephadex column.

For the determination of ODN/ODN $T_d$ from the ODN-bead, fluorescently-labeled ODN is incubated in various hybridization solutions with a complementary ODN immobilized on ODN-beads. From 5 to 5000 ng of ODN are hybridized in 300–400 μl volumes at various temperatures (19–65° C.) for 5–30 minutes with constant agitation. The beads are washed with 3×1 ml of the respective hybridization solution, and then once with the respective melting solution at the starting temperature of the melting process. The beads in 300–400 μl of the respective melting solution are then placed in a 0–15° C. water bath. At 5 minute intervals, the temperature is raised 5° C., the solution decanted into a well of a microtiter plate, and fresh solution (5° C. below the next increment) is added to the beads. The "melting" or duplex dissociation is conducted over a temperature range of 15° C. to 95° C. Fluorescence is measured with a commercial fluorescence plate reader.

To calculate the $T_d$, cumulative counts eluted at each temperature are plotted against temperature. The temperature at which 50% of the material is dissociated from the bead is the $T_d$.

For determining RNA/ODN or DNA/ODN $T_d$ from nylon membranes (Schleicher & Schuell, Keene, N. H.), $^{32}$P-labeled ODN (3'-labeled with terminal transferase) is incubated with 0.5 cm² pieces of membrane, in the specified hybridization solutions. For the (non-covalent) immobilization of genomic DNA onto nylon membranes, purified DNA is denatured in 0.3 M NaOH at 20° C. for 10 minutes. An equal volume of 2 M ammonium acetate is added and the sample was applied to Nytran membranes assembled in a slot blot apparatus. RNA was denatured in 4.6 M formaldehyde-6×SSC (0.9 M NaCl, 90 mM sodium citrate) for 15 min. at 60° C. and applied to the membranes as above. After immobilization of the nucleic acids, the filters were baked at 80° C. for 2 hours, then stored dry at ambient temperature. The hybridizations and dissociations were then performed as described above for the nylon bead solid supports.

To determine the $T_{opt}$ODN (the temperature at which the maximum rate of hybridization of target nucleic acid to ODNs occurs, under near stringent to stringent conditions (–20 to –5° C. below the $T_d$)), complementary $^{32}$P-labeled ODN is hybridized (to the $C_0t_{1/2}$) to either covalently immobilized ODN sequences on the ODN-bead as described above, or in a sandwich assay format when RNA is used as the target nucleic acid. The hybridizations are performed over a 40° C. range (+ or –20° C. around the $T_d$ of the respective duplex in 5° C. increments). The extent of hybridization is then measured as a function of temperature at the $C_0t_{1/2}$ of the respective hybridization.

Thermal transitions determined in solution ($T_m$) are recorded at 260 nm using a Gilford System 2600 UV-VIS spectrophotometer equipped with a Gilford 2527 Thermoprogrammer. ODNs (2 mM/strand) are dissolved in the respective hybridization or melting solutions. The ODN mixtures were heated to 85° C., then cooled to 10–15° C. to allow hybridization. The samples were slowly heated to 85° C. employing a temperature increase of 0.5° C./min. Absorbance versus time is recorded, and the first derivative is computed automatically. The $T_m$ values are determined using the first derivative maxima.

The helical coil transition of an oligonucleotide or nucleic acid duplex can be measured essentially as described by Martinson (*Biochemistry* 12:145–165, 1973) for the thermal elution of DNA or RNA duplexes or hybrids from hydroxylapatite. For the determination of the helical coil transition from a solid support, fluorescently-labeled oligonucleotide (ODN) was incubated in various hybridization solutions with a complementary ODN immobilized on ODN-beads.

From 5 to 5000 ng of ODN were hybridized in 300–400 μl volumes at various temperatures (19–65° C.) for 5–30 minutes with constant agitation. The beads were washed with 3×1 ml of the respective hybridization solution, and then once with the respective melting solution at the starting temperature of the melting process. The beads in 300–400 μl of the respective melting solution were then placed in a 0–15° C. water bath. At 5 minute intervals, the temperature was raised 5° C., the solution decanted into a well of a microtiter plate, and fresh solution (5° C. below the next increment) was added to the beads. The "melting" or duplex dissociation was conducted over a temperature range of 15° C. to 95° C. Fluorescence was measured with a commercial fluorescence plate reader. To calculate the $T_d$, cumulative counts eluted at each temperature were plotted against temperature. The temperature at which 50% of the material had been dissociated from the bead was taken as the $T_d$. The helical coil transition is defined as the temperature at which a value of a equals 0.2 for a given oligonucleotide duplex (or nucleic acid duplex, containing or not containing a mismatch at any place in the duplex) to the temperature at which a value for α equals 0.8 for the same given oligonucleotide duplex (or nucleic acid duplex).

Oligonucleotides were bound to the tips described herein. In these studies, the oligonucleotides were attached to the tips using the approach described by Van Ness et al., *Nucl. Acids Res.* 19:3345, 1991. The oligonucleotide-tips contained 0.1 to 1.2 μg/tip of covalently immobilized oligonucleotide.

Preparation and Use of Nylon Tip Supports (ODN-Tip)

To label the probe oligonucleotides, amine oligonucleotides were reacted with amine-reactive fluorochromes. The derived oligonucleotide preparation was divided into three portions and each portion was reacted with either (a) 20-fold molar excess of Texas Red sulfonyl chloride (Molecular Probes, Eugene, Oreg.), with (b) 20-fold molar excess of Lissamine sulfonyl chloride (Molecular Probes, Eugene, Oreg.), or (c) 20-fold molar excess of fluorescein isothiocyanate. The final reaction conditions consisted of 0.15 M sodium borate (pH 8.3) for one hour at room temperature. The unreacted fluorochromes were removed by size exclusion chromatography on a G-50 Sephadex column.

Figure 26:
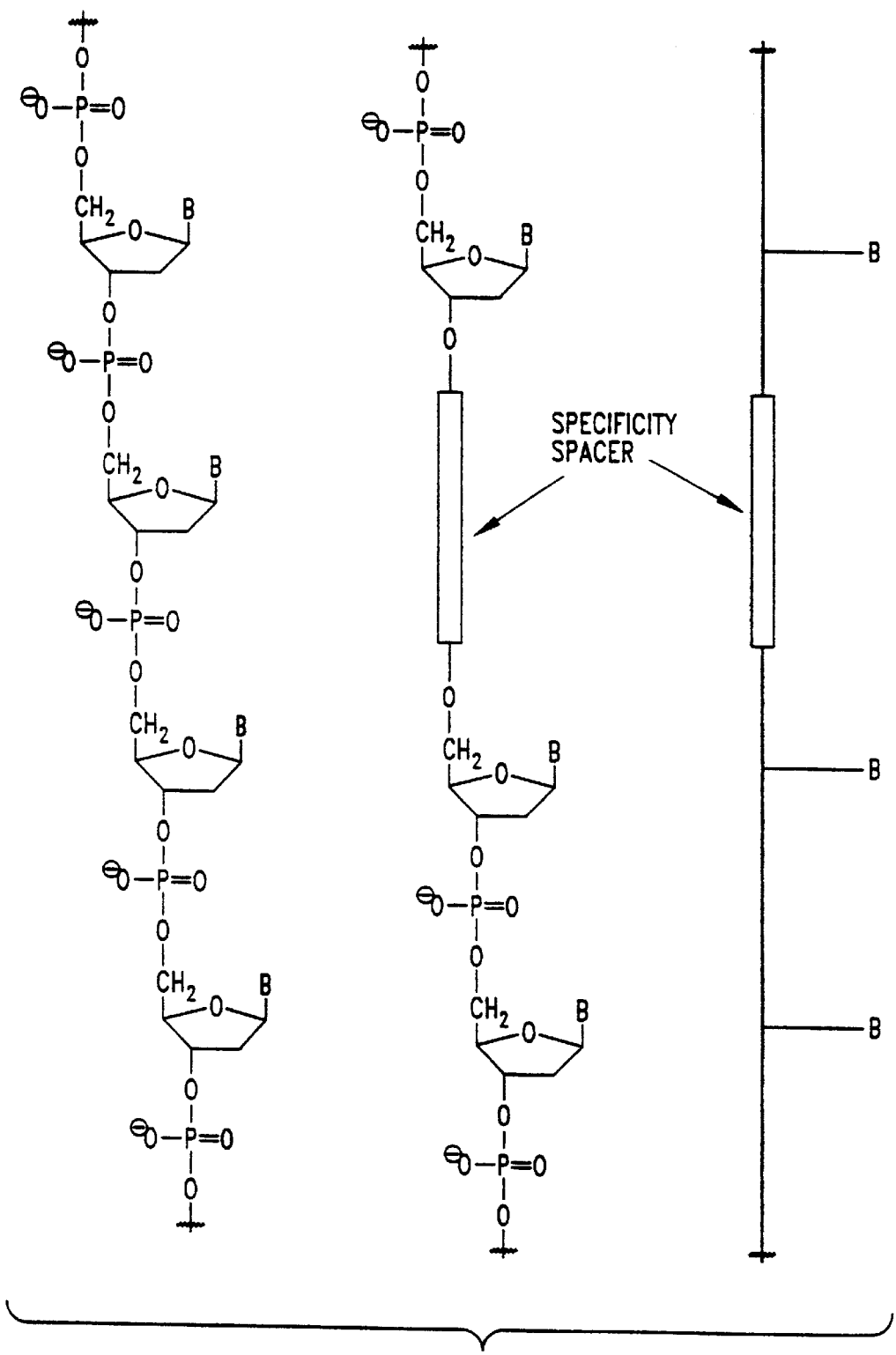
FIG. 26 explains a convention used herein to denote oligonucleotides having a specificity spacer.

A high throughput method for the measurement of the thermodynamic properties of oligonucleotide duplexes has been developed. The method allows thousands of solution samples to be scanned for their ability to modulate the thermodynamic parameters of the helical to coil transition of oligonucleotide duplexes. This method employs a solid support which has been designed to fit in a Cetus plate (or the well of a plate designed for 96 well PCR format) and requires about 40 μl of volume to be completely covered by liquid. The design of the tip is shown in FIG. 26. This tip is also designed to be compatible with the square end of a spring probe that can be used as an attachment site in order to array the nylon tips in a 1×8, 1×12, 4×8, 4×12, or 8×12 format. A depiction of such a device is shown in FIG. 27.

One member of the oligonucleotide duplex is immobilized on the nylon tip as described by Van Ness and Chen, *Nucleic Acids Res.* 19:5143, 1991. A hybridization step is then used to form the oligonucleotide duplexes on a tip. The hybridization step can be performed en masse in a single container or individually in the wells of a plate used for the PCR. It is therefore possible for every tip of a 96 member array of tips to possess a different oligonucleotide duplex.

After the hybridization step, the tips are washed and then placed in a PCR plate mounted on a thermocycler. In the case of the 1×8 or 1×12 format, the tips are then moved through a series of wells each time the temperature is increased by 5° C. Typically, the temperature increments are in 5° C. steps and the period of the melting at each temperature is 1 to 5 minutes. For example, tips in a 1×12 format are placed in row H at 10° C. The thermocycler is then programmed to ramp through 16 steps at 2 minute intervals with 5° C. increments of temperature. The tip array is moved from row to row 15 seconds prior to the temperature increase. In this format, 12 solutions can be studied using two plates of solution. In a 96 tip format, entire plates of solution are moved off and on the thermocycler at the timed interval.

Fluorescent probes are commonly used in this format and have little effect on the measured $T_d$ values described herein. The use of radiolabeled or fluorescent probes permit a wide variety of solutions to be measured since there is no requirement of optical clarity, in contrast to the case for melt curves derived by UV spectrometry (hyperchromicity shifts). Fluorescence is measured with a microtiter plate fluorescence reader, the data are directly imported into a spreadsheet program, such as Excel, which then calculates the stability, enthalpy, helical coil transition, and temperature range, and then graphs the results. Typically, a 1×2 format that measures 12 solutions at once can be completed within one hour, including set up and data reduction.

For the determination of oligonucleotide/oligonucleotide $T_d$ from the oligonucleotide-tip, fluorescently-labeled oligonucleotide is incubated in various hybridization solutions with a complementary oligonucleotide immobilized on oligonucleotide-tips. From 5 to 5000 ng of oligonucleotide are hybridized in 300–400 Zμl volumes at various temperatures (19–65° C.) for 5 to 30 minutes. The tips are washed three times with one milliliter of the respective hybridization solution, and then once with the respective melting solution at the starting temperature of the melting process. The tips in 100 μl of the respective melting solution are then placed on top of a thermocycler. At one to five minute intervals, the temperature is raised 5° C., and the tip is moved into a new well of the microtiter plate. The melting, or duplex dissociation, is conducted over a temperature range of 10° C. to 95° C. Fluorescence is measured with a commercial fluorescence plate reader.

To calculate the $T_d$, cumulative relative fluorescent units (RFUs) eluted at each temperature were platted against temperature. The temperature at which 50% of the material had been dissociated from the tip is the $T_d$ or $T_m$. The helical coil transition is defined as the temperature at which a value of a equals 0.2 for a given oligonucleotide duplex (or nucleic acid duplex, containing or not containing a mismatch at any place in the duplex) to the temperature at which a value for a equals 0.8 for the same given oligonucleotide duplex (or nucleic acid duplex).

The $T_d$ s set forth in Table 7 are obtained in the hybridizations using either ODN-Beads or ODN-Tips as described above:

TABLE 7

| Solution Type | Length of Probe | $T_d$ (Mutant) (° C.) | $T_d$ (Wild Type) (° C.) | Δ-$T_d$ (° C.) | HCT (° C.) |
|---|---|---|---|---|---|
| 2.5 m LiTCA | 30-mer | 27 | 33 | 6 | 13/14 |
| 2.5 m LiTCA | 24-mer | 25.5 | 32 | 6.5 | 13/14.5 |
| 2.5 m LiTCA | 18-mer | 24 | 31 | 7 | 9/14 |
| 0.5 M EP | 30-mer | 56 | 60 | 4 | 28/30 |
| 0.5 M EP | 24-mer | 54 | 58 | 4 | 28/30 |

TABLE 7-continued

| Solution Type | Length of Probe | $T_d$ (Mutant) (° C.) | $T_d$ (Wild Type) (° C.) | Δ-$T_d$ (° C.) | HCT (° C.) |
|---|---|---|---|---|---|
| 0.5 M EP | 18-mer | 51 | 56 | | 25/27 |
| 0.5 m DMCHAA | 30-mer | 32 | 37 | 5 | 15.5/18.5 |
| 0.5 m DMCHAA | 24-mer | 30 | 35 | 5 | 15/18 |
| 0.5 m DMCHAA | 18-mer | 29 | 34 | 5 | 15.5/18 |
| 0.5 m DMHAA | 30-mer | 45 | 49 | 5 | 18/21 |
| 0.5 m DMHAA | 24-mer | 44 | 49 | 5 | 18/22 |
| 0.5 m DMHAA | 18-mer | 42 | 47 | 5 | 18/20 |
| 0.5 M DMABTFA | 30-mer | 40 | 44 | 4 | 22/25 |
| 0.5 M DMABTFA | 24-mer | 38 | 43 | 5 | 22/25 |
| 0.5 M DMABTFA | 18-mer | 36 | 42 | 6 | 21/24 |
| 2.0 m LiTCA | 30-mer | 42 | 47 | 5 | 13.5/16 |
| 2.0 m LiTCA | 24-mer | 38 | 44 | 6 | 14/15 |
| 2.0 m LiTCA | 18-mer | 37 | 43 | 6 | 14.5/16.5 |
| 3.0 m GuSCN | 30-mer | 37 | 42.5 | 5.5 | 13.5/17.5 |
| 3.0 m GuSCN | 24-mer | 34.5 | 41 | 6.6 | 12.5/17 |
| 3.0 m GuSCN | 18-mer | 33.5 | 40.5 | 7 | 14.5/15 |
| 3.0 m GuHCl | 30-mer | 55.5 | 60 | 4.5 | 16/21 |
| 3.0 m GuHCl | 24-mer | 52.5 | 58 | 5.5 | 15/20 |
| 3.0 m GuHCl | 18-mer | 50 | 57 | 7 | 18/20 |
| Rapid Hybe | 30-mer | 80 | 80 | 0 | na* |
| Rapid Hybe | 24-mer | 80 | 80 | 0 | na |
| Rapid Hybe | 18-mer | 68 | 70 | 2 | 18/23 |
| 5x SSC | 30-mer | 72.5 | 72.5 | 0 | 18/18 |
| 5x SSC | 24-mer | 69 | 70 | 1 | 18/18 |
| 5x SSC | 18-mer | 67 | 72 | 5 | 16/18 |
| 0.1 m DMABA | 30-mer | 44 | 50 | 6 | 22/24 |
| 0.1 m DMABA | 24-mer | 42 | 50 | 8 | 22/24 |
| 0.1 m DMABA | 18-mer | 40 | 48 | 8 | 21/24 |
| Promega QY | 30-mer | 80 | 80 | 0 | na |
| Promega QY | 24-mer | 80 | 80 | 0 | na |
| Promega QY | 18-mer | 62 | 65 | 3 | 20/23 |

*na indicates not applicable or too large to accurately determine.

In Table 7, EP is 1-ethyl-piperidine acetate, DMCHAA is dimethylcyclohexylamine acetate, DMHAA is dimethylhexylamine acetate, DMABA is dimethylaminobutane acetate, and DMABTFA is dimethylaminobutane trifluoroacetate. The data indicate that the hybotropic solutions (LiTCA, DMCHAA, DMHAA, GuSCN GuHCl, DMABTFA and DMABA) permit the detection of a single base-pair mismatch in a 24-mer and 30-mer probe whereas the detection of a single base-pair mismatch in standard hybridization solutions (Rapid Hybe, Promega QY or 5xSSC) is not possible.

A similar experiment is performed for the 24-mers described above in a series of hybridization solutions.

TABLE 8

| Hybridization Solution Type | Slope ([..], k) | HCT | Δ$T_d$ |
|---|---|---|---|
| LiTCA, 3 M | 19 | 8 C. | 7.5 C. |
| GuSCN, 3 M | 13 | 10 | 6.0 |
| NaSCN, 3 M | 8.5 | 11 | 5.5 |
| NaClO₄, 3 M | 7 | 12 | 4.5 |
| KI, 3 M | 5 | 15 | 3.0 |
| NaCl, 0.165 M | 4.5 | 17.5 | 1.5 |
| GuCl, 3 M | 3.5 | 18 | 1.2 |
| CsTFA, 2 M | 2.5 | 18 | 1.2 |
| 30% formamide | ND | 20 | 1.5 |

$T_d$(wt) is the $T_d$ of a perfectly base-paired oligonucleotide duplex and $T_d$ (mt) is the $T_d$ of an oligonucleotide duplex containing a single mismatch. The values are for a 24-mer duplex of sequence described in Example 1. From the data presented in Table 8 above, the stringency factor is directly proportional to the difference between a perfectly base paired duplex and a duplex containing a mismatch. That is, the stringency factor predicts the ability of given hybridization solution to discriminate mismatched duplexes.

Example 3

Effect of Concentration of Salt or Hybotrope on HCT and $T_D$

The discrimination between mismatched oligonucleotides (mutant abbreviated as "mt") and perfected based-paired oligonucleotides (abbreviated as "wt") does not appear to be a function of concentration of a particular hybotrope but rather a function of hybotrope type. HCT is defined as the temperature range over which a duplex melts during a melting process under defined conditions. To calculate HCT, the temperature at which 80% of the duplexes are melted is subtracted from the temperature at which 20% melting is observed. Surprisingly, for the hybotropes LiTCA, GuSCN, GuHCl, NaClO₄ the HCT does not change over about the range of 0.5 M to about 6.0 M. The slope of the mt duplex is always observed to be greater than for wt duplexes (see Table 8). Another parameter which does not change as a function of concentration is the difference between the $T_d$ of the wt duplex and the mutant duplex (Δ$T_d$). The $T_d$ of the mt and wt duplexes is observed to be strictly dependent on concentration in a precisely linear relation. In Table 9, the HCT and $T_d$ for mt and wt 30-mer duplexes and mt and wt 18-mers are presented.

The effect of concentration and hybotrope type on HCT, Δ$T_d$, and $T_d$.

TABLE 9

| Hybotrope | Conc. | Oligo Length | HCT | Δ$T_d$ | $T_d$ |
|---|---|---|---|---|---|
| GuSCN | 0.5 M | 24-mer wt | 12.5 C. | | 70 C. |
| GuSCN | 0.5 M | 24-mer mt | 10.0 C. | 4.0 C. | 74 |
| GuSCN | 1.0 M | 24-mer wt | 12.5 C. | | 65 |
| GuSCN | 1.0 M | 24-mt mt | 10.0 C. | 3.5 C. | 68.5 |
| GuSCN | 2.0 M | 24-mer wt | 12.5 C. | | 52 |
| GuSCN | 2.0 M | 24-mer mt | 10.0 C. | 4.0 C. | 56 |
| GuSCN | 2.5 M | 24-mer wt | 12.5 C. | | 46.5 |
| GuSCN | 2.5 M | 24-mer mt | 12.5 C. | 3.5 C. | 50 |

Figure 9:
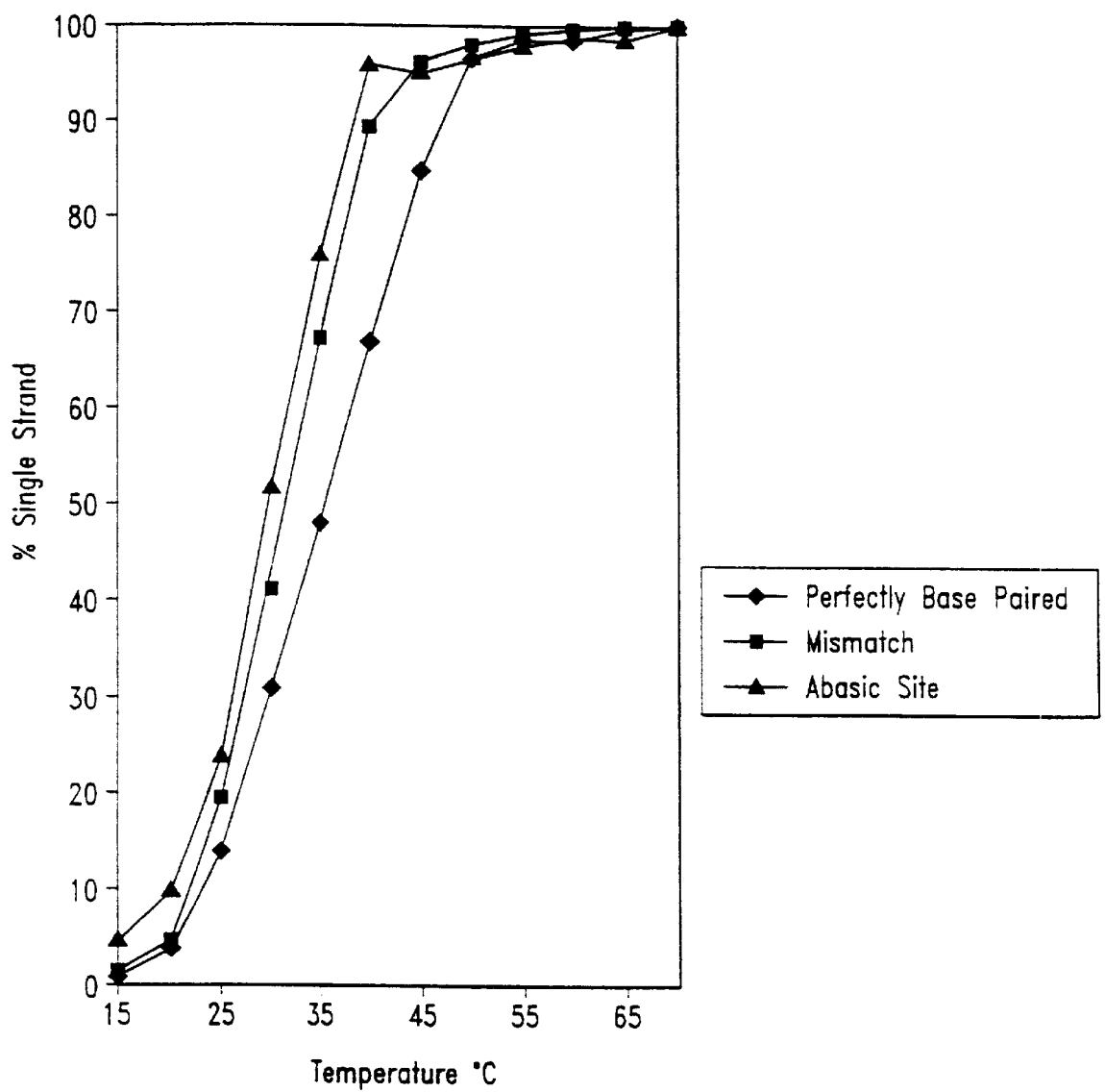
FIG. 9 is a graph illustrating melting profiles for an 18-mer oligonucleotide duplex that is perfectly based paired and the same oligonucleotide duplex that contains either a central mismatch (A/A) or abasic substitution at position 9. The melting profiles are determined in GuSCN. The % single strand (y-axis) is plotted versus temperature (° C.; x-axis).
Figure 10:
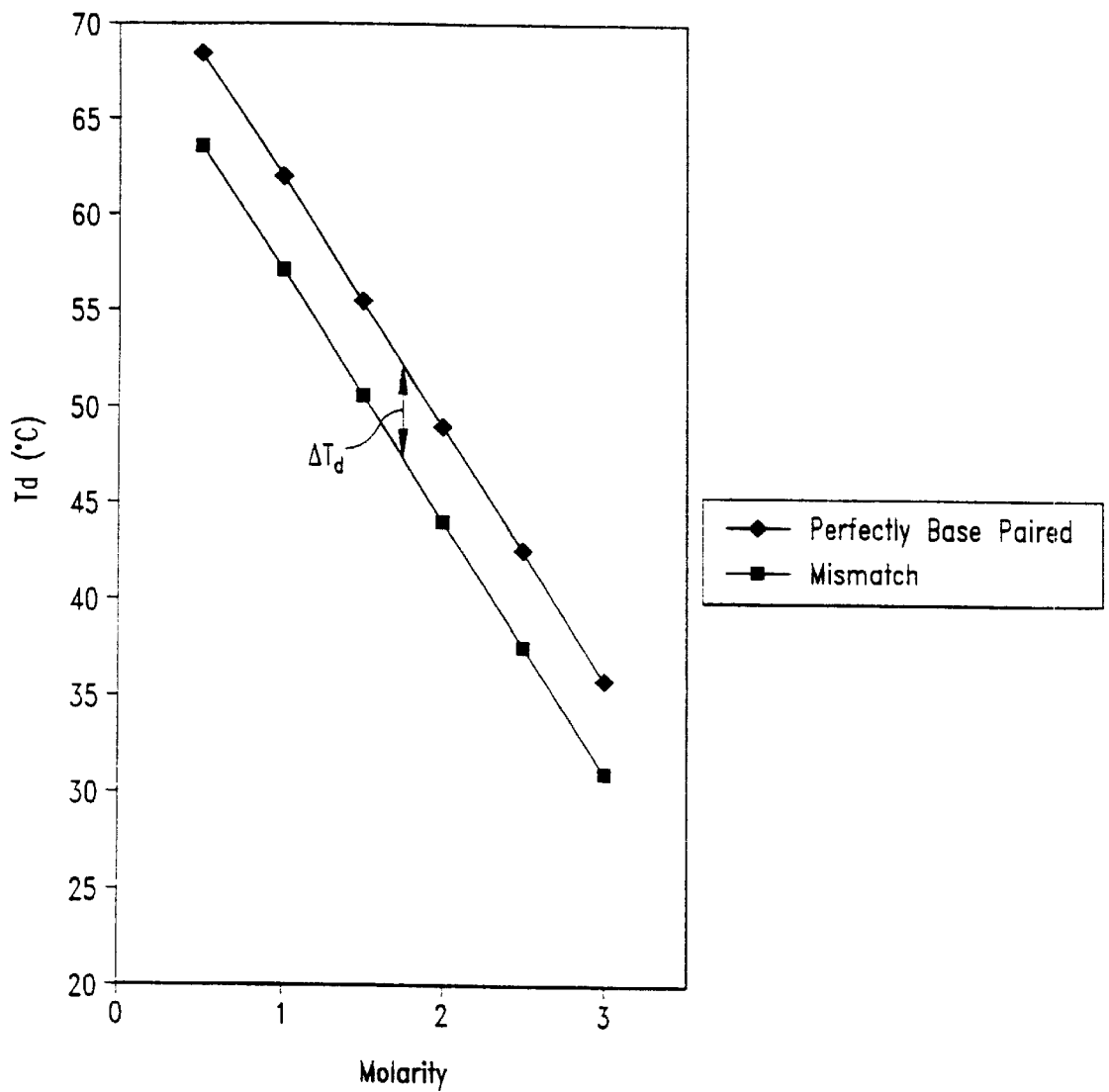
FIG. 10 is a graph showing the relationship between molarity and $T_d$ of the data obtained from the melting curves described in FIG. 9. The $T_d$ on the y-axis is plotted versus the molarity of GuSCN on the x-axis.
Figure 11:
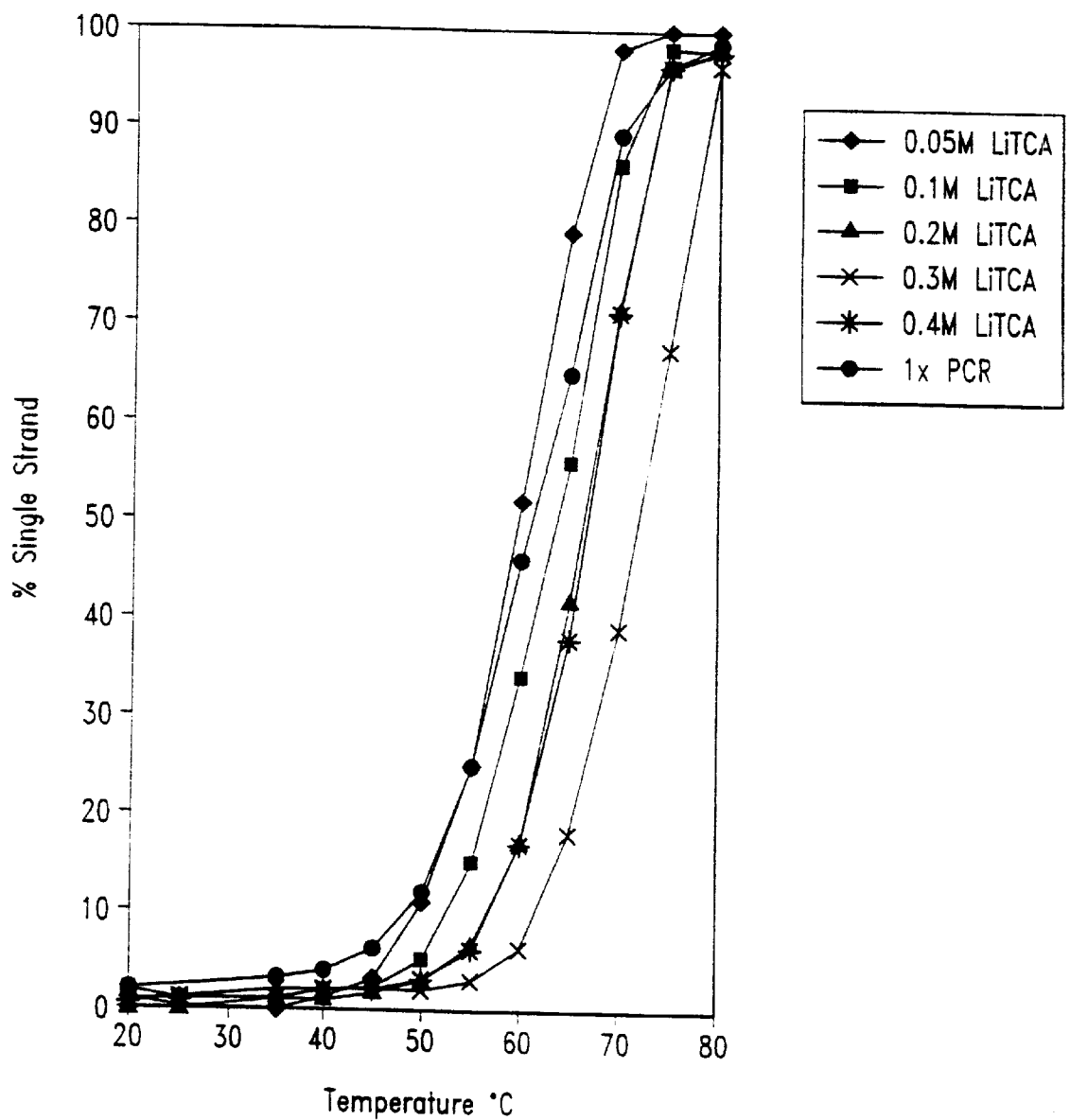
FIG. 11 is a graph illustrating melting profiles for an 18-mer oligonucleotide duplex that is perfectly based paired in 1×PCR buffer or LiTCA over a concentration range of 0.05 M to 0.4 M. The % single strand (y-axis) is plotted versus temperature (x-axis).

The data from Table 9 is graphically represented in FIG. 9.

Because Δ$T_d$ does not change over a wide concentration range for the hybotropic solutions described above, a wide temperature range can be employed for conducting oligonucleotide-based assays (i.e., 20 to 80° C.). In addition, relatively low concentrations (e.g., 0.5 M) of oligonucleotide can be employed in assays and polymerase based assays.

Example 4

Detection of a Single Base-Pair Mismatch on a Solid Phase

This example describes the detection of a single-base pair mismatch in an immobilized probe using complementary fluorescently labeled oligonucleotides. The set of probe oligonucleotides consists of one probe which forms perfect base-pairing and one oligonucleotide which contains the mismatch when hybridized. The two oligonucleotides are labeled with different fluorochromes, and after hybridization is allowed to occur at the $T_d$ of the mismatch, the ratio of hybridized fluorochromes is determined.

A "target" oligonucleotide (DMO501: 5'-TTGATTCCCAATTATGCGAAGGAG-3'; SEQ ID NO:22) was immobilized on a set of solid supports. ODN-beads (3/32nd inch diameter) were prepared as previously described (Van Ness et al., *Nucl. Acids Res.* 19:3345, 1991). The ODN-beads contained 0.01 to 1.2 mg/bead of covalently immobilized ODN. DMO578 is the complement to DMO501 (perfect complement). DMO1969 is the complement to DMO501 with a G→T change at position 11. DMO1971 is the complement to DMO501 with a A→T change at position 12. Each probe oligonucleotide was labeled with either BODIPY, TAMRA or Texas Red. Hybridization reactions were assembled in 3 M GuSCN, 0.01 M Tris pH 7.6, 5 mM EDTA at 50 ng/ml respective probe. Equal molar ratios of each probe type were used in each hybridization in the presence of 3 solid supports per tube. Hybridizations are performed at 42° C. for 30 minutes with constant agitation. The beads were washed twice with 3 M GuSCN at 42° C. and then with SDS/FW 5 times.

To denature the probe oligonucleotide, the solid supports are placed in 200 μl TE (TE is 0.01 M Tris, pH 7.0, 5 mM EDTA). The mixture is incubated for 10 minutes at 100° C. Fluorescence is measured in a black microtiter plate. The solution is removed from the incubation tubes (200 microliters) and placed in a black microtiter plate (Dynatek Laboratories, Chantilly, Va.). The plates are then read directly using a Fluoroskan II fluorometer (Flow Laboratories, McLean, Va.) using an excitation wavelength of 495 nm and monitoring emission at 520 nm for fluorescein, using an excitation wavelength of 591 nm and monitoring emission at 612 nm for Texas Red, and using an excitation wavelength of 570 nm and monitoring emission at 590 nm for lissamine or TAMRA.

The results are set forth in Table 10:

TABLE 10

| Probe Mix | Fluorochrome ratio in hybridization mix | Fluorochrome ratio after denaturing |
| --- | --- | --- |
| 578TR/578BD | 1.9/1 | 1.9/1 |
| 578TR/1969BD | 2.0/1 | 25/1 |
| 578TR/1971TA | 0.025/1 | 0.58/1 |
| 578BD/1971TA | 0.014/1 | 0.48/1 |

The results indicate that there is no effect of the fluorochrome on the hybridization as indicated in line 1 that Texas Red (TR) 578 oligonucleotide and 578-BD (BODIPY) competed evenly for hybridization to the immobilized target since the ratio of labels did not change after hybridization. There is an average of a 20-fold enrichment of perfectly based probes over the mismatched probes in GuSCN allowing certain detection of base-pair mismatches.

Example 5

Determination of the Helical Coil Transitions in Amplification Solutions and in Low Molarity Hybotrope Solutions The observation that $\Delta T_d$ does not change as a function of concentration of hybotrope has substantial utility for uses in DNA, RNA or nucleic acid amplifications based on primer extension by polymerases (e.g., Taq DNA polymerase in polymerase chain reaction). The observation that mismatched probes as long as 30-mer oligonucleotides can be distinguished on the basis of thermal melting in 0.5 M LiTCA and 1-ethyl-piperidine permits the possibility of a substantial improvement in priming efficiency in amplification reactions. As currently configured, PCR buffer is optimized for the polymerase rather for specific priming.

Commercially available PCR buffers were examined with respect to the melting behavior of 18-mers, 24-mers and 30-mers in both the wild-type (wt) and mutant (mt) forms. In Table 11, the level of discrimination achieved in PCR buffer versus a low molarity concentration of hybotrope is presented.

TABLE 11

$\Delta T_d$ for PCR Buffers and Low Molarity Hybotropes

| Hybotrope | Conc. | Oligo Length | HCT | $\Delta T_d$ | $T_d$ |
| --- | --- | --- | --- | --- | --- |
| PCR buffer | 1x | 24-mer wt | 15 C. | | 61 C. |
| PCR buffer | 1x | 24-mer mt | 14 C. | 1 C. | 60 C. |
| EP 0.1 M | | 24-mer wt | 28 C. | | 60.5 |
| EP 0.1 M | | 24-mer mt | 25 C. | 5.5 C. | 54.0 |
| LiTCA 0.1 M | | 24-mer wt | 12 C. | | 65.5 |
| LiTCA 0.1 M | | 24-mer wt | 8 C. | 4 C. | 61.5 |

As shown, the HCT for standard PCR buffer is about 15° C. whereas the HCT for 0.1 M LiTCA is about 12° and for EP (1-ethyl piperidine) it is about 28° C. The $\Delta T_d$ for the 1×PCR buffer is 1° C. for the 24-mer whereas the $\Delta T_d$ in 0.1 M LiTCA is 4° and the $\Delta T_d$ in 0.1 M EP is 5.5° C. Thus, priming specificity is significantly improved in a 0.1 M EP versus 1×PCR buffer.

Example 6

Introduction of an Abasic Site into an Oligonucleotide Increases the HCT of the Oligonucleotide and Improves Priming Specificity As demonstrated above (Example 3), an abasic site or mismatched site introduced into an oligonucleotide primer decreases the $T_d$ and HCT of the respective derived primer compared to a perfectly based pair "sister" primer. Abasic sites in polynucleotides or oligonucleotides can be introduced by the chemical or enzymatic hydrolysis of the glycosidic bond. The resulting structure is apurinic or apyrimidinic which lacks the coding information and fails to base pair. The CE phosphoramidite of the tetrahydrofuran derivative is commercially available (dSPACER, Glenn Research, Sterling, Va.) as well as other spacer phosphoramidites (Glenn Research, Sterling, Va.). In addition, abasic sites can be introduced by phosphoramidite synthesis.

The effect of abasic substitutions on the HCT of a set of oligonucleotides is shown in Table 12.

TABLE 12

| Buffer Type | Oligo Type | HCT* | $T_d$* | Stringency Factor |
| --- | --- | --- | --- | --- |
| 1X PCR buffer | normal | 24 | 65 | |
| 1X PCR buffer | deoxynebularine | 22 | 64 | |
| 0.5 M DMCHAA | normal | 18 | 37 | |
| 0.5 M DMCHAA | deoxynebularine | 14 | 32 | |
| 1X PCR buffer | normal | 18 | | |
| 1X PCR buffer | abasic (dSPACER) | 12 | | |
| 1X PCR buffer | abasic (C3 spacer) | 12 | | |
| 0.5 M TMATCA | normal | 14 | | |
| 0.5 M TMATCA | abasic (dSPACER) | 8 | | |
| 0.5 M TMATCA | abasic (C3 spacer) | 8 | | |
| 2.0 M LiTCA | normal | 12.5 | 44.5 | 4.97 |
| 2.0 M LiTCA | abasic (dSPACER)deoxynebularine | 10 | 39 | 6.37 |
| 2.0 M LiTCA | abasic (dSPACER) | 10 | 39 | 6.37 |
| 2.0 M LiTCA | abasic (C3 spacer) | 10 | 39 | 6.25 |
| 3.0 M GuSCN | normal | 16 | 35.5 | 3.85 |
| 3.0 M GuSCN | deoxynebularine | 12.5 | 32 | 5.24 |

*= ° C.

In Table 12, DMCHAA is dimethycyclohexylamine acetate. The oligonucleotide is a 24-mer with the following sequence: 5'-hexylamine-TGTGGATCAGCA-spacer-GCAGGAGTATG-3' where the spacer is either the C3-spacer or dSPACER or deoxynebularine from Glenn Research (Sterling, Va.).

Example 7

Detection of a Single Base-Pair Mismatch using Abasic Substituted Oligonucleotides This example describes the hybridization of an oligonucleotide containing an abasic site to an immobilized oligonucleotide using fluorescent tags. The set of probe oligonucleotides consists of one probe which forms perfect base-pairing and one oligonucleotide which contains the an abasic site when hybridized. The two oligonucleotides are labeled with different fluorochromes, and after hybridization at the $T_d$ of the mismatch, the ratio of hybridized fluorochromes is determined.

A "target" oligonucleotide (DMO501: 5'-TTGATTCCCAATTATGCGAAGGAG-3'; SEQ ID NO:22) was immobilized on a set of solid supports. ODN-beads (3/32nd inch diameter) were prepared as previously described (Van Ness et al., Nuc. Acids Res. 19:3345, 1991). The ODN-beads contained 0.01 to 1.2 mg/bead of covalently immobilized ODN. DMO578 is the complement to DMO501 (perfect complement). DMO1969 is the complement to DMO501 with an abasic site at position 11. DMO1971 is the complement to DMO501 with an abasic site at position 12. Each probe oligonucleotide is labeled with either BODIPY, TAMRA or Texas Red. Hybridization reactions were assembled in 3 M GuSCN, 0.01 M Tris pH 7.6, 5 mM EDTA at 50 ng/ml respective probe. Equal molar ratios of each probe type were used in each hybridization in the presence of 3 solid supports per tube. Hybridizations were at 42° C. for 30 minutes with constant agitation. The beads were washed twice with 3 M GuSCN at 42° C. and then with SDS/FW 5 times.

To denature the probe oligonucleotide, the solid supports were placed in 200 μl TE (TE is 0.01 M Tris, pH 7.0, 5 mM EDTA). The mixture is incubated for 10 minutes at 100° C. Fluorescence is measured in a black microtiter plate. The solution is removed from the incubation tubes (200 microliters) and placed in a black microtiter plate (Dynatek Laboratories, Chantilly, Va.). The plates are then read directly using a Fluoroskan II fluorometer (Flow Laboratories, McLean, Va.) using an excitation wavelength of 495 nm and monitoring emission at 520 nm for fluorescein, using an excitation wavelength of 591 nm and monitoring emission at 612 nm for Texas Red, and using an excitation wavelength of 570 nm and monitoring emission at 590 nm for lissamine or TAMRA. The results are set forth in Table 13.

TABLE 13

| Probe Mix | Fluorochrome ratio in hybridization mix | Fluorochrome ratio after denaturing |
| --- | --- | --- |
| 578TR/578BD | 2.1/1 | 2.1/1 |
| 578TR/1969BD | 1.8/1 | 25/1 |
| 578TR/1971TA | 0.024/1 | 0.6/1 |
| 578BD/1971TA | 0.015/1 | 0.36/1 |

The results indicate that there is no effect of the fluorochrome on the hybridization. As indicated in line 1, Texas Red (TR) 578 oligonucleotide and 578-BD (BODIPY) competed evenly for hybridization to the immobilized target since the ratio of labels did not change after hybridization. There is an average of a 20-fold enrichment of perfectly based probes over the abasic modified in GuSCN; allowing much higher levels of discrimination in hybridization reactions.

Example 8

Effects of Introducing Deoxynebularine or Abasic Residues into an Oligonucleotide Primer Used in Amplificaiton This example describes the use of oligonucleotide primers substituted with either abasic or deoxyNebularine residues to increase the specificity of priming in amplification reactions.

The primers used in this experiment are described by Rychlik (Rychlik, BioTechniques, 18:84–90, 1995). Primers may be synthesized or obtained as gel-filtration grade primers from Midland Certified Reagent Company (Midland Tex.).

Amplification reactions are either Taq DNA polymerase-based (10 mM Tris-HCl pH 8.3, 1.5 mM $MgCl_2$, 50 mM KCl), or Pfu DNA polymerase based (20 mM Tris-HCl pH 8.75, 2.0 mM $MgCl_2$, 10 mM KCl, 10 mM $(NH_4)_2SO_4$, 0.1% Triton X-100, 0.1 mg/ml bovine serum albumin (BSA)). The total deoxynucleoside triphosphate (dNTPs) concentration in the reactions is 0.8 mM, the primer concentration is 200 nM (unless otherwise stated) and the template amount is 0.25 ng of bacteriophage lambda DNA per 25 μl reaction. The amplification cycles consist of a denaturation step at 94° C. for 5 minutes followed by 30 cycles of: 94° C. for 45 seconds, 52° C. for 45 seconds, at 72° C. for 30 seconds, followed by a single step of 72° C. for 5 minutes. Amplified DNA fragments are electrophoresed along with DNA standards through a 2% agarose gel in 0.5×TBE buffer (45 mM Tris-borate, pH 8.0, 0.1 mM EDTA) and visualized after staining with ethidium bromide. DNA is quantitated by densitometry. Each experiment is performed twice.

Two regions in the bacteriophage lambda DNA sequence (GenBank Accession #J02459) are chosen as the priming sites for amplification. The 5' primer has a stable GC-rich 3' end; the 3' primer is chosen so that a 381 bp product will result from the amplification. The primers used in this example are as follows:

Forward (5') primers:
H17: 5'-GAACGAAAACCCCCCGC-3' (SEQ ID NO: 23)
H14: 5'-CTTCGAAAACCCCCCGC-3' (SEQ ID NO: 24)
H11: 5'-CTTGCTAAACCCCCCGC-3' (SEQ ID NO: 25)
AB1: 5'-GAACGA(dS)AACCCC(dS)CGC-3' (SEQ ID NO: 26)
AB2: 5'-GAACGA(dS)AACCC(dS)CCGC-3' (SEQ ID NO: 27)
AB3: 5'-GAACGA(dS)AACCCCCCG(dS)C-3' (SEQ ID NO: 28)
DN1: 5'-GAACGA(dS)AACCCC(dN)CGC-3' (SEQ ID NO: 26)
DN2: 5'-GAACGA(dNAACCC(dN)CCGC-3' (SEQ ID NO: 27)
DN3: 5'-GAACGA(dN)AACCCCCCG(dN)C-3' (SEQ ID NO: 28)
DN4: 5'-GAACG(dN)AAACCC(dN)CCGC-3' (SEQ ID NO: 29)
DN5: 5'-GAACG(dN)AAACC(dN)CCCGC-3' (SEQ ID NO: 30)
DN6: 5'-CTTCGAAAACCC(dN)CCGC-3' (SEQ ID NO: 31)

Reverse (3') primer:
reverse: 5'-GATCGCCCCCAAAACACATA-3' (SEQ ID NO: 32)
(dS) represents "dSPACER" residue and (dN) represents deoxyNebularine residue.

The forward primers are designed with their 5' ends variably mismatched to the target DNA. The H17 primer is a perfect match to the intended target, whereas the primer H14 is complementary only for the 14 nucleotides at the 3' end (the 3 nucleotides at the 5' end are mismatched). All of the primer pairs are used in separate amplification reactions, and the annealing temperature is varied from 25° C. to 65° C. A set of typical results are presented in Table 14, wherein "dNeb." stands for deoxyNebularine. Similar results are obtained for both Taq and Pfu polymerases.

TABLE 14

| Primer Name | Number mismatches @ position in primer | Substitutions | Temp. Range (° C.) that amplifications observed |
|---|---|---|---|
| H17 | none | none | 25 ---> 65 |
| H14 | 3 @ 5' | none | 25 ---> 65 |
| H11 | 6 @ 5 | none | 25 ---> 50 |
| AB1 | 2, @ 7, 14 | dSpacer ™ | no amplification |
| AB2 | 2, @ 7, 13 | dSpacer ™ | no amplification |
| AB3 | 2, @ 7, 16 | dSpacer ™ | no amplification |
| DN1 | 2, @ 7, 14 | dNeb. | 25 ---> 35 |
| DN2 | 2, @ 7, 13 | dNeb. | 25 ---> 35 |
| DN3 | 2, @ 7, 16 | dNeb. | 25 ---> 30 |
| DN4 | 2, @ 6, 13 | dNeb. | 25 ---> 35 |
| DN5 | 2, @ 6, 12 | dNeb. | 25 ---> 35 |
| DN6 | 2, 3 @ 5', 13 | dNeb. | 25 ---> 30 |

These results indicate that the dSpacer substitution prevents the Taq or Pfu DNA polymerase from "reading through" the abasic site. That is, when the polymerase encounters an abasic residue, chain extension is terminated. Therefore, the priming site is not conserved during the second strand synthesis, and amplification of the target nucleic acid is not achieved. However, the polymerases can read through deoxyNebularine residues present in the oligonucleotide primers. Most likely, but not verified, deoxythymidine is inserted as the complementary base to deoxyNebularine. However, the temperature range over which amplification is achieved is reduced compared to the temperature range for amplification using the H17 primer (from 25° C.–65° C. down to 25° C. to approximately 35° C.). It is therefore apparent that the deoxyNebularine substituted primers can substantially increase the specificity of the PCR reaction. Priming was improved which led to the amplification of a specific amplicon.

Figure 12:
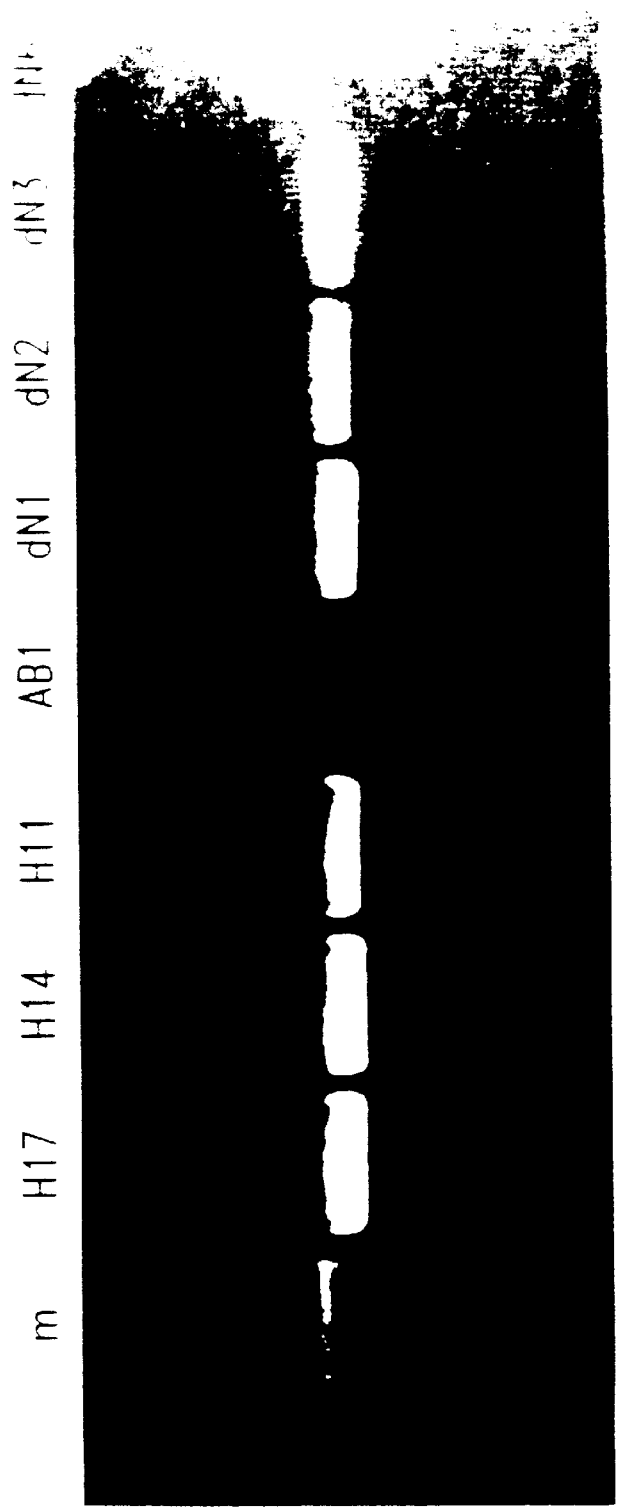
FIG. 12 is a photograph of a 2% agarose gel that shows the presence or absence of an amplicon 381 bp in length. "m", marker; and H17, H14, H11, AB1, dN1, dN2, dN3 and dN6 are the 5' primers used in amplification.

In a second series of experiments, the primer pairs are used in separate amplification reactions utilizing an annealing temperature of 42° C. The results are presented in FIG. 12. Similar results are obtained for both the Taq and Pfu polymerases. As expected, the H17, H14 and H11 primers all give rise to a 381 bp amplicon, despite the 3 base mismatches at the 5' end for the H 14 primer and the 6 base mismatches at the 5' end for the H11 primer. As above, no amplification is observed using the AB1 primer containing abasic residues. In contrast, the DN1, DN2, and DN3 primers all give rise to a 381-bp amplicon, although no amplification is observed using the DN6 primer, probably due to the mismatch of 3 bases at the 5'-end of the primer and the deoxyNebularine substitution at the 3' end of the primer. Thus, deoxyNebularine substituted primer can greatly increase the specificity of priming in the polymerase chain reaction.

Example 9
Effects of a Deoxynebularine Residue on the HCT of the Oligonucleotide In Example 3, the introduction of an abasic site or mismatched site into an oligonucleotide primer decreases the $T_d$ and HCT of the modified primer as compared to a perfectly based pair "sister" primer. The effect of deoxyNebularine substitutions on the HCT is also investigated.

DeoxyNebularine modified oligonucleotides can be synthesized by standard methods utilizing phosphoramidites. The CE phosphoramidite of the tetrahydrofuran derivative, as well as other spacer phosphoramidites are commercially available (deoxyNebularine, Glenn Research, Sterling, Va.). The oligonucleotide for the following experiments is synthesized as a 24-mer having the following sequence:
5'-hexylamine-TGTGGATCAGCA(dN)GCAGGAGTATG-3' (SEQ ID NO: 9)

The effect of the deoxyNebularine (dN) substitution on the HCT of a set of oligonucleotides is shown in Table 15.

TABLE 15

| Buffer Type | Oligo Type | ΔHCT* | $T_d$* | Stringency Factor |
|---|---|---|---|---|
| 1X PCR buffer | normal | 24 | 65 | |
| 1X PCR buffer | abasic | 22 | 64 | |
| 1X PCR buffer | deoxyNebularine | 22 | 64 | |
| 0.5 M DMCHAA | normal | 18 | 37 | |
| 0.5 M DMCHAA | abasic | 12 | 32 | |
| 0.5 M DMCHAA | deoxyNebularine | 12 | 32 | |
| 0.5 M EP | normal | 28 | 58 | |
| 0.5 M EP | abasic | 25 | 53 | |
| 0.5 M EP | deoxyNebularine | 25 | 53 | |
| 0.5 M DMCHAA | normal | 18 | 37 | |
| 0.5 M DMCHAA | abasic | 12 | 32 | |
| 0.5 M DMCHAA | deoxyNebularine | 12 | 32 | |
| 0.5 M EP | normal | 28 | 58 | |
| 0.5 M EP | abasic | 25 | 53 | |
| 0.5 M EP | deoxyNebularine | 25 | 53 | |
| 0.5 M DMCHAA | normal | 18 | 37 | |
| 0.5 M DMCHAA | abasic | 12 | 32 | |
| 0.5 M DMCHAA | deoxyNebularine | 12 | 32 | |
| 0.5 M EP | normal | 28 | 58 | |
| 0.5 M EP | abasic | 25 | 53 | |
| 0.5 M EP | deoxyNebularine | 25 | 53 | |
| 3.0 M GuSCN | normal | 16 | 35 | |
| 3.0 M GuSCN | abasic | 12.5 | 32 | |
| 3.0 M GuSCN | deoxyNebularine | 12.5 | 31 | |
| 1X PCR buffer | normal | 18 | | |
| 1X PCR buffer | abasic | 12 | | |
| 1X PCR buffer | deoxyNebularine | 12 | | |
| 0.5 M TMATCA | normal | 14 | | |
| 0.5 M TMATCA | abasic | 8 | | |
| 0.5 M TMATCA | deoxyNebularine | 8 | | |
| 2.0 M LiTCA | normal | 12 | 44 | 5.0 |
| 2.0 M LiTCA | abasic | 10 | 39 | 6.3 |
| 2.0 M LiTCA | deoxyNebularinne | 10 | 39 | 6.3 |
| 3.0 M GuSCN | normal | 16 | 35 | 3.9 |
| 3.0 M GuSCN | abasic | 12.5 | 32 | 5.2 |
| 3.0 M GuSCN | deoxyNebularine | 12.5 | 31 | 5.3 |

*= ° C.

In Table 15, EP is 1-ethyl-piperidine, DMCHAA is dimethylcyclohexylamine acetate. The deoxyNebularine substituted oligonucleotide showed the same decrease in the HCT as the abasic substituted oligonucleotide.

Example 10

Detection of a Single Base-Pair Mismatch on a Solid Phase Using Deoxynebularine Substituted Oligonucleotides This example describes the hybridization of an oligonucleotide containing a deoxyNebularine site to an immobilized oligonucleotide (target). The set of probe oligonucleotides consists of one probe that is perfectly complementary to the target, and a second oligonucleotide that contains a deoxyNebularine site. The probe oligonucleotides are labeled with fluorescent tags to aid in detection of hybridization. For this data, the two oligonucleotides are labeled with different fluorochromes, and after hybridization at the $T_d$ of the mismatch, the ratio of hybridized fluorochromes is determined.

A target oligonucleotide, 5'-TTGATTCCCAATTATGCGAAGGAG-3' (DMO501; SEQ ID NO: 22), is immobilized on a solid support. Oligonucleotide containing beads (ODN-beads) that are 3/32nd inch diameter are prepared as previously described (Van Ness et al., *Nuc. Acids Res.* 19:3345, 1991). The ODN-beads contain from 0.01 to 1.2 mg/bead of covalently immobilized ODN. Probe oligonucleotides include DMO578, which is the perfect complement to DMO501. DMO1969, which is the complement to DMO501 but has a deoxyNebularine residue at position 11, DMO1971, which is the complement to DMO501 but has a deoxyNebularine site at position 12. Each probe oligonucleotide is labeled with either BODIPY, TAMRA or Texas Red. Hybridization reactions contain 50 ng/ml of each probe in a solution comprising 3 M GuSCN, 0.01 M Tris pH 7.6, and 5 mM EDTA. Equal molar ratios of each probe are used for each hybridization to 3 solid supports contained in a tube. Hybridizations are carried out at 42° C. for 30 minutes with constant agitation. The beads are washed twice with 3 M GuSCN at 42° C. followed by five washes of SDS/FW.

To denature the probe/target duplexes, the solid supports are placed in 200 μl TE (0.01 M Tris, pH 7.0, 5 mM EDTA) and incubated for 10 minutes at 100° C. The solution (200 μl) is removed from the incubation tubes and placed in a black microtiter plate (Dynatek Laboratories, Chantilly, Va.) for measurement of fluorescence. The plates are then read directly in a Fluoroskan II fluorometer (Flow Laboratories, McLean, Va.) using an excitation wavelength of 495 nm and monitoring emission at 520 nm for fluorescein, using an excitation wavelength of 591 nm and monitoring emission at 612 nm for Texas Red, and using an excitation wavelength of 570 nm and monitoring emission at 590 nm for lissamine or TAMRA.

The results are presented in Table 16:

TABLE 16

| Probe Mix | Fluorochrome ratio in hybridization mix | Fluorochrome ratio after denaturing |
|---|---|---|
| 578TR/578BD | 5.6/1 | 5.6/1 |
| 578TR/1969BD | 2.0/1 | 36/1 |
| 578TR/1971TA | 0.018/1 | 0.7/1 |
| 578BD/1971TA | 0.022/1 | 0.48/1 |

The results indicate an average of 20-fold enrichment of perfectly based probes over the deoxyNebularine modified probes in GuSCN; allowing much higher levels of discrimination in hybridization reactions. This enrichment is not due to the presence of the fluorochrome, as the fluorochrome has no measurable effect on the hybridization. As indicated in line 1, Texas Red (TR) 578 oligonucleotide and 578-BD (BODIPY) competed equivalently for hybridization to the immobilized target as evidenced by the same ratio of labels before and after hybridization.

Example 11

Detection of a Single Base-Pair Mismatch on a Solid Phase Using Abasic Substituted Oligonucleotides This example describes the use of abasic substituted oligonucleotide probes to detect single base pair mismatches. As shown herein, an increase in efficiency is observed in detecting single base-pair mismatches using abasic substituted oligonucleotide probes as compared to standard probes.

Target oligonucleotides are covalently attached to membrane filters (Magna Graph nylon membrane filters, Micron Separations, Westboro, Mass.) (Van Ness et al., *Nuc. Acids Res.* 19:3345, 1991). The target oligonucleotides are based on the sequence: 5'-TGTGGATCAGCAAGCAGGAGTATC-3' (SEQ ID NO: 2) and contain either a G→A, T→C, T→T, G→T, or T→G mismatch at positions 13 or 14 in the target oligonucleotides. After attachment of the oligonucleotides to the membrane, the sheet is blocked for 10 min with gentle mixing in a succinnic anhydride solution (2.5 g of succinnic anhydride dissolved in 25 ml m-pyrol mixed with 125 ml 0.1 M NaBorate pH 8.5). The sheets are then washed 5 times with a solution of 10 mM Tris, 5 mM EDTA (TE). The sheets are additionally blocked for 30 min with gentle mixing with a solution of 1% bovine serum albumin (Fraction 5, Sigma) and containing 100 μg/ml fragmented, single strand herring sperm DNA. The sheets were then washed 5 times in TE. The following biotinylated probes control probe: 5'-ACACCTAGTCGTTCGTCCTCATAC-3', (SEQ ID NO: 33)

8S abasic probe: 5'-ACACCT(dS)GTCGTTCGTCCTCATAC-3' (SEQ ID NO: 34), and 6S abasic probe: 5'-ACACCT(dS)GTCGTTCGTCCTC(dS)TAC-3' (SEQ ID NO: 35)

are added to the sheet at a final concentration of 10 ng/ml in 1 ml of 3 M GuSCN, and the sheets are incubated at 28° C. for 30 minutes. The sheets are then rinsed four times in 1×SSC/0.1% SDS for 1 minute each wash, followed by two rinses in Wash Solution (0.01 M Tris pH 7.2, 0.1 M NaCl, 0.005 M EDTA, 0.1% Tween 20).

The streptavidin/alkaline phosphatase conjugate (Vector, Burlingame, Calif.) is diluted 1:10,000 in wash solution. The sheets are then incubated in this solution for 1 hour at room temperature with shaking. The sheets are subsequently rinsed four times with wash solution and once with detection buffer (0.1 M NaCl, 0.01 M Tris pH 8.5, 0.05 M MgCl$_2$) for 5 minutes. The alkaline phosphatase substrate is prepared by dissolving a BCIP/NBT tablet (Schleicher and Schuell, part #78349, Keene, N. H.) in 30 ml dH$_2$O. The reaction is carried out for 0.5 to 4 hours at room temperature. The sheets are then rinsed with water and dried. A text scanner is used to detect signal.

Figure 13:
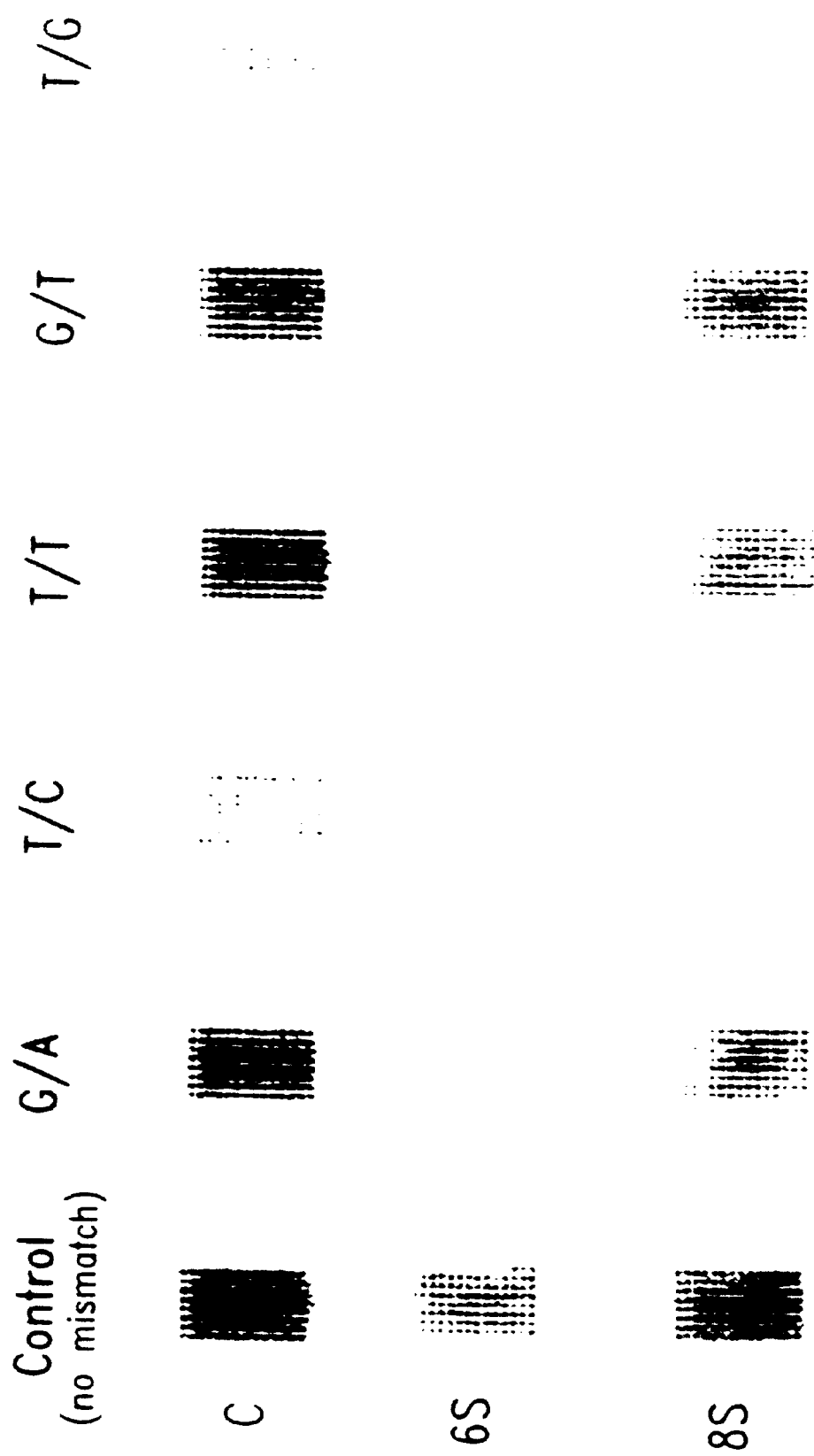
FIG. 13 is the text scan of a set of arrayed oligonucleotides that when duplexed with probe contain the mismatch indicated in the top row. "C" indicates control probe, "6S" indicates the 6S abasic substituted probe and "8S" indicates the 8S abasic substituted probe. The figure is a compilation of 3 separate filters.

As shown in FIG. 13, hybridization to the control probe is observed for each target oligonucleotide, even for those that are mismatched. However, the 6S abasic-modified probe hybridized nearly exclusively to the perfect match target oligonucleotide. The 8S abasic-modified probe also hybridized preferentially to the perfect match target oligonucleotide. The density for each target is presented in Table 17, in relative intensity units:

TABLE 17

| Oligo | None | G/A | C/T | T/T | G/T | T/G |
|---|---|---|---|---|---|---|
| Control | 90 | 82 | 26 | 90 | 91 | 45 |
| 6S | 52 | 0 | 0 | 0 | 10 | 3 |
| 8S | 76 | 35 | 2 | 35 | 45 | 30 |

Table 18 presents the ratio of mismatch density to control density.

TABLE 18

| Oligo | None | G/A | C/T | T/T | G/T | T/G |
|---|---|---|---|---|---|---|
| Control | 1 | 0.91 | 0.28 | 1 | 1.01 | 0.5 |
| 6S | 1 | 0 | 0 | 0 | 0.19 | 0.06 |
| 8S | 1 | 0.46 | 0.03 | 0.46 | 0.59 | 0.39 |

Example 12

High throughput Analysis of Helical Coil Transitions of Oligonucleotides

A capture oligonucleotide (36-mer) was covalently linked to nylon bead via a C6-amine tail as previously described (Van Ness et al., *Nuc. Acids Res.* 19:3345, 1991). Oligonucleotides (of various lengths as described in the text) were labeled via a C6 amine arm with Texas Red (fluorescein, lissamine or TAMRA can also be used) and were hybridized to the capture oligonucleotide in a 1.5 M guanidinium thiocyanate solution (other hybridization solutions as described in the text can also be used).

Specifically, the "signal" oligonucleotide was synthesized by Midland Certified Reagent Company (Midland, Tex.) at 1μM scale. The oligo was diluted to 250 μL in TE buffer which was used as a stock solution. The signal oligo was further diluted for hybridization by removing 25 μL of the stock solution and mixing it into 975 μL of 1.5 M guanidinium thiocyanate solution (other hybridization solutions as described in the text can also be used). This working stock was aliquoted into a Cetus tube (100 uL/tube). A nylon pin was immersed in the solution for 15 minutes at ambient temperature to allow the signal oligo to hybridize to the immobilized capture oligo. The beads were then washed to remove unhybridized signal oligonucleotide 1× with 0.01 M Tris pH 7.0, 5 mM EDTA, and 0.1 M NaCl; 2× with 0.01 M Tris pH 7.0, 5 mM EDTA, 0.1 M NaCl, and 0.1% SDS; 1× with 0.01 M Tris pH 7.0, 5 mM EDTA, and 0.1 M NaCl (TEN: 0.01M Tris pH 7.5, 1 mM EDTA, 110 mM NaCl; TENS: 0.01 M Tris pH 7.5, 1 mM EDTA, 100 mM NaCl, 0.1% SDS).

Test solutions were aliquoted into wells of a polycarbonate thermowell plate (Coming Costar Corp., Cambridge, Mass.) and the plate placed in an MJ thermal cycler (MJ Research Company, Watertown, Mass.). The beads were serially transferred between the wells of the plate; every 2.5 to 5 minutes the temperature increases by 5° C. starting at 10° C. and reaching 85 to 100° C. at the final point. After the melting process was completed, the liquid in the polycarbonate thermowell plates was transferred to a black 96 well microtiter plate (Dynatek Laboratories, Chantilly, Va.). The plates were then read directly using a Fluoroskan II fluorometer (Flow Laboratories, McLean, Va.) using an excitation wavelength of 495 nm and monitoring emission at 520 nm for fluorescein, using an excitation wavelength of 591 nm and monitoring emission at 612 nm for Texas Red, and using an excitation wavelength of 570 nm and monitoring emission at 590 nm for lissamine or TAMRA. The level of fluorescence correlates with the amount of signal oligonucleotide that has melted from the capture oligo.

To calculate the $T_d$, cumulative counts eluted at each temperature were plotted against temperature. The temperature at which 50% of the material dissociates from the bead is the $T_d$. The data was exported into a spreadsheet and melt curves were generated for each solution. From these melt curves, $T_d$, $\Delta HCT$, and $\Delta T_d$ were calculated.

Example 13

Identificaiton of Hybridization Solutions which Effectively Neutralize the G+C Content of Nucleic Acid Duplexes This example describes the identification and use of novel compounds that reduce or eliminate the effects of G+C content on the melting behavior of nucleic acid duplexes. Also, as shown herein, an increase in efficiency is observed in detecting single base-pair mismatches using modified oligonucleotide probes as compared to standard probes.
Solutions and Reagents Filter wash (FW) is 0.09 M NaCl, 540 mM Tris pH 7.6, 25 mM EDTA. SDS/FW is FW with 0.1% sodium dodecyl sulfate (SDS). Hybridization solutions contain the text specified concentration of hybotrope of G+C neutralizing compound, 0.1 to 2% N-lauroylsarcosine (sarcosyl), 50 mM Tris pH 7.6 (in some cases) and 0.5 to 25 mM EDTA. Formamide hybridization solution contains 30% formamide, 0.09 M NaCl, 40 mM Tris-HCl pH 7.6, 5 mM EDTA and 0.1% SDS. GuSCN is purchased from Kodak (Rochester, N.Y.). GuCi, lithium hydroxide, trichloroacetic acid, NaSCN, NaClO₄ and KI, are purchased from Sigma (St. Louis, Mo.). CsTFA is purchased from Pharmacia (Piscataway, N.J.). The amine based compounds were purchased from Sigma (St. Louis, Mo.), Aldrich (Milwaukee, Wis.) or from Fluka (Ronkonkoma, N.Y.).

Preparation of LiTCA, TMATCA and TEATCA and other Amine-based TCA, TFA and Acetate Salts LiTCA and TMATCA, and TEATCA are prepared by the dropwise titration of a 3 N solution of LiOH, TEAOH and TMAOH respectively, with trichloroacetic acid (100% w/v, 6.1 N) to pH 7.0 on ice with constant stirring. The salt is evaporated to dryness under vacuum, washed once with ether and dried. The acetate, trichloroacetate, or trifluoroacetate salts of the amine containing compounds were synthesized by neutralizing the respective amines with acetic acid, trichloroacetic acid or with trifluoroacetate to pH 6.0 to pH 8.5, depending upon the application. The resulting salt solution was then diluted to the concentration desired as stated in the Figures or Tables in this example. In some cases the salt was then dissolved in water to a final concentration of 0.1 to 3.0 M. The resulting salt solution was in some cases then buffered with Tris-HCl, pH 7.0–8.5, and detergents, such as sarkosyl, are added to about 0.1%, and optionally EDTA is added to 0.5 to 5 mM. The oligonucleotide that was tethered to the bead was DMO-2060: 5'-hexylamine-GTCATACTCCTGCTTGCTGATCCACATCTG-3' (oligonucleotide immobilized on the nylon bead; SEQ ID NO: 1); and the probe oligonucleotides were: DMO-2055: 5'-Texas Red-TGTGGATCAGCAAGCAGGAGTATG-3' (perfect complement; SEQ ID NO: 2); DMO-2058; 5'-Texas Red-TGTGGATCAGGAAGCAGGAGTATG-3' (mismatch complement; SEQ ID NO: 3); and DMO-2058-dN: 5'-Texas Red-TGTGGATCAG(deoxyNebularine)

AAGCAGGAGTATG-3' (deoxyNebularine mismatch complement; SEQ ID NO: 4).

In general, the amine-based compounds may be synthesized into acetate salts, trichloroacetate salts, trifluoroacetate salts and the like by neutralization of the base with acetic acid, trichloroacetic acid, or trifluoroacetic acid. Stock solutions of 1–6 M were prepared. In some cases the base amine was re-distilled prior to use. In some cases the resulting salt solution is then dried under vacuum to complete dryness and the mass is determined. The salt is then dissolved in water to a final concentration of 0.5 to 3.0 M. In some cases the resulting salt solution is then buffered with a buffer such as Tris-HCl, pH 7.0–8.5, and detergents, such as sarkosyl, are added to about 0.1%, and optionally EDTA is added to 0.5 to 5 mM.

Tetramethyl ammonium- and tetraethyl ammonium-trichloroacetate are synthesized by neutralizing tetramethyl ammonium- and tetraethyl ammonium-hydroxide with trichloroacetate to pH 7.0 to pH 8.5, depending upon the application. The resulting salt solution is then dried under vacuum to complete dryness and the mass is determined. The salt is then dissolved in water to a final concentration of 0.5 to 3.0 M. The resulting salt solution is then buffered with a buffer such as Tris-HCl, pH 7.0–8.5, and detergents, such as sarkosyl, are added to about 0.1%, and optionally EDTA is added to 0.5 to 5 mM.

The oligonucleotide that was tethered to the bead was DMO-2060: 5'-hexylamine-GTCATACTCCTGCTTGCTGATCCACATCTG-3' (oligonucleotide immobilized on the nylon bead; SEQ ID NO. 1); and the probe oligonucleotides were: DMO-2055: 5'-Texas Red-TGTGGATCAGCAAGCAGGAGTATG-3' (perfect complement; SEQ ID NO: 2); DMO-2058; 5'-Texas Red-TGTGGATCAGGAAGCAGGAGTATG-3' (mismatch complement; SEQ ID NO: 3); and DMO-2058-dN: 5'-Texas Red-TGTGGATCAG(deoxyNebularine)AAGCAGGAGTATG-3' (deoxyNebularine mismatch complement; SEQ ID NO: 4).

TABLE 19

| Stock Solution | Stock pH | 1 M $\Delta T_m$ (27–83 GC) | 500 mM $\Delta T_m$ (27–83 GC) | 100 mM $\Delta T_m$ (27–83 GC) |
|---|---|---|---|---|
| 1-ethylpiperidine acetate | 7 | 0 | 1 | 6 |
| 1-ethylpiperidine trichloroacetate | 8.6 | −1 | 0 | 5 |
| 1-ethylpiperidine trifluoroacetate | 6.6 | −1 | 0 | 5 |
| 1-methylimidizole acetate | 6.6 | 8 | 7 | 14 |
| 1-methylpiperidine acetate | 7 | 4 | 14 | 7 |
| 1-methylpiperidine trichloroacetate | 8.4 | 3 | 4 | 8 |
| 1-methylpyrrolidine acetate | 7 | −1 | −5 | 7 |
| 1-methylpyrrolidine trichloroacetate | 8.4 | 6 | 7 | 8 |
| 1-methylpyrrolidine trifluoroacetate | 7.2 | 2 | 4 | 8 |
| 2-methoxyethylamine acetate | 7 | 9 | −1 | 6 |
| 2-methoxyethylamine trifluoroacetate | 7.6 | 3 | 11 | 12 |
| 3-methoxypropylamine acetate | 6.8 | 9 | 3 | 6 |
| betaine in 1X THE | 7.7 | 9 | 13 | 11 |
| Bis(2-methoxyethyl)amine acetate | 6.2 | 4 | 5 | 4 |
| bis(2-methoxyethyl)amine trifluoroacetate | 7.6 | 3 | 5 | 9 |
| Diallylamine acetate | 6.5 | 2 | 2 | 5 |
| diallylamine trifluoroacetate | 7.6 | 5 | 4 | 8 |
| dibutylamine acetate | 6.5 | 3 | 4 | 4 |
| Dicyclohexylamine Acetate | 6.7 | 3 | 4 | 5 |
| diisobutylamine acetate | 6.6 | 3 | 6 | 5 |
| diisopropylamine acetate | 6.9 | 1 | 2 | 4 |
| diisopropylamine trifluoroacetate | 6.9 | 6 | 2 | −1 |
| dipropylamine acetate | 6.5 | 2 | 4 | 4 |
| N,N,N',N'-tetraethylethylenediamine acetate | 7.3 | 0 | 3 | 2 |
| N,N-dimethylaminobutane acetate | 7 | 3 | 2 | 5 |
| N,N-dimethylaminobutane trichloroacetate | 8.2 | 5 | 4 | 9 |
| N,N-dimethylaminobutane trifluoroacetate | 6.2 | −1 | 7 | 0 |
| N,N-dimethylbutylamine acetate | 6.9 | 0 | 2 | 6 |
| N,N-dimethylcyclohexylamine acetate | 7.1 | 1 | 4 | 5 |
| N,N-dimethylcyclohexylamine trifluoroacetate | 7.3 | −5 | 13 | 12 |
| N,N-dimethylcyclohexylamine/TE/Sark | | 2 | 3 | 8 |
| N,N-dimethylheptylamine acetate | 6.5 | 3 | 5 | 5 |
| N,N-dimethylheptylamine acetate | 7.7 | 5 | 6 | 10 |
| N,N-dimethylhexylamine acetate | 6.6 | 3 | 3 | 3 |
| N,N-dimethylhexylamine acetate | 7.1 | 4 | 2 | 10 |
| N,N-dimethylisopropylamine acetate | 6.9 | 3 | 6 | 9 |
| N,N-dimethylisopropylamine trichloroacetate | 8.5 | 2 | 3 | 13 |
| N,N-dimethyloctylamine trifluoroacetate | 7 | 5 | 6 | −2 |
| n-ethylbutylamine acetate | 6 | 1 | 1 | 6 |
| n-ethylbutylamine trifluoroacetate | 6.1 | 6 | 6 | 8 |
| triethanolamine acetate | 6.5 | −4 | 4 | 12 |
| triethylamine acetate | 7 | 2 | 2 | 7 |
| triethylamine trichloroacetate | | 5 | 9 | 8 |
| tripropylamine acetate | 6.5 | −1 | 4 | 7 |
| tetraethylammonium acetate | | 0 | 8 | |
| tetra ethylammonium acetate 3 M | | −3 | | |
| formamide 20%/TE/Sark | | 14 | | |
| 1X PCR Buffer | | 14 | | |
| 1X SSC | | 13 | | |

As shown in Table 19, numerous amine-based hybridization solutions (in the 100 mM concentration range, 500 mM concentration range and 1000 mM concentration range) have been identified which give rise to a $\Delta T_d$ of 9° C. or less between oligonucleotide duplexes of G+C content of 27% to 83%. Novel hybridization solutions were prepared which demonstrate properties not previously described for a hybridization solution.

These hybridization solutions possess the property of neutralizing the differences in G+C and A+T base-pairing strength. Some of the solutions (most notably those containing tripropylamine acetate, bis(2-methoxyethyl)amine trifluoroacetate, diisopropylamine trifluoroacetate, N,N dimethylaminobutane trifluoroacetate at 100 mM; triethanolamine acetate, notably N,N dimethylcyclohexylamine trifluoroacetate, N,N dimethylheptylamine acetate at 500 mM; notably N,N dimethylcyclohexylamine trifluoroacetate, tripropylamine acetate, dibutylamine acetate, N,N dimethylheptylamine acetate, dimethylhexylamine acetate, dicyclohexylamine acetate at 1000 mM) simultaneously lowers the $T_d$ and $\Delta T_d$. Others (e.g., 1-ethylpiperidine acetate, etc.) increase $\Delta T_d$. In Table 19, the characteristics of the novel hybridization solutions and hybotropes are described. The following $\Delta T_d$s as a function of G+C content were obtained from the melt curves described below: Novel hybridization solutions have also been identified which neutralize the effects of G+C content on the melting behavior of nucleic acid duplexes. These solutions are in some cases hybotropes and in other cases can be used as PCR buffers or as hybridization solutions which minimize the effects of G+C content on nucleic acid duplexes. These new hybridization solutions, their properties, and their preparation are described in Examples 2, 12 and 13.

FIG. 14 is a graph showing the difference in $T_d$ between three duplexes, that vary in G+C content from 27% to 83%. The capture oligonucleotide is a 36-mer (DMO-GC36cap: 5'-hexylamine-GCAGCCTCGCGGAGGCGGATGA-TCGTCATTAGTATT-3'; SEQ ID NO: 5) and three complementary oligos which are labeled with the fluorochrome are DMO-83GC: 5'-Texas Red-CCGCCTCCGCGAGGCTGC-3' (SEQ ID NO: 6); DMO-SOGC: 5'-Texas Red-AATGACGATCATCCGCCT-3' (SEQ ID NO: 7); DMO-27GC: -Texas Red-AATACTAATGACGATCAT-3' (SEQ ID NO: 8). The temperature difference between any two $T_d$s at $\alpha=0.5$ is defined as the $\Delta T_d$. The percentage of single strand DNA (y-axis) is plotted versus temperature (° C.; x-axis). The melting solution was 100 mM 2-methoxyethylamine trifluoroacetate. The maximum difference between the 3 melting curves in the $T_d$ was 6° C. The helical coil transition of the 27% G+C content was 21° C., 50% G+C was 33° C. and for the 83% G+C duplex was 29° C. Note that the helical coil transitions (HCTs) of the 3 different G+C content oligonucleotides is different. This is in contrast to the case with diisobutylamine as shown in FIG. 15.

FIG. 15 is a graph showing the difference in $T_d$ between three duplexes, that vary in G+C content from 27% to 83% (the same system as described in FIG. 14. The temperature difference between any two $T_d$s at $\alpha=0.5$ is defined as the $\Delta T_d$. The percentage of single strand DNA (y-axis) is plotted versus temperature (° C.; x-axis). The melting solution was 100 mM diisobutylamine acetate. The maximum difference between the 3 melting curves in the $T_d$ was 5° C. The helical coil transition of the 27% G+C content was 22° C., 50% G+C was 26° C. and for the 83% G+C duplex was 25° C. The helical coil transitions for the three oligonucleotide duplexes are very similar. This is the behavior that is preferred for use in array hybridizations or polymerase chain reactions.

In FIG. 16 the inability of GuSCN to neutralize G+C content is shown. FIG. 16 is a graph showing the difference in $T_d$ between three duplexes, that vary in G+C content from 27% to 83% (the same capture and probe oligonucleotides as described in FIG. 14). The temperature difference between any two $T_d$s at $\alpha=0.5$ is defined as the $\Delta T_d$. The percentage of single strand DNA (y-axis) is plotted versus temperature (° C.; x-axis). The melting solution was 2 M Guanidinium thiocyanate. The maximum difference between the 3 melting curves in the $T_d$ or $T_m$ is 16° C. The helical coil transition of the 27% G+C content was 28° C., for the 50% G+C duplex was 30° C. and for the 83% G+C duplex was 32° C. Similar results were obtained with 1×PCR buffer (FIG. 17) and 1×SSC buffer (FIG. 18). There was also no neutralization of G+C content with 20% formamide (FIG. 19). Similar results were obtained with 1×PCR and 1×SSC buffer.

Figure 17:
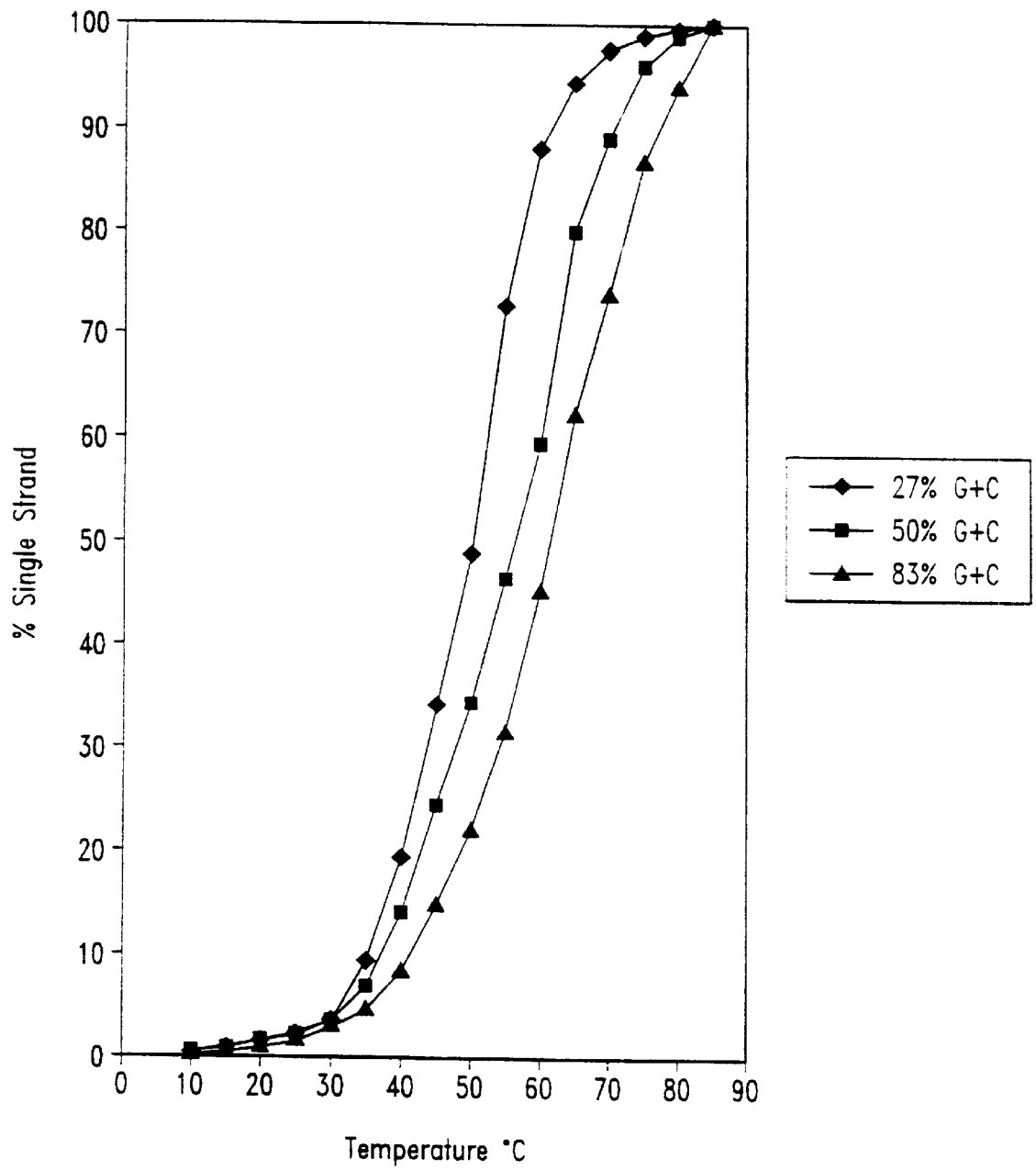
FIG. 17 is a graph showing the difference in $T_d$ between three duplexes, that vary in G+C content from 27% to 83%. The percentage of single strand DNA (y-axis) is plotted versus temperature (° C.; x-axis). The melting solution was 1×PCR buffer.

FIG. 17 is a graph showing the difference in $T_d$ between three duplexes, that vary in G+C content from 27% to 83% (the same duplex system as described in FIG. 14). The temperature difference between any two $T_d$s at $\alpha=0.5$ is defined as the $\Delta T_d$. The percentage of single strand DNA (y-axis) is plotted versus temperature (° C.; x-axis). The melting solution was 1×PCR buffer. The maximum difference between the 3 melting curves in the $T_d$ was 14° C. The helical coil transition of the 27% G+C content was 17° C., for the 50% G+C duplex was 22° C. and for the 83% G+C duplex was 23° C.

FIG. 18 is a graph showing the difference in $T_d$ between three duplexes, that vary in G+C content from 27% to 83%. The temperature difference between any two $T_d$s at $\alpha=0.5$ is defined as the $\Delta T_d$. The percentage of single strand DNA (y-axis) is plotted versus temperature (° C.; x-axis). The melting solution was 1×SSC. The maximum difference between the 3 melting curves in the $T_d$ is 13° C. The helical coil transition of the 27% G+C content was 20° C., for the 50% G+C duplex was 22° C. and for the 83% G+C duplex was 23° C.

FIG. 19 is a graph showing the difference in $T_d$ between three duplexes, that vary in G+C content from 27% to 83%. The temperature difference between any two $T_d$s at $\alpha=0.5$ is defined as the $\Delta T_d$. The percentage of single strand DNA (y-axis) is plotted versus temperature (° C.; x-axis). The melting solution was 20% formamide, 10 mM Tris pH 7.6, and 5 mM EDTA with 0.1 % sarkosyl. The maximum difference between the 3 melting curves in the $T_d$ is 14° C. The helical coil transition of the 27% G+C content was 15° C., for the 50% G+C duplex was 16° C. and for the 83% G+C duplex was 20° C.

In contrast to the situation in FIGS. 17, 18 and 19, FIG. 20 shows the melting behavior of the 3 different G+C oligonucleotide duplexes in 1 M dicyclohexylamine acetate. FIG. 20 is a graph showing the difference in $T_d$ between three duplexes, that vary in G+C content from 27% to 83%. The temperature difference between any two $T_d$s at $\alpha=0.5$ is defined as the $\Delta T_d$. The percentage of single strand DNA (y-axis) is plotted versus temperature (° C.; x-axis). The melting solution was 1 M dicyclohexylamine acetate. The maximum difference between the 3 melting curves in the $T_d$ was 3° C. The helical coil transition of the 27% G+C content was 13° C., for the 50% G+C duplex was 17° C. and for the 83% G+C duplex was 19° C. This is an ideal profile for a hybotrope. In contrast, the narrow helical coil transition observed in FIG. 20, a much wider HCT is observed with 500 mM n-ethylbutylamine acetate. FIG. 21 is a graph showing the difference in $T_d$ between three duplexes, that vary in G+C content from 27% to 83%. The capture oligonucleotide is a 36-mer (DMO-GC36cap: 5'-hexylamine- GCAGCCTCGCGGAGGCGGATGATCGTCATTAGTA-TT-3'; SEQ ID NO: 5) and three complementary oligos which are labeled with the fluorochrome are DMO-83GC: 5'-Texas Red-CCGCCTCCGCGAGGCTGC-3' (SEQ ID NO: 6); DMO-50GC: 5'-Texas Red-AATGACGATCATCCGCCT-3' (SEQ ID NO: 7); DMO-27GC: -Texas Red-AATACTAATGACGATCAT-3' (SEQ ID NO:8). The temperature difference between any two $T_d$s at α=0.5 is defined as the $\Delta T_d$. The percentage of single strand DNA (y-axis) is plotted versus temperature (° C.; x-axis). The melting solution was 500 mM n-ethylbutylamine acetate. The maximum difference between the 3 melting curves in the $T_d$ was 1 ° C. The helical coil transition of the 27% G+C content was 22° C., for the 50% G+C duplex was 22° C. and for the 83% G+C duplex was 26° C.

The ability of some of the G+C neutralizing buffer to act as hybotropes is illustrated in FIG. 22. FIG. 22 is a graph showing the difference in $T_d$ between three duplexes, one that is perfectly based-paired and the other two that contains a mismatch or a deoxyNebularine substitution. The temperature difference between any two $T_d$s at α=0.5 is defined as the $\Delta T_d$. The percentage of single strand DNA (y-axis) is plotted versus temperature (° C.; x-axis). DMO-2060: 5'-hexylamine-GTCATACTCCTGCTTGCTGATCCACATCTG-3' (oligonucleotide immobilized on the nylon bead SEQ ID NO:1).; DMO-2055: 5'-Texas Red-TGTGGATCAGCAAGCAGGAGTATG-3' (perfect complement; SEQ ID NO: 2); DMO-2058; 5'-Texas Red-TGTGGATCAGGAAGCAGGAGTATG-3' (mismatch complement; SEQ ID NO: 3); and DMO-2058-dN: 5'-Texas Red-TGTGGATCAG(deoxyNebularine)AAGCAGGAGTATG-3' (deoxyNebularine mismatch complement; SEQ ID NO: 4). The melting solution was 1 M diisopropylamine acetate. The maximum difference between the 3 melting curves in the $T_d$ was 6° C. The helical coil transition (HCT) of the true mismatch was 14° C.; the HCT for the deoxyNebularine mismatch duplex was 14° C. and the HCT for the perfectly based paired duplex was 16° C.

Figure 23:
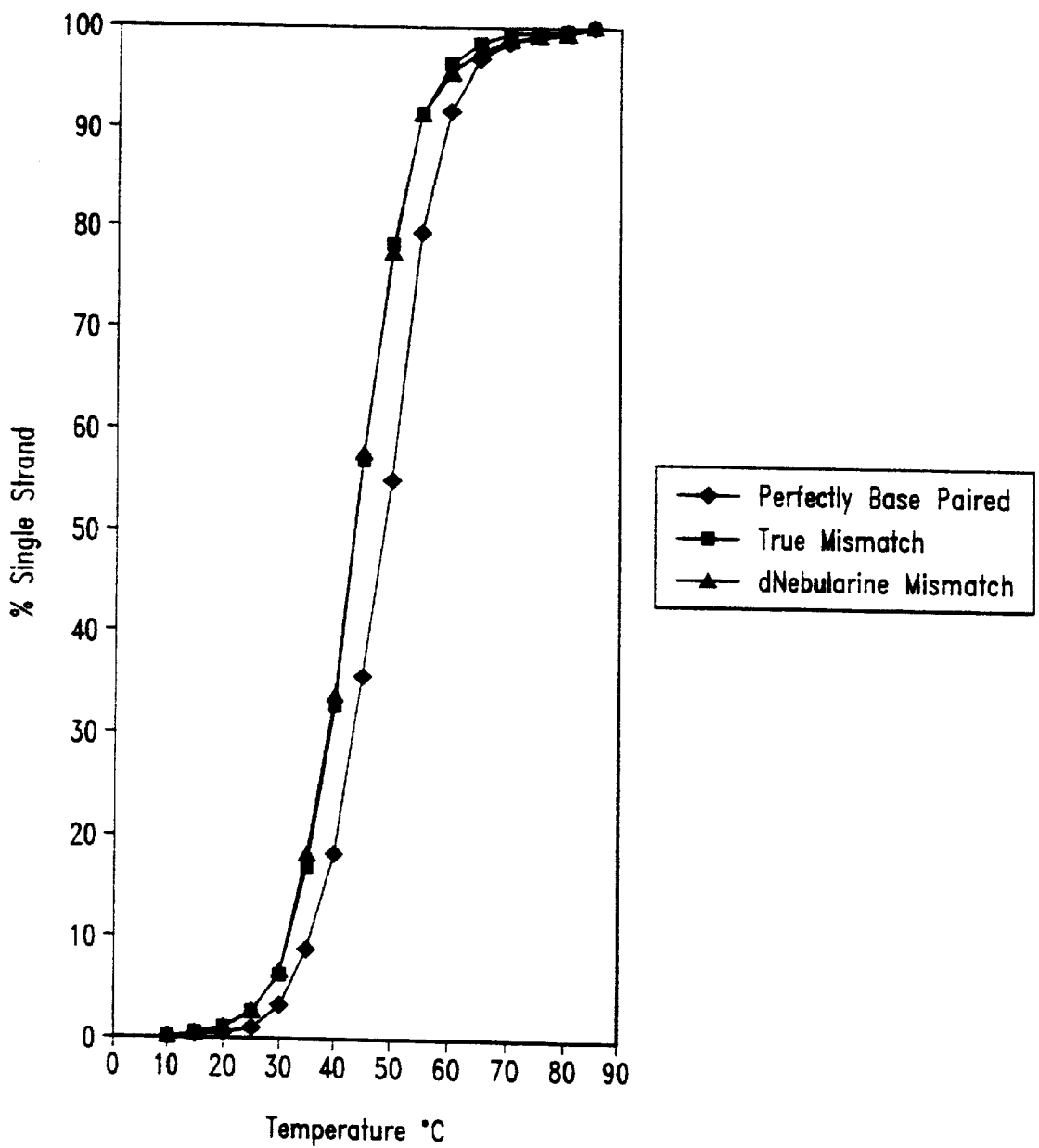
FIG. 23 is a graph showing the difference in $T_d$ between three duplexes, one that is perfectly based-paired and the other two that contains a mismatch or a deoxyNebularine substitution. The temperature difference between any two $T_d$s at $\alpha$=0.5 is defined as the $\Delta T_d$. The percentage of single strand DNA (y-axis) is plotted versus temperature (° C.; x-axis). DMO-2060: 5'-hexylamine-GTCATACTCCTGCTTGCTGATCCACATCTG-3' (oligonucleotide immobilized on the nylon bead.; SEQ ID NO: 1DMO-2055: 5'-Texas Red-TGTGGATCAGCAAGCAGGAGTATG-3' (perfect complement SEQ ID NO: 2); DMO-2058; 5'-Texas Red-TGTGGATCAGGAAGCAGGAGTATG-3' (mismatch complement) SEQ. ID NO:3; and DMO-2058-dN: 5'-Texas Red-TGTGGATCAG(deoxyNebularine)-AAGCAGGAGTATG-3' (deoxyNebularine mismatch complement SEQ ID NO: 4). The melting solution was 1 M N,N-dicyclohexylamine acetate. The maximum difference between the 3 melting curves in the $T_d$ was 4° C. The helical coil transition (HCT) of the true mismatch was 15° C.; the HCT for the deoxyNebularine mismatch duplex was 15° C. and the HCT for the perfectly based paired duplex was 15° C.

The same situation was observed for 1 M diisopropylamine acetate (FIG. 22), 1 M N,N-dimethylcyclohexylamine acetate (FIG. 23) and 1 M dicyclohexylamine acetate (FIG. 24) and N,N-dimethylhexylamine acetate (FIG. 25). FIG. 23 is a graph showing the difference in $T_d$ between three duplexes, one that is perfectly based-paired and the other two that contains a mismatch or a deoxyNebularine substitution. The temperature difference between any two $T_d$s at α=0.5 is defined as the $\Delta T_d$. The percentage of single strand DNA (y-axis) is plotted versus temperature (° C.; x-axis). DMO-2060: 5'-hexylamine-GTCATACTCCTGCTTGCTGATCCACATCTG-3' (oligonucleotide immobilized on the nylon bead; SEQ ID NO: 1).; DMO-2055: 5'-Texas Red-TGTGGATCAGCAAGCAGGAGTATG-3' (perfect complement; SEQ ID NO: 2); DMO-2058; 5'-Texas Red-TGTGGATCAGGAAGCAGGAGTATG-3' (mismatch complement; SEQ ID NO: 3); and DMO-2058-dN: 5'-Texas Red- TGTGGATCAG(deoxyNebularine)AAGCAGGAGTATG-3' (deoxyNebularine mismatch complement; SEQ ID NO: 4). The melting solution was 1 M N,N-dicyclohexylamine acetate. The maximum difference between the 3 melting curves in the $T_d$ or $T_m$ is 4° C. The helical coil transition (HCT) of the true mismatch was 15° C.; the HCT for the deoxyNebularine mismatch duplex was 15° C. and the HCT for the perfectly based paired duplex was 15° C.

Figure 24:
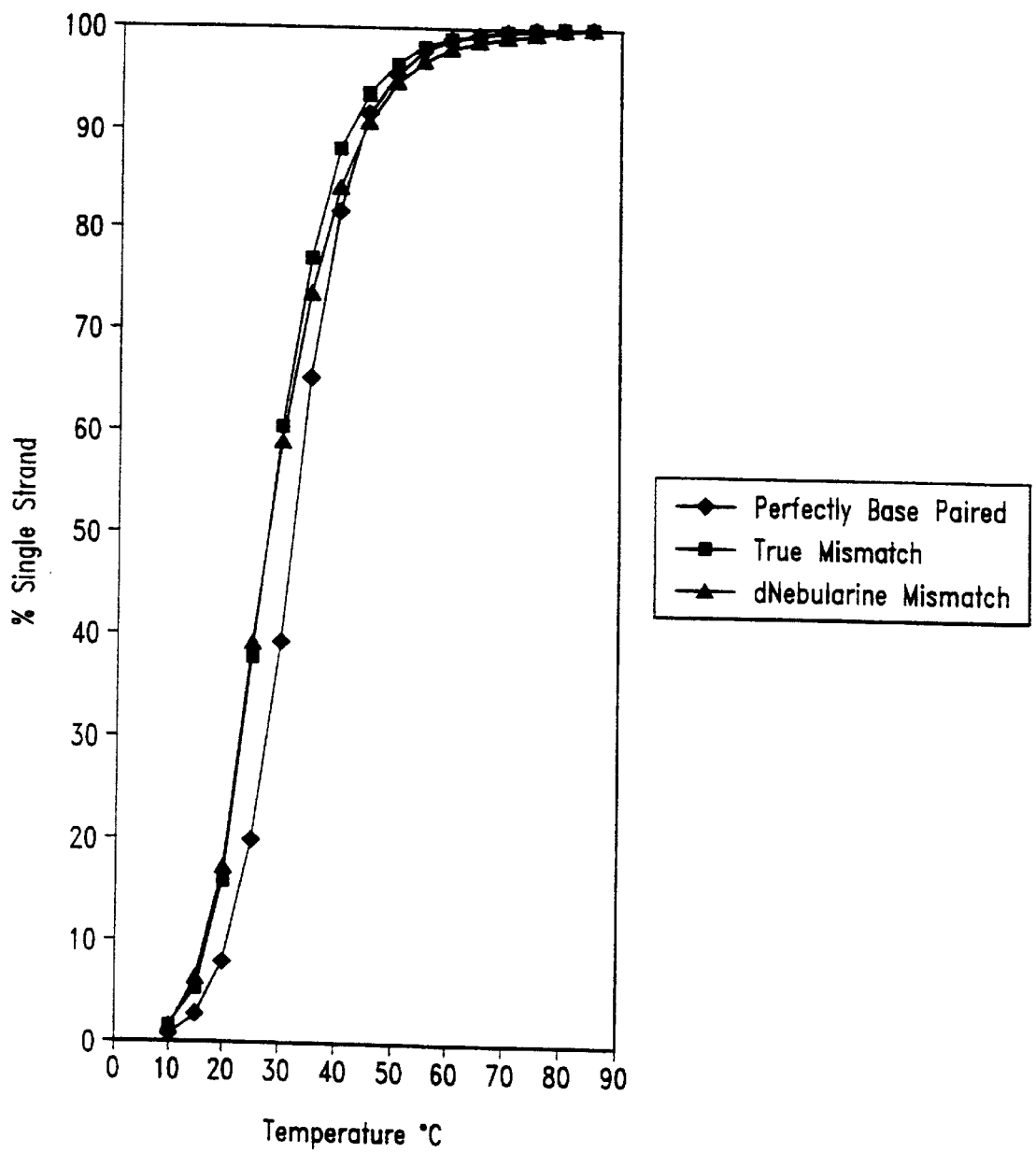
FIG. 24 is a graph showing the difference in $T_d$ between three duplexes, one that is perfectly based-paired and the other two that contains a mismatch or a deoxyNebularine substitution. The temperature difference between any two $T_d$s at α=0.5 is defined as the $\Delta T_d$. The percentage of single strand DNA (y-axis) is plotted versus temperature (° C.; x-axis). DMO-2060: 5'-hexylamine-GTCATACTCCTGCTTGCTGATCCACATCTG-3' (oligonucleotide immobilized on the nylon bead. SEQ ID NO: 1; DMO-2055: 5'-Texas Red-TGTGGATCAGCAAGCAGGAGTATG-3' (perfect complement SEQ ID NO: 2); DMO-2058; 5'-Texas Red-TGTGGATCAGGAAGCAGGAGTATG-3' (mismatch complement SEQ ID NO: 3); and DMO-2058-dN: 5'-Texas Red-TGTGGATCAG(deoxyNebularine)-AAGCAGGAGT/ATG-3' (deoxyNebularine mismatch complement SEQ ID NO: 4). The melting solution was 1 M N,N-dicyclohexylamine acetate. The maximum difference between the 3 melting curves in the $T_d$ was 4° C. The helical coil transition (HCT) of the true mismatch was 17° C.; the HCT for the deoxyNebularine mismatch duplex was 17° C. and the HCT for the perfectly based paired duplex was 15° C.
Figure 25:
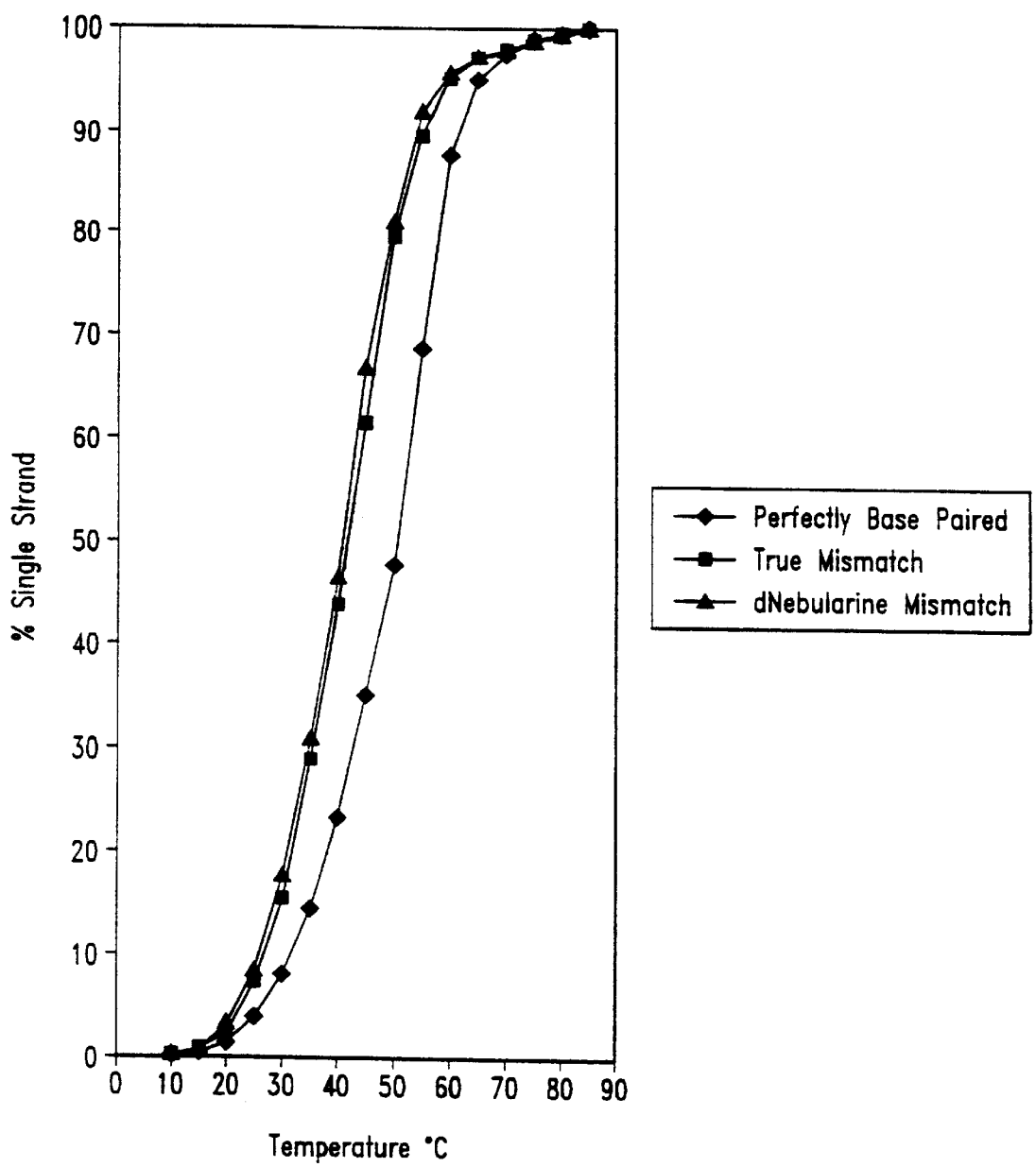
FIG. 25 is a graph showing the difference in $T_d$ between three duplexes, one that is perfectly based-paired and the other two that contains a mismatch or a deoxyNebularine substitution. The temperature difference between any two $T_d$s at α=0.5 is defined as the $\Delta$-$T_d$. The percentage of single strand DNA (y-axis) is plotted versus temperature (° C.; x-axis). DMO-2060: 5'-hexylamine-GTCATACTCCTGCTTGCTGATCCACATCTG-3' (oligonucleotide immobilized on the nylon bead, SEQ ID NO: 1); DMO-2055: 5'-Texas Red-TGTGGATCAGCAAGCAGGAGTATG-3' (perfect complement SEQ ID NO: 2); DMO-2058; 5'-Texas Red-TGTGGATCAGGAAGCAGGAGTATG-3' (mismatch complement) SEQ ID NO: 3; and DMO-2058-dN: 5'-Texas Red-TGTGGATCAG(deoxyNebularine) AAGCAGGAGTATG-3' (deoxyNebularine mismatch complement) SEQ ID NO: 4. The melting solution was 100 mM N,N-dimethylhexylamine acetate. The maximum difference between the 3 melting curves in the $T_d$ was 9° C. The helical coil transition (HCT) of the true mismatch was 15° C.; the HCT for the deoxyNebularine mismatch duplex was 15° C. and the HCT for the perfectly based paired duplex was 15° C.

FIG. 24 is a graph showing the difference in $T_d$ between three duplexes, one that is perfectly based-paired and the other two that contains a mismatch or a deoxyNebularine substitution. The temperature difference between any two $T_d$s at α=0.5 is defined as the $\Delta T_d$. The percentage of single strand DNA (y-axis) is plotted versus temperature (° C.; x-axis). DMO-2060: 5'-hexylamine-GTCATACTCCTGCTTGCTGATCCACATCTG-3' (oligonucleotide immobilized on the nylon bead.; SEQ ID NO: 1); DMO-2055: 5'-Texas Red-TGTGGATCAGCAAGCAGGAGTATG-3' (perfect complement; SEQ ID NO: 2); DMO-2058; 5'-Texas Red-TGTGGATCAGGAAGCAGGAGTATG-3' (mismatch complement); and DMO-2058-dN: 5'-Texas Red-TGTGGATCAG(deoxyNebularine)AAGCAGGAGTATG-3' (deoxyNebularine mismatch complement; SEQ ID NO: 4). The melting solution was 1 M N,N-dicyclohexylamine acetate. The maximum difference between the 3 melting curves in the $T_d$ is 4° C. The helical coil transition (HCT) of the true mismatch was 17° C.; the HCT for the deoxyNebularine mismatch duplex was 17° C. and the HCT for the perfectly based paired duplex was 15° C.

FIG. 25 is a graph showing the difference in $T_d$ between three duplexes, one that is perfectly based-paired and the other two that contains a mismatch or a deoxyNebularine substitution. The temperature difference between any two $T_d$s at α=0.5 is defined as the $\Delta T_d$. The percentage of single strand DNA (y-axis) is plotted versus temperature (° C.; x-axis). The melting solution was 100 mM N,N-dimethylhexylamine acetate. The maximum difference between the 3 melting curves in the $T_d$ is 9° C. The helical coil transition (HCT) of the true mismatch was 15° C.; the HCT for the deoxyNebularine mismatch duplex was 15° C. and the HCT for the perfectly based paired duplex was 15° C.

Example 14

Amplification Specificity Using Hybotropic-Based Buffers

This example describes a second generation of buffers that increase the specificity of polymerase chain reaction (PCR). The increase in specificity is effected via the ability to extend only perfectly base-paired 3'-hydroxyls of primers. Any primer in which the 3'-terminal base is mismatched is not extended in the new buffers described here. This permits amplification as an assay for the detection of single nucleotide polymorphism's.

In this experiment, the priming efficiency of PCR is examined using the model system described by Rychlik W., *BioTechniques* 18:84–90 (1995). In this system, DNA of the bacteriophage lambda (GenBank Accession #J02459) is amplified using the following primers: forward primer, 5'-GAACGAAAACCCCCCGC-3' (SEQ ID NO: 23); reverse primer, 5'-GATCGCCCCCAAAACACATA-3' (SEQ ID NO: 32). Note that the forward primer is heavily GC rich at the 3' end of the primer. The forward primer is also synthesized with an "A," "G," or "T" mismatch at the 3'-end. This primer pair amplifies a 381 base pair product. The amplification buffer is 10 mM Tris pH 8.3, 50 mM KCl, 1.5 mM MgC$_2$, and 100 mM ethyl piperidine acetate, pH 7.0 or 100 mM dipropylammonium acetate, pH 6.5. The bacteriophage lambda template is diluted to 0.25 ng/µl and human genomic DNA (used as a source of background DNA to increase complexity) is diluted to 0.25 ng/µl prior to use in the reaction. The total dNTP concentrations are 0.8 mM, the primer concentration is 200 nM, and 0.25 ng of template DNA is used per reaction. 0.5 units of Taq polymerase (Perkin Elmer, Norwalk, Conn.), was used per reaction. Amplification consisted of 25 cycles of 15 second at 94° C., 1 minute at 52° C., and 1 minute at 72° C. Amplified products are separated along with DNA standards by electrophoresis, through 2% agarose gel in 0.5% TBE (45 mM Tris-borate, pH 8.0, 0.1 mM EDTA) and visualized by staining with ethidium bromide.

Individual PCR reactions are performed with the 4 forward primers (perfectly matched or containing the "A," "G," or "T" mismatch at the 3'-end) in buffer containing 100 mM ethyl piperidine. In addition, the primers contain a deoxyNebularine 5 nucleotides in from the 3' end of the primer.

The results indicate the following:

| | |
|---|---|
| 5'--------------------dN--------->3' | base-paired (G/C) = product |
| 5'--------------------dN--------->3' | mismatch (G/T) = no product |
| 5'--------------------dN--------->3' | mismatch (G/A) = no product |
| 5'--------------------dN--------->3' | mismatch (G/G) = no product |

These results indicate a substantial difference in amplification between standard PCR buffer and buffer containing 100 mM ethyl piperidine acetate in terms of the fidelity of priming a 3' mismatch.

All publications and patent applications mentioned in this specification are herein incorporated by reference to the same extent as if each individual publication or patent application was specifically and individually incorporated by reference.

Example 15

Polymorphism Detection inf the YP2D6 Gene P4502D6 Assay

It was chosen to study the CYP2D6 polymorphisms which are responsible for the metabolism of debrisoquine 4-hydroxylase. This particular P450 cytochrome is important in the metabolism of more than 30 drugs and xenobiotic compounds. Thirty CEPH DNA samples were genotyped at 8 polymorphic loci by RFLP (See table for RFLP enzymes, fragment size, etc.) and seventy-eight Newfoundland DNA samples were genotyped at 8 polymorphic loci by sequencing. (See table for sequencing results). RFLP/Sequencing will serve as the "gold standard" for the CMST-based assay. The mutations selected for study include C188T, G212A, delT1795, G1846T/A, G1934A, delA2637, C2938T, and G4268C. Nucleotide numbering follows that established by Kimura et al (1989). The RFLPS were detected by gel electrophoresis as previously described (Gough et. al., 1990, Nature, 347, p773–776). Primers used for RFLP corresponds to those used by Sachse et al (Am. J. Hum. Genet., 1997, 60:284–295) or Sequencing reactions were performed on an ABI 377 instrument (ABI, Foster City, Calif.). Primers used for sequencing corresponds to those used by Meyer et al (Pharmacogenetics, 1995, 5, 373–384)

The principle of the CMST-based assay was to immobilize one strand of the amplified CYP2D6 exon on a solid phase (in this case magnetic particles), hybridize the modified oligonucleotide probes, wash away unhybridized material, elute the hybridized probe and then detect the mass spec tag by mass spectrometry after cleaving the tag from the probe. The utility of the method is proportional to the number of tags than can be simultaneously detected with a mass spectrometer.

Streptavidin magnetic particles (Promega Magnesphere, binding capacity of 80 pmol biotin/100 μg particles) were washed with low salt wash and binding buffer (LSWBB, 100 mM NaCl, 1 mM EDTA, 10 mM Tris, pH 7.5) and then resuspended in high salt wash and binding buffer (HSWBB, 2 M NaCl, 1 mM EDTA, and 10 mM Tris pH 7.5) at a concentration of 2000 μg/ml. The biotinylated PCR products were incubated with the streptavidin particles for 2 hours at 21 C. with constant rotary mixing. The particles were washed twice with 200 μl of HSWBB and once with 200 μl of LSWBB. The bound PCR amplicons were then denatured by treatment with 50 μl of 0.1 N NaOH for 10 minutes at 21 C. The particles were then washed once with 50 μl of 0.1 N NaOH and three times with 200 μl LSWBB. The particle-bound amplicons were then hybridized with equal molar mixtures of wild-type (wt) and mutant (mt) probes possessing different mass tags. Fifty picomoles of respective probe was placed in 200 μl of 0.5 M 1-ethyl-piperidine, 5 mM EDTA and 50 μof the hybridization solution was placed with the particles. Hybridization was for 1 hour at 21 C. with constant rotary mixing. The particles were washed 5 times with LSWBB and the tubes were changed after the second wash. The hybridized probes were eluted from the particles by treatment of the particles with 20 μl of 0.1 N NaOH and a following wash of 9 μl of 0.1 N NaOH. The solution was then neutralized with 3 μl of 1 M acetic acid. Five μl of this solution was then injected into the mass spectrometer (HP 1100 series LC/MS equipped with a vacuum degasser, binary pump, autosampler and diode array detector. The mass spectrometer was used with the APCI source option. HP LC/MSD Chemstation software was used for system control, data acquisition and data analysis installed on a HP vectra XA with the Windows NT workstation version 4.0 operating system). The flow steam into the MS consists of 50% acetonitrile in ultra-pure water at a flow rate of 800 μl/minute. The photochemical cleavage device consisted of 254 nm low pressure mercury lamp, a UV transparent reactor coil and a lamp holder (Aura Industries).

Representative results are as follows:

| Individual | Exon | mAU (wt) | mAU (mt) | CMST call | RFLP call |
|---|---|---|---|---|---|
| 1362 PF 13 | 4 | 0 | 190,000 | M/M | M/M |
| 1362 PM 14 | 4 | 152,000 | 0 | W/W | W/W |
| 1362 MF 15 | 4 | 149,000 | 53,000 | W/M | W/M |
| 1377 C1 19 | 6 | 0 | 271,000 | M/M | M/M |
| 1377 C2 20 | 6 | 104,000 | 88,000 | W/M | W/M |
| 1377 C3 21 | 6 | 290,000 | 0 | W/W | W/W |
| 1377 C1 19 | 9 | 0 | 74,000 | M/M | M/M |
| 1377 C2 20 | 9 | 38,000 | 41,0001 | W/M | W/M |
| 1377 C3 21 | 9 | 149,000 | 0 | W/W | W/W |
| CONTROL | | 0 | 0 | NONE | NONE |

The results indicate that both wildtype and mutant alleles can be easily typed using this technique.

P4502D6 Validation Assay

Primers that flank the 2D6 gene (Sachse et. al) were used to amplify a 4,681 b.p. genomic DNA fragment containing all of the relevant gene sequence. The PCR reaction was composed of 1×Expand HF buffer, 1.5 mM MgCl2, 200 μM dNTP's, 0.5 μM primers P100 & P200, 0.5% formamide, 100 ng gDNA, and 1.1U Expand™ High Fidelity enzyme mix (Boehringer Mannheim). Thermocycling conditions were as follows: 94 C. for 3 minutes; 10 cycles of 94 C. for 30 seconds, 62 C. for 30 seconds, and 68 C. for 4 minutes; 20 cycles of 94 C. for 30 seconds, 62C. for 30 seconds, and 68 C. for 4 minutes +20 seconds/cycle; 68 C. for 10 minutes. Product were visualized on a 1.0 % agarose gel stained with ethidium bromide.

CYP p450 RFLP Assay

The nested PCR reactions consisted of 10 mM Tris-HCl pH 8.3, 50 mM KCI, 1.25 mM MgC12, 200 µM dNTP's, 0.5% formamide, 5pM primer A&B as specified in table 1, 1/250 dilution of the 4.6 KB template , and 1.25 units of TAQ polymerase. The thermocycling conditions were 94 C. for 3 minutes, 25 cycles of 94 C. for 30 seconds, 60 C. for 30 seconds, 72 C. for 1 minute, and a final extension step of 72 C. for 5 minutes. PCR products were visualized on an agarose gel (2.5%) stained with ethidium bromide. Primers for the CYP2D6 exon amplification were designed according to Sachse et. al. See Table ? for RFLP results.

Sequencing Standard Assay

1×PCR buffer consisted of 10 mM Tris-HCl pH 8.3, 50 mM KCl, 1.0–1.5 mM MgC12, 200 µM dNTP's, 0.5 µM primer A&B as specified in table 2, 1/250 dilution of the 4.6 KB template , and 1.25 units of TAQ polymerase. The thermocycling conditions were 94 C. for 3 minutes, 35 cycles of 94 C. for 30 seconds, 59 C. for 30 seconds, 72 C. for 1 minute, and a final extension step of 72 C. for 5 minutes. PCR products were visualized on an agarose gel (2.5%) stained with Ethidium Bromide. Prior to sequencing the reactions were purified via a Qiagen BioRobot 9600. Primers for the CYP2D6 exon amplification were designed according to Meyer et al. See Table 2 for sequencing results.

All publications and patent applications mentioned in this specification are herein incorporated by reference to the same extent as if each individual publication or patent application was specifically and individually incorporated by reference.

From the foregoing it will be appreciated that, although specific embodiments of the invention have been described herein for purposes of illustration, various modifications may be made without deviating from the spirit and scope of the invention. Accordingly, the invention is not limited except as by the appended claims.

We claim:

1. A composition comprising a nucleic acid molecule and a salt, the salt comprising an anion and a cation, the anion selected from halogenated acetate, propionate and halogenated propionate, the cation selected from primary, secondary and tertiary ammonium comprising 1–36 carbon atoms.

2. The composition of claim 1 wherein the anion is trichloroacetate.

3. The composition of claim 1 wherein the anion is trifluoroacetate.

4. The composition of claim 1 wherein the cation is formed from atoms selected from 2–20 carbons, 0–5 oxygens and 1–5 nitrogens.

5. The composition of claim 1 wherein the cation has the structure $HN(R)_3$ wherein the nitrogen is positively charged, R is a $C_1$–$C_{12}$ hydrocarbyl and any two R groups may join together to form a cyclic structure with the nitrogen.

6. The composition of claim 5 wherein R is independently selected from the group consisting of $C_1$–$C_{12}$ alkyl, $C_3$–$C_{12}$ cycloalkyl and $C_7$–$C_{12}$ arylalkyl.

7. The composition of claim 1 wherein the cation has the structure $N(H)_2(R)_2$ wherein the nitrogen is positively charged, R is a $C_1$–$C_{12}$ hydrocarbyl and the two R groups may join together to form a cyclic structure with the nitrogen.

8. The composition of claim 7 wherein R is independently selected from the group consisting of $C_1$–$C_{12}$ alkyl, $C_3$–$C_{12}$ cycloalkyl and $C_7$–$C_{12}$ arylalkyl.

9. The composition of claim 1 wherein the cation is selected from the group consisting of ethylbutylammonium, 1-methylimidizole, 1-methylpiperidine, 1-methylpyrrolidine, 3-methoxypropylamine, triethylamine, bis(2-methoxyethyl)amine, diallylamine, dibutylamine, diisobutylamine, N,N-dimethylaminobutane, N,N-dimethylcyclohexylamine, N,N-dimethylheptylamine, N,N-dimethylhexylamine, triethanolamine, 1-ethylpiperidine, dicyclohexylamine, diisopropylamine, dipropylamine, N,N-dimethylisopropylamine, N-ethylbutylamine, tripropylamine, 2-methoxyethylamine, and N,N-dimethyloctylamine, and the anion is selected from the group consisting of trichloroacetate and trifluoroacetate.

10. The composition of claim 1 wherein the nucleic acid molecule comprises 6–100 nucleotides.

11. The composition of claim 1 wherein the nucleic acid molecule is DNA.

12. The composition of claim 1 wherein the nucleic acid molecule is immobilized on a solid support.

13. The composition of claim 1 wherein the nucleic acid molecules are arranged in an array on a solid support.

14. The composition of claim 1 further comprising an enzyme selected from polymerase and ligase.

15. The composition of claim 1 further comprising water.

16. The composition of claim 15 wherein the salt is completely dissolved in the water at a concentration of from 50 mM to 6 M at room temperature.

17. The composition of claim 15 wherein the nucleic acid molecule is present at a concentration of from $10^{-6}$ to $10^{-18}$ g/mL.

18. The composition of claim 15 further comprising at least one of a buffer, detergent and chelator.

19. A composition which is non-flowing comprising a nucleic acid molecule of 6–100 nucleotides and a salt, the salt comprising an anion and a cation, the anion selected from acetate, halogenated acetate, propionate, and halogenated propionate, the cation selected from primary, secondary and tertiary ammonium comprising 1–36 carbons.

20. A composition which is free from organic solvent, comprising a nucleic acid molecule of 6–100 nucleotides and a salt, the salt comprising an anion and a cation, the anion selected from acetate, halogenated acetate, propionate, and halogenated propionate, the cation selected from primary, secondary and tertiary ammonium comprising 1–36 carbons.

21. The composition of any of claims 19 or 20 wherein the anion is acetate.

22. The composition of claim 19 wherein the cation is formed from atoms selected from 2–20 carbons, 0–5 oxygens, and 1–5 nitrogens.

23. The composition of claim 19 wherein the cation has the structure $HN(R)_3$ wherein the nitrogen is positively charged, R is a $C_1$–$C_{12}$ hydrocarbyl and any two R groups may join together to form a cyclic structure with the nitrogen.

24. The composition of claim 19 wherein the cation has the structure $N(H)_2(R)_2$ wherein the nitrogen is positively charged, R is a $C_1$–$C_{12}$ hydrocarbyl and the two R groups may join together to form a cyclic structure with the nitrogen.

25. The composition of claim 19 wherein the nucleic acid molecule is DNA.

26. The composition of claim 19 wherein the nucleic acid molecules are arranged in an array on a solid support.

27. The composition of claim 19 further comprising water.

28. The composition of claim 27 wherein the salt is completely dissolved in the water at a concentration of from 50 mM to 6 M at room temperature.

29. A composition comprising a nucleic acid and a salt, the nucleic acid immobilized on a solid support, the salt comprising an anion and a cation, the anion selected from acetate, halogenated acetate, propionate and halogenated propionate, the cation selected from primary, secondary and tertiary ammonium comprising 1–36 carbons.

30. The composition of claim 29 wherein the anion is selected from acetate, trifluoroacetate and trichloroacetate.

31. The composition of claim 29 wherein the cation is formed from atoms selected from 2–20 carbons, 0–5 oxygens, and 1–5 nitrogens.

32. The composition of claim 29 wherein the cation has the structure $HN(R)_3$ wherein the nitrogen is positively charged, R is a $C_1$–$C_{12}$hydrocarbyl and any two R groups may join together to form a cyclic structure with the nitrogen.

33. The composition of claim 29 wherein the cation has the structure $N(H)_2(R)_2$ wherein the nitrogen is positively charged, R is a $C_1$–$C_{12}$hydrocarbyl and the two R groups may join together to form a cyclic structure with the nitrogen.

34. The composition of claim 29 wherein the cation is selected from the group consisting of ethylbutylammonium, 1-methylimidizole, 1-methylpiperidine, 1-methylpyrrolidine, 3-methoxypropylamine, triethylamine, bis(2-methoxyethyl)amine, diallylamine, dibutylamine, diisobutylamine, N,N-dimethylaminobutane, N,N-dimethylcyclohexylamine, N,N-dimethylheptylamine, N,N-dimethylhexylamine, triethanolamine, 1-ethylpiperidine, dicyclohexylamine, diisopropylamine, dipropylamine, N,N-dimethylisopropylamine, N-ethylbutylamine, tripropylamine, 2-methoxyethylamine, and N,N-dimethyloctylamine, and the anion is selected from the group consisting of trichloroacetate and trifluoroacetate.

35. The composition of claim 29 wherein the solid support is selected from materials having a planar surface and comprising quartz, gold, nylon-6,6, nylon, polystyrene, glass, and silicon.

36. The composition of claim 35 wherein the solid support is selected from a glass plate and a silicon wafer.

37. The composition of claim 29 wherein the nucleic acid molecules are arranged in separated domains in an array, where the number of domains present in an array is selected from the ranges 10 to 50, 50 to 400, and 400 to 800.

38. The composition of claim 37 wherein the domains are substantially circular, where the circles have an average diameter of about 10 microns to 200 microns.

39. The composition of claim 29 wherein the nucleic acids comprise a plurality of sequences.

40. A salt selected from the group consisting of:
   (a) an acetate salt of a cation of the formula $HN(CH_3)_2R_a$ wherein the nitrogen is positively charged and $R^a$ is a $C_4$–$C_7$hydrocarbyl;
   (b) a halogenated acetate salt of a cation of the formula $HN(CH_3)_2R_b$ wherein the nitrogen is positively charged and $R_b$ is a $C_7$–$C_{12}$hydrocarbyl;
   (c) acetate and halogenated acetate salts of a cation of the formula $H_2N(C_5$–$C_7$cycloalkyl)$R_c$ where the nitrogen is positively charged and $R_c$ is a $C_1$–$C_{12}$hydrocarbyl;
   (d) acetate and halogenated acetate salts of N-substituted piperidine, wherein the nitrogen of piperidine is positively charged and substituted with $C_1$–$C_{12}$hydrocarbyl.

41. The salt of claim 40 wherein hydrocarbyl is selected from alkyl, alkenyl, alkynyl, cycloalkyl, cycloalkenyl, aryl, aralkyl, and alkylaryl.

42. The salt of claim 40 which is an acetate salt of a cation of the formula $HN(CH_3)_2R_a$ wherein the nitrogen is positively charged and $R_a$ is a $C_4$–$C_7$hydrocarbyl.

43. The salt of claim 40 which is a halogenated acetate salt of a cation of the formula $HN(CH_3)_2R_b$ wherein the nitrogen is positively charged and $R_b$ is a $C_7$–$C_{12}$hydrocarbyl.

44. The salt of claim 40 which is an acetate or halogenated acetate salt of a cation of the formula $H_2N(C_5$–$C_7$cycloalkyl)$R_c$ where the nitrogen is positively charged and $R_c$ is a $C_1$–$C_{12}$hydrocarbyl.

45. The salt of claim 40 which is an acetate or halogenated acetate salt of N-substituted piperidine, wherein the nitrogen of piperidine is positively charged and substituted with $C_1$–$C_{12}$hydrocarbyl.

46. An oligonucleotide in solution comprising a plurality of fragments, each fragment shown schematically by structure (1)

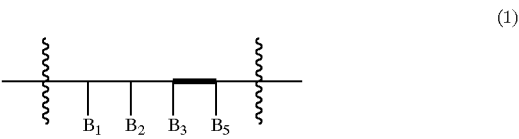

wherein

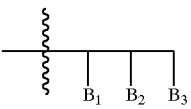

represents a sequence of at least three nucleotides as found in wild-type DNA, where "B" represents a base independently selected at each location;

—— represents a series of covalent chemical bonds termed a "specificity spacer," which separates and connects two bases $B_3$ and $B_5$, wherein all nearest specificity spacers are separated by 8–12 nucleotides having a wild-type sequence;

the specificity spacer having steric and chemical properties such that (a) it does not prevent hybridization between a fragment of structure (1) and an oligonucleotide fragment having a complementary base sequence, as shown schematically as structure (2)

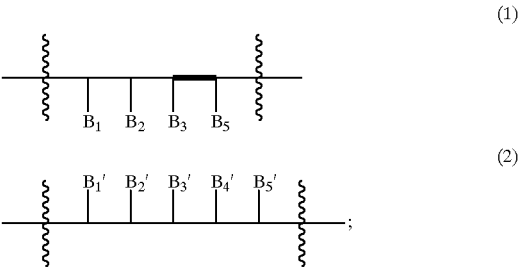

and (b) it cannot enter into hydrogen bonding with a base positioned opposite itself in a hybridized complementary base sequence of structure (2).

47. The oligonucleotide of claim 46 wherein the specificity spacer has the formula

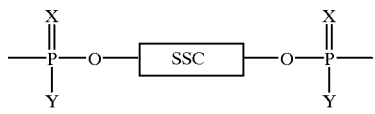

wherein

Y is selected from oxygen, sulfur, methyl and amino when X is oxygen, or Y is selected from oxygen and sulfur when X is sulfur; and SSC represents a specificity spacer component having a chain of 2–5 carbons shown in the formula

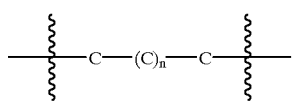

wherein n is 0, 1, 2 or 3, and each of the shown 2–5 carbons of the specificity spacer component may be independently substituted with $C_1$–$C_{10}$hydrocarbyl or $C_1$–$C_{10}$hydrocarbyloxy, and any two of the shown 2–5 carbon atoms which are bonded directly to one another may form a carbocyclic or heterocyclic 5–6 membered ring.

48. The oligonucleotide of claim 46 wherein n of the specificity spacer component is 1, and the specificity spacer component has the formula (2)

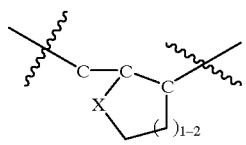

(2)

wherein n is 1 and X is selected from carbon, oxygen and sulfur, such that any carbon shown in formula (2), including X when it is carbon, may be substituted with hydrogen, $C_1$–$C_5$hydrocarbyl, $C_1$–$C_5$hydrocarbyloxy, a non-hydrogen bonding purine base analog or a non-hydrogen bonding pyrimidine base analog.

49. The oligonucleotide of claim 47 wherein the specificity spacer component has the formula (3)

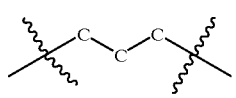

wherein each of the three shown carbons may be substituted with hydrogen, $C_1$–$C_{10}$hydrocarbyl or $C_1$–$C_{10}$hydrocarbyloxy.

50. The oligonucleotide of claim 47 having a plurality of specificity spacers, where specificity spacers constitute 15–60% of the positions occupied by specificity spacers and nucleotides having a wild-type sequence.

51. An array comprising a plurality of oligonucleotides immobilized in an array format to a solid support, each oligonucleotide of the plurality comprising a plurality of fragments, each fragment shown schematically by structure (1)

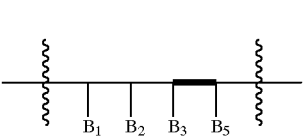
(1)

wherein,

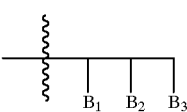

represents a sequence of at least three nucleotides as found in wild-type DNA, where "B" represents a base independently selected at each location;

—— represents a series of covalent chemical bonds termed a "specificity spacer," which separates and connects two bases $B_3$ and $B_5$, wherein all nearest specificity spacers are separated by 8–12 nucleotides having a wild-type sequence;

the specificity spacer having steric and chemical properties such that (a) it does not prevent hybridization between a fragment of structure (1) and an oligonucleotide fragment having a complementary base sequence, as shown schematically as structure (2)

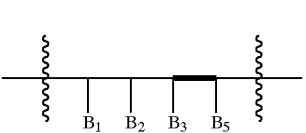
(1)

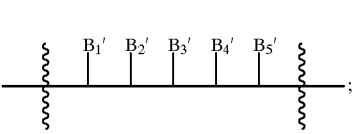
(2)

and (b) it cannot enter into hydrogen bonding with a base positioned opposite itself in a hybridized complementary base sequence of structure (2).

52. The array of claim 51 wherein the specificity spacer has the formula

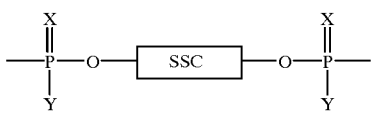

wherein

Y is selected from oxygen, sulfur, methyl and amino when X is oxygen, or Y is selected from oxygen and sulfur when X is sulfur; and SSC represents a specificity spacer component having a chain of 2–5 carbon atoms shown in the formula

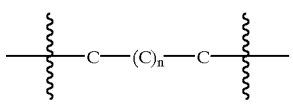

wherein n is 0, 1, 2 or 3, and each of the shown 2–5 carbon atoms of the specificity spacer component may be independently substituted with $C_1$–$C_{10}$hydrocarbyl or $C_1$–$C_{10}$hydrocarbyloxy, and any two of the shown 2–5 carbon atoms which are bonded directly to one another may form a carbocyclic or heterocyclic 5–6 membered ring.

53. The array of claim 51 wherein n of the specificity spacer component is 1, and the specificity spacer component has the formula (2)

(2)

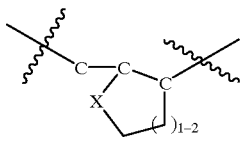

wherein n is 1 and X is selected from carbon, oxygen and sulfur, such that any carbon shown in formula (2), including X when it is carbon, may be substituted with hydrogen, $C_1$–$C_5$hydrocarbyl, $C_1$–$C_5$hydrocarbyloxy, a non-hydrogen bonding purine base analog or non-hydrogen bonding pyrimidine base analog.

54. The array of claim 51 wherein the specificity spacer component has the formula (3)

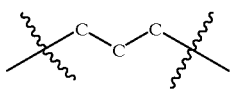

wherein each of the three shown carbons may be substituted with hydrogen, $C_1$–$C_{10}$hydrocarbyl or $C_1$–$C_{10}$hydrocarbyloxy.

55. The array of claim 51 wherein each of the plurality of oligonucleotides have a plurality of specificity spacers, where specificity spacers constitute 15–60% of the positions occupied by specificity spacers and nucleotides having wild-type sequence.

56. An oligonucleotide in solution comprising a plurality of fragments, each fragment shown schematically by structure (1)

(1)

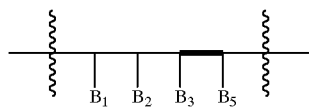

wherein,

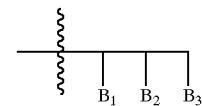

represents a sequence of at least three nucleotides as found in wild-type DNA, where "B" represents a base independently selected at each location;
—— represents a series of covalent chemical bonds termed a "specificity spacer," which separates and connects two bases $B_3$ and $B_5$, wherein all nearest specificity spacers are separated by 8–12 nucleotides having a wild-type sequence;
the specificity spacer having steric and chemical properties such that
(a) it does not prevent hybridization between a fragment of structure (1) and an oligonucleotide fragment having a complementary base sequence, as shown schematically as structure (2)

(1)

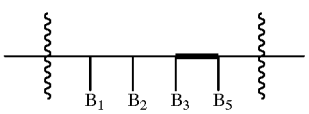

(2)

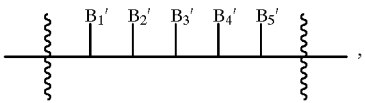

(b) it enters into hydrogen bonding with a base positioned opposite itself in a hybridized complementary base sequence of structure (2); and
(c) it does not hydrogen-bond through any of adenine, guanine, cytosine, thymine or uracil.

57. The oligonucleotide of claim 56 wherein the specificity spacer has the formula

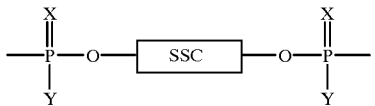

wherein
Y is selected from oxygen, sulfur, methyl and amino when X is oxygen, or Y is selected from oxygen and sulfur when X is sulfur; and
SSC represents a specificity spacer component having a chain of 2–5 carbon atoms shown in the formula

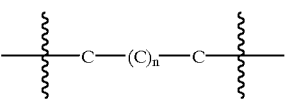

wherein n is 0, 1, 2 or 3, and each of the shown 2–5 carbon atoms of the specificity spacer component may be independently substituted with $C_1$–$C_{10}$hydrocarbyl or $C_1$–$C_{10}$hydrocarbyloxy, and any two of the shown 2–5 carbon atoms which are bonded directly to one another may form a carbocyclic or heterocyclic 5–6 membered ring.

58. The oligonucleotide of claim 57 wherein n of the specificity spacer component is 1, and the specificity spacer component has the formula (2)

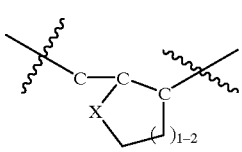

(2)

wherein n is 1 and X is selected from carbon, oxygen and sulfur, such that any carbon shown in formula (2), including X when it is carbon, may be substituted with hydrogen, $C_1$–$C_5$hydrocarbyl, $C_1$–$C_5$hydrocarbyloxy, a purine base analog or a pyrimidine base analog, where the purine base analog and the pyrimidine base analog may hydrogen bond to a complementary strand.

59. The oligonucleotide of claim 57 wherein the specificity spacer component has the formula (3)

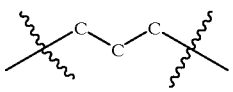

wherein each of the three shown carbon atoms may be substituted with hydrogen, $C_1$–$C_{10}$hydrocarbyl or $C_1$–$C_{10}$hydrocarbyloxy.

60. The oligonucleotide of claim 56 having a plurality of specificity spacers, where specificity spacers constitute 15–60% of the positions occupied by specificity spacers and wild-type nucleotides.

61. An array comprising a plurality of oligonucleotides immobilized in an array format to a solid support, each oligonucleotide of the plurality comprising a plurality of fragments, each fragment shown schematically by structure (1)

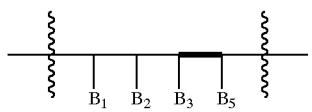

(1)

wherein,

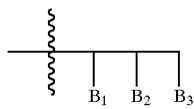

represents a sequence of at least three nucleotides as found in wild-type DNA, where "B" represents a base independently selected at each location;

—— represents a series of covalent chemical bonds termed a "specificity spacer," which separates and connects two bases $B_3$ and $B_5$, wherein all nearest specificity spacers are separated by 8–12 nucleotides having a wild-type sequence;

the specificity spacer having steric and chemical properties such that (a) it does not prevent hybridization between a fragment of structure (1) and an oligonucleotide fragment having a complementary base sequence, as shown schematically as structure (2)

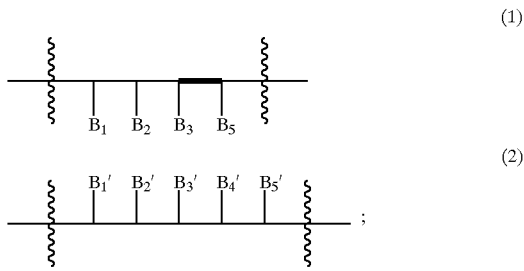

(b) it enters into hydrogen bonding with a base positioned opposite itself in a hybridized complementary base sequence of structure (2); and
(c) it does not hydrogen-bond through any of adenine, guanine, cytosine, thymine or uracil.

62. The array of claim 61 wherein the specificity spacer has the formula

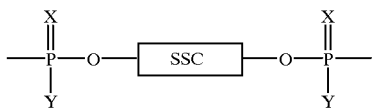

wherein
Y is selected from oxygen, sulfur, methyl and amino when X is oxygen, or Y is selected from oxygen and sulfur when X is sulfur; and
SSC represents a specificity spacer component having a chain of 2–5 carbon atoms shown in the formula

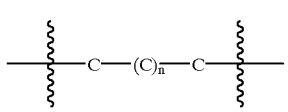

wherein n is 0, 1, 2 or 3, and each of the shown 2–5 carbon atoms of the specificity spacer component may be independently substituted with $C_1$–$C_{10}$hydrocarbyl or $C_1$–$C_{10}$hydrocarbyloxy, and any two of the shown 2–5 carbon atoms which are bonded directly to one another may form a carbocyclic or heterocyclic 5–6 membered ring.

63. The array of claim 62 wherein n of the specificity spacer component is 1, and the specificity spacer component has the formula (2)

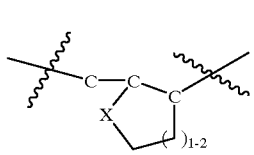

(2)

wherein n is 1 and X is selected from carbon, oxygen and sulfur, such that any carbon shown in formula (2), including X when it is carbon, may be substituted with hydrogen, $C_1$–$C_5$hydrocarbyl, $C_1$–$C_5$hydrocarbyloxy, a purine base, a pyrimidine base, a non-hydrogen bonding purine base analog or a non-hydrogen bonding pyrimidine base.

64. The array of claim 62 wherein the specificity spacer component has the formula (3)

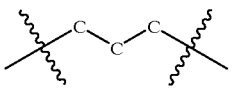

wherein each of the three shown carbon atoms may be substituted with hydrogen, $C_1$–$C_{10}$hydrocarbyl or $C_1$–$C_{10}$hydrocarbyloxy.

65. The array of claim 61 wherein each of the plurality of oligonucleotides have a plurality of specificity spacers, where specificity spacers constitute 15–60% of the positions occupied by specificity spacers and nucleotides having wild-type sequence.

66. A method of distinguishing between hybridizations of a complementary nucleic acid target and a nucleic acid probe in which the probe and target are perfectly complementary and in which the probe and target have one or more base mismatches, comprising:
(a) mixing the nucleic acid target with the nucleic acid probe in a solution comprising a hybotrope, the hybotrope comprising an anion and a cation, the anion selected from acetate, halogenated acetate, propionate and halogenated propionate, and the cation selected from primary, secondary and tertiary ammonium comprising 1–36 carbon atoms;
(b) hybridizing at a discriminating temperature; and
(c) detecting hybridized probe and target,
thereby determining whether the nucleic acid probe and target are perfectly complementary or mismatched.

67. The method according to claim 66 wherein the nucleic acid probe is labeled with a radioactive molecule, fluorescent molecule, mass-spectrometry tag or enzyme.

68. The method according to claim 66 wherein the nucleic acid probe is from 6 to 40 bases.

69. The method according to claim 66 wherein the target nucleic acid probe is from 6 to 40 bases.

70. The method according to claim 66 wherein the hybotrope is selected from the group consisting of bis(2-methoxyethyl)amine acetate, 1-ethylpiperidine acetate, 1-ethylpiperidine trichloroacetate, 1-ethylpiperidine trifluoroacetate, 1-methylimidizole acetate, 1-methylpiperidine acetate, 1-methylpiperidine trichloroacetate, 1-methylpyrrolidine acetate, 1-methylpyrrolidine trichloroacetate, 1-methylpyrrolidine trifluoroacetate, 2-methoxyethylamine acetate, N,N-dimethylcyclohexylamine acetate, N,N-dimethylcyclohexylamine trifluoroacetate, N,N-dimethylcyclohexylamine, N,N-dimethylheptylamine acetate, N,N-dimethylheptylamine acetate, N,N-dimethylhexylamine acetate, N,N-dimethylhexylamine acetate, N,N-dimethylisopropylamine acetate, N-ethylbutylamine acetate, N-ethylbutylamine trifluoroacetate, N,N-dimethylaminobutane trichloroacetate, N,N-dimethylisopropylamine trichloroacetate, triethanolamine acetate, triethylamine acetate, triethylamine trichloroacetate, and tripropylamine acetate.

71. The method according to claim 66 wherein the hybotrope is a compound that has a $pK_1$ of less than 2.2 in water at 25° C.

72. The method according to claim 66 wherein the hybotrope is present at a molarity of from about 0.5 M to about 6 M.

73. The method according to claim 66 wherein the probe nucleic acid is DNA or RNA.

74. The method according to claim 66 wherein the target nucleic acid is genomic DNA, RNA, or cDNA.

75. The method according to claim 66 wherein the target nucleic acid is affixed to a solid substrate.

76. A method of distinguishing between hybridizations of a complementary nucleic acid target and a nucleic acid probe in which the probe and target are perfectly complementary and in which the probe and target have one or more base mismatches, comprising:
(a) mixing a nucleic acid target with a nucleic acid probe containing at least one abasic residue or base analog in the presence of a hybotrope, the hybotrope present at a molarity of from about O.5M to about 6M;
(b) hybridizing at a discriminating temperature; and
(c) detecting hybridized probe and target,
thereby determining whether the nucleic acid probe and target are perfectly complementary or mismatched.

77. The method according to claim 76 wherein the base analog is deoxyNebularine.

78. The method according to claim 76 wherein the nucleic acid probe is labeled with a radioactive molecule, fluorescent molecule, mass-spectrometry tag or enzyme.

79. The method according to claim 76 wherein the nucleic acid probe is from 6 to 40 bases.

80. The method according to claim 76 wherein the target nucleic acid probe is from 6 to 40 bases.

81. The method according to claim 76 wherein the hybotrope is selected from the group consisting of bis(2-methoxyethyl)amine acetate, 1-ethylpiperidine acetate, 1-ethylpiperidine trichloroacetate, 1-ethylpiperidine trifluoroacetate, 1-methylimidizole acetate, 1-methylpiperidine acetate, 1-methylpiperidine trichloroacetate, 1-methylpyrrolidine acetate, 1-methylpyrrolidine trichloroacetate, 1-methylpyrrolidine trifluoroacetate, 2-methoxyethylamine acetate, N,N-dimethylcyclohexylamine acetate, N,N-dimethylcyclohexylamine trifluoroacetate, N,N-dimethylcyclohexylamine, N,N-dimethylheptylamine acetate, N,N-dimethylheptylamine acetate, N,N-dimethylhexylamine acetate, N,N-dimethylhexylamine acetate, N,N-dimethylisopropylamine acetate, N-ethylbutylamine acetate, N-ethylbutylamine trifluoroacetate, N,N-dimethylaminobutane trichloroacetate, N,N-dimethylisopropylamine trichloroacetate, triethanolamine acetate, triethylamine acetate, triethylamine trichloroacetate, tripropylamine acetate, and tetraethylammonium acetate.

82. The method according to claim 76 wherein the probe nucleic acid is DNA or RNA.

83. The method according to claim 76 wherein the target nucleic acid is genomic DNA, RNA or cDNA.

84. The method according to claim 76 wherein the target nucleic acid is affixed to a solid substrate.

85. A method of increasing discrimination in a nucleic acid synthesis procedure, comprising:
(a) mixing a single-stranded nucleic acid target with an oligonucleotide primer in a solution comprising a hybotrope and a polymerase, where the hybotrope is present at a molarity of from about 0.5 M to about 6 M;
(b) annealing the primer to the target at a discriminating temperature; and
(c) synthesizing a complementary strand to the target to form a duplex.

86. The method according to claim 85 wherein the nucleic acid primer is labeled with a radioactive molecule, fluorescent molecule, mass-spectrometry tag or enzyme.

87. The method according to claim 85 wherein the nucleic acid primer is from 6 to 40 bases.

88. The method according to claim 85 wherein the hybotrope is selected from the group consisting of bis(2-methoxyethyl)amine acetate, 1-ethylpiperidine acetate, 1-ethylpiperidine trichloroacetate, 1-ethylpiperidine trifluoroacetate, 1-methylimidizole acetate, 1-methylpiperidine acetate, 1-methylpiperidine trichloroacetate, 1-methylpyrrolidine acetate, 1-methylpyrrolidine trichloroacetate, 1-methylpyrrolidine trifluoroacetate, 2-methoxyethylamine acetate, N,N-dimethylcyclohexylamine acetate, N,N-dimethylcyclohexylamine trifluoroacetate, N,N-dimethylcyclohexylamine, N,N-dimethylheptylamine acetate, N,N-dimethylheptylamine acetate, N,N-dimethylhexylamine acetate, N,N-dimethylhexylamine acetate, N,N-dimethylisopropylamine acetate, N-ethylbutylamine acetate, N-ethylbutylamine trifluoroacetate, N,N-dimethylaminobutane trichloroacetate, N,N-dimethylisopropylamine trichloroacetate, triethanolamine acetate, triethylamine acetate, triethylamine trichloroacetate, tripropylamine acetate, and tetraethylammonium acetate.

89. The method according to claim 85 wherein the hybotrope is an amine-based salt selected from the group consisting of ethylpiperidine acetate, ethylbutylamine acetate, bismethoxyamine acetate, dipropylamine acetate and diisopropylamine acetate.

90. The method according to claim 85 wherein the hybotrope is ethyl piperidine.

91. The method according to claim 85 wherein the hybotrope is present at a molarity of from about 10 M to about 1 M.

92. The method according to claim 85 wherein the steps of (a), (b), and (c) are repeated multiple times.

93. A method of distinguishing a single base change in a nucleic acid molecule from a wild-type sequence, comprising:

(a) mixing a single-stranded nucleic acid target with an oligonucleotide primer in a solution comprising a hybotrope and a polymerase, where the hybotrope is present at a molarity of from about 0.5 M to about 6 M, and wherein the oligonucleotide primer has a 3'-most base complementary to the wild-type sequence or the single base change;

(b) annealing the primer to the target at a discriminating temperature;

(c) extending the primer, wherein a complementary strand to the target is synthesized when the 3'-most base of the primer is complementary to the target; and (d) detecting the extension of the primer.

94. The method of claim 93, further comprising in step (a) a second primer having a wild-type sequence, wherein the second primer anneals to the strand synthesized in step (c).

95. The method of claim 94 wherein steps (a), (b) and (c) are performed multiple times.

96. The method of claim 94 wherein the hybotrope is selected from the group consisting of bis(2-methoxyethyl)amine acetate, 1-ethylpiperidine acetate, 1-ethylpiperidine trichloroacetate, 1-ethylpiperidine trifluoroacetate, 1-methylimidizole acetate, 1-methylpiperidine acetate, 1-methylpiperidine trichloroacetate, 1-methylpyrrolidine acetate, 1-methylpyrrolidine trichloroacetate, 1-methylpyrrolidine trifluoroacetate, 2-methoxyethylamine acetate, N,N-dimethylcyclohexylamine acetate, N,N-dimethylcyclohexylamine trifluoroacetate, N,N-dimethylcyclohexylamine, N,N-dimethylheptylamine acetate, N,N-dimethylheptylamine acetate, N,N-dimethylhexylamine acetate, N,N-dimethylhexylamine acetate, N,N-dimethylisopropylamine acetate, N-ethylbutylamine acetate, N-ethylbutylamine trifluoroacetate, N,N-dimethylaminobutane trichloroacetate, N,N-dimethylisopropylamine trichloroacetate, triethanolamine acetate, triethylamine acetate, triethylamine trichloroacetate, tripropylamine acetate, and tetraethylammonium acetate.

97. The method of claim 94 wherein the hybotrope is 1-ethylpiperidine acetate.

* * * * *

UNITED STATES PATENT AND TRADEMARK OFFICE
CERTIFICATE OF CORRECTION

PATENT NO. : 6,361,940 B1
DATED : March 26, 2002
INVENTOR(S) : Jeffrey Van Ness et al.

It is certified that error appears in the above-identified patent and that said Letters Patent is hereby corrected as shown below:

<u>Column 119,</u>
Line 29, "The oligonucleotide of claim 46" should read -- The oligonucleotide of claim 47 --.

Signed and Sealed this

Thirtieth Day of July, 2002

*Attest:*

*Attesting Officer*

JAMES E. ROGAN
*Director of the United States Patent and Trademark Office*

SEQUENCE LISTING (1) GENERAL INFORMATION:

(iii) NUMBER OF SEQUENCES: 35

(2) INFORMATION FOR SEQ ID NO:1:

(i) SEQUENCE CHARACTERISTICS:
      (A) LENGTH: 30 base pairs
      (B) TYPE: nucleic acid
      (C) STRANDEDNESS: single
      (D) TOPOLOGY: linear (xi) SEQUENCE DESCRIPTION: SEQ ID NO:1:

GTCATACTCC TGCTTGCTGA TCCACATCTG          30

(2) INFORMATION FOR SEQ ID NO:2:

(i) SEQUENCE CHARACTERISTICS:
      (A) LENGTH: 24 base pairs
      (B) TYPE: nucleic acid
      (C) STRANDEDNESS: single
      (D) TOPOLOGY: linear (xi) SEQUENCE DESCRIPTION: SEQ ID NO:2:

TGTGGATCAG CAAGCAGGAG TATG          24

(2) INFORMATION FOR SEQ ID NO:3:

(i) SEQUENCE CHARACTERISTICS:
      (A) LENGTH: 24 base pairs
      (B) TYPE: nucleic acid
      (C) STRANDEDNESS: single
      (D) TOPOLOGY: linear (xi) SEQUENCE DESCRIPTION: SEQ ID NO:3:

TGTGGATCAG GAAGCAGGAG TATG          24

(2) INFORMATION FOR SEQ ID NO:4:

(i) SEQUENCE CHARACTERISTICS:
      (A) LENGTH: 24 base pairs
      (B) TYPE: nucleic acid
      (C) STRANDEDNESS: single
      (D) TOPOLOGY: linear

```
    (ix) FEATURE:
        (A) NAME/KEY: -
        (B) LOCATION: 11
        (D) OTHER INFORMATION: /note= "Where N is an unnatural
             nucleotide (i.e., a nucleotide having a chemical moiety
             which is not one of A,G,C,T or U at the position normally
             occupied by A,G,C,T or U) or a molecular spacer that
             provides an equal linear distance, as a natural
             nucleotide, along the DNA phosphate sugar backbone"

(xi) SEQUENCE DESCRIPTION: SEQ ID NO:4:

TGTGGATCAG NAAGCAGGAG TATG                                       24

(2) INFORMATION FOR SEQ ID NO:5:

(i) SEQUENCE CHARACTERISTICS:
        (A) LENGTH: 36 base pairs
        (B) TYPE: nucleic acid
        (C) STRANDEDNESS: single
        (D) TOPOLOGY: linear (xi) SEQUENCE DESCRIPTION: SEQ ID NO:5:

GCAGCCTCGC GGAGGCGGAT GATCGTCATT AGTATT                          36

(2) INFORMATION FOR SEQ ID NO:6:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (xi) SEQUENCE DESCRIPTION: SEQ ID NO:6:

CCGCCTCCGC GAGGCTGC                                              18

(2) INFORMATION FOR SEQ ID NO:7:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (xi) SEQUENCE DESCRIPTION: SEQ ID NO:7:

AATGACGATC ATCCGCCT                                              18

(2) INFORMATION FOR SEQ ID NO:8:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (xi) SEQUENCE DESCRIPTION: SEQ ID NO:8:

AATACTAATG ACGATCAT                                              18

(2) INFORMATION FOR SEQ ID NO:9:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (ix) FEATURE:
        (A) NAME/KEY: -
        (B) LOCATION: 13
        (D) OTHER INFORMATION: /note= "Where N is an unnatural
``` nucleotide (i.e., a nucleotide having a chemical moiety
which is not one of A,G,C,T or U at the position normally
occupied by A,G,C,T or U) or a molecular spacer that
provides an equal linear distance, as a natural
nucleotide, along the DNA phosphate sugar backbone"

(xi) SEQUENCE DESCRIPTION: SEQ ID NO:9:

TGTGGATCAG CANGCAGGAG TATG                                           24

(2) INFORMATION FOR SEQ ID NO:10:

(i) SEQUENCE CHARACTERISTICS:
        (A) LENGTH: 19 base pairs
        (B) TYPE: nucleic acid
        (C) STRANDEDNESS: single
        (D) TOPOLOGY: linear (xi) SEQUENCE DESCRIPTION: SEQ ID NO:10:

AAATAATTCA GGGTCAAAA                                                 19

(2) INFORMATION FOR SEQ ID NO:11:

(i) SEQUENCE CHARACTERISTICS:
        (A) LENGTH: 19 base pairs
        (B) TYPE: nucleic acid
        (C) STRANDEDNESS: single
        (D) TOPOLOGY: linear (xi) SEQUENCE DESCRIPTION: SEQ ID NO:11:

CTGTCGTAGG TAAATAACT                                                 19

(2) INFORMATION FOR SEQ ID NO:12:

(i) SEQUENCE CHARACTERISTICS:
        (A) LENGTH: 19 base pairs
        (B) TYPE: nucleic acid
        (C) STRANDEDNESS: single
        (D) TOPOLOGY: linear (xi) SEQUENCE DESCRIPTION: SEQ ID NO:12:

AAAAAGTGGG GAAGTGAGT                                                 19

(2) INFORMATION FOR SEQ ID NO:13:

(i) SEQUENCE CHARACTERISTICS:
        (A) LENGTH: 19 base pairs
        (B) TYPE: nucleic acid
        (C) STRANDEDNESS: single
        (D) TOPOLOGY: linear (xi) SEQUENCE DESCRIPTION: SEQ ID NO:13:

GTGTTAACTT CCGCTCCTC                                                 19

(2) INFORMATION FOR SEQ ID NO:14:

(i) SEQUENCE CHARACTERISTICS:
        (A) LENGTH: 19 base pairs
        (B) TYPE: nucleic acid
        (C) STRANDEDNESS: single
        (D) TOPOLOGY: linear (xi) SEQUENCE DESCRIPTION: SEQ ID NO:14:

GGCGTAGGTC TGTCGTGCT                                                 19

(2) INFORMATION FOR SEQ ID NO:15:

(i) SEQUENCE CHARACTERISTICS:

(A) LENGTH: 19 base pairs
        (B) TYPE: nucleic acid
        (C) STRANDEDNESS: single
        (D) TOPOLOGY: linear (xi) SEQUENCE DESCRIPTION: SEQ ID NO:15:

GGTGTGGGTC CGTCGTGCC                                                    19

(2) INFORMATION FOR SEQ ID NO:16:

(i) SEQUENCE CHARACTERISTICS:
        (A) LENGTH: 30 base pairs
        (B) TYPE: nucleic acid
        (C) STRANDEDNESS: single
        (D) TOPOLOGY: linear (xi) SEQUENCE DESCRIPTION: SEQ ID NO:16:

CAGATGGGTA TCAGCAAGCA GGAGTATGAC                                         30

(2) INFORMATION FOR SEQ ID NO:17:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (xi) SEQUENCE DESCRIPTION: SEQ ID NO:17:

ATGGGTATCA GCAAGCAGGA GTAT                                               24

(2) INFORMATION FOR SEQ ID NO:18:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (xi) SEQUENCE DESCRIPTION: SEQ ID NO:18:

GGTATCAGCA AGCAGGAG                                                      18

(2) INFORMATION FOR SEQ ID NO:19:

(i) SEQUENCE CHARACTERISTICS:
        (A) LENGTH: 30 base pairs
        (B) TYPE: nucleic acid
        (C) STRANDEDNESS: single
        (D) TOPOLOGY: linear (xi) SEQUENCE DESCRIPTION: SEQ ID NO:19:

CAGATGGGTA TCAGGAAGCA GGAGTATGAC                                         30

(2) INFORMATION FOR SEQ ID NO:20:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (xi) SEQUENCE DESCRIPTION: SEQ ID NO:20:

ATGGGTATCA GGAAGCAGGA GTAT                                               24

(2) INFORMATION FOR SEQ ID NO:21:

(i) SEQUENCE CHARACTERISTICS:
        (A) LENGTH: 18 base pairs (B) TYPE: nucleic acid
        (C) STRANDEDNESS: single
        (D) TOPOLOGY: linear (xi) SEQUENCE DESCRIPTION: SEQ ID NO:21:

GGTATCAGGA AGCAGGAG                                                        18

(2) INFORMATION FOR SEQ ID NO:22:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (xi) SEQUENCE DESCRIPTION: SEQ ID NO:22:

TTGATTCCCA ATTATGCGAA GGAG                                                 24

(2) INFORMATION FOR SEQ ID NO:23:

(i) SEQUENCE CHARACTERISTICS:
        (A) LENGTH: 17 base pairs
        (B) TYPE: nucleic acid
        (C) STRANDEDNESS: single
        (D) TOPOLOGY: linear (xi) SEQUENCE DESCRIPTION: SEQ ID NO:23:

GAACGAAAAC CCCCCGC                                                         17

(2) INFORMATION FOR SEQ ID NO:24:

(i) SEQUENCE CHARACTERISTICS:
        (A) LENGTH: 17 base pairs
        (B) TYPE: nucleic acid
        (C) STRANDEDNESS: single
        (D) TOPOLOGY: linear (xi) SEQUENCE DESCRIPTION: SEQ ID NO:24:

CTTCGAAAAC CCCCCGC                                                         17

(2) INFORMATION FOR SEQ ID NO:25:

(i) SEQUENCE CHARACTERISTICS:
        (A) LENGTH: 17 base pairs
        (B) TYPE: nucleic acid
        (C) STRANDEDNESS: single
        (D) TOPOLOGY: linear (xi) SEQUENCE DESCRIPTION: SEQ ID NO:25:

CTTGCTAAAC CCCCCGC                                                         17

(2) INFORMATION FOR SEQ ID NO:26:

(i) SEQUENCE CHARACTERISTICS:
        (A) LENGTH: 17 base pairs
        (B) TYPE: nucleic acid
        (C) STRANDEDNESS: single
        (D) TOPOLOGY: linear (ix) FEATURE:
        (A) NAME/KEY: -
        (B) LOCATION: 7
        (D) OTHER INFORMATION: /note= "Where N is an unnatural
            nucleotide (i.e., a nucleotide having a chemical moiety
            which is not one of A,G,C,T or U at the position normally
            occupied by A,G,C,T or U) or a molecular spacer that
            provides an equal linear distance, as a natural
            nucleotide, along the DNA phosphate sugar backbone"

```
       (ix) FEATURE:
             (A) NAME/KEY: -
             (B) LOCATION: 14
             (D) OTHER INFORMATION: /note= "Where N is an unnatural
                 nucleotide (i.e., a nucleotide having a chemical moiety
                 which is not one of A,G,C,T or U at the position normally
                 occupied by A,G,C,T or U) or a molecular spacer that
                 provides an equal linear distance, as a natural
                 nucleotide, along the DNA phosphate sugar backbone"

(xi) SEQUENCE DESCRIPTION: SEQ ID NO:26:

GAACGANAAC CCCNCGC                                                        17

(2) INFORMATION FOR SEQ ID NO:27:

(i) SEQUENCE CHARACTERISTICS:
             (A) LENGTH: 17 base pairs
             (B) TYPE: nucleic acid
             (C) STRANDEDNESS: single
             (D) TOPOLOGY: linear (ix) FEATURE:
             (A) NAME/KEY: -
             (B) LOCATION: 7
             (D) OTHER INFORMATION: /note= "Where N is an unnatural
                 nucleotide (i.e., a nucleotide having a chemical moiety
                 which is not one of A,G,C,T or U at the position normally
                 occupied by A,G,C,T or U) or a molecular spacer that
                 provides an equal linear distance, as a natural
                 nucleotide, along the DNA phosphate sugar backbone"

(ix) FEATURE:
             (A) NAME/KEY: -
             (B) LOCATION: 13
             (D) OTHER INFORMATION: /note= "Where N is an unnatural
                 nucleotide (i.e., a nucleotide having a chemical moiety
                 which is not one of A,G,C,T or U at the position normally
                 occupied by A,G,C,T or U) or a molecular spacer that
                 provides an equal linear distance, as a natural
                 nucleotide, along the DNA phosphate sugar backbone"

(xi) SEQUENCE DESCRIPTION: SEQ ID NO:27:

GAACGANAAC CCNCCGC                                                        17

(2) INFORMATION FOR SEQ ID NO:28:

(i) SEQUENCE CHARACTERISTICS:
             (A) LENGTH: 18 base pairs
             (B) TYPE: nucleic acid
             (C) STRANDEDNESS: single
             (D) TOPOLOGY: linear (ix) FEATURE:
             (A) NAME/KEY: -
             (B) LOCATION: 7
             (D) OTHER INFORMATION: /note= "Where N is an unnatural
                 nucleotide (i.e., a nucleotide having a chemical moiety
                 which is not one of A,G,C,T or U at the position normally
                 occupied by A,G,C,T or U) or a molecular spacer that
                 provides an equal linear distance, as a natural
                 nucleotide, along the DNA phosphate sugar backbone"

(ix) FEATURE:
             (A) NAME/KEY: -
             (B) LOCATION: 17
             (D) OTHER INFORMATION: /note= "Where N is an unnatural
                 nucleotide (i.e., a nucleotide having a chemical moiety
                 which is not one of A,G,C,T or U at the position normally
                 occupied by A,G,C,T or U) or a molecular spacer that
                 provides an equal linear distance, as a natural
                 nucleotide, along the DNA phosphate sugar backbone"

(xi) SEQUENCE DESCRIPTION: SEQ ID NO:28:

GAACGANAAC CCCCCGNC                                                       18
```

(2) INFORMATION FOR SEQ ID NO:29:

(i) SEQUENCE CHARACTERISTICS:
        (A) LENGTH: 17 base pairs
        (B) TYPE: nucleic acid
        (C) STRANDEDNESS: single
        (D) TOPOLOGY: linear (ix) FEATURE:
        (A) NAME/KEY: -
        (B) LOCATION: 6
        (D) OTHER INFORMATION: /note= "Where N is an unnatural
            nucleotide (i.e., a nucleotide having a chemical moiety
            which is not one of A,G,C,T or U at the position
            normally occupied by A,G,C,T or U) or a molecular spacer
            that provides an equal linear distance, as a natural
            nucleotide, along the DNA phosphate sugar backbone"

(ix) FEATURE:
        (A) NAME/KEY: -
        (B) LOCATION: 13
        (D) OTHER INFORMATION: /note= "Where N is an unnatural
            nucleotide (i.e., a nucleotide having a chemical moiety
            which is not one of A,G,C,T or U at the position
            normally occupied by A,G,C,T or U) or molecular spacer
            that provides an equal linear distance, as a natural
            nucleotide, along the DNA phosphate sugar backbone"

(xi) SEQUENCE DESCRIPTION: SEQ ID NO:29:

```
GAACGNAAAC CCNCCGC                                                    17
```

(2) INFORMATION FOR SEQ ID NO:30:

(i) SEQUENCE CHARACTERISTICS:
        (A) LENGTH: 17 base pairs
        (B) TYPE: nucleic acid
        (C) STRANDEDNESS: single
        (D) TOPOLOGY: linear (ix) FEATURE:
        (A) NAME/KEY: -
        (B) LOCATION: 6
        (D) OTHER INFORMATION: /note= "Where N is an unnatural
            nucleotide (i.e., a nucleotide having a chemical moiety
            which is not one of A,G,C,T or U at the position
            normally occupied by A,G,C,T or U) or a molecular spacer
            that provides an equal linear distance, as a natural
            nucleotide, along the DNA phosphate sugar backbone"

(ix) FEATURE:
        (A) NAME/KEY: -
        (B) LOCATION: 12
        (D) OTHER INFORMATION: /note= "Where N is an unnatural
            nucleotide (i.e., a nucleotide having a chemical moiety
            which is not one of A,G,C,T or U at the position normally
            occupied by A,G,C,T or U) or a molecular spacer that
            provides an equal linear distance, as a natural
            nucleotide, along the DNA phosphate sugar backbone"

(xi) SEQUENCE DESCRIPTION: SEQ ID NO:30:

```
GAACGNAAAC CNCCCGC                                                    17
```

(2) INFORMATION FOR SEQ ID NO:31:

(i) SEQUENCE CHARACTERISTICS:
        (A) LENGTH: 17 base pairs
        (B) TYPE: nucleic acid
        (C) STRANDEDNESS: single
        (D) TOPOLOGY: linear (ix) FEATURE:
        (A) NAME/KEY: -
        (B) LOCATION: 13

(D) OTHER INFORMATION: /note= "Where N is an unnatural
    nucleotide (i.e., a nucleotide having a chemical moiety
    which is not one of A,G,C,T or U at the position
    normally occupied by A,G,C,T or U) or a molecular spacer
    that provides an equal linear distance, as a natural
    nucleotide, along the DNA phosphate sugar backbone"

(xi) SEQUENCE DESCRIPTION: SEQ ID NO:31:

CTTCGAAAAC CCNCCGC                                            17

(2) INFORMATION FOR SEQ ID NO:32:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (xi) SEQUENCE DESCRIPTION: SEQ ID NO:32:

GATCGCCCCC AAAACACATA                                    20

(2) INFORMATION FOR SEQ ID NO:33:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (xi) SEQUENCE DESCRIPTION: SEQ ID NO:33:

ACACCTAGTC GTTCGTCCTC ATAC                              24

(2) INFORMATION FOR SEQ ID NO:34:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (ix) FEATURE:
        (A) NAME/KEY: -
        (B) LOCATION: 7
        (D) OTHER INFORMATION: /note= "Where N is an unnatural
            nucleotide (i.e., a nucleotide having a chemical moiety
            which is not one of A,G,C,T or U at the position
            normally occupied by A,G,C,T or U) or a molecular
            spacer that provides an equal linear distance, as a
            natural nucleotide, along the DNA phosphate sugar
            backbone"

(xi) SEQUENCE DESCRIPTION: SEQ ID NO:34:

ACACCTNGTC GTTCGTCCTC ATAC                              24

(2) INFORMATION FOR SEQ ID NO:35:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (ix) FEATURE:
        (A) NAME/KEY: -
        (B) LOCATION: 7
        (D) OTHER INFORMATION: /note= "Where N is an unnatural
            nucleotide (i.e., a nucleotide having a chemical moiety
            which is not one of A,G,C,T or U at the position
            normally occupied by A,G,C,T or U) or a molecular
            spacer that provides an equal linear distance, as a
            natural nucleotide, along the DNA phosphate sugar -continued

```
        backbone"
(ix) FEATURE:
    (A) NAME/KEY: -
    (B) LOCATION: 21
    (D) OTHER INFORMATION: /note= "Where N is an unnatural
        nucleotide (i.e., a nucleotide having a chemical
        moiety which is not one of A,G,C,T or U at the
        position normally occupied by A,G,C,T or U) or a
        molecular spacer that provides an equal linear distance,
        as a natural nucleotide, along the DNA phosphate sugar
        backbone"

(xi) SEQUENCE DESCRIPTION: SEQ ID NO:35:

ACACCTNGTC GTTCGTCCTC NTAC                                          24
```